(12) United States Patent
Jenekhe et al.

(10) Patent No.: US 9,172,049 B2
(45) Date of Patent: Oct. 27, 2015

(54) SOLUTION-PROCESSABLE ELECTRON-TRANSPORT MATERIALS AND RELATED ORGANIC OPTOELECTRONIC DEVICES

(71) Applicant: University of Washington through its Center for Commercialization, Seattle, WA (US)

(72) Inventors: Samson A. Jenekhe, Seattle, WA (US); Taeshik Earmme, Seattle, WA (US); Eilaf Ahmed, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 106 days.

(21) Appl. No.: 13/767,243

(22) Filed: Feb. 14, 2013

(65) Prior Publication Data

US 2013/0285021 A1 Oct. 31, 2013

Related U.S. Application Data

(63) Continuation of application No. PCT/US2011/047305, filed on Aug. 10, 2011.

(60) Provisional application No. 61/374,204, filed on Aug. 16, 2010.

(51) Int. Cl.
*H01B 1/00* (2006.01)
*H01L 51/00* (2006.01)
*C07D 215/06* (2006.01)
(Continued)

(52) U.S. Cl.
CPC .......... *H01L 51/0072* (2013.01); *C07D 215/06* (2013.01); *C07D 215/12* (2013.01); *C07D 401/14* (2013.01); *H01L 51/0037* (2013.01); *H01L 51/0042* (2013.01);
(Continued)

(58) Field of Classification Search
CPC ............................ C07D 215/06; C07D 215/12
USPC ................................ 252/500; 257/40; 438/82
See application file for complete search history.

(56) References Cited

U.S. PATENT DOCUMENTS 5,645,948 A 7/1997 Shi

FOREIGN PATENT DOCUMENTS

| JP | 2003-59670 A | 2/2003 |
| JP | 20030-86381 A | 3/2003 |
| WO | 2006/029226 A1 | 3/2006 |

OTHER PUBLICATIONS

Buu-Hoï, N. P., et al., "Nitrogen Hetrocyclic Analogs of Polyaryls," Journal of Heterocyclic Chemistry 2(1):7-10, Mar. 1965.
(Continued)

*Primary Examiner* — Douglas Menz
(74) *Attorney, Agent, or Firm* — Christensen O'Connor Johnson Kindness PLLC

(57) ABSTRACT

Charge transport compounds are provided. The compounds are useful in optoelectronic devices that include the compounds incorporated as a charge-transport layer. Methods for forming films of the compounds are also provided. Additionally, methods are provided for forming films of a charge-transport layer on an active layer of an optoelectronic device. The films are formed from a solution with solubility orthogonal to the solubility of the active layer, such that the active layer is not solvated during deposition of the charge-transport layer.

54 Claims, 55 Drawing Sheets

(51) Int. Cl.
 C07D 215/12 (2006.01)
 C07D 401/14 (2006.01)
 H01L 51/50 (2006.01)
(52) U.S. Cl.
 CPC ........ H01L 51/0085 (2013.01); H01L 51/5072 (2013.01); H01L 2051/0063 (2013.01)

(56) References Cited

OTHER PUBLICATIONS

Earmme, T., et al., "Solution-Processed Highly Efficient Blue Phosphorescent Polymer Light-Emitting Diodes Enabled by a New Electron Transport Material," Advanced Materials 22(42):4744-4748, Nov. 2010.
International Search Report and Written Opinion mailed Jun. 20, 2012, issued in corresponding International Application No. PCT/US2011/047305, filed Aug. 10, 2011, 15 pages.
Kitazawa, D., et al., Database WPI, Week 200342, Thomson Scientific, London, AN 2003-444152, Mar. 20, 2003.
Rodriguez, J.G., et al., "Synthesis of n-Chloroquinolines and n-Ethynylquinolines (n=2, 4, 8): Homo and Heterocoupling Reactions," Tetrahedron 61(38):9042-9051, Sep. 2005.
Kim, F.S., et al., "One-Dimensional Nanostructures of π-Conjugated Molecular Systems: Assembly, Properties, and Applications From Photovoltaics, Sensors, and Nanophotonics to Nanoelectronics," Chemistry of Materials 23(3):682-732, Feb. 2011.
Kim, K.H., et al., "Small Molecule Host System for Solution-Processed Red Phosphorescent OLEDs," Synthetic Metals 160(7-8):631-635, Apr. 2010.
Kim, S.H., et al., "Stable efficiency Roll-Off in Phosphorescent Organic Light-Emitting Diodes," Applied Physics Letters 92(2):023513-1-023513-3, Jan. 2008.
Kulkarni, A.P., and S.A. Jenekhe, "Blue-Green, Orange, and White Organic Light-Emitting Diodes Based on Exciplex Electroluminescence of an Oligoquinoline Acceptor and Different Hole-Transport Materials," Journal of Physical Chemistry C 112(13):5174-5184, Apr. 2008.
Kulkarni, A.P., et al., "Electron Transport Materials for Organic Light-Emitting Diodes," Chemistry of Materials 16(23):4556-4573, Nov. 2004.
Kwon, T.W., et al., "n-Type Conjugated Dendrimers: Convergent Synthesis, Photophysics, Electroluminescence, and Use as Electron-Transport Materials for Light-Emitting Diodes," Chemistry of Materials 16(23):4657-4666, Nov. 2004.
Lai, W.Y., et al., "A Phosphorescent Poly(dendrimer) Containing Iridium(III) Complexes: Synthesis and Light-Emitting Properties," Macromolecules 43(17):6986-6994, Sep. 2010.
Lee, S.-J., et al., "Synthesis and Characterization of Red-Emitting Iridium(III) Complexes for Solution-Processable Phosphorescent Organic Light-Emitting Diodes," Advanced Functional Materials 19(14):2205-2212, Jul. 2009.
Lee, T.-W., et al., "Characteristics of Solution-Processed Small-Molecule Organic Films and Light-Emitting Diodes Compared With Their Vacuum-Deposited Counterparts," Advanced Functional Materials 19(10):1625-1630, May 2009.
Li, H., et al., "First-Principles Theoretical Investigation of the Electronic Couplings in Single Crystals of Phenanthroline-Based Organic Semiconductors," Journal of Chemical Physics 126(16):164704-1-164704-7, Apr. 2007.
Li, Y.-J., et al., "Highly Efficient Green Phosphorescent OLED Based on Pyridine-Containing Starburst Electron-Transporting Materials," Chemistry Letters 39(2):140-141, 2010.
Liu, B., et al., "Blue-Light-Emitting Cationic Water-Soluble Polyfluorene Derivatives With Tunable Quaternization Degree," Macromolecules 35(13):4975-4982, Jun. 2002.
Liu, Z-Y. et al., "Solution-Processed Small Molecular Electron Transport Layer for Multilayer Polymer Light-Emitting Diodes," Synthetic Metals 161(5-6):426-430, Mar. 2011.
Lo, S.C. et al., "High-Triplet-Energy Dendrons: Enhancing the Luminescence of Deep Blue Phosphorescent Indium(III) Complexes," Journal of the American Chemical Society 131(46):16681-16688, Nov. 2009.
Lo, S.-C., et al., "Solution-Processible Phosphorescent Blue Dendrimers Based on Biphenyl-Dendrons and Fac-tris (phenyltriazolyl)iridium(III) Cores," Advanced Functional Materials 18(19):3080-3090, Oct. 2008.
Ma, B., et al., "Multifunctional Crosslinkable Iridium Complexes as Hole Transporting/Electron Blocking and Emitting Materials for Solution-Processed Multilayer Organic Light-Emitting Diodes," Advanced Functional Materials 19(7):1024-1031, Apr. 2009.
Mori, T., et al., "Electroluminescent Properties in Organic Light-Emitting Diode Doped With Two Guest Dyes," Japanese Journal of Applied Physics 40(9A):5346-5349, Sep. 2001.
Mori, T., et al., "Electronic Structure of 8-hydroxyquinoline Aluminum/LiF/Al Interface for Organic Electroluminescent Device Studied by Ultraviolet Photoelectron Spectroscopy," Applied Physics Letters 73(19):2763-2765, Nov. 1998.
Murgatroyd, P.N., "Dimensional Considerations for Space-Charge Conduction in Solids," Journal of Physics D: Applied Physics 3(10):1488-1490, Oct. 1970.
Naka, S., et al., "High Electron Mobility in Bathophenanthroline," Applied Physics Letters 76(2):197-199, Jan. 2000.
Nakada, H., et al., "Blue Organic Electroluminescent Devices Using Phenanthroline Derivatives as an Electron Transport Layer," Polymer Preprints Japan (English Edition) 43(7):2450-2451, 1994.
O'Brien, F.O., et al., "Improved Energy Transfer in Electrophosphorescent Devices," Applied Physics Letters 74(3):442-444, Jan. 1999.
Osaheni, J.A., and S.A. Jenekhe, "Efficient Blue Luminescence of a Conjugated Polymer Exciplex," Macromolecules 27(3):739-742, May 1994.
Oyamada, T., et al., "Efficient Electron Injection Characteristics of Triazine Derivatives for Transparent OLEDs (TOLEDs)," Chemistry Letters 33(8):1034-1035, 2004.
Park, J.J., et al., "Small Molecule Interlayer for Solution Processed Phosphorescent Organic Light Emitting Device," Organic Electronics 10(1):189-193, Feb. 2009.
Rajagopal, A., and A. Kahn, "Molecular-Level Offset at the PTCDA/$Alq_3$ Heterojunction," Advanced Materials 10(2):140-144, Jan. 1998.
Rehmann, N., et al., "Highly Efficient Solution-Processed Phosphorescent Multilayer Organic Light-Emitting Diodes Based on Small-Molecule Hosts," Applied Physics Letters 91(10):103507-1-103507-3, Sep. 2007.
Reineke, S., et al., "White Organic Light-Emitting Diodes With Fluorescent Tube Efficiency," Nature 459(7244):234-239, May 2009.
Rodríguez, J.G., et al., "Synthesis of n-chloroquinolines and n-ethynylquinolines (n=2,4,8): Homo and Heterocoupling Reactions," Tetrahedron 61(38):9042-9051, Sep. 2005.
Rodríguez, J.G., et al., "Thermal Analysis of 1,4-di[n'-(quinolyl)]buta-1,3-diynes, Structure, and Topo-Oligomerization: Polymerization of 3-ethynylquinoline With the triethyl Aluminum/Vanadium 2,4-Pentanedionate Catalyst System," Journal of Polymer Science Part A: Polymer Chemistry 42(23):6031-6040, Dec. 2004.
Sasabe, H. and J. Kido, "Multifunctional Materials for High-Performance OLEDs: Challenges for Solid-State Lighting," Chemistry of Materials 23(3):621-630, Feb. 2011.
Sasabe, H., et al., "Influence of Substituted Pyridine Rings on Physical Properties and Electron Mobilities of 2-Methylpyrimidine Skeleton-Based Electron Transporters," Advanced Functional Materials 21(2):336-342, Jan. 2011.
Sasabe, H., et al., "Wide-Energy-Gap Electron-Transport Materials Containing 3,5-Dipyridylphenyl Moieties for an Ultra High Efficiency Blue Organic Light-Emitting Device," Chemistry of Materials 20(19):5951-5953, Oct. 2008.
Sax, S., et al., "Efficient Blue-Light-Emitting Polymer Heterostructure Devices: The Fabrication of Multilayer Structures From Orthogonal Solvents," Advanced Materials 22(18):2087-2091, May 2010.
Sax, S., et al., "Intrinsic Electrochemical Doping in Blue Light Emitting Polymer Devices Utilizing a Water Soluble Anionic Conjugated Polymer," Organic Electronics 8(6):791-795, Dec. 2007.

(56) References Cited

OTHER PUBLICATIONS

Shih, P.-I., and C.-F. Shu, "Efficient White-Light-Emitting Diodes Based on poly(N-vinylcarbazole) Doped With Blue Fluorescent and Orange Phosphorescent Materials," Applied Physics Letters 88(25):251110-1-251110-3, Jun. 2006.
So, F., et al., "Organic Light-Emitting Devices for Solid-State Lighting," MRS Bulletin 33(7):663-669, Jul. 2008.
So., F., et al., "Recent Progress in Solution Processable Organic Light Emitting Devices," Journal of Applied Physics 102(9):091101-1-091101-21, Nov. 2007.
Su, S.-J., et al., "Pyridine-Containing Triphenylbenzene Derivatives With High Electron Mobility for Highly Efficient Phosphorescent OLEDs," Advanced Materials 20(11):2125-2130, Jun. 2008.
Su, S.-J., et al., "Structure-Property Relationship of Pyridine-Containing Triphenyl Benzene Electron-Transport Materials for Highly Efficient Blue Phosphorescent OLEDs," Advanced Functional Materials 19(8):1260-1267, Apr. 2009.
Sun, Y., et al., "Management of Singlet and Triplet Excitons for Efficient White Organic Light-Emitting Devices," Nature 440(7086):908-912, Apr. 2006.
Tang, M.L., and Z. Bao, "Halogenated Materials as Organic Semiconductors," Chemistry of Materials 23(3):446-455, Feb. 2011.
Tonzola, C.J., et al., "Blue-Light-Emitting Oligoquinolines: Synthesis, Properties, and High-Efficiency Blue-Light-Emitting Diodes," Advanced Functional Materials 17(6):863-874, Apr. 2007.
Tonzola, C.J., et al., "New n-Type Organic Semiconductors: Synthesis, Single Crystal Structures, Cyclic Voltammetry, Photophysics, Electron Transport, and Electroluminescence of a Series of Diphenylanthrazolines," Journal of the American Chemical Society 125(44):13548-13558, Nov. 2003.
Tonzola, C.J., et al., "New Soluble n-Type Conjugated Copolymer for Light-Emitting Diodes," Advanced Materials 14(15):1086-1090, Aug. 2002.
Tonzola, C.J., et al., "New Soluble n-Type Conjugated Polymers for Use as Electron Transport Materials in Light-Emitting Diodes," Macromolecules 37(10):3554-3563, May 2004.
Tonzola, C.J., et al., "A New Synthetic Route to Soluble Polyquinolines With Tunable Photophysical, Redox, and Electroluminescent Properties," Macromolecules 38(23):9539-9547, Nov. 2005.
Tsai, M.-H., et al., "Highly Efficient Organic Blue Electrophosphorescent Devices Based on 3,6-Bis(triphenylsilyl) Carbazole as the Host Material," Advanced Materials 18(9):1216-1220, May 2006.
Wang, C., et al., "Tuning the Optoelectronic Properties of Pyridine-Containing Polymers for Light-Emitting Devices," Advanced Materials 12(3):217-222, Feb. 2000.
Wang, L., et al., "Highly Efficient and Color-Stable Deep-Blue Organic Light-Emitting Diodes Based on a Solution-Processible Dendrimer," Advanced Materials 21(47):4854-4858, Dec. 2009.
Adachi, C., et al., "High-Efficiency Organic Electrophosphorescent Devices With tris(2-phenylpyridine)iridium Doped Into Electron-Transporting Materials," Applied Physics Letters 77(6):904-906, Aug. 2000.
Adamovich, V.I., et al., "New Charge-Carrier Blocking Materials for High Efficiency OLEDs," Organic Electronics 4(2-3):77-87, Sep. 2003.
Agrawal, A.K., and S.A. Jenekhe, "Electrochemical Properties and Electronic Structures of Conjugated Polyquinolines and Polyanthrazolines," Chemistry of Materials 8(2):579-589, Feb. 1996.
Agrawal, A.K., and S.A. Jenekhe, "New Conjugated Polyanthrazolines Containing Thiophene Moieties in the Main Chain," Macromolecules 24(25):6806-6808, Dec. 1991.
Ahmed, E., et al., "High Mobility Single-Crystal Field-Effect Transistors From Bisindoloquinoline Semiconductors," Journal of the American Chemical Society 130(4):1118-1119, Jan. 2008.
Ahmed, E., et al., "New Solution-Processable Electron Transport Materials for Highly Efficient Blue Phosphorescent OLEDs," Advanced Functional Materials, 21(20):3889-3899, Oct. 2011.
Ahmed, E., et al., "Novel n-Type Conjugated Ladder Heteroarenes: Synthesis, Self-Assembly of Nanowires, Electron Transport, and Electroluminescence of Bisindenoanthrazolines," Chemistry of Materials 22(20):5786-5796, Oct. 2010.
Alam, M.M., and S.A. Jenekhe, "Efficient Solar Cells From Layered Nanostructures of Donor and Acceptor Conjugated Polymers," Chemistry of Materials 16(23):4647-4656, Nov. 2004.
Alam, M.M., and S.A. Jenekhe, "Polybenzobisazoles Are Efficient Electron Transport Materials for Improving the Performance and Stability of Polymer Light-Emitting Diodes," Chemistry of Materials 14(11):4775-4780, Nov. 2002.
Arias, A.C., et al., "Materials and Applications for Large Area Electronics: Solution-Based Approaches," Chemical Reviews 110(1):3-24, Jan. 2010.
Baldo, M.A., et al., "Highly Efficient Phosphorescent Emission From Organic Electroluminescent Devices," Nature 395(6698):151-154, Sep. 1998.
Baldo, M.A., et al., "Very High-Efficiency Green Organic Light-Emitting Devices Based on Electrophosphorescence," Applied Physics Letters 75(1):4-6, Jul. 1999.
Briseno, A.L., et al., "Perylenediimide Nanowires and Their Use in Fabricating Field-Effect Transistors and Complementary Inverters," Nano Letters 7(9):2847-2853, Sep. 2007.
Cai, M., et al., "High-Efficiency Solution-Processed Small Molecule Electrophosphorescent Organic Light-Emitting Diodes," Advanced Materials 23(31):3590-3596, Aug. 2011.
Campbell, A.J., et al., "Space-Charge Limited Conduction With Traps in Poly(phenylene vinylene) Light Emitting Diodes," Applied Physics Letters 82(12):6326-6342, Dec. 1997.
Chan, M.Y., et al., "Efficient Organic Photovoltaic Devices Using a Combination of Exciton Blocking Layer and Anodic Buffer Layer," Journal of Applied Physics 100(9):094506-1-094506-4, Nov. 2006.
Chopra, N., et al., "High Efficiency Blue Phosphorescent Organic Light-Emitting Device," Applied Physics Letters 93(14):143307-1-143307-3, Oct. 2008.
Chopra, N., et al., "High-Efficiency Blue Emitting Phosphorescent OLEDs," IEEE Transactions on Electron Devices 57(1):101-107, Jan. 2010.
Choudhury, K.R., et al., "LiF as an n-Dopant in Tris(8-hydroxyquinoline) Aluminum Thin Films," Advanced Materials 20(8):1456-1461, Apr. 2008.
Chu, T.-Y., and O.-K. Song, "Hole Mobility of N,N'-bis(naphthalen-1-yl)-N,N'-bis(phenyl) Benzidine Investigated by Using Space-Charge-Limited Currents," Applied Physics Letters 90(2):203512-1-203512-3, May 2007.
Cui, Y., et al., "Thiophene-Linked Polyphenylquinoxaline: A New Electron Transport Conjugated Polymer for Electroluminescent Devices," Macromolecules 32(11):3824-3826, Jun. 1999.
Ding, J., et al., "Solution-Processable Carbazole-Based Conjugated Dendritic Hosts for Power-Efficient Blue-Electrophosphorescent Devices," Advanced Materials 21(48):4983-4986, Dec. 2009.
Earmme, T., and S.A. Jenekhe, "High-Performance Multilayered Phosphorescent OLEDs by Solution-Processed Commercial Electron-Transport Materials," Journal of Materials Chemistry 22(22):4660-4668, Mar. 2012.
Earmme, T., et al., "Highly Efficient Phosphorescent Light-Emitting Diodes by Using an Electron-Transport Material With High Electron Affinity," Journal of Physical Chemistry C 113(43):18448-18450, Oct. 2009.
Endo, A., et al., "Efficient Up-Conversion of Triplet Excitons Into a Singlet State and Its Application for Organic Light Emitting Diodes," Applied Physics Letters 98(8):083302-1-083302-3, Feb. 2011.
Forrest, S.R., "The Path to Ubiquitous and Low-Cost Organic Electronic Appliances on Plastic," Nature 428(6986):911-918, Apr. 2004.
Friend, R.H., et al., "Electroluminescence in Conjugated Polymers," Nature 397(6715):121-128, Jan. 1999.
Fukagawa, H., et al., "Efficient White Organic Light Emitting Diodes With Solution Processed and Vacuum Deposited Emitting Layers," Organic Electronics 10(5):798-802, Aug. 2009.
Gather, M.C., et al., "White Organic Light-Emitting Diodes," Advanced Materials 23(2):233-248, Jan. 2011.
Gong, S., et al., "Biopolar Tetraarylsilanes as Universal Hosts for Blue, Green, Orange, and White Electrophosphorescence With High

(56) References Cited

OTHER PUBLICATIONS

Efficiency and Low Efficiency Roll-Off," Advanced Functional Materials 21(6):1168-1178, Mar. 2011.
Gong, X., et al., "High-Efficiency Polymer-Based Electrophosphorescent Devices," Advanced Materials 14(8):581-585, Apr. 2002.
Gong, X., et al., "Multilayer Polymer Light-Emitting Diodes: White-Light Emission With High Efficiency," Advanced Materials 17(17):2053-2058, Sep. 2005.
Grimsdale, A.C., "Synthesis of Light-Emitting Conjugated Polymers for Applications in Electroluminescent Devices," Chemical Reviews 109(3):897-1091, Mar. 2009.
Grozea, D., et al., "Chemical Structure of Al/LiF/Alq Interfaces in Organic Light-Emitting Diodes," Applied Physics Letters 81(17):3173-3175, Oct. 2002.
Haldi, A., et al., "Highly Efficient Green Phosphorescent Organic Light-Emitting Diodes With Simplified Device Geometry," Applied Physics Letters 92(25):253502-1-253502-3, Jun. 2008.
Hancock, J.M., and S.A. Jenekhe, "Unusual Protonation-Induced Continuous Tunability of Optical Properties and Electroluminescence of π-Conjugated Heterocyclic Oligomer," Macromolecules 41(19):6864-6867, Oct. 2008.
Holmes, R.J., et al., "Efficient, Deep-Blue Organic Electrophosphorescence by Guest Charge Trapping," Applied Physics Letters 83(18):3818-3820, Nov. 2003.
Hoven, C.V., et al., "Recent Applications of Conjugated Polyelectrolytes in Optoelectronic Devices," Advanced Materials 20(20):3793-3810, Oct. 2008.
Hsu, F.-M., et al., "Phosphine-Oxide-Containing Biopolar Host Material for Blue Electrophosphorescent Devices," Chemistry of Materials 21(6):1017-1022, Mar. 2009.
Huang, F., et al., "High-Efficiency, Environment-Friendly Electroluminescent Polymers with Stable High Work Function Metal as a Cathode: Green- and Yellow-Emitting Conjugated Polyfluorene Polyelectrolytes and Their Neutral Precursors," Journal of the American Chemical Society 126(31):9845-9853, Aug. 2004.
Hughes, G., and M.R. Bryce, "Electron-Transporting Materials for Organic Electroluminescent and Electrophosphorescent Devices," Journal of Materials Chemistry 15(1):94-107, 2005.
Hung, L.S., et al., "Enhanced Electron Injection in Organic Electroluminescence Devices Using an Al/LiF Electrode," Applied Physics Letters 70(2):152-154, Jan. 1997.
Jenekhe, S.A., and J.A. Osaheni, "Excimers and Exciplexes of Conjugated Polymers," Science 265(5173):765-768, Aug. 1994.
Jenekhe, S.A., and S.J. Yi, "Efficient Photovoltaic Cells From Semiconducting Polymer Heterojunctions," Applied Physics Letters 77(17):2635-2637, Oct. 2000.
Jiang, Z., et al., "Star-Shaped Oligotriarylamines With Planarized Triphenylamine Core: Solution-Processable, High-Tg Hole-Injecting and Hole-Transporting Materials for Organic Light-Emitting Devices," Chemistry of Materials 23(3):771-777, Feb. 2011.
Kamtekar, K.T., et al., "Recent Advances in White Organic Light-Emitting Materials and Devices (WOLEDs)," Advanced Materials 22(5):572-582, Feb. 2010.
Kawamura, Y., et al., "Energy Transfer in Polymer Electrophosphorescent Light Emitting Devices With Single and Multiple Doped Luminescent Layers," Journal of Applied Physics 92(1):87-93, Jul. 2002.
Khan, M.A., et al., "Electron Mobility of 4,7-diphyenyl-1,10-phenanthroline Estimated by Using Space-Charge-Limited Currents," Journal of Applied Physics 103(1):014509-1-014509-4, Jan. 2008.
Kido, J., et al., "1,2,4-Triazole Derivative as an Electron Transport Layer in Organic Electroluminescent Devices," Japanese Journal of Applied Physics 32(7A):L917-L920, Jul. 1993.
Kido, J., et al., "Multilayer White Light-Emitting Organic Electroluminescent Device," Science 267(5202):1332-1334, Mar. 1995.
Wei, G.D., et al., "Efficient, Ordered Bulk Heterojunction Nanocrystalline Solar Cells by Annealing of Ultrathin Squaraine Thin Films," Nano Letters 10(9):3555-3559, Sep. 2010.
Wei, G.D., et al., "Solution-Processed Squaraine Bulk Heterojunction Photovoltaic Cells," ACS Nano 4(4):1927-1934, Apr. 2010.
Wu, F.-I., et al., "Efficient White-Electrophosphorescent Devices Based on a Single Polyfluorene Copolymer," Advanced Functional Materials 17(7):1085-1092, May 2007.
Wu, H., et al., "Efficient Electron Injection from a Bilayer Cathode Consisting of Aluminum and Alcohol-/Water-Soluble Conjugated Polymers," Advanced Materials 16(20):1826-1830, Oct. 2004.
Xiao, L., et al., "Recent Progresses on Materials for Electrophosphorescent Organic Light-Emitting Devices," Advanced Materials 23(8):926-952, Feb. 2011.
Xu, Y., et al., "Solvent Effects on the Architecture and Performance of Polymer White-Light-Emitting Diodes With Conjugated Oligoelectrolyte Electron-Transport Layers," Advanced Materials 21(5):584-588, Feb. 2009.
Yang, C.-H., et al., "Blue-Emitting Heteroleptic Iridium(III) Complexes Suitable for High-Efficiency Phosphorescent OLEDs," Angewandte Chemie International Edition 119(14):2470-2473, Mar. 2007.
Yang, X.H., et al., "Blue Polymer Electrophosphorescent Devices With Different Electron-Transporting Oxadiazoles," Applied Physics Letters 88(2):021107-1-021107-3, Jan. 2006.
Ye, S., et al., "Solution-Processed Solid Solution of a Novel Carbazole Derivative for High-Performance Blue Phosphorescent Organic Light-Emitting Diodes," Advanced Materials 22(37):4167-4171, Oct. 2010.
Ye, T., et al., "Efficient Phosphorescent Polymer Yellow-Light-Emitting Diodes Based on Solution-Processed Small Molecular Electron Transporting Layer," Applied Materials & Interfaces 3(2):410-416, Feb. 2011.
Yeh, S.-J., et al., "New Dopant and Host Materials for Blue-Light-Emitting Phosphorescent Organic Electroluminescent Devices," Advanced Materials 17(3):285-289, Feb. 2005.
Yook, K.S., and J.Y. Lee, "Solution Processed White Phosphorescent Organic Light-Emitting Diodes With a Double Layer Emitting Structure," Organic Electronics 12(2):291-294, Feb. 2011.
Yook, K.S., et al., "Fabrication and Efficiency Improvement of Soluble Blue Phosphorescent Organic Light-Emitting Diodes Using a Multilayer Structure Based on an Alcohol-Soluble Blue Phosphorescent Emitting Layer," Advanced Materials 22(40):4479-4483, Oct. 2010.
You, J.-D., et al., "All-Solution-Processed Blue Small Molecular Organic Light-Emitting Diodes With Multilayer Device Structure," Organic Electronics 10(8):1610-1614, Dec. 2009.
Zhang, X., et al., "Electroluminescence of Multicomponent Conjugated Polymers. 2. Photophysics and Enhancement of Electroluminescence From Blends of Polyquinolines," Macromolecules 35(2):382-393, Jan. 2002.
Zhang, X.J.et al., "Electroluminescence and Photophysical Properties of Polyquinolines," Macromolecules 32(22):7422-7429, Nov. 1999.
Zheng, Y., et al., "Efficient Deep-Blue Phosphorescent Organic Light-Emitting Device With Improved Electron and Exciton Confinement," Applied Physics Letters 92(22):223301-1-223301-3, Jun. 2008.
Zhu, M., et al., "Highly Efficient Solution-Processed Green and Red Electrophosphorescent Devices Enabled by Small-Molecule Bipolar Host Material," Journal of Materials Chemistry 21(25):9326-9331, Jun. 2011.

(a) Vacuum deposited TQB (b) Solution deposited TQB

SOLUTION-PROCESSABLE ELECTRON-TRANSPORT MATERIALS AND RELATED ORGANIC OPTOELECTRONIC DEVICES

CROSS-REFERENCE TO RELATED APPLICATIONS

This application is a continuation of International Application No. PCT/US2011/047305, filed Aug. 10, 2011, which claims the benefit of U.S. Provisional Application No. 61/374,204, filed Aug. 16, 2010, the disclosures of which are expressly incorporated by reference herein in their entirety.

STATEMENT OF GOVERNMENT LICENSE RIGHTS

This invention was made with Government support under Grant No. DMR-0805259, awarded by the National Science Foundation. The Government has certain rights in the invention.

BACKGROUND

Organic light-emitting diodes (OLEDs) are of broad interest for applications in full-color display panels, flexible displays, and solid-state lighting. Much progress has been made in developing phosphorescent OLEDs (PhOLEDs) in which nearly 100% internal quantum efficiency has been achieved. However, blue emitting PhOLEDs remain challenging because high-energy triplet excitons tend to flow out without radiative decay in the emissive layer (EML). Insertion of a wide-energy-gap electron-transport material between the cathode and the blue-phosphorescent EML represents a successful strategy for confining excitons to the EML and for blocking holes, facilitating a good charge balance in the EML. Current high-performance blue PhOLEDs have been achieved by vacuum deposition of small molecules to fabricate multilayered device structures. Although it is economically highly desired to produce high-performance PhOLEDs by solution-based fabrication processes, new small-molecule or polymer-based electron transport/hole blocking materials and novel solution-processing strategies are essential to realize this goal.

Solution-based device fabrication methods, such as spray-on or spin-on deposition, ink jet printing, screen printing, and roll-to-roll printing processes, are considered critical to next generation, low cost, large area, high performance light-emitting devices. In contrast to the considerable progress in developing highly efficient PhOLEDs using vacuum deposition, reports on solution-processed devices are still relatively few. Surprisingly, nearly all prior reports on solution-processable PhOLEDs are multilayered structures that included a vacuum-deposited electron-transport layer (ETL)/hole-blocking layer (HBL). High-performance polymer-based PhOLEDs without a vacuum-deposited ETL/HBL also include a vacuum-deposited thin layer of low work function metals (e.g., Ba, Ca) or interfacial materials (e.g., LiF, CsF) inserted between the EML and cathode metals such as Al or Ag.

The longstanding challenge in solution-based fabrication of high performance PhOLEDs and other organic electronic devices is achieving orthogonal sequential solution deposition of multilayered structures. This requirement that the solvent used to deposit the overlayer thin film not dissolve or swell the underlying layer can conflict with the factors essential to good surface wetting properties of the second solution on top of the underlying layer. Others have exploited polyfluorene-based polyelectrolytes as electron transport layers in multilayered OLEDs. However, the ionic groups in such polyelectrolytes can result in undesired electrochemical doping effects and reduce the air-stability of high work function electrodes such as Al. Thus, there remains a need to develop new materials and novel processing strategies that can enable the achievement of solution-processed high-performance PhOLEDs and multilayered electronic devices in general.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, compounds are provided. In one embodiment, the compound has a formula (Compound 1):

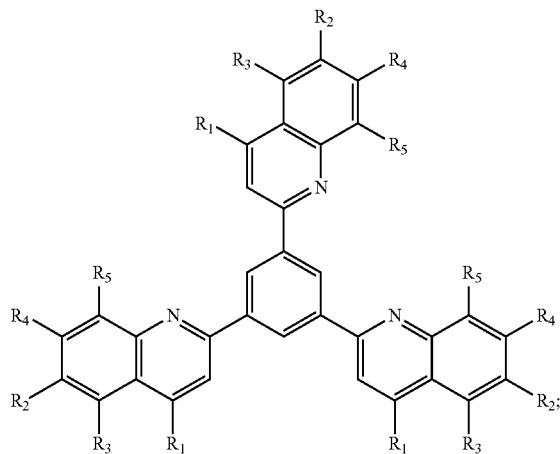

wherein $R_1$ is selected from the group consisting of H, alkyl, aromatic, heteroaromatic,

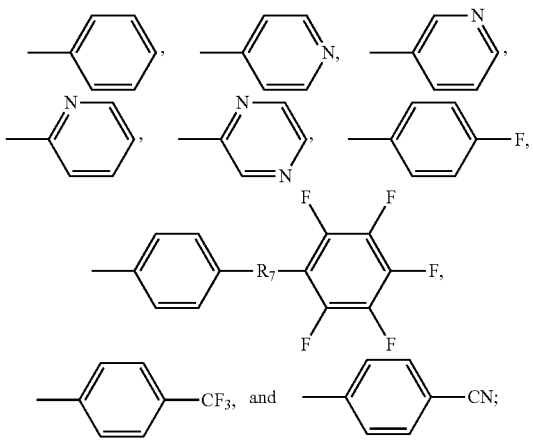

wherein $R_6$ is any one of $R_1$ or $R_2$; wherein $R_2$ is independently selected from the group consisting of H, alkyl, aromatic, heteroaromatic,

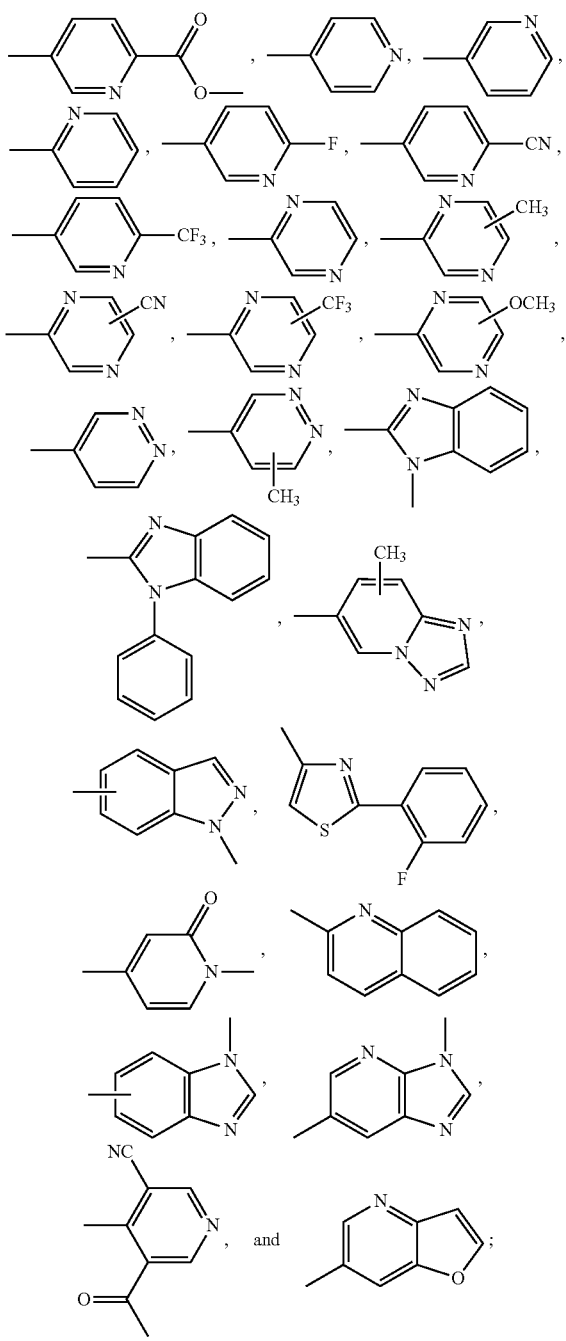

wherein R₃, R₄, and R₅ are each independently selected from the group consisting of H and R₁; and wherein R₁-R₅ are not all H.

In another aspect, devices (e.g., OLEDs) incorporating the compounds are disclosed.

In yet another aspect, methods for solution depositing an ETL of an OLED are provided.

DESCRIPTION OF THE DRAWINGS

The foregoing aspects and many of the attendant advantages of the embodiments of invention will become more readily appreciated as the same become better understood by reference to the following detailed description, when taken in conjunction with the accompanying drawings, wherein:

FIGS. 4A-4D graphically illustrate the performance of representative blue PhOLEDs of the invention, wherein FIG. 4A illustrates current density versus voltage; FIG. 4B illustrates luminescence versus voltage; FIG. 4C illustrates luminesence efficiency versus luminescence; and FIG. 4D illustrates the electroluminescence spectra at the maximum luminescence value;

FIGS. 9A and 9B graphically illustrate the performance of representative green PhOLEDs of the invention, wherein FIG. 9A illustrates current density versus voltage; and FIG. 9B illustrates luminescence versus voltage;

FIGS. 10A and 10B graphically illustrate the performance of representative green PhOLEDs of the invention, wherein FIG. 10A illustrates luminesence efficiency versus luminescence; and FIG. 10B illustrates the electroluminescence spectra at the maximum luminescence value;

FIG. 11B illustrates luminesence efficiency versus luminescence;

FIGS. 12A-12C graphically illustrate the performance of representative green PhOLEDs fabricated according to the methods disclosed herein, wherein FIG. 12A illustrates luminescence versus voltage; FIG. 12B illustrates the electroluminescence spectra at the maximum luminescence value; and FIG. 12C illustrates luminesence efficiency versus luminescence;

FIG. 23A: current density (J)-voltage (V), FIG. 23B: luminance (L)-voltage (V), FIG. 23C: luminous efficiency (LE)-luminance (L) curves of blue PhOLEDs with solution-deposited ETLs using a formic acid/water (3:1 v/v) mixture, and FIG. 23D: electroluminescence (EL) spectra of the blue PhOLEDs at the maximum luminance value;

FIG. 26A Current density (J)-voltage (V); FIG. 26B luminance (L)-voltage (V); FIG. 26C luminous efficiency (LE)-luminance (L); and FIG. 26D power efficiency (PE)-luminance (L) curves, wherein the device structures are as follows: device IA: ITO/PEDOT:PSS/EML/vacuum-deposited TmPyPB/Al and devices IB, IC, and ID: ITO/PEDOT:PSS/EML/solution-deposited TmPyPB/Al with TmPyPB deposited from 8, 16, and 24 mg mL$^{-1}$ solution, respectively;

FIG. 27A Current density (J)-voltage (V); FIG. 27B luminance (L)-voltage (V); FIG. 27C luminous efficiency (LE)-luminance (L); and FIG. 27D power efficiency (PE)-luminance (L) curves, wherein the device structures are as follows: device IIA: ITO/PEDOT:PSS/EML/vacuum-deposited BPhen/Al and devices IIB, IIC, and IID: ITO/PEDOT:PSS/EML/solution-deposited BPhen/Al with BPhen deposited from 16, 20, and 24 mg mL$^{-1}$ solution, respectively;

FIG. 28A Current density (J)-voltage (V); and FIG. 28B luminance (L)-voltage (V); wherein the device structures are as follows: device IIA: ITO/PEDOT:PSS/EML/vacuum-deposited BPhen/Al and devices IIB, IIC, and IID: ITO/PEDOT:PSS/EML/solution-deposited BPhen/Al with BPhen deposited from 16, 20, and 24 mg mL$^{-1}$ solution, respectively;

DETAILED DESCRIPTION

Figure 1:
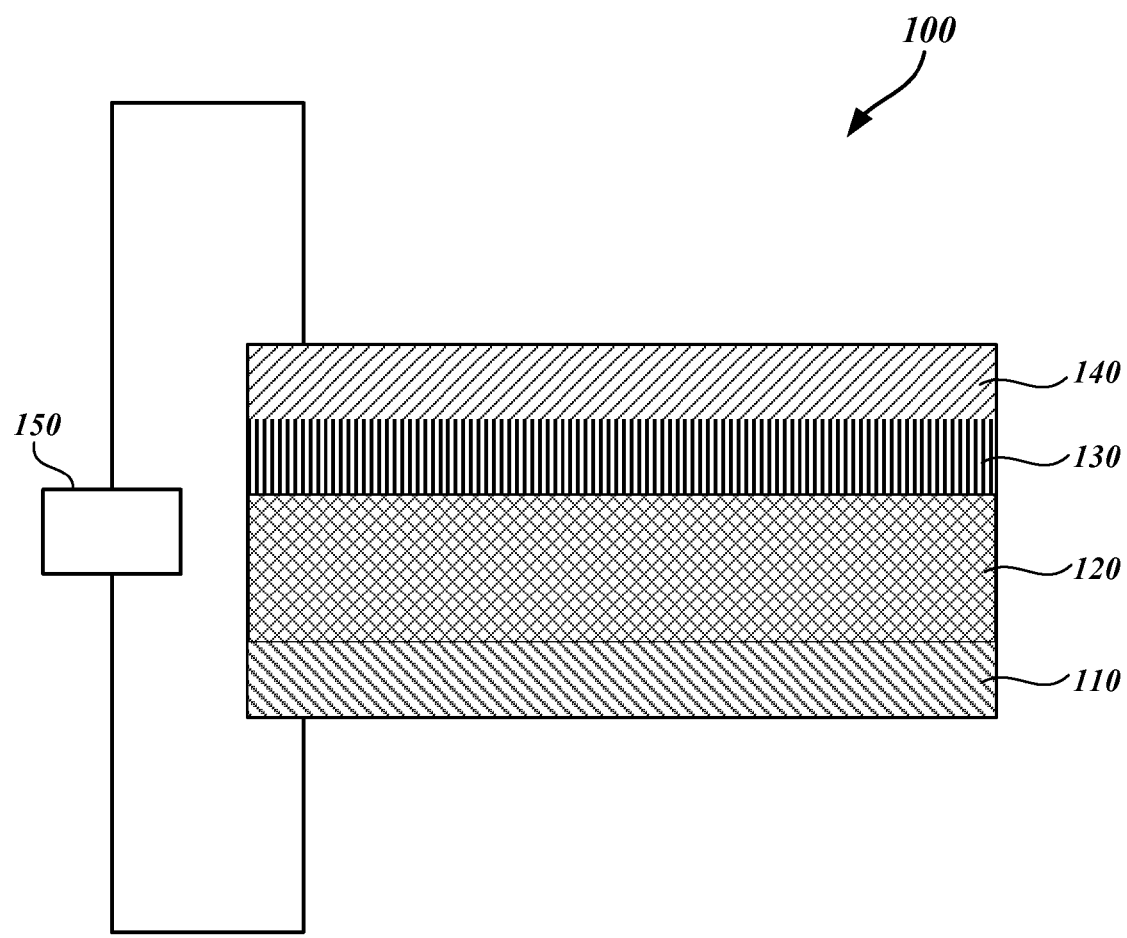
FIG. 1 illustrates a representative device of the invention.

The present invention provides compounds useful as charge transport materials, optoelectronic devices that include the compounds, methods for forming the optoelectronic devices, and general methods for forming optoelectronic devices (i.e., devices with or without the compounds as the charge transport materials).

In one aspect, compounds are provided. The compounds of the invention have solubility orthogonal to the solubility of traditional emissive layer (EML) materials used for organic light-emitting diodes (OLEDs), such that solution-based deposition of the compounds onto the EML is possible. Additionally, the compounds enable optoelectronic devices to be fabricated with high work-function cathode materials that outperform, and are more stable than, similar devices fabricated with low work-function cathode materials.

In certain embodiments, the compounds are useful as electron-transport materials in optoelectronic devices. Specifically, the compounds can be vacuum or solution-deposited to provide high-efficiency OLED devices. In certain embodiments, the compounds are soluble in a solution that is orthogonal to the solubility of an OLED EML, upon which the compound is deposited in the solution to form an ETL.

As used herein, "R" refers to a substituent on an atom. Unless otherwise specifically assigned, R represents any single atom or any one of the substituent groups defined below. When there is more than one R in a molecule, the "R" may independently at each occurrence refer to a single atom or any one of the substituent groups defined below.

Unless specified otherwise, R, $R_1$, $R_2$, $R_3$, $R_4$, $R_5$, $R_6$, and $R_7$ are, at each instance, independently selected from hydrogen, alkyl, alkoxy, halogen (i.e., fluoro, chloro, bromo, iodo), unsubstituted aromatic, unsubstituted heteroaromatic, substituted aromatic, and substituted heteroaromatic.

As used herein, the term "aromatic" refers to aromatic groups having only carbon atoms in the aromatic ring. Representative aromatic groups include C6 aromatic groups such as phenyl and benzo groups, C10 aromatic groups such as naphthyl groups, and C14 aromatic groups such as anthracenyl groups.

The term "heteroaromatic" refers to aromatic groups that include one or more heteroatoms (e.g., oxygen, nitrogen, sulfur, or phosphorus) in the aromatic ring. Representative heteroaromatic groups that include a single heteroatom in the aromatic ring include furanyl, pyridinyl, pyrrolyl, and thiophenyl groups. Representative heteroaromatic groups that include more than one heteroatom in the aromatic ring include $C_4N_2$, $C_3N_3$, $C_3N_2$, $C_3NO$, $C_3NS$, and $C_2N_3$ groups. Heteroaromatic groups additionally include n-heteroaryl groups such as $C_6N_3$, $C_7N_2$, $C_7NO$, and $C_8N$.

In certain embodiments, the aromatic and heteroaromatic groups are further substituted with one or more substituents independently selected from alkyl, alkoxy, haloalkyl, haloalkoxy, halo, and cyano groups. As used herein, the term "alkyl or alkoxy substituted" refers to replacement (substitution) of a hydrogen atom bound to a carbon of the aromatic ring of an aromatic compound with an alkyl or alkoxy group or to replacement of a hydrogen atom bound to a carbon or nitrogen of the aromatic ring of a heteroaromatic compound with an alkyl or alkoxy group.

The term "alkyl" refers to C1-C20 straight chain and branched alkyl groups. Representative straight chain alkyl groups include methyl, ethyl, n-propyl, n-butyl, n-pentyl, and n-hexyl groups. Alkyl additionally refers to halogenated and fluorinated alkyls.

The term "alkoxy" refers to alkoxy (—OR) groups including C1-C20 straight chain and branched alkyl groups (R). Representative straight chain alkyl groups include methoxy, ethoxy, n-propoxy, n-butoxy, n-pentoxy, and n-hexoxy groups. Representative branched alkyl groups include s-propoxy, s-butoxy, t-butoxy, s-pentoxy, neopentoxy, and s-hexoxy groups.

In one embodiment, the compound has a formula (Compound 1):

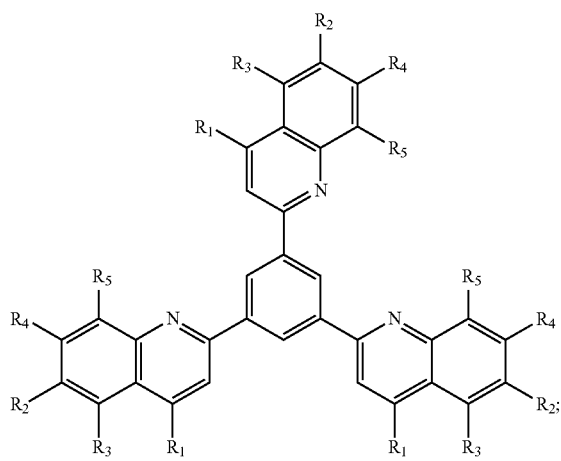

1 wherein $R_1$ is selected from the group consisting of H, alkyl, aromatic, heteroaromatic,

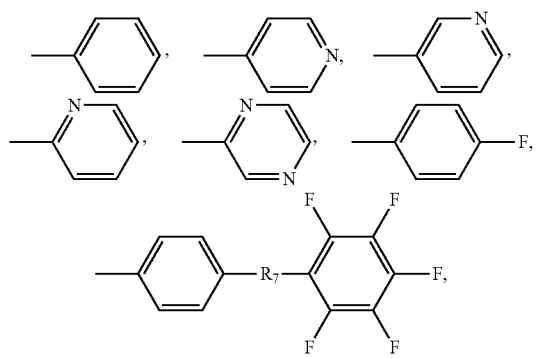

-continued

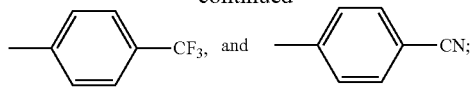

wherein $R_6$ is any one of $R_1$ or $R_2$;
wherein $R_2$ is independently selected from the group consisting of H, alkyl, aromatic, heteroaromatic,

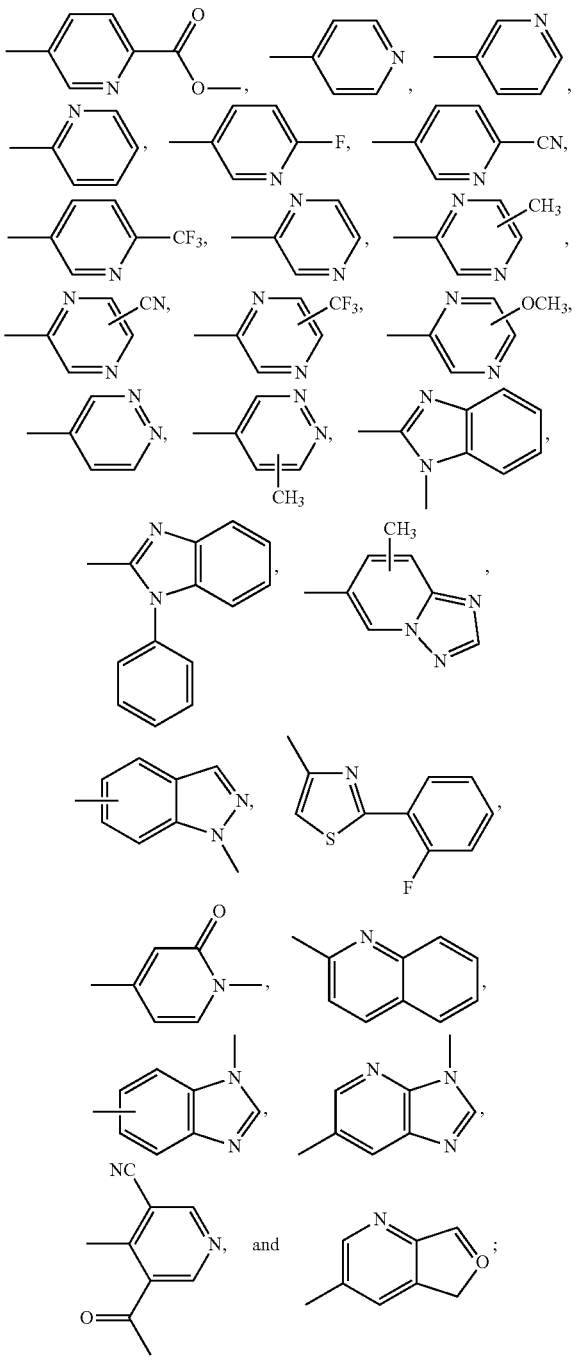

wherein $R_3$, $R_4$, and $R_5$ are each independently selected from the group consisting of H and $R_1$; and
wherein $R_1$-$R_5$ are not all H.

In another embodiment, the compound has a formula (Compound 2):
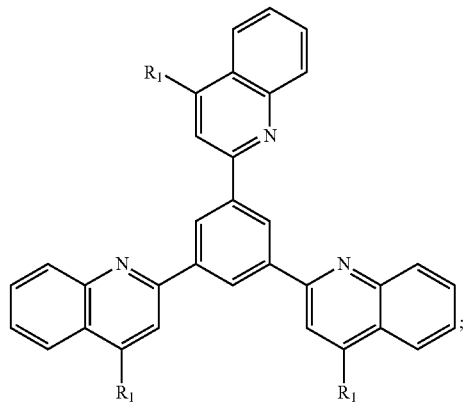
2
wherein $R_1$ is selected from the group consisting of, alkyl, aromatic, heteroaromatic,
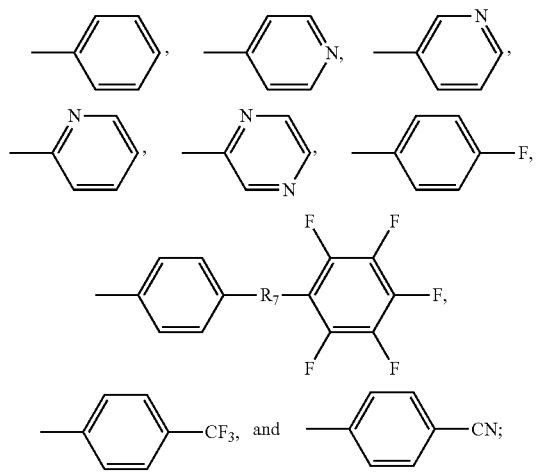
wherein $R_6$ is any one of $R_1$ or $R_2$; and
wherein $R_2$ is independently selected from the group consisting of H, alkyl, aromatic, heteroaromatic,
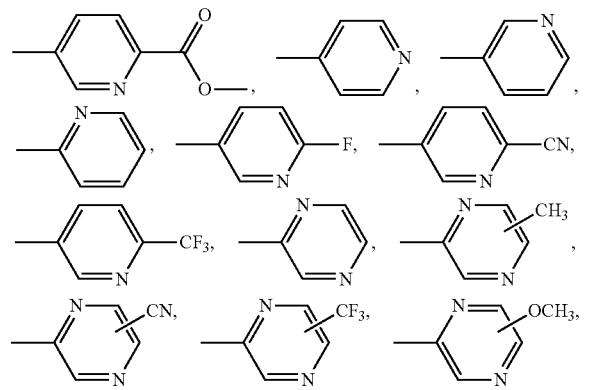
In another embodiment, the compound has a formula (Compound 3):
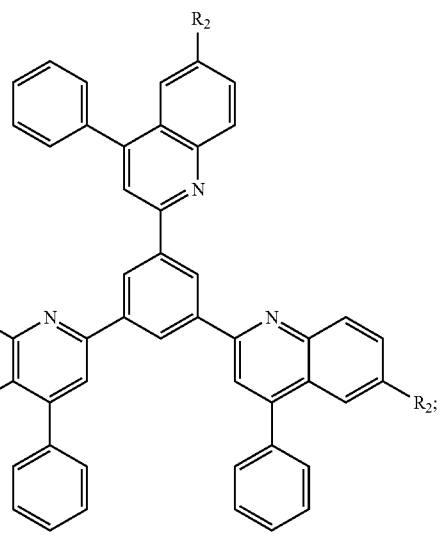
3 wherein $R_2$ is independently selected from the group consisting of H, alkyl, aromatic, heteroaromatic,
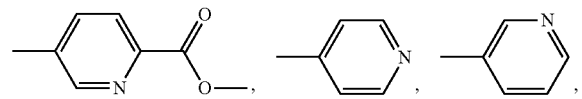
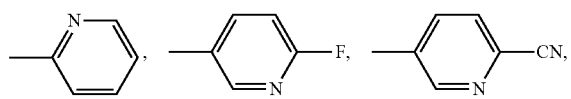
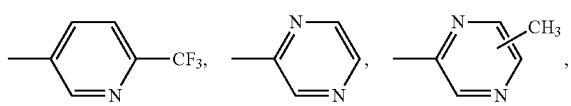
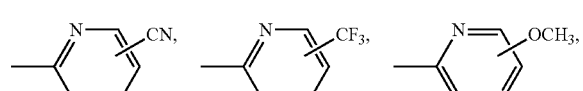
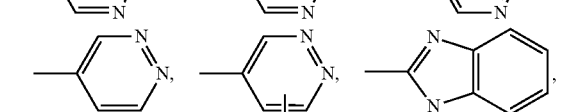
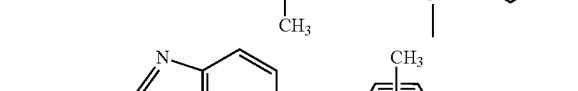
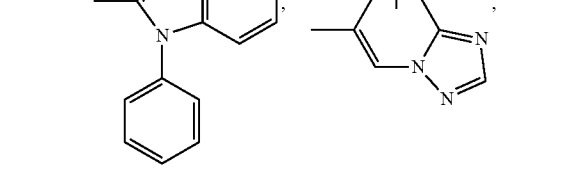
-continued
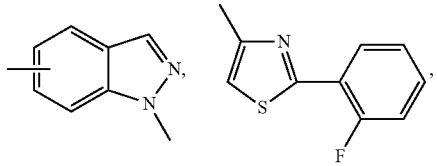
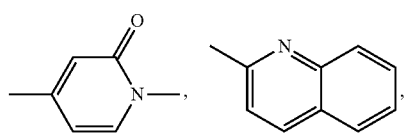
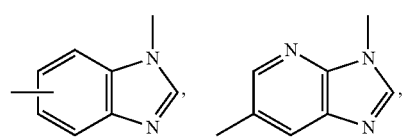
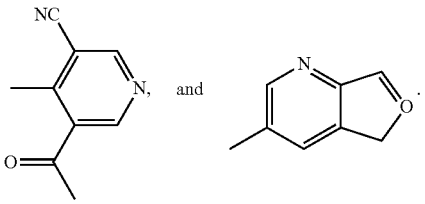
In another embodiment, the compound has a formula (Compound 4):
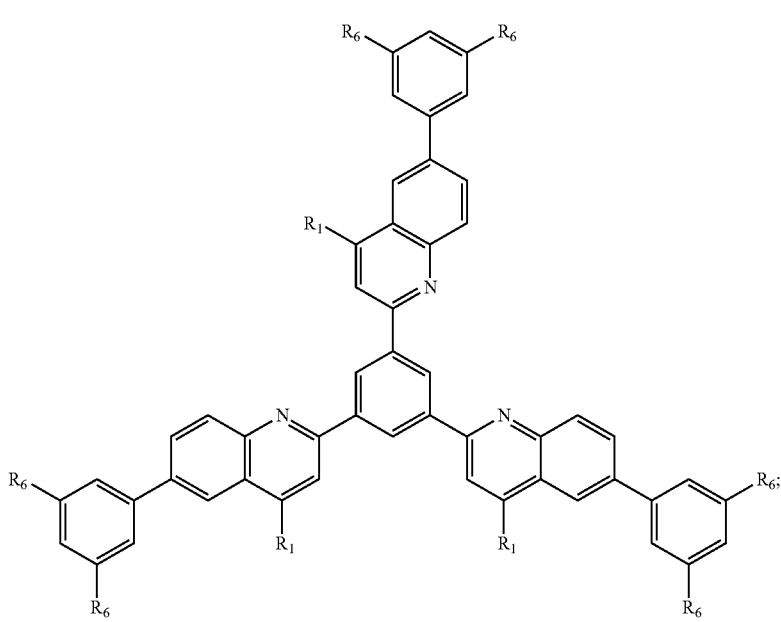

wherein $R_1$ is independently selected from the group consisting of H, alkyl, aromatic, heteroaromatic,
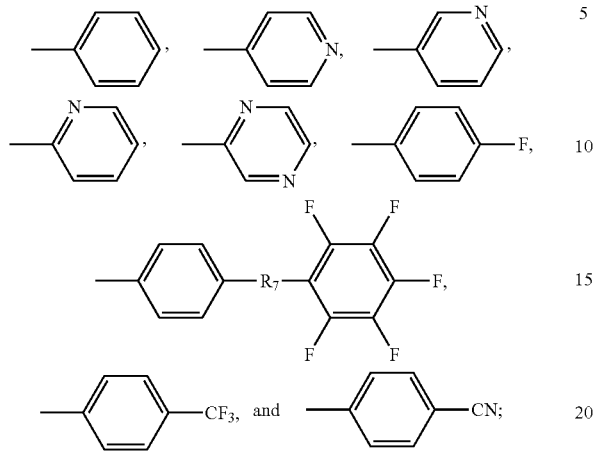
wherein $R_7$ is any one of $R_1$ or $R_2$;
wherein $R_2$ is any of H, alkyl, aromatic, heteroaromatic,
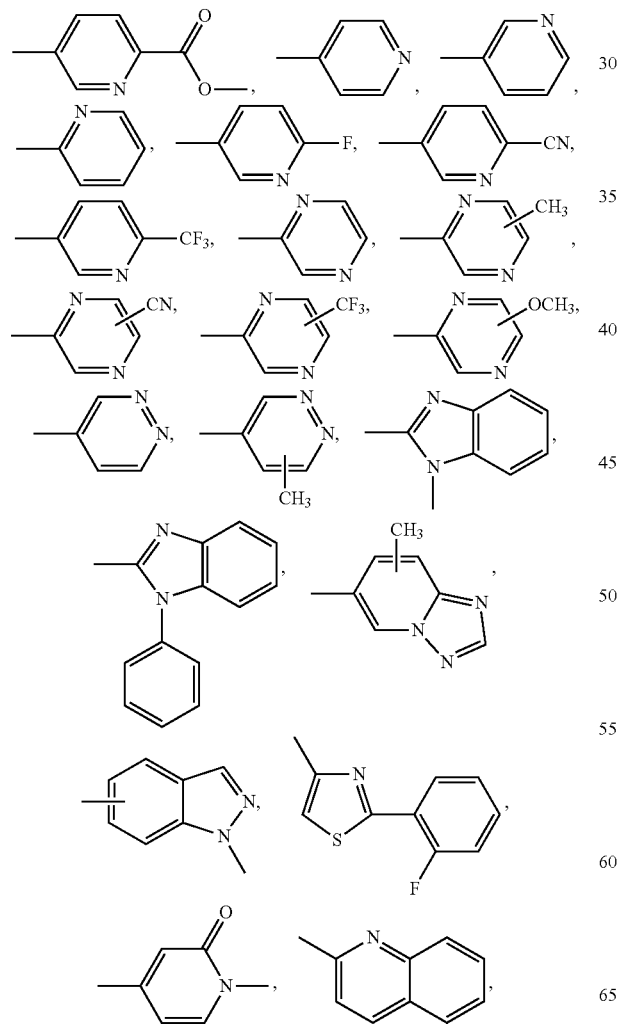
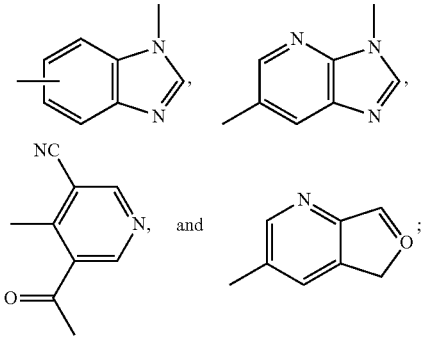
and wherein R6 is independently selected from the group consisting of
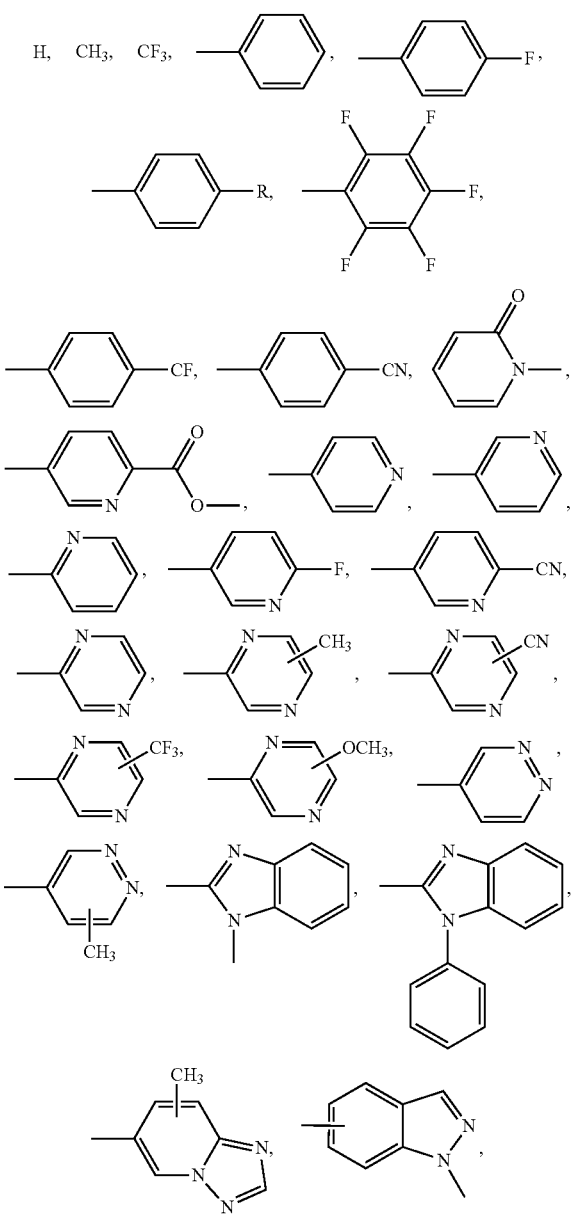

-continued

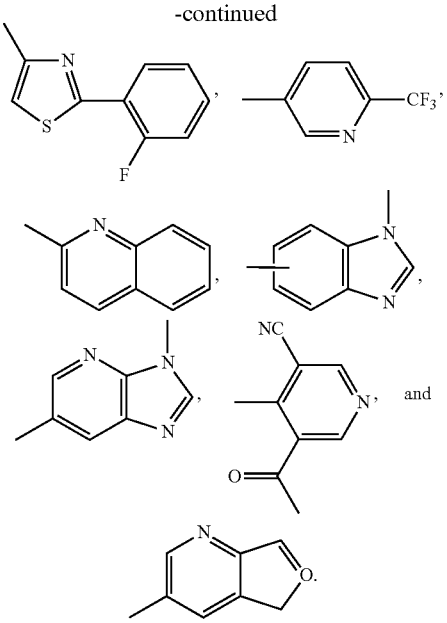

The general synthesis of representative Compounds 1-4 are described in Example 5.

The synthesis of a number of specific compounds are also provided in Examples 6-8: 1,3,5-tris(4-methylquinolin-2-yl)benzene (TMQB) (Example 6); 1,3,5-tris(4-(4-fluorophenyl)quinolin-2-yl)benzene (TFQB) (Example 7); and 1,3,5-tris(4-pyridinquinolin-2-yl)benzene (TPQB) (Example 8).

In another embodiment, the compound is 1,3,5-tris(4-phenylquinolin-2-yl)benzene (TQB) (Compound 5), which is a species of the genus of Compounds 1 and 2 above. TQB has the structure:

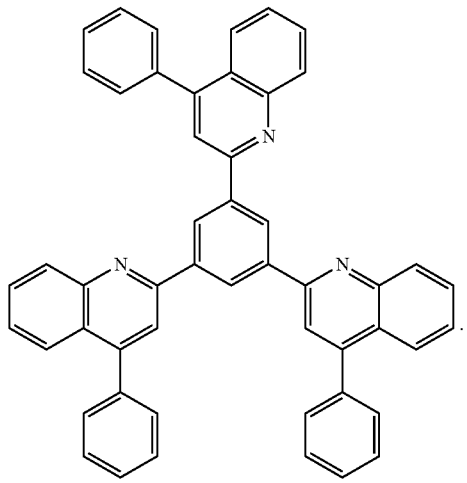

1

The synthesis of TQB and related compounds are set forth in Examples 1 and 9, below.

In another aspect, the present invention provides an optoelectronic device. In one embodiment, the optoelectronic device includes a first electrode; a second electrode; an active layer intermediate the first and second electrodes; and a transport layer intermediate the second electrode and the active layer, where the transport layer includes a compound selected from any of Compounds 1-5.

The incorporation of Compound 5 (TQB) into OLEDs (PhOLEDs, specifically) are set forth below in Example 2 (blue PhOLED) and Example 3 (green PhOLED).

The transport layer is a layer that facilitates the transfer of electrical charges (e.g., electrons) between layers of an optoelectronic device (e.g., electroluminescent or photovoltaic devices). When a transport layer is intermediate a cathode and an emissive layer (EML) in an optoelectronic device, it can be referred to as an electron transport layer (ETL).

Embodiments of the invention provide highly efficient polymer-based blue PhOLEDs that are fabricated by sequential solution-processing, made possible by the solution-processable, wide-energy-gap electron-transport materials as provided herein. for example, the aqueous solution-processed TQB electron-transport material has enabled achievement of high performance PhOLEDs while eliminating the need for interfacial materials (LiF, CsF) or low work function metals (Ba, Ca) as cathode materials in OLEDs. Additionally, the inventors believe that this is the first small molecule electron-transport layer/hole blocking layer (ETL/HBL) that can be solution-processed to fabricate high-performance PhOLEDs instead of using vacuum deposition for the ETL/HBL.

Representative optoelectronic devices of the invention include electroluminescent devices (e.g., OLEDs) and photovoltaic devices. The active layer of the device partially defines the function of the device. An electroluminescent device has an electroluminescent active layer and a photovoltaic device has a photovoltaic active layer. In one embodiment, the optoelectronic device is an electroluminescent device. Electroluminescent devices of the invention can be fabricated using well-known microelectronic and semiconductor processing techniques known to those skilled in the art. One type of electroluminescent device embodied by the present invention is the organic light-emitting diode (OLED), also called a polymer light-emitting diode (PLED) when a polymer is used as the electroluminescent layer. Furthermore, an OLED having an active layer that operates by way of phosphorescent photoluminescence can be specifically referred to as a phosphorescent OLED (PhOLED).

A representative optoelectronic device 100 is illustrated in FIG. 1 and includes a first electrode 110. In one embodiment, the first electrode 110 is an anode. In one embodiment, the first electrode 110 is either indium-tin-oxide (ITO) or fluorine-tin-oxide. Any transparent conductive material is useful as the first electrode 110. Conductive organic films, including conductive plastics and conductive organic/inorganic hybrid composites, are additional representative examples of transparent conductive materials.

An active layer 120 (e.g., an EML) is coplanar to, and abuts, the first electrode 110 in the device 110. In certain embodiments, electroluminescent film-forming materials in liquid form are deposited on the first electrode 110, typically by spin coating, drop coating, or other solution-based deposition techniques to form the active layer 120. The film deposition technique forms a solid film that can then be cured (e.g., at an elevated temperature) so as to evaporate any remaining solvent to provide the active layer 120 (e.g., an electroluminescent layer). In one embodiment, the active layer 120 includes an emissive material that is a triplet emitter-doped poly(N-vinylcarbazole) (PVK).

An electron injection layer 130 is coplanar to, and abuts, the active layer 120 in the device 100. In certain embodiments, the electron injection layer 130 is formed by a solution-based deposition technique. The electron injection layer 130 layer includes a compound of embodiments of the invention (e.g., TQB).

A second electrode 140 is coplanar to, and abuts, the electron injection layer 130 in the device 100. In one embodiment, the second electrode 140 is a cathode. In one embodiment, the second electrode 140 is a high work-function material. As used herein, the term "high work-function material" refers to an electrode material with a work function greater than (i.e., more negative than) about −3.5 eV. A representative second electrode 140 is a metallic electrode deposited by an evaporation or sputtering technique. Representative second electrode 140 materials include gold, silver, aluminum, magnesium, calcium, cesium fluoride, lithium fluoride, combinations of the materials (i.e., aluminum-capped CsF), and other electrode materials known to those skilled in the art.

Electroluminescent devices of the invention may also incorporate hole- or additional electron-transporting materials, or both, into the overall device structure. These charge-transporting materials allow for both efficient injection of charges from the electrodes into the electroluminescent layer and also allow for tuning of the number and location of holes and/or electrons in the device. In addition, the hole-transporting layer can also function as an electron-blocking and exciton-confining layer at the anode side, and the electron-transporting layer can function as a hole-blocking and exciton-confining layer at the cathode side.

Figure 2:
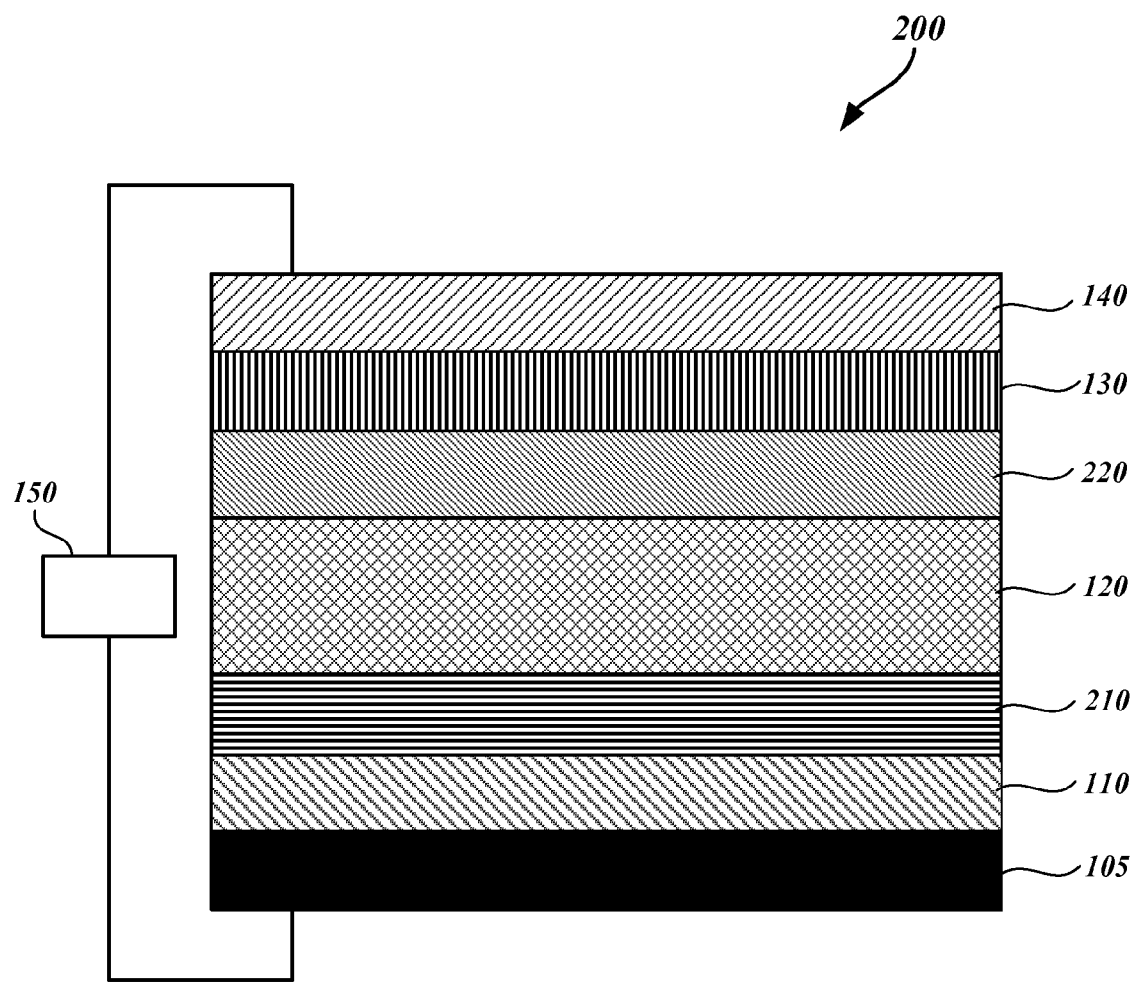
FIG. 2 illustrates another representative device of the invention.

A representative device 200, as illustrated in FIG. 2, optionally includes a hole-injection/transport layer 210 incorporated into the device 200 to improve charge injection and transport. A second electron-injection/transport layer 220 can optionally be inserted intermediate the active layer 120 and the electron injection layer 130.

In the representative devices (e.g., 100 and 200) described above, the first electrode 110 will act as an anode and will produce holes in the device. To improve the efficiency of hole injection into the device, a hole injection layer 210 may be deposited on the first electrode 110 before the active layer 120 is formed. A hole-injection layer 210 can be deposited either by solution-based or vapor-based techniques. In one embodiment, the device includes a hole-injection layer 210 intermediate the active layer 120 and the first electrode 110. In a further embodiment, the hole-injection layer 210 includes poly(3,4-ethylene dioxythiophene):poly(styrene sulfonic acid) or polyaniline.

To improve the efficiency of electron injection into the device 220, a second electron injection layer 220 may be deposited on the active layer 120 before the electron injection layer 130 is formed. The second electron-injection layer 220 can be deposited either by solution-based or vapor-based techniques. In one embodiment, the device 200 has a second electron-injection layer 220 intermediate the active layer 120 and the electron injection layer 130.

The completed device (either 100 or 200) can be operated by attaching the first electrode 110 (e.g., anode) and second electrode 140 (e.g., cathode) to an electrical power supply 150. When the device is run in forward bias, the electrons and holes produced at the cathode and anode, respectively, will migrate through any charge-transporting layers and will recombine in the active layer 120 to produce light.

In one embodiment, electroluminescent devices (e.g., 100 or 200) of the invention also include a substrate 105 adjacent the first electrode 110 (as illustrated in FIGS. 1 and 2) or second electrode 140. Because the representative transparent conductor ITO is traditionally commercially available as a thin-film coating on glass or plastic, representative electroluminescent devices are fabricated using ITO (as the first electrode 110 (anode)) supported on a substrate 105 (e.g., glass). In a further embodiment, the substrate 105 is glass or plastic.

In a further embodiment, the substrate 105 is adjacent to the first electrode 110, and the substrate 105 is glass and the first electrode 110 is ITO.

From the substrate 105 to the second electrode 140, the layers of a representative electroluminescent device 100 are: substrate 105, first electrode 110 (anode), active layer 120, electron injection layer 130, and second electrode 140 (cathode). More complex electroluminescent devices may optionally include a hole-injection/transport layer 210 intermediate the first electrode 110 and the active layer 120 and/or a second electron-injection/transport layer 220 intermediate the active layer 120 and the electron injection layer 130.

The representative devices illustrated in FIGS. 1 and 2 (100 and 200, respectively) can also be used as photovoltaic devices. In one embodiment, the device is a photovoltaic device. For photovoltaic device operation, the active layer is a photovoltaic material and the electrical power supply 150 is a device in need of electricity (e.g., a depleted rechargeable battery) and the device will operate to convert electromagnetic radiation into electricity. The operation of both electroluminescent and photovoltaic devices is known to those of skill in the art.

In another aspect, methods are provided for the solution-based deposition of transport layers (e.g., ETLs) onto emissive layers of optoelectronic devices. Specifically, the methods provide solution-based deposition of ETLs in a solvent that is orthogonal to the EML material (i.e., the EML is not solvated by the ETL solvent).

In certain embodiments, the solvent is neutrally charged (e.g., non-ionic).

With regard specifically to Compounds 1-5, representative solvents $C_1$-$C_4$ carboxylic acids, including traditional hydrogen-substituted carboxylic acids, halogenated analogs, fluorinated analogs, and combinations thereof. Table 1 provides a list of representative organic acids that can be used as a solvent to solution-deposit a layer of Compounds 1-5. The acids are selected based on boiling point (Bp~70-160° C.) and pKa lower than that of quinoline (pKa=4.97). The acids can be used independently to as a solvent for the Compounds; a mixture of one or more acids can be used; and one or more acids can be mixed with a polar solvent. Representative polar solvents include water, acetonitrile, acyclic alkane alcohols (e.g., methanol and ethanol), and dimethylformide.

TABLE 1

Acids useful for solvent-based deposition of representative compounds.

| Acid | Structure | m.p. | b.p. | pKa |
|---|---|---|---|---|
| Formic acid | HCOOH | | 100 | 3.74 |
| Acetic acid | $CH_3COOH$ | | 118 | 4.79 |
| 2-X-acetic acid | $CH_2XCOOH$ X = F, Cl | | 165-189 | 2.66-3.17 |
| 2-Propenoic acid | $CH_2CHCOOH$ | | 141 | 4.25 |
| 2-Propynoic acid | CHCHCOOH | | 144 | 2.0 |
| Lactic acid | $CH_3CHOHCOOH$ | | 122 | 3.86 |
| Maleic acid | HOOCCHCHCOOH | | 135 | 2.39 |
| Trifluoroacetic acid | $CF_3COOH$ | | 72 | .05 |
| Perfluoropropanoic acid | $CF_3CF_2COOH$ | | 96 | 0.38 |
| Trifluorobutanoic acid | $CF_3CH_2CH_2COOH$ | | 120 | 0.37 |
| Trifluoropropionic acid | $CF_3CH_2COOH$ | | 144 | 3.16 |

In another aspect, methods are provided for solution-depositing a layer of any ETL heterocyclic compounds containing two or more imine nitrogens. As all of Compounds 1-5 are heterocyclic compounds containing two or more imine nitrogens, the above embodiments described with reference to Compounds 1-5 also apply to embodiments of the present aspect. However, the embodiments of the method of this aspect are not limited to Compounds 1-5.

Exemplary compounds compatible with the method for solution-based deposition include 2,9-dimethyl-4,7-diphenyl-1,10-phenanthroline (BCP); (2,2',2'-(1,3,5-Benzinetriyl)-tris(1-phenyl-1-H-benzimidazole) (TPBI); 4,7-diphenyl-1,10-phenanthroline (BPhen); 2-(4-biphenyl)-5-(4-tert-butylphenyl)-1,3,4-oxadiazole (PBD); 3-(4-biphenyl)-4-phenyl-5-tert-butylphenyl-1,2,4-triazole (TAZ); 1,3-bis[2-(4-tert-butylphenyl)-1,3,4-oxadiazo-5-yl]benzene (OXD-7); tris(2,4,6-trimethyl-3-(pyridine-3-yl)phenyl)borane (3 TPYMB); 3,3',5,5'-tetra[(m-pyridyl)-phen-3-yl]biphenyl (BP4mPy); 1,3,5-tri[(3-pyridyl)phen-3-yl]benzene (TmPyPB); and 1,3-bis[3,5-di(pyridine-3-yl)phenyl]benzene (BmPyPhB). Example 4 describes the formation of a highly-efficient green PhOLED using 2,9-dimethyl-4,7-diphenyl-1,10-phenanthroline (BCP) deposited by the provided solvent-deposition method.

Referring to exemplary ETL BCP, the compound has heretofore been deposited in OLED devices (e.g., on an EML) only by vacuum deposition. The results of Examples 4 and 10 demonstrate that the solution-based deposition method of the provided embodiments not only enables the use of BCP as a solution-deposited ETL, but the OLEDs produced using solution processing are superior in performance compared to similar OLEDs having vacuum-deposited BCP ETLs.

In one embodiment, a method of fabricating a portion (e.g., the portion formed is an ETL on an EML) of an optoelectronic device is provided, comprising forming a transport layer on an active layer from a solution comprising a charge-transport compound and a solvent, wherein the charge-transport compound has a solubility in the solvent orthogonal to the solubility of the active layer in the solvent, and wherein the active layer is not solvated during forming of the transport layer.

In one embodiment, the charge-transport compound is a heterocyclic compound containing two or more imine nitrogens.

In one embodiment, the organic active layer comprises a mixture of one or more polymers and one or more phosphorescent triplet emitters.

In one embodiment, the organic active layer is selected from the group consisting of poly(N-vinylcarbazole) (PVK), N,N'-Bis(3-methylphenyl)-N,N'-bis(phenyl)-benzidine (TPD), Di-[4-(N,N-ditolyl-amino)-phenyl]cyclohexane (TAPC), 4,4'-Bis(carbazol-9-yl)biphenyl (CBP), 1,3-bis(2-(4-tert-butylphenyl)-1,3,4-oxadiazo-5-yl)benzene (OXD-7), 2-(4-Biphenyl)-5-(4-tert-butylphenyl)1-3,4-oxadiazole (PBD), and combinations thereof.

In one embodiment, the polymer is selected from the group consisting of poly(N-vinylcarbazole) (PVK), poly(alkylfluorene) (PFO), and poly(p-phenylene) (PPP).

In one embodiment, the polymer has the band gap ($E_g$) greater than 2.5 eV.

In one embodiment, the phosphorescent triplet emitter is selected from the group consisting of Iridium-, Ruthenium-, and Osmium-based metal-complexes.

In one embodiment, the phosphorescent triplet emitter is selected from the group consisting of Tris(2-phenylpyridine) iridium(III) (Ir(ppy)$_3$), Bis(2-phenylpyridine)(acetylacetonate)iridium(III) (Ir(ppy)$_2$(acac)), Tris[2-(p-tolyl)pyridine] iridium(III) (Ir(mppy)$_3$), Bis(3,5-difluoro-2-(2-pyridyl) phenyl-(2-carboxypyridyl)iridium III (FIrpic), Bis(2,4-difluorophenylpyridinato)tetrakis(1-pyrazolyl)borate iridium III (FIr6), Bis(2-benzo[b]thiophen-2-yl-pyridine) (acetylacetonate)iridium(III) (Ir(btp)2(acac)), Tris(1-phenylisoquinoline)iridium(III) (Ir(piq)$_3$) Bis(1-phenylisoquinoline)(acetylacetonate)iridium (III) (Ir(piq)$_2$(acac)), Bis[1-(9,9-dimethyl-9H-fluoren-2-yl)-isoquinoline](acetylacetonate) iridium(III) (Ir(fliq)$_2$(acac)), Bis[2-(9,9-dimethyl-9H-fluoren-2-yl)-quinoline](acetylacetonate)iridium(III) (Ir(flq)$_2$(acac)), Bis(2-phenylbenzothiazolato)(acetylacetonate)iridium(III) (Bt$_2$Ir(acac)), Osmium(II) bis(3-trifluoromethyl-5-(2-pyridyl)-pyrazolate)dimethylphenylphosphine (Os(fppz)$_2$(PPhMe$_2$)$_2$) Osmium(II) bis(3-(trifluoromethyl)-5-(4-tert-butylpyridyl)-1,2,4-triazolate)diphenylmethylphosphine (Os(bpftz)$_2$(PPh2Me)$_2$), and combinations thereof.

In one embodiment, the organic active layer further comprises a charge transport compound.

In one embodiment, the charge transport compound is selected from the group consisting of 1,3-bis(2-(4-tert-butylphenyl)-1,3,4-oxadiazo-5-yl)benzene (OXD-7), 2-(4-Biphenyl)-5-(4-tert-butylphenyl)-1,3,4-oxadiazole (PBD), 3-(4-Biphenyl)-4-phenyl-5-tert-butylphenyl-1,2,4-triazole (TAZ), and combinations thereof.

In one embodiment, the charge transport compound is selected from the group consisting of N,N'-Bis(3-methylphenyl)-N,N'-bis(phenyl)-benzidine (TPD), Di-[4-(N,N-ditolylamino)-phenyl]cyclohexane (TAPC), 4,4'-Bis(carbazol-9-yl) biphenyl (CBP), N,N'-Bis(naphthalen-1-yl)-N,N'-bis (phenyl)-benzidine (NPB), and combinations thereof.

In one embodiment, the charge transport compound has ionization potential value (IP) lower than 6.0 eV.

Example 9 further describes the synthesis, characterization, and device fabrication using the exemplary compounds of the invention TMQB, TQB, TFQB, and TPyQB.

The following examples are provided for the purpose of illustrating, not limiting, the invention.

EXAMPLES

Example 1

Synthesis of
1,3,5-tris(4-phenylquinolin-2-yl)benzene (TQB)

Figure 3:
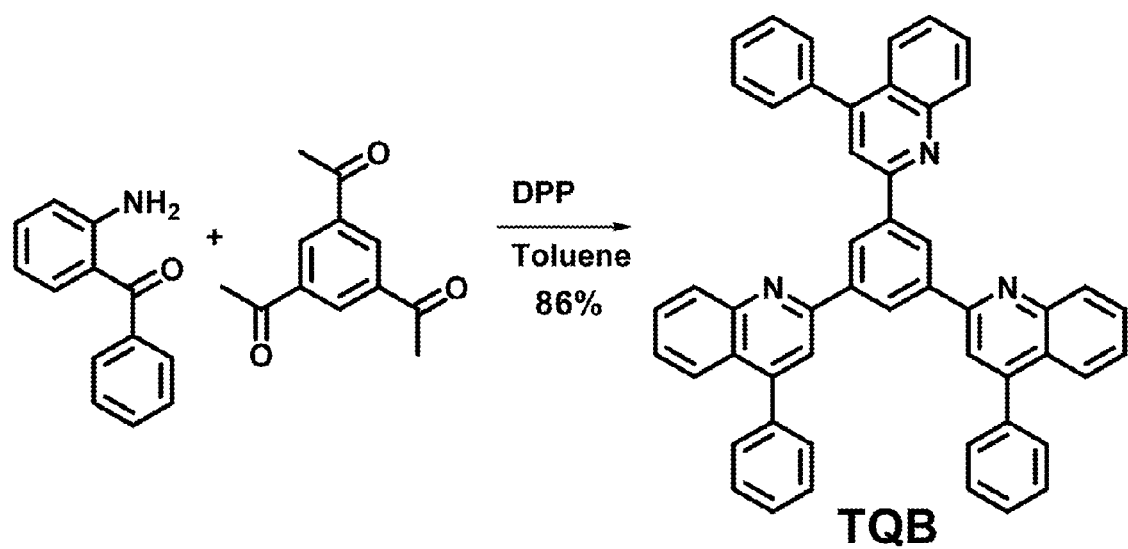
FIG. 3 illustrates the synthesis of a representative compound of the invention.

The new electron transport molecule, TQB, was synthesized in high yield via Friedlander condensation of 1,2-aminobenzophenone and 1,3,5-triacetylbenzene using diphenylphosphate (DPP) as the acid catalyst as shown in FIG. 3.

All chemical were purchased from Sigma-Aldrich and used without further purification. A mixture of 2-aminobenzophenone (1.86 g, 9.44 mmol), 1,3,5-triacetylbenzene (0.6 g, 2.94 mmol) and diphenyl phosphate (DPP, 8 equiv.) in 12 mL of toluene was refluxed in argon overnight. The reaction mixture was precipitated into 10% methanol/triethylamine and the solid was collected by vacuum filtration. The product was recrystallized twice from tetrahydrofuran/methanol solvent mixture (2:1, v/v) and the off-white solid was collected in 86% yield. $^1$H-NMR, $^{13}$C-NMR and high resolution mass spectrometry confirmed the structure. $^1$H-NMR and $^{13}$C-NMR were recorded on a Bruker AV300 at 300 MHz using CDCl$_3$ as the solvent, and high-resolution mass spectrum was obtained from JEOL/HX-110 using 2-nitrobenzyl alcohol as a matrix. $^1$H-NMR (300 MHz, CDCl3): δ ppm=9.175 (s, 3H), 8.3714 (d, 3H), 8.139 (s, 3H), 7.979 (d, 3H), 7.784 (t, 3H), 7.679-7.5067 (m, 18H). $^{13}$C-NMR (300 MHz, CDCl3): δ ppm=156.4905, 149.3806, 148.8507, 140.9459, 130.2619, 129.7142, 129.5713, 128.8807, 128.6283, 128.4425, 127.7615, 126.4845, 125.7167, 125.3298, 119.5872. HRMS (FAB) calcd for $C_{51}H_{34}N_3$, M+1=688.27551. Found M+1 688.27619.

The thin film absorption edge optical band gap ($E_g$) of TQB was determined to be 3.4 eV. The LUMO and HOMO energy levels of TQB, estimated from cyclic voltammetry low-lying LUMO energy level of TQB suggests the potential for good electron-injection from high work function metals such as Al. Its deep HOMO energy level, which is much lower-lying than those of typical triplet emitters and hosts, suggests that good confinement of holes within an emissive layer can be achieved. The space-charge-limited current (SCLC) electron mobility of solution-deposited TQB thin films was determined to be $3.6 \times 10^{-4}$ $cm^2$ $V^{-1}$ $s^{-1}$ at a maximum electric field of $3.8 \times 10^5$ V $cm^{-1}$ (FIG. 5), which is about two orders magnitude higher than those of current electron-transport materials, such as $Alq_3$ or TAZ.

Figure 6:
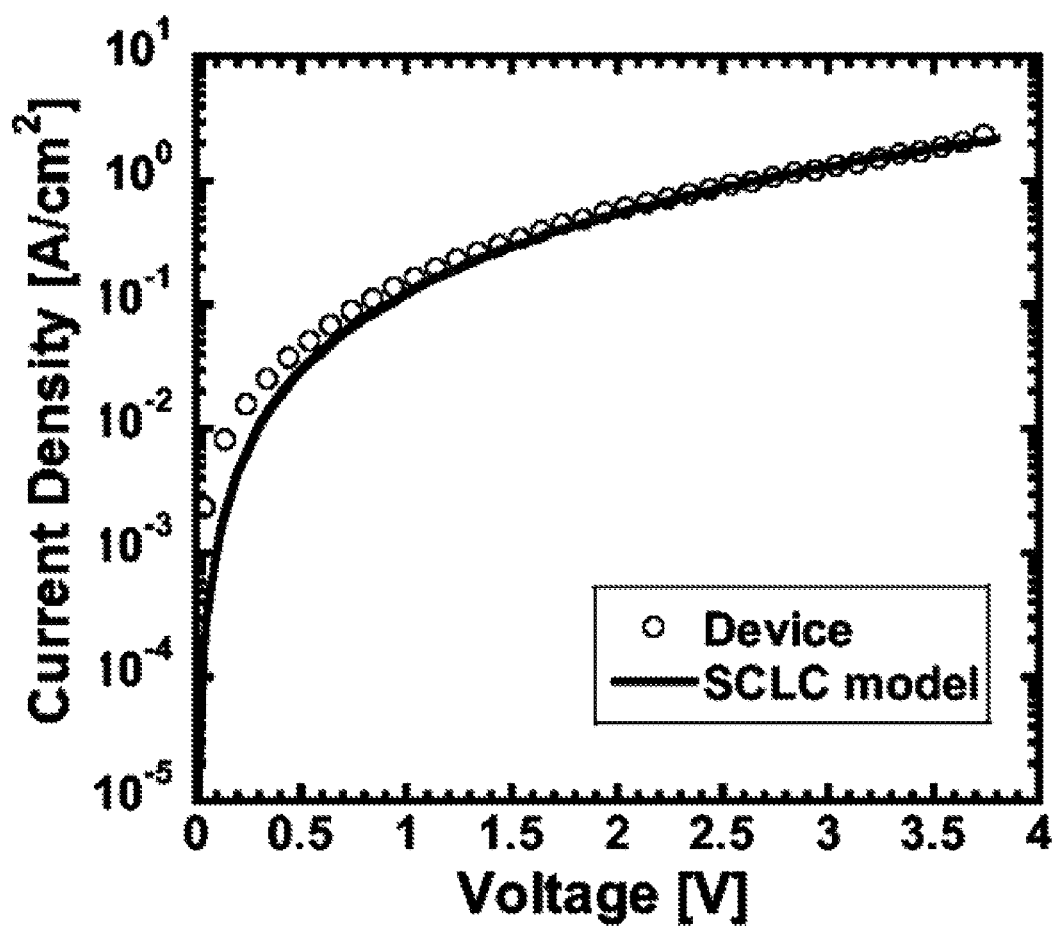
FIG. 6 graphically illustrates current density versus voltage for a representative film of TQB.

Charge-carrier mobility of TQB was evaluated by space-charge limited current (SCLC). FIG. 6 shows the current density-voltage (J-V) characteristic of the device, ITO/TQB/Al, in ambient conditions. The mobility was extracted by using a nonlinear least-squares fitting to the modified Mott-Gurney equation, $$J = \frac{9}{8}\varepsilon\varepsilon_0\mu\frac{V^2}{L^3}\exp\left(0.89\beta\frac{\sqrt{V}}{\sqrt{L}}\right)$$

where J is the current density, V is the applied bias, L is the thickness of active layer (100 nm), μ is the mobility, ε is the relative permittivity, $\varepsilon_0$ is the permittivity of free space, and β is the field-activation factor.

Example 2

Blue PhOLEDs Incorporating TQB as an Electron-Transport Layer

Blue PhOLEDs were fabricated using blends of PVK and 1,3-bis(2-(4-tert-butylphenyl)-1,3,4-oxadiazo-5-yl)benzene (OXD-7) as the host with doped bis(3,5-difluoro-2-(2-pyridyl)phenyl-(2-carboxypyridyl)iridium (FIrpic) blue triplet emitter in the EML as described in Example 1.

The blue EML consisted of a blend of poly(N-vinyl carbazole) (PVK, $M_w$=135,600, $M_n$=56,400, Polysciences) and 1,3-bis(2-(4-tert-butylphenyl)-1,3,4-oxadiazo-5-yl)benzene (OXD-7, LumTec., Taiwan) (PVK:OXD-7=60:40, wt/wt) as a host and 10 wt % bis(3,5-difluoro-2-(2-pyridyl)phenyl-(2-carboxypyridyl)iridium (FIrpic, LumTec., Taiwan) as the dopant. A solution of PEDOT:PSS (poly-(ethylenedioxythiophene)-polystyrenesulfonate, H. C. Starck, Clevios PVP A14083) in water was spin-coated to make a 30-nm hole-injection layer onto a pre-cleaned ITO glass and annealed at 150° C. under vacuum. The 80-nm blue EML was obtained by spin coating of the PVK:OXD-7:FIrpic blends in chlorobenzene onto the PEDOT:PSS layer and vacuum dried at 100° C. A 20-nm TQB was evaporated in a vacuum (<$6.0 \times 10^{-7}$ torr) or spun cast using different solvents (formic acid (FA):water=9:1, 7:1, 5:1, 3:1, 2:1) onto the EML, followed by an vacuum drying at 50° C. After drying, 100-nm Al was deposited onto the TQB layer. The structure of devices II and III was identical: ITO/PEDOT:PSS (30 nm)/EML (80 nm)/TQB (20 nm)/Al (100 nm). Device characterization, including external quantum efficiency (EQE), was performed using known methods. All device fabrication and characterization steps was performed under ambient laboratory air.

Device testing results are summarized in Table 2.

TABLE 2

Device characteristics of blue PhOLEDs. [a]

| Device [b] | ETL deposition | $V_{on}$[c] | Drive voltage [V] | Current density [mA $cm^{-2}$] | Luminance [cd $m^{-2}$] | Device efficiency [cd $A^{-1}$, (% EQE)] |
|---|---|---|---|---|---|---|
| Device I | None | 10.2 | 16.7 | 39.6 | 21.6 | 0.05, (0.02) |
|  |  |  | *13.9* | *1.8* | *4.0* | *0.2, (0.13)* |
| Device III | Vacuum | 9.6 | 16.6 | 54.9 | 4020 | 7.3, (4.0) |
|  |  |  | *14.0* | *8.7* | *1060* | *12.2, (6.9)* |
| Device IIIA | FA:$H_2O$ = 9:1 | 9.3 | 14.4 | 104.1 | 8260 | 8.9, (4.7) |
|  |  |  | *13.0* | *30.7* | *3780* | *12.3, (7.3)* |
| Device IIIB | FA:$H_2O$ = 7:1 | 9.3 | 13.9 | 120.0 | 8990 | 7.6, (4.6) |
|  |  |  | *12.5* | *31.1* | *3800* | *12.2, (7.4)* |
| Device IIIC | FA:$H_2O$ = 5:1 | 8.6 | 13.3 | 112.1 | 10900 | 9.8, (5.4) |
|  |  |  | *12.2* | *25.7* | *3730* | *14.5, (7.9)* |
| Device IIID | FA:$H_2O$ = 3:1 | 6.9 | 12.4 | 85.8 | 12400 | 14.4, (7.6) |
|  |  |  | *10.0* | *9.8* | *2790* | *28.3, (15.5)* |
| Device IIIE | FA:$H_2O$ = 2:1 | 8.6 | 13.7 | 73.3 | 10200 | 14.0, (7.5) |
|  |  |  | *12.2* | *20.3* | *4250* | *20.9, (13.4)* |

[a] Values in italic correspond to those at maximum device efficiencies.
[b] Device I, without TQB; device II, with vacuum-deposited TQB and device III, with solution-deposited TQB ETL using different solvent composition (FA:$H_2O$).
[c] Turn-on voltage (at brightness of 1 cd m−2).

Figure 7A:
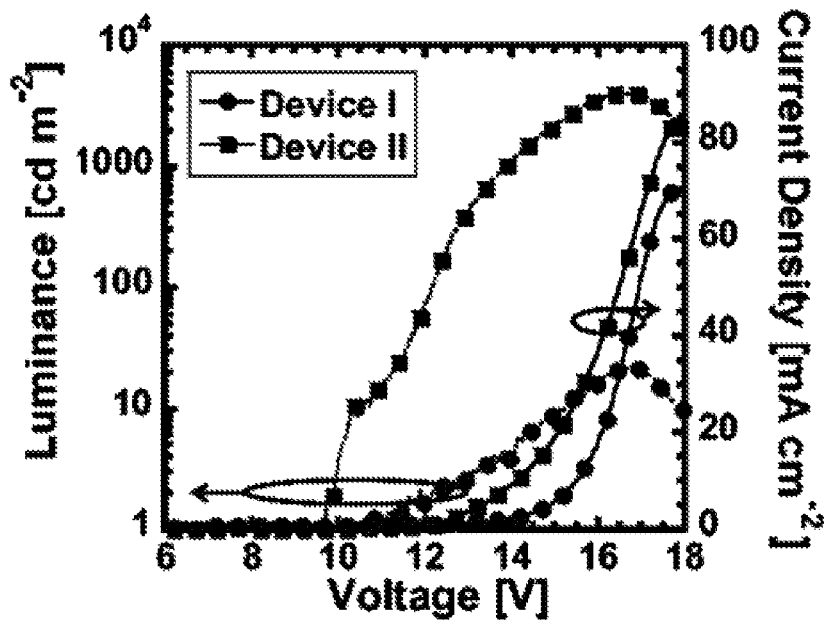
FIGS. 7A and 7B graphically illustrate luminescence versus voltage (FIG. 7A) and luminous efficiency versus current density (FIG. 7B) comparing representative devices of the invention with control devices.
Figure 7B:
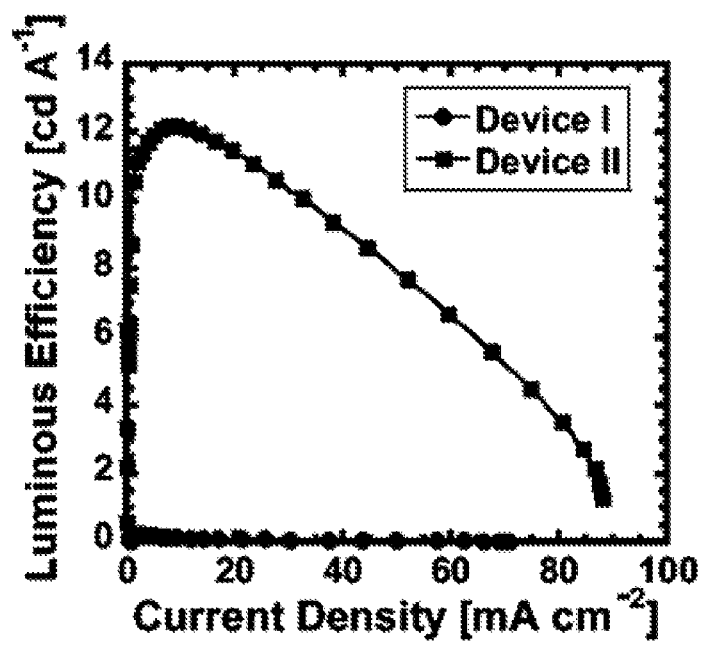

Two sets of devices were initially fabricated to verify the effectiveness of TQB as an ETL: device I, ITO/PEDOT:PSS/EML/Al without TQB as a reference; and device II, ITO/PEDOT:PSS/EML/TQB/Al with a thermally evaporated TQB inserted between the EML and Al cathode. From the luminance (L)-voltage (V)-current density (J) and luminous efficiency (LE)-current density (J) curves for devices I and II (FIGS. 7A-7B), we observed poor performance in device I without TQB layer, showing a turn-on voltage (at brightness of 1 cd $m^{-2}$) of 10.2 V, a maximum brightness of only 21.6 cd $m^{-2}$ (at 16.7 V) and a maximum LE value of 0.2 cd $A^{-1}$ with an EQE of 0.13%. Device II containing an evaporated TQB layer showed a dramatic improvement in performance with a brightness of 4020 cd $m^{-2}$ (at 16.6 V), an EQE of 6.9% and a LE value of 12.2 cd A$^{-1}$ (at 1060 cd m$^{-2}$); the turn-on voltage was also lower at 9.6 V. The enhanced performance of device II shows that TQB acts as a good ETL/FIBL by facilitating charge-injection from Al cathode as well as by facilitating a good confinement of holes to the EML.

Figure 8A:
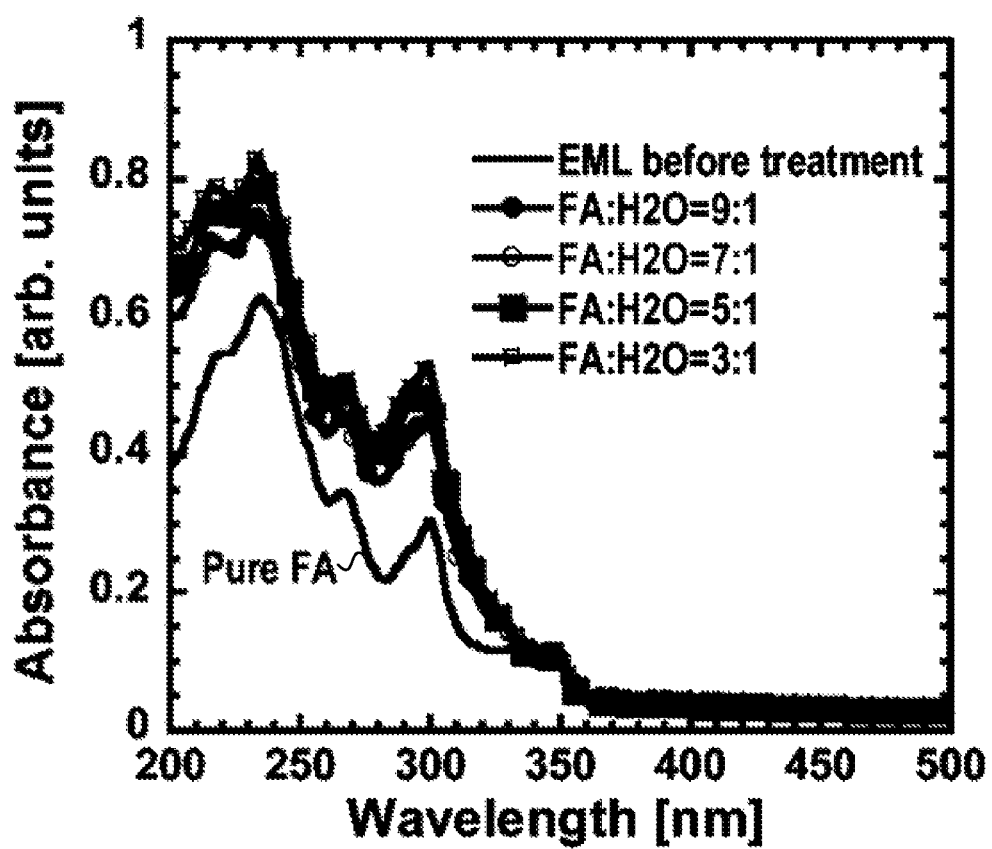
FIG. 8A graphically illustrates the absorption spectra of a film of a representative compound of the invention before and after treatment with various solvents.
Figure 8B:
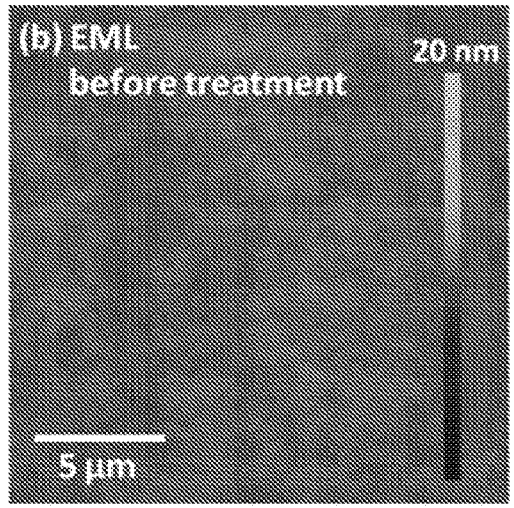
FIGS. 8B-8E are atomic force micrographs of films of a representative compound of the invention before and after treatment with various solvents.
Figure 8C:
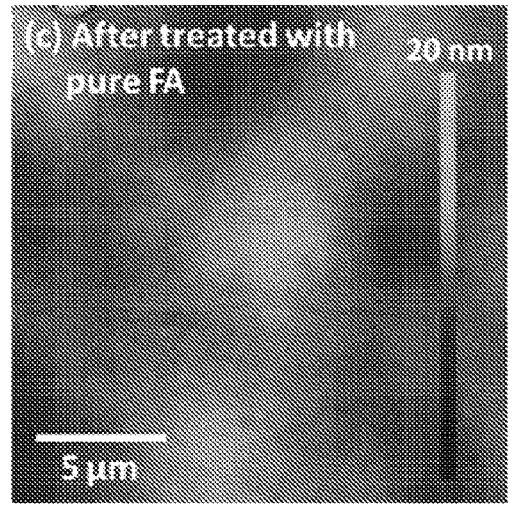
Figure 8D:
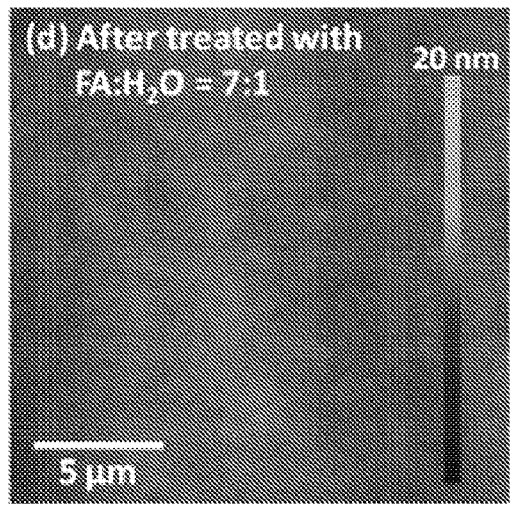
Figure 8E:
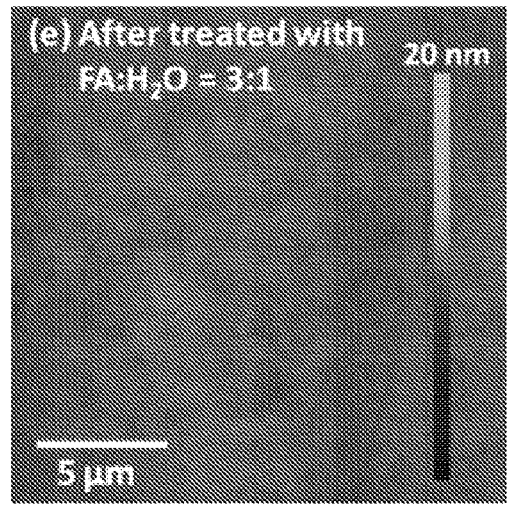

Next, the solution-processability of TQB as an ETL/HBL onto PVK-based EML was investigated. Based on the known solubility of oligo-/polyquinolines in formic acid (FA) and miscibility of formic acid with water (H$_2$O), we tested the orthogonal nature of FA/water mixed solvent system by examining the absorption spectrum and surface morphology of 40-nm EML (PVK:OXD-7:FIrpic) treated with FA/water mixtures of various compositions (FA:H$_2$O=10:0 [pure FA], 9:1, 7:1, 5:1, 3:1, 2:1, v/v). It should also be noted that FA and water have comparable boiling points (100° C.) and vapor pressures. Compared to the reference absorption spectrum of the untreated EML (PVK:OXD-7:FIrpic), the absorbance decreased significantly when treated with pure FA. In contrast, the EML absorbance was unchanged when treated with FA/water mixture at 3:1 but decreased slightly with mixtures of higher FA content (FIG. 8A). Similar studies of the EML (PVK:FIrpic), without OXD-7, showed unchanged absorption spectrum when treated with pure FA and all compositions of FA/water. These results suggest that the observed significant absorbance change when treated with pure FA is due to some extraction of OXD-7, resulting in a change in the composition of the EML. These studies, including the surface morphology revealed by AFM imaging of untreated and treated EML (FIGS. 8B-8E, demonstrate that the orthogonality of solvents required for sequential solution processing of PhOLEDs can be achieved by processing TQB as an ETL/HBL from FA:H$_2$0 mixed solvent system.

The surface morphology revealed by AFM imaging of untreated and treated EML (FIGURE S3b to S3e) showed that the surface roughness as characterized by the root-mean-square (rms) value was high (2.20 nm) for pure FA but comparable to the untreated (0.476 nm) in the case of all FA/water ratios (0.575-0.746 nm).

Figure 4A:
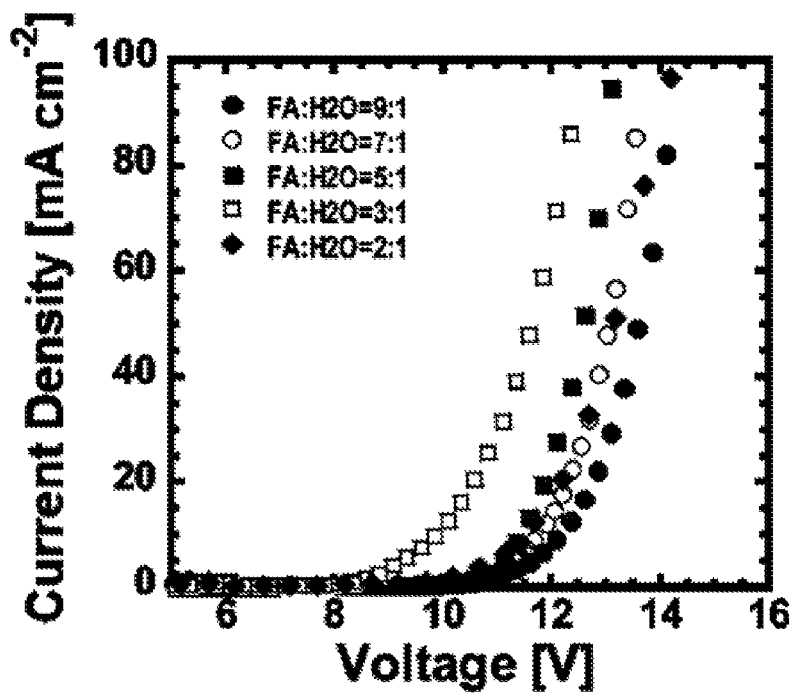
Figure 4B:
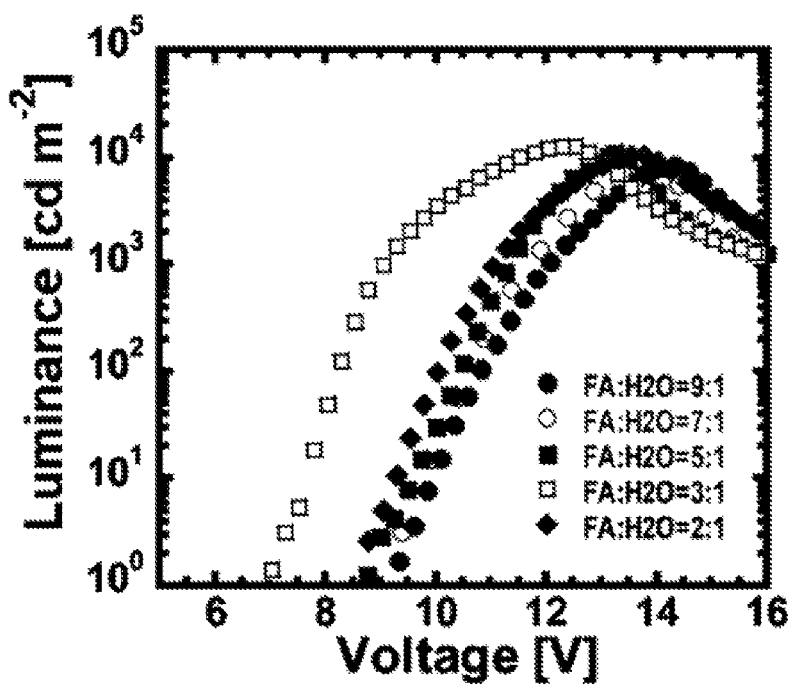
Figure 4C:
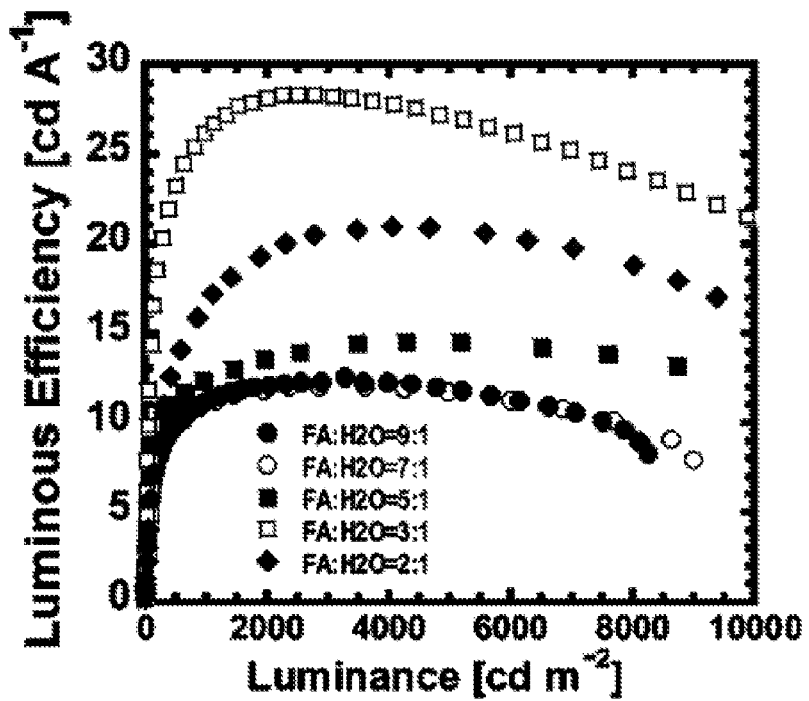

High performance blue PhOLEDs were fabricated by sequential spin coating of the PVK-based phosphorescent EML followed by deposition of the TQB ETL/HBL from its solution in FA/water mixture. Five sets of device III with the structure ITO/PEDOT:PSS/EML/TQB/Al were fabricated as a function of the solvent (FA/water) composition. The J-V, L-V and the luminous efficiency (LE)-luminance (L) characteristics of the PhOLEDs are shown in FIGS. 4A-4C.

Device IIIA made by processing TQB from the solvent FA:H$_2$0=9:1 had a maximum brightness of 8260 cd m$^{-2}$ (at 14.4 V) and a LE value of 12.3 cd A$^{-1}$ (at 3780 cd m$^{-2}$) with an EQE of 7.3%. This performance is already superior to that of device II with a vacuum-deposited TQB (Table 2). The performance of device IIIB containing TQB spin coated from a solvent with slightly increased water content (FA:H$_2$O=7:1) was similar to that of device IIIA. As shown in FIGS. 4A-4C and Table 2, the best device performance was achieved in device IIID in which TQB was spin coated from FA:H$_2$O=3:1. The PhOLEDs of device IIID had the lowest turn-on voltage (6.9 V), a maximum brightness of 12 400 cd/m$^2$, and a maximum luminous efficiency of 28.3 cd A$^{-1}$ (an EQE of 15.5%) at a high brightness of 2790 cd m$^{-2}$. This is the highest reported observed to date in polymer-based blue PhOLEDs. Even at a remarkably high brightness of 10 000 cd m$^{-2}$, the PhOLEDs of device IIID were still very efficient (>20 cd A$^{-1}$). The performance of device IIIE with TQB spin-coated from a solvent with even higher water content (FA:H$_2$0=2:1) while still excellent (LE=20.9 cd A$^{-1}$ at 4250 cd m$^{-2}$), is not as good as device IIID These results (devices IIIA-IIIE) show how high-performance multilayer PhOLEDs can be readily obtained by solution-deposition of the ETL/HBL from a binary solvent system which allows tuning of the surface wetting and interfacial morphology.

Figure 4D:
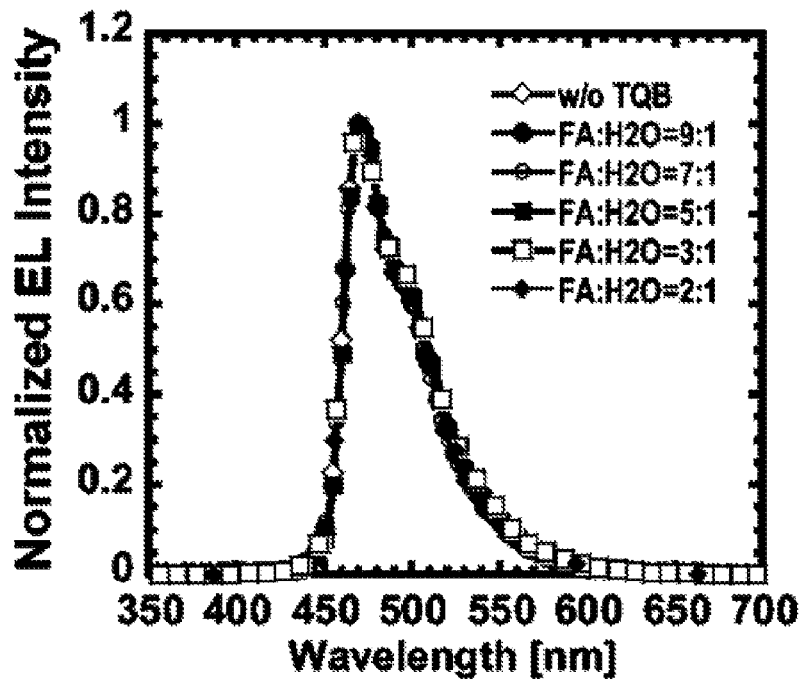

The electroluminescence (EL) spectra of the PhOLEDs without TQB and with the solution-processed TQB (devices I and III) are shown in FIG. 4D. The EL spectra of all the devices are identical in line shape with a maximum peak at 472 nm, which is characteristic of the FIrpic blue triplet emitter. The Commission Internationale de L'Eclairage (CIE) 1931 coordinates of all the devices were identical at (0.14, 0.28). These results show that the solution-processed TQB thin films function exclusively as the ETL/HBL in these PhOLEDs and can be expected to similarly work when used with blue triplet emitters other than FIrpic.

Figure 5A:
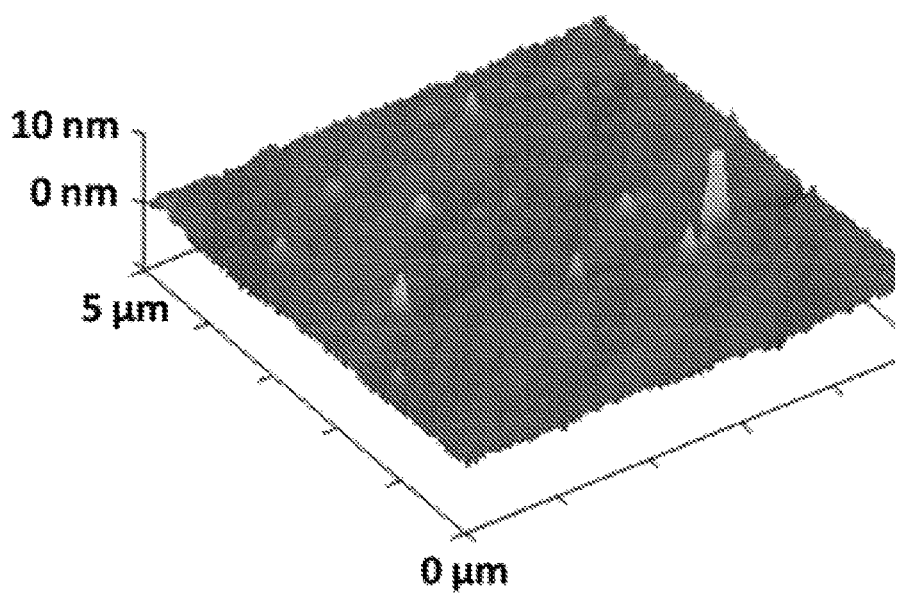
FIG. 5A is an atomic force micrograph of a layer of a representative compound of the invention (TQB) formed by vacuum deposition.
Figure 5B:
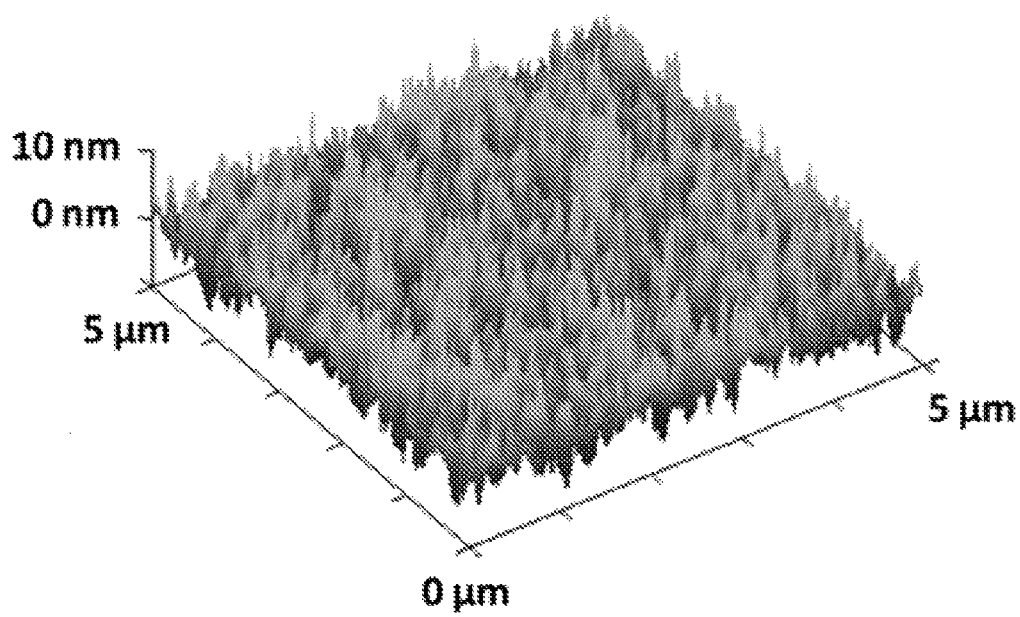
FIG. 5B is an atomic force micrograph of a layer of TQB formed by solution deposition.

The more than two-fold superior device performance of the PhOLEDs with a solution-deposited TQB ETL/HBL (e.g., LE=28.3 cd A$^{-1}$ at 2790 cd m$^{-2}$) compared to those with a vacuum-deposited TQB ETL/HBL (12.2 cd A$^{-1}$ at 1060 cd m$^{-2}$) is very important since the most common method of incorporating small-molecule ETL/HBL into OLEDs is by vacuum deposition. FIGS. 5A and 5B show the AFM topographical images of the surface morphology of vacuum-deposited and spin-cast TQB thin films, respectively. The vacuum-deposited TQB layer has a very smooth surface with an rms value of 0.553 nm. In contrast, the solution-deposited TQB layer has a very rough surface with an rms value of 2.54 nm (FIG. 5B). The observed large difference in surface roughness of the ETL/HBL can have a large impact on the quality of the TQB/Al contact and thus electron injection into the PhOLEDs. The rough TQB surface formed by solution-processing enables a high quality TQB/Al interface formation, resulting in efficient injection of electrons into the devices. The nature of the TQB/Al interface is likely similar to the polyquinoline/Al interface which is thought to be formed by chemical bonding of Al to the nitrogen heteroatoms in the organic material.

Figure 5C:
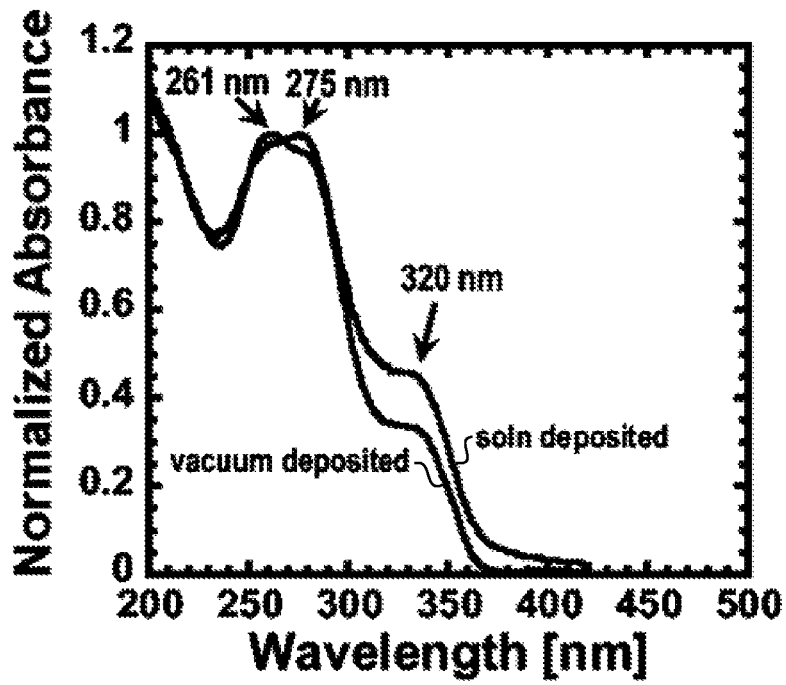
FIGS. 5C and 5D graphically illustrate absorption spectra (FIG. 5C) and photoluminescence spectra (FIG. 5D) of vacuum- and solution-deposited TQB films.
Figure 5D:
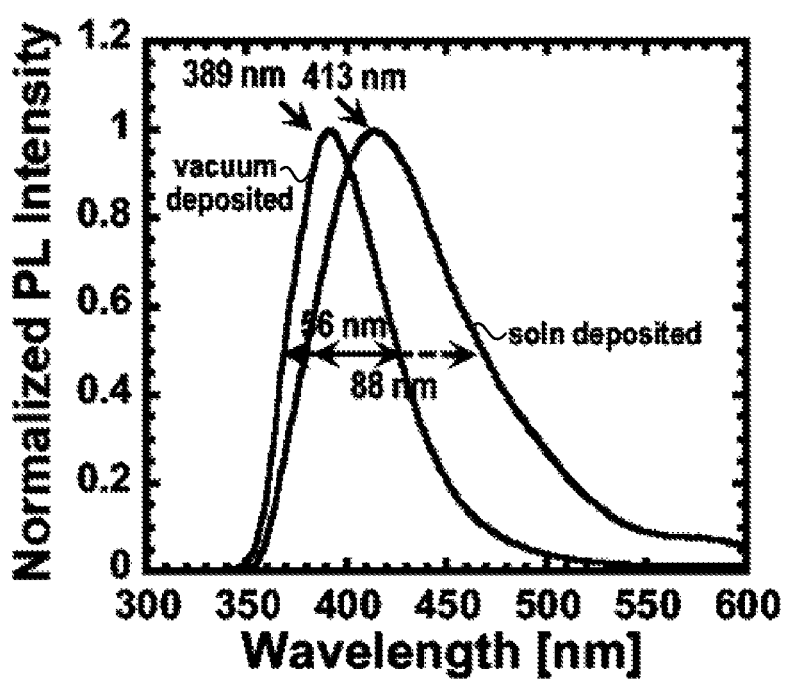

Formation of the rough surface of solution-processed TQB layer is enabled by oriented self-aggregation of the molecules from solution. Comparative absorption and photoluminescence (PL) spectroscopic analysis on the vacuum-deposited and solution-deposited TQB thin films provide evidence of a significant difference in photophysical properties. Although the optical band gap (E$_g$=3.4 eV), is identical in both TQB thin films, evaporated or spin cast, there is significant difference in the absorption spectra (FIG. 5C). The shoulder absorption peaks at 320 and 275 nm are enhanced in the solution-deposited TQB thin films, suggesting more aggregated molecules than in the evaporated thin films. The PL emission spectrum of vacuum evaporated TQB thin film has a peak centered at 389 nm with a full-width-at-half-maximum (fwhm) of 56 nm (FIG. 5D). In contrast, the PL emission spectrum of solution-deposited TQB thin film is red shifted and much broadened with a peak at 413 nm and an fwhm of 88 nm. The red-shifted and broadened PL emission of spin cast TQB thin film is consistent with aggregation and strong intermolecular interactions.

Example 3

Green PhOLEDs Incorporating TQB as an Electron-Transport Layer

Highly efficient green PhOLEDs were fabricated by sequential solution-processing of multilayered structures. Using a solution-processable electron-transport layer (ETL)/hole-blocking layer (HBL), multilayered green PhOLEDs demonstrate a large improvement of device efficiency and brightness compared to a vacuum deposited ETL. The devices incorporate TQB, which functions as an ETL/HBL in the devices without the aid of interfacial materials (LiF, CsF) or low work function metals (Ba, Ca) as cathode materials. In addition, LiF has been inserted between solution-deposited TQB and Al cathode, resulting in the determination that the cathode interfacial material (LiF) is unnecessary when applying the solution-processed TQB as an ETL/HBL in green PhOLEDs.

The polymer-based emission layer (EML) in green PhOLEDs was fabricated using blends of poly(N-vinylcarbazole) (PVK) and 1,3-bis(2-(4-tert-butylphenyl)-1,3,4-oxadiazo-5-yl)benzene (OXD-7) (PVK:OXD-7=60:40 wt/wt) as the host doped with 1.0 wt % fac-tris(2-phenylpyridine)iridium ($Ir(ppy)_3$) as the green triplet emitter in the EML. For the hole injection layer, a solution of poly(ethylenedioxythiophene):poly(styrenesulfonate) (PEDOT:PSS), H. C. Starck, Clevios P VP Al 4083) in water was spin-coated to make a 30-nm thick layer onto a pre-cleaned ITO glass and annealed at 150° C. under vacuum. A 70-nm thick EML was obtained by spin-coating of the PVK/OXD-7/$Ir(ppy)_3$ blend in chlorobenzene onto the PEDOT:PSS layer and vacuum-dried overnight at 100° C. A 15-nm thick TQB layer was evaporated in a vacuum ($<6.0 \times 10^{-7}$ torr) or spun cast from its solution in a formic acid (FA)/water ($H_2O$) mixture (FA:$H_2O$=4:1) onto the EML, followed by vacuum drying at 50° C. After drying, 100-nm Al or LiF/Al were deposited onto the TQB layer.

Figure 9A:
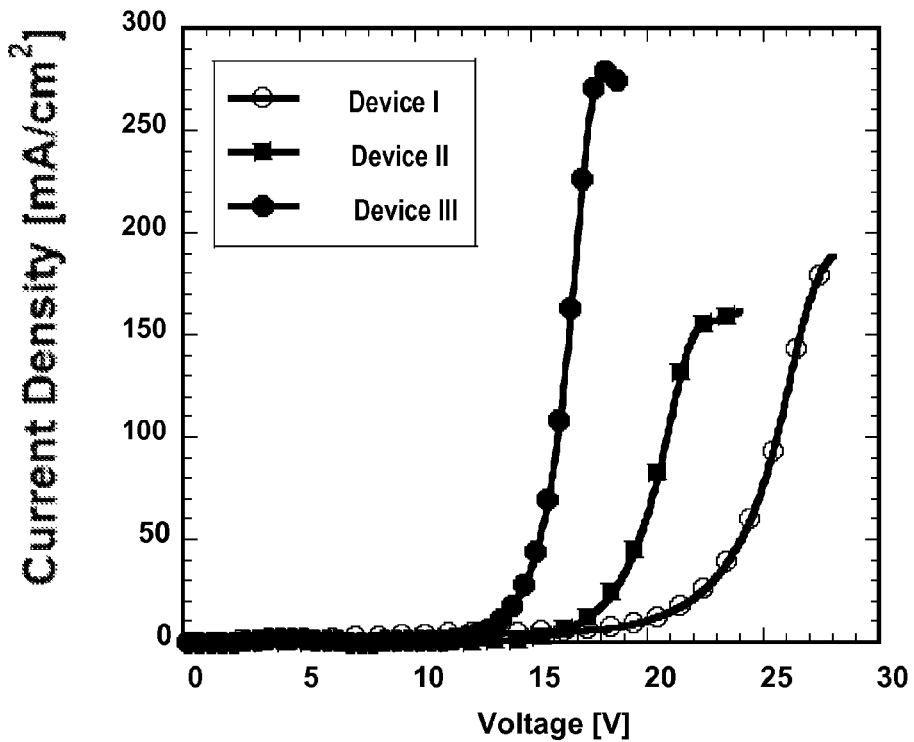
Figure 9B:
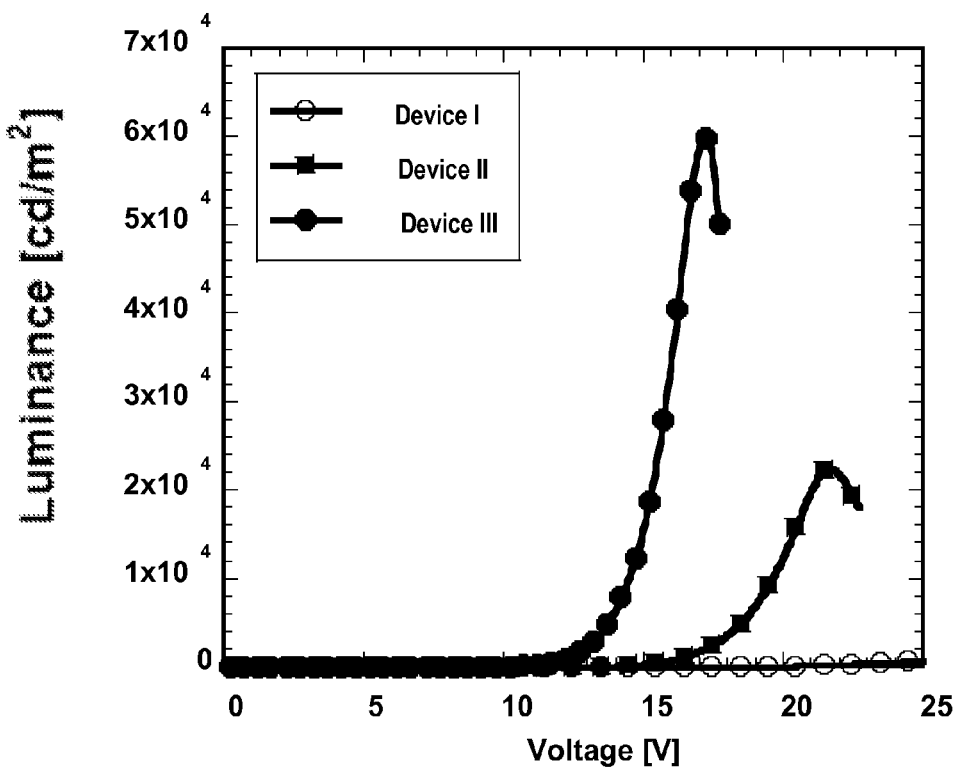

To verify the effectiveness of TQB as an ETL/HBL in the green PhOLEDs, three sets of devices were fabricated: device I, ITO/PEDOT:PSS/EML/Al without TQB as a reference; device II, ITO/PEDOT:PSS/EML/TQB/Al with a vacuum-deposited TQB; and device III, ITO/PEDOT:PSS/EML/TQB/Al with a solution-deposited TQB. The only difference between devices II and III was the method of deposition of the TQB ETL/HBL onto the EML: vacuum-deposited or solution-deposited. The current density-voltage (J-V) characteristics of the devices are shown in FIG. 9A. Compared to devices I and II, device III having a solution-deposited TQB showed superior electron-injection as seen from its greater current density. In FIG. 9B, the luminance-voltage (L-V) curves are also shown. The maximum brightness (luminance) of device I without an ETL was only 580 cd/m² at a high drive voltage of 24.7 V. However, device II with vacuum-deposited TQB as an ETL showed a brightness of 22 500 cd/m² at a lower drive voltage of 21.6 V than device I, an almost 40-fold increase in brightness. In contrast, device III with solution-deposited TQB showed an ultrahigh brightness of 60 000 cd/m² at even lower drive voltage of 17.2 V, which represents 100-fold increase compared to device I without TQB and nearly 3-fold increase in brightness compared to device II with vacuum-deposited TQB.

Figure 10A:
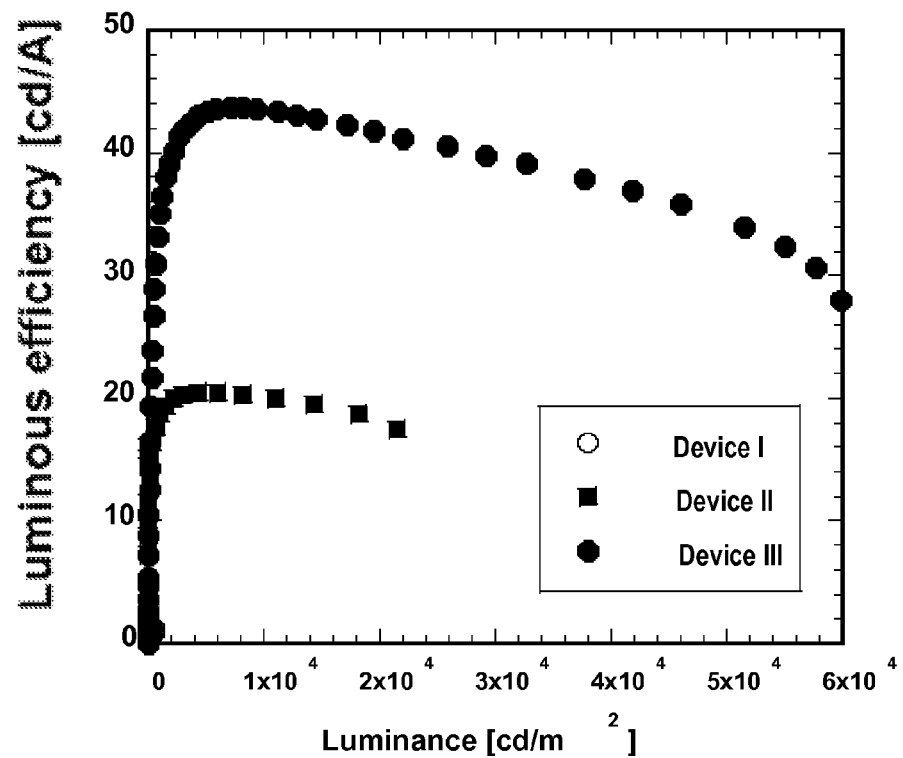

The luminous efficiency-luminance (LE-L) curves of the three devices are shown in FIG. 10A. The LE value of device III was 43.9 cd/A with an EQE of 14.0% at a brightness of 6530 cd/m², which is more than double the efficiency of device II, 20.4 cd/A with an EQE of 6.5% at a brightness of 5270 cd/m². Even at an ultrahigh brightness of ~60 000 cd/m², the LE of device III remained as high efficiency (>27.0 cd/A). These result clearly show that solution-processed TQB is a superior ETL than vacuum-deposited TQB in green PhOLEDs.

Figure 10B:
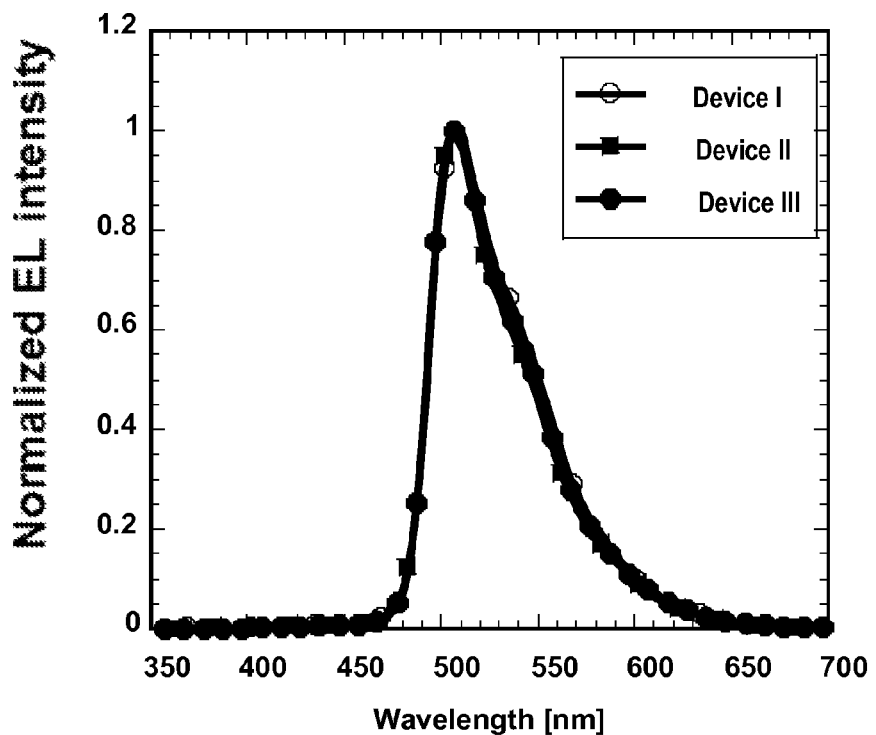

The normalized EL spectra of devices I, II, and III are shown in FIG. 10B. The EL spectra are all identical in line shape with a maximum peak of 512 nm. The Commision Internationale de L'Eclairage (CIE) 1931 color coordinates of the three devices were all identical at (0.24, 0.63) due to the green triplet emitter $Ir(ppy)_3$. These results demonstrate that TQB functions exclusively as an electron-transporting layer, showing good confinement of charge carriers and excitons inside the EML.

Figure 11A:
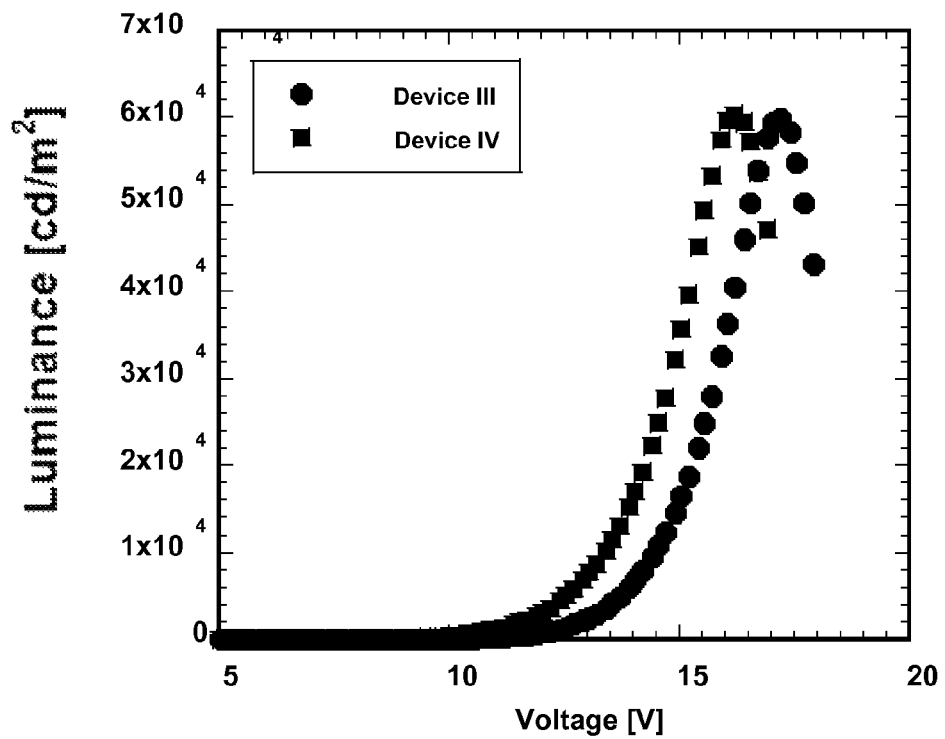
FIGS. 11A and 11B graphically illustrate the performance of representative green PhOLEDs of the invention, wherein FIG. 11A luminescence versus voltage.

The influence of lithium fluoride (LiF) inserted between solution-deposited TQB layer and Al cathode was determined by fabricating device IV, ITO/PEDOT:PSS/EML/TQB/LiF/Al. It is well-known that insertion of a thin layer of LiF between the organic layer (EML or ETL) and the metal cathode usually results in reduced driving voltage of OLEDs. In addition, it was also reported that energy-band bending at organic layer/LiF interface leads to enhancement of electron-injection from Al cathode into the organic layer. However, green PhOLEDs (device IV) with a solution-processed TQB ETL showed a lower efficiency when LiF was inserted between the TQB ETL and Al cathode. A PhOLED with 1-nm LiF between TQB ETL and Al cathode was fabricated and compared with the device without LiF (device III). In FIG. 11A, the luminance-voltage (L-V) curves of the two devices (III versus IV) are shown. The drive voltage at a maximum brightness was slightly reduced from 17.2 V to 16.2 V when LiF was inserted, while showing the same maximum brightness.

Figure 11B:
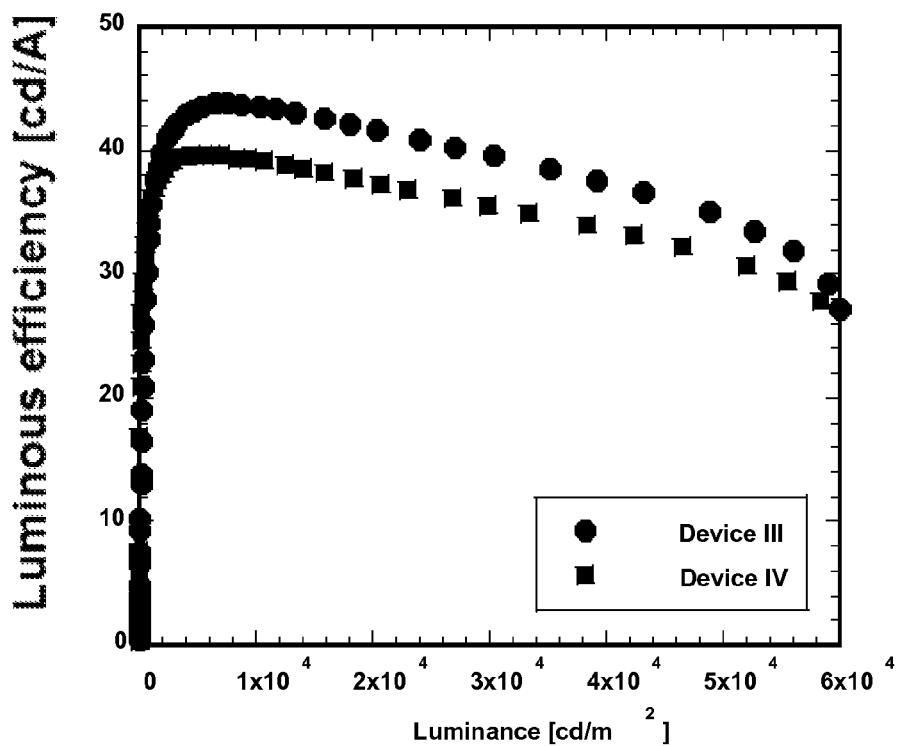

In FIG. 11B, the luminous efficiency curves of the two devices (III versus IV) are shown. The luminous efficiency of device IV decreased to 39.7 cd/A (at a brightness of 5920 cd/m²) compared to device III (without LiF) which had a higher efficiency of 43.9 cd/A at a brightness of 6530 cd/m². Many previous studies have shown that LiF is a highly effective cathode interfacial layer that enhances electron-injection from Al cathode, leading to enhanced performance of devices. However, in the case of devices containing solution-processed TQB ETL, LiF does not enhance performance. Although the driving voltage of the PhOLED was slightly reduced in device IV compared to device III, the luminous efficiency of device IV decreased. Note that both PhOLEDs with LiF (device IV) and without LiF (Device III) had similar maximum power efficiency (~10.4 lm/W). Therefore, insulating inorganic interfacial materials such as LiF are not needed when utilizing the solution-processed TQB ETL in PhOLEDs using Al cathode.

Example 4

PhOLEDs Fabricated Using a Solution-Deposited Electron-Transport Layer from a Solvent Orthogonal in Solubility to the Emissive Layer The fabrication of highly-efficient green PhOLEDs by solution-processing of an electron-transport material, 2,9-dimethyl-4,7-diphenyl-1,10-phenanthroline (BCP) as an electron-transport layer/hole-blocking layer (ETL/HBL) is provided. BCP is a well-known commercial electron-transport material having a high electron affinity (3.2 eV) and good hole-blocking property (HOMO level of −6.7 eV), but to date it is processed only by thermal evaporation method. However, in this Example, BCP is solution-deposited as an ETL, leading to bright and high-efficiency in the green PhOLEDs.

The polymer-based emission layer (EML) for green PhOLEDs are blends of poly(N-vinylcarbazole) (PVK) and 1,3-bis(2-(4-tert-butylphenyl)-1,3,4-oxadiazo-5-yl)benzene (OXD-7) (PVK:OXD-7=60:40 wt/wt), as the host, doped with 2.0 wt % fac-tris(2-phenylpyridine)iridium ($Ir(ppy)_3$), as the green triplet emitter in the EML. For the hole injection layer, a solution of poly(ethylenedioxythiophene):poly(styrenesulfonate) (PEDOT:PSS), H. C. Starck, Clevios P VP Al 4083) in water was spin-coated to make a 30-nm thick layer onto a pre-cleaned ITO glass and annealed at 150° C. under vacuum. A 70-nm thick EML was obtained by spin-coating of the PVK:OXD-7:Ir(ppy)$_3$ blend in chlorobenzene onto the PEDOT:PSS layer and vacuum-dried overnight at 100° C. A 20-nm thick BCP was spun cast from its solution in a formic acid (FA)/water (H$_2$O) mixture (FA:H$_2$O=3:1) onto the EML, followed by overnight vacuum drying at 50° C. After drying, 100-nm Al was deposited onto the EML or BCP layer.

Figure 12A:
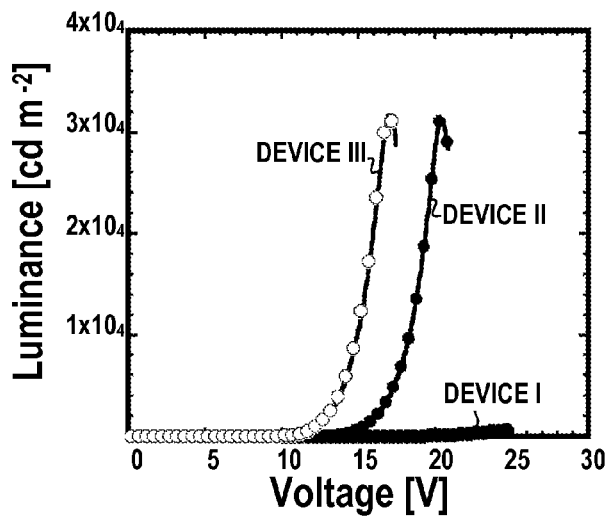
Figure 12B:
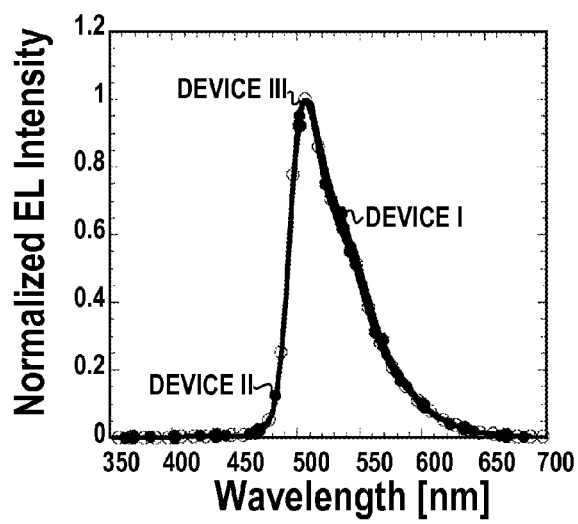
Figure 12C:
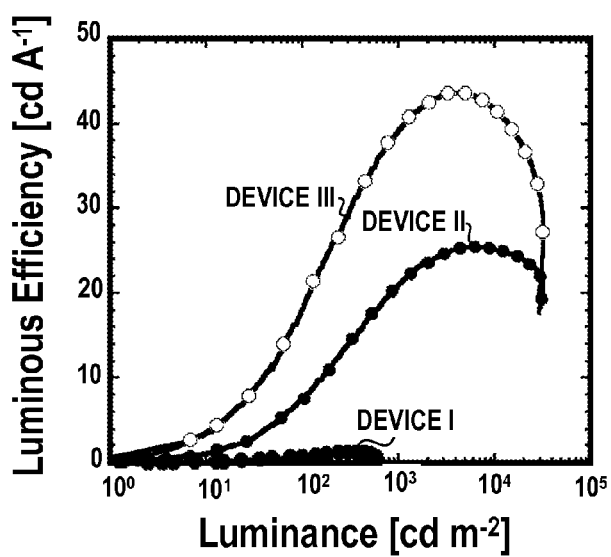

To verify the effectiveness of solution-deposited BCP as an ETL/HBL in the green PhOLEDs, two sets of devices were fabricated: device I, ITO/PEDOT:PSS/EML/Al without BCP layer as a reference; device II, ITO/PEDOT:PSS/EML/BCP/Al with a vacuum-deposited BCP; and device III, ITO/PEDOT:PSS/EML/BCP/Al with a solution-deposited BCP. The luminance-voltage (L-V) characteristics of the devices are shown in FIG. 12A; the electroluminescence is shown in FIG. 12B, and the luminous efficiency is shown in FIG. 12C. The maximum brightness (luminance) of device I without a BCP layer was only 580 cd/m$^2$ at a high drive voltage of 24.7 V. Device II with vacuum-deposited BCP layer showed much increased brightness of 31 300 cd/m$^2$ at a drive voltage of 20.4 V, which represents over 50-fold increase compared to device I without ETL. Device III with solution-deposited BCP layer showed a similar brightness of 31 700 cd/m$^2$ even at a lower drive voltage of 17.0 V. However, the luminous efficiency (FIG. 12C) of device III was 43.7 cd/A with an EQE of 13.9% at a brightness of 4270 cd/m$^2$, which is almost twice higher than the efficiency of device II showing 25.5 cd/A with an EQE of 8.1% at a brightness of 5230 cd/m$^2$. These results demonstrate that the solution-deposited BCP works as a good ETL in PhOLEDs compared to vacuum-deposited BCP.

Example 5

Synthetic Schema for Representative Compounds of the Provided Embodiments

As set forth above, various genera of compounds are provided in the disclosed embodiments. These compounds are generally synthesized in the same manner as provided in Example 1 with regard to TQB, which is a species of genus 1, 2, and 3 set forth below. The symbolic schema for the synthesis of the representative compounds are provided below in Schemes 1-5.

Synthesis:

Scheme 1. Synthesis of 1.

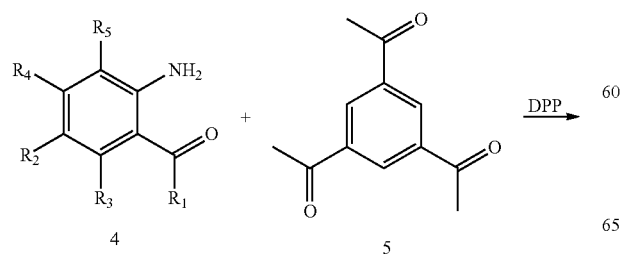

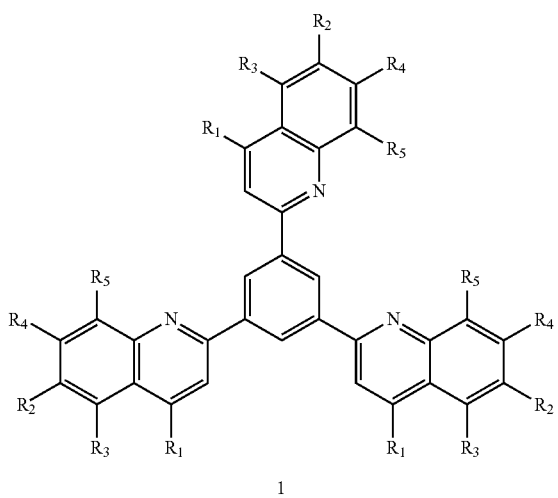

1

Scheme 2. Synthesis of 2.

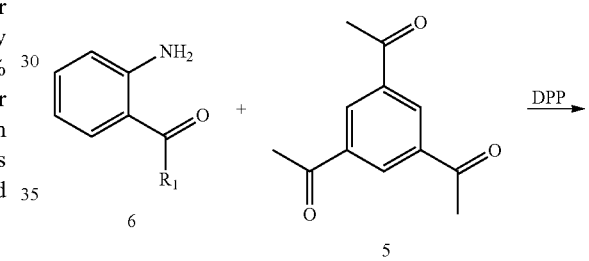

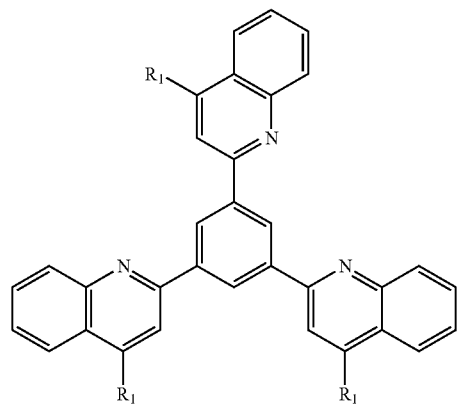

2

Example 1
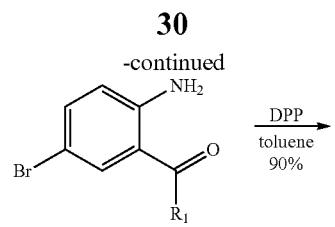
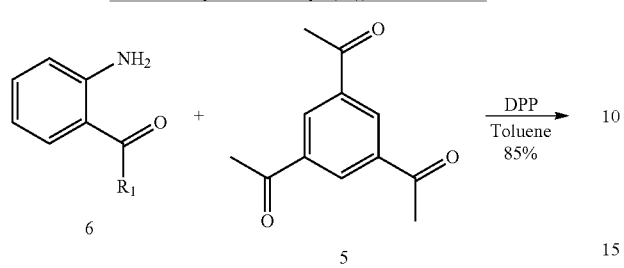
Scheme 3. Synthesis of TQB (2a), derivative of 2.
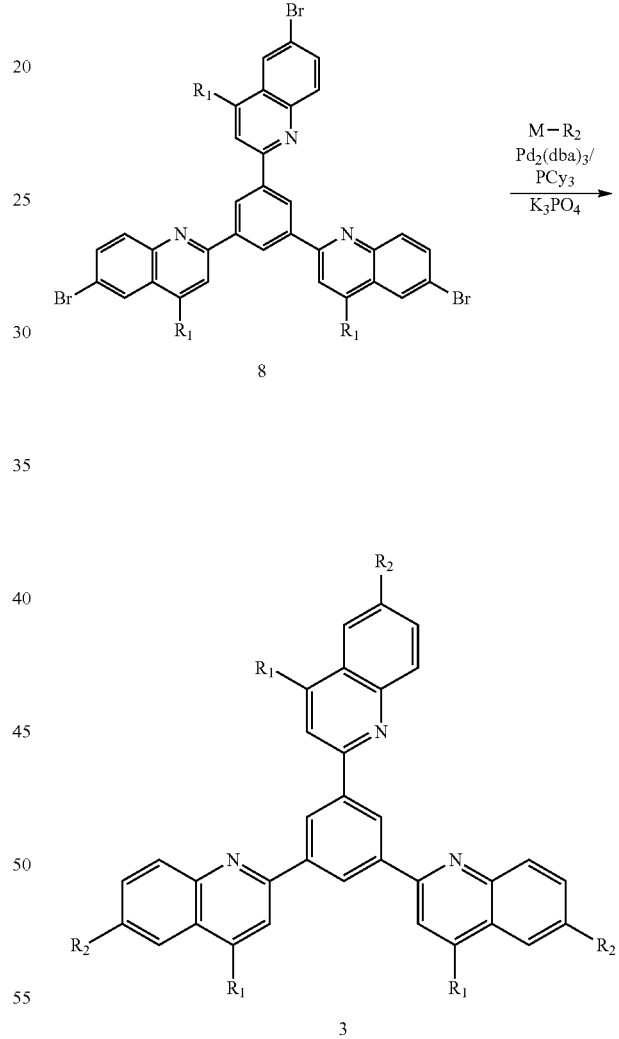
$R_1$ = phenyl
Scheme 4. Synthesis of compound 3.
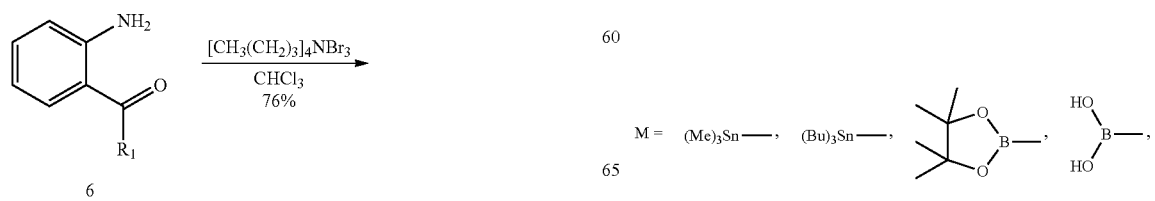

Scheme 5. Synthesis of compound 4.
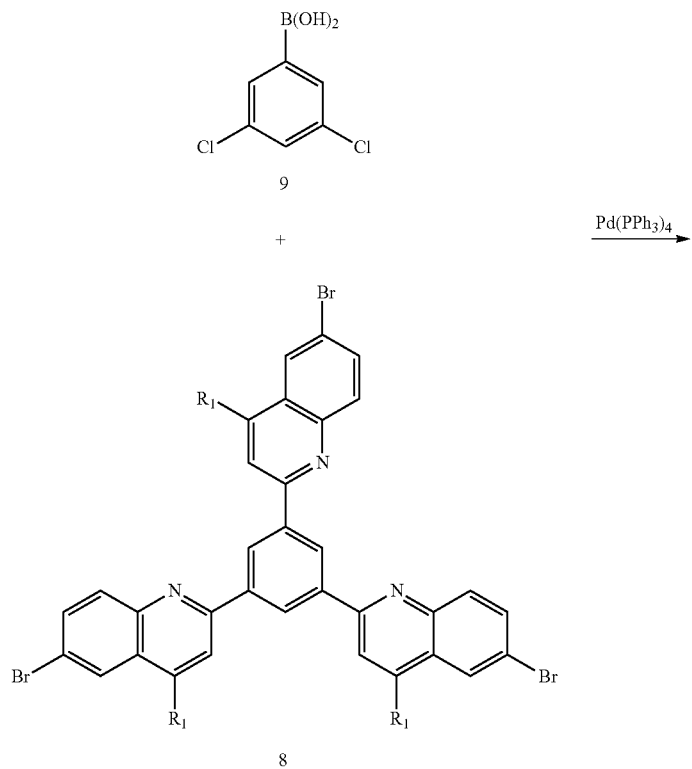
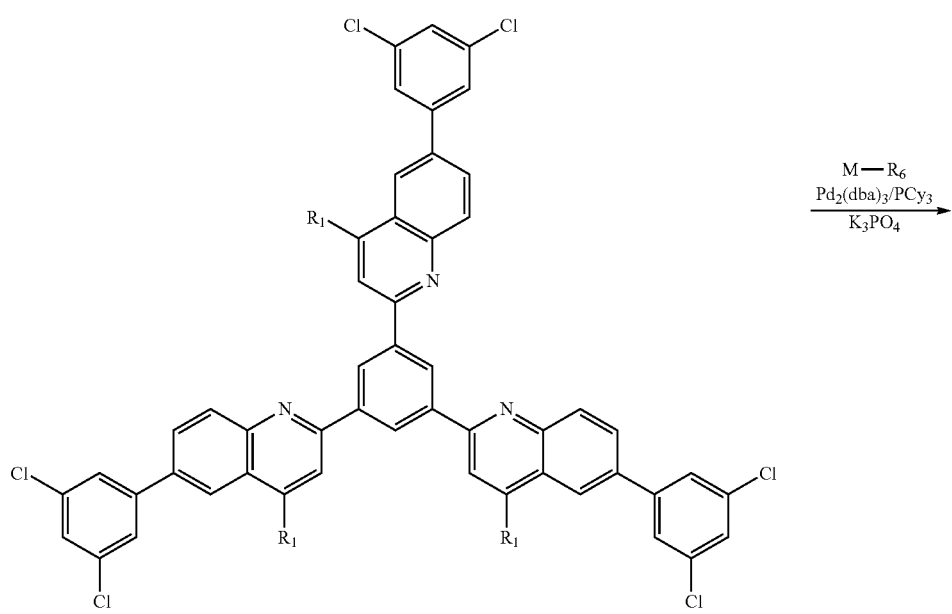

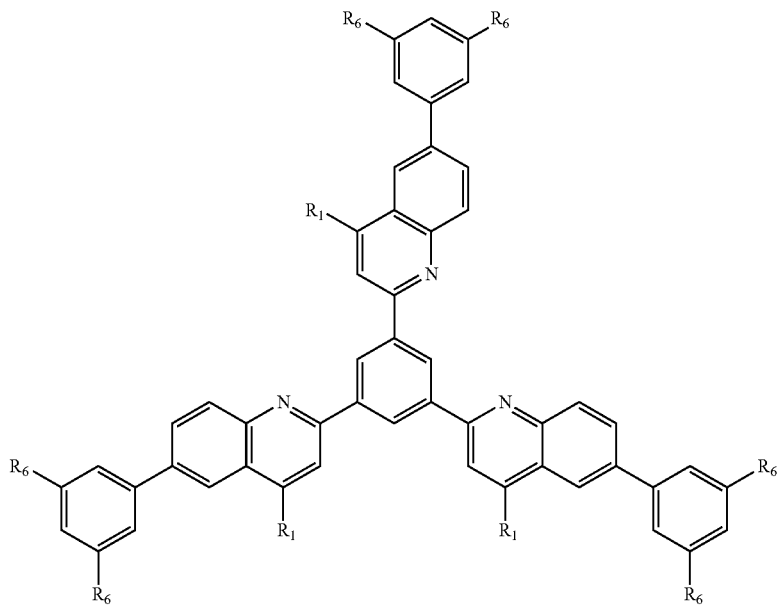

4

Example 6

Synthesis of 1,3,5-tris(4-methylquinolin-2-yl)benzene (TMQB)

TMQB was synthesized (as illustrated in Scheme 6) from 2-aminoacetophenone and 1,3,5-triacetylbenzene via Friedlander condensation using diphenyl phosphate (DPP) as an acid catalyst. The final product was precipitated from 10% methanol/triethylamine mixture. The product was then recrystallized twice from dichloromethane and once from THF/MeOH mixture (2:1 v:v).

Scheme 6. Synthesis of 1,3,5-tris(4-methylquinolin-2-yl)benzene (TMQB).

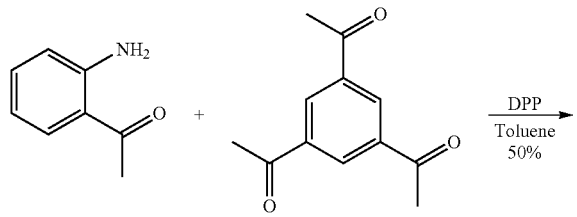

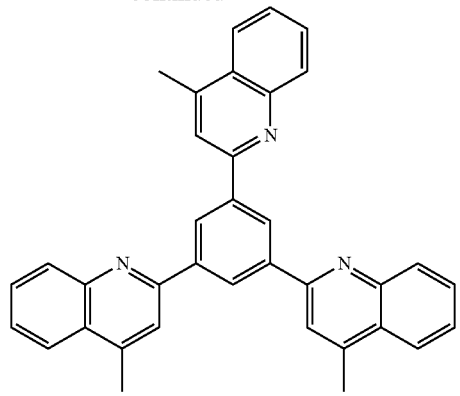

TMQB

A mixture of 2-aminoacetophenone (3.0 g, 14.7 mmol), 1,3,5-triacetylbenzene (6.2 g, 45.5 mmol) and diphenyl phosphate (8 equiv) in 12 mL of toluene were refluxed under argon overnight. The reaction mixture was precipitated from 10% methanol/triethylamine and the solid was collected by vacuum filtration. The product was purified by flash column chromatography using dichloromethane and acetonitrile mixture (9.5:0.5). The product was then recrystallized twice from dichloromethane and once from THF/MeOH mixture (2:1 v:v) and the white solid was collected in 50% yield. $^1$H-NMR (300 MHz, CDCl$_3$): δ ppm=9.102 (s, 3H), 8.325 (d, J=8.0 Hz, 3H), 8.101-8.068 (m, 6H), 7.788 (t, J=8.1 Hz, 3H), 7.614 (m, 3H), 2.882 (s, 9H). $^{13}$C-NMR (500 MHz, CDCl$_3$): δ ppm=156.76, 148.20, 144.99, 140.90, 130.40, 129.38, 127.53, 126.16, 123.73, 120.14, 19.08. LC-Mass calcd=C$_{37}$H$_{27}$N$_3$ 501.62 Found M+1 502.5.

Example 7

Synthesis of 1,3,5-tris(4-(4-fluorophenyl)quinolin-2-yl)benzene (TFQB)

TFQB was synthesized (as illustrated in Scheme 7) from 2-amino-4'-fluorobenzophenone and 1,3,5-triacetylbenzene via Friedlander condensation using diphenyl phosphate (DPP) as an acid catalyst. The final product was precipitated from 10% methanol/triethylamine mixture. The product was purified by flash column chromatography using chloroform/acetonitrile (9.5:0.5 v/v) as eluent solvent. The product was then recrystallized from chloroform and methanol mixture (1:1 v/v).

Scheme 7. Synthesis of 1,3,5-tris(4-(4-fluorophenyl)quinolin-2-yl)benzene (TFQB).

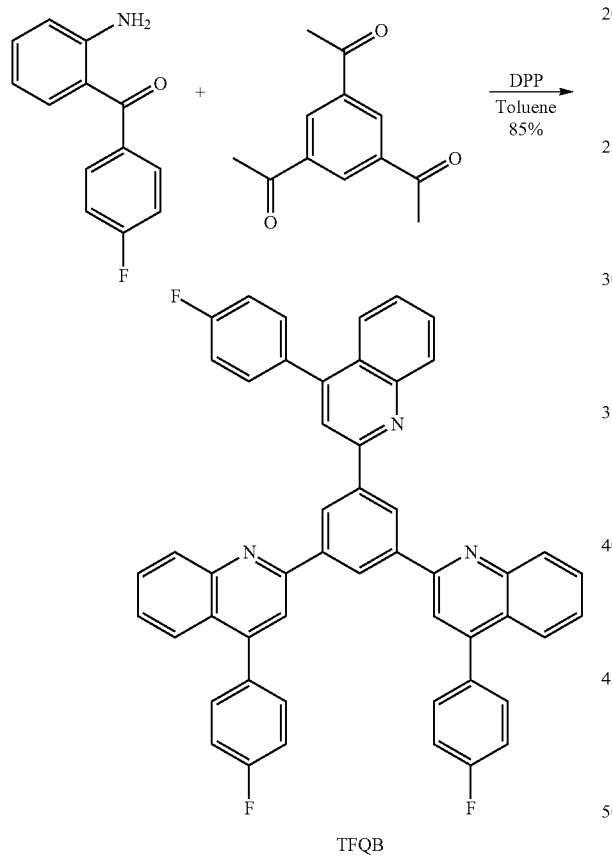

TFQB

A mixture of 2-amino-4'-fluorobenzophenone (3.2 g, 14.9 mmol), 1,3,5-triacetylbenzene (1.0 g, 4.9 mmol) and diphenyl phosphate (8 equiv) in 12 mL of toluene were refluxed under argon overnight. The reaction mixture was precipitated from 10% methanol/triethylamine and the solid was collected by vacuum filtration. The product was purified by flash column chromatography using chloroform and acetonitrile mixture (9.5:0.5). The product was then recrystallized from chloroform/MeOH mixture (1:1 v:v) and the white solid was collected in 85% yield. $^1$H-NMR (300 MHz, CDCl$_3$): δ ppm=9.158 (s, 3H), 8.352 (d, J=8.4 Hz, 3H), 8.106 (s, 3H), 7.927 (d, J=8.1 Hz, 2H), 7.787 (t, 3H), 7.620 (m, 9H), 7.328 (m, 6H), 2.882 (s, 9H). $^{13}$C-NMR (500 MHz, CDCl$_3$): δ ppm=163.972, 161.997, 156.400, 148.824, 148.351, 140.845, 134.304, 131.452, 130.275, 129.744, 127.761, 126.717, 125.991, 125.479, 119.640, 115.816, 115.644. LC-Mass calcd=C$_{51}$H$_{30}$F$_3$N$_3$ 741.8 Found M+1 742.8.

Example 8

Synthesis of 1,3,5-tris(4-pyridinquinolin-2-yl)benzene (TPQB)

Synthesis of 1,3,5-tris(4-pyridinquinolin-2-yl)benzene (TPQB) is shown below in Scheme 8. TPQB was synthesized from 4-(2-aminobenzoyl)pyridine and 1,3,5-triacetylbenzene via Friedlander condensation using diphenyl phosphate (DPP) as an acid catalyst. The final product was precipitated from 10% methanol/triethylamine mixture. The product was then recrystallized from dichloromethane and methanol mixture (1:1 v/v).

Scheme 8. Synthesis of 1,3,5-tris(4-pyridinquinolin-2-yl)benzene (TPQB).

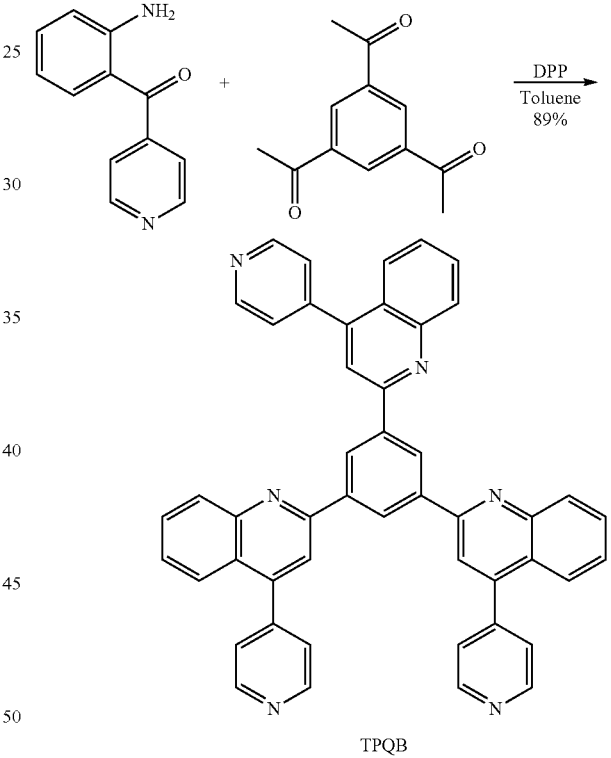

TPQB

A mixture of 4-(2-aminobenzoyl)pyridine (1.0 g, 5.04 mmol), 1,3,5-triacetylbenzene (0.338 g, 1.66 mmol) and diphenyl phosphate (8 equiv) in 12 mL of toluene were refluxed under argon overnight. The reaction mixture was precipitated from 10% methanol/triethylamine and the solid was collected by vacuum filtration. The product was then recrystallized from dichloromethane/MeOH mixture (1:1 v:v) and the white solid was collected in 89% yield. $^1$H-NMR (300 MHz, CDCl$_3$): δ ppm=9.184 (s, 3H), 8.887 (d, J=6.0 Hz, 6H), 8.391 (d, J=8.4 Hz, 3H), 8.120 (s, 3H), 7.886-7.813 (m, 6H), 7.602-7.582 (m, 9H). $^{13}$C-NMR (500 MHz, CDCl$_3$): δ ppm=156.24, 150.25, 148.77, 146.60, 146.22, 140.70, 130.47, 130.18, 127.83, 127.28, 125.04, 124.96, 124.45, 119.12. LC-Mass calcd=C$_{48}$H$_{30}$N$_3$ 690.8 Found M+1 691.9.

Example 9

Synthesis and Testing of Synthesis of Dendritic Oligoquinolines

In this example, the synthesis, electrochemical properties, and photophysics of a series of dendritic oligoquinolines and their use as electron-transport layers in solution-processed highly efficient polymer-based blue PhOLEDs, is described. The molecular structures of the oligoquinolines (TMQB, TQB, TFQB, and TPyQB) are as follows:

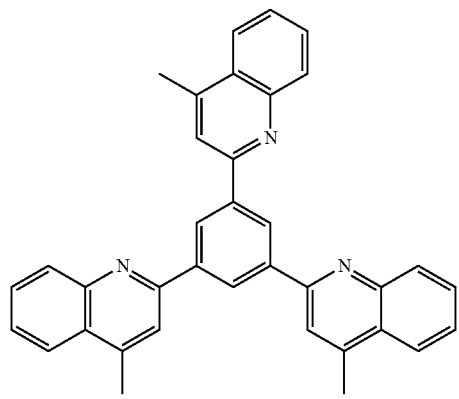

TMQB

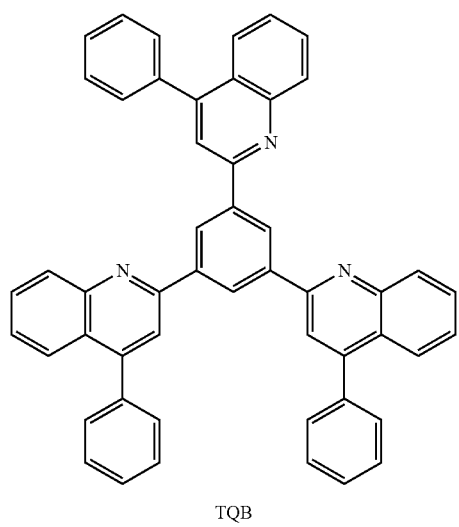 [SMILES: c1ccc2c(-c3ccncc3)cc(-c3cc(-c4cc(-c5ccncc5)c5ccccc5n4)cc(-c4cc(-c5ccncc5)c5ccccc5n4)c3)nc2c1]

TQB

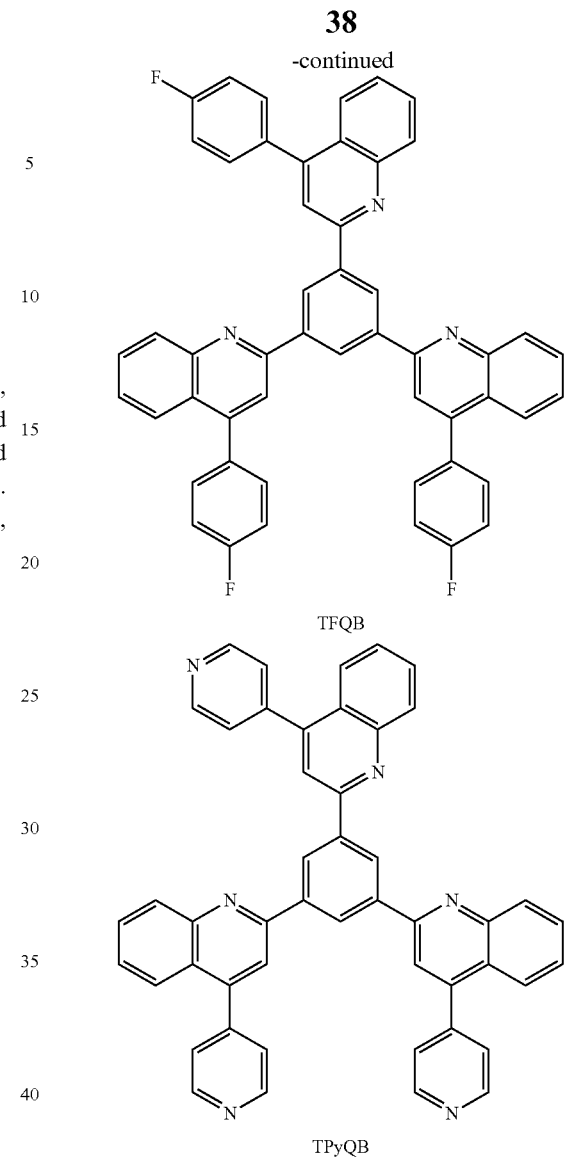

TFQB

TPyQB

The molecular design of these oligoquinolines is focused on connecting tris(quinolin-2-yl)benzene with meta-linkage to confine the π-conjugation length and thus to enable wide-energy-gap. Various substitutions ($R_1$=methyl, phenyl, 4-fluorophenyl, and 4-pyridyl) on the quinoline rings were examined towards tuning the electronic and solid-state properties. Variation of the $R_1$ group in the quinoline rings leads to a 100-fold variation in charge carrier mobility among the four oligoquinolines.

Blue PhOLEDs based on FIrpic triplet emitter-doped poly (N-vinylcarbazole) (PVK) emission layer and a solution-processed oligoquinoline electron-transport layer (ETL) gave a high luminous efficiency of 30.5 cd $A^{-1}$ at a brightness of 4130 cd $m^{-2}$ with an external quantum efficiency (EQE) of 16.0%. These solution-processed PhOLEDs exhibit the highest performance observed to date in polymer-based blue PhOLEDs, to the best of the inventors' knowledge. The approach of using solution-processed oligoquinoline ETLs has resulted in high performance blue PhOLEDs while eliminating the need for a cathode interfacial layer (e.g., LiF, CsF) in OLEDs. The results also clearly demonstrate that small-molecule electron-transport layer/hole-blocking layer (ETL/HBL) can be solution-processed to fabricate high-performance PhOLEDs instead of using vacuum-deposition. It was also determined that solution-processed ETL films exhibit a unique morphology that facilitates improved carrier mobility, higher device performance, and better ETL/electrode interface compared with vacuum deposited films. Structure-property relationships of the series of oligoquinolines were investigated by cyclic voltammetry, photophysical measurements, space-charge-limited current (SCLC) measurements of electron mobility, electrophosphorescent devices, and atomic force microscopy (AFM).

Synthesis and Characterization.

The synthesis of the four dendritic oligoquinolines, 1,3,5-tris(4-methylquinolin-2-yl)benzene (TMQB), 1,3,5-tris(4-phenylquinolin-2-yl)benzene (TQB), 1,3,5-tris(4-(4-fluorophenyl)quinolin-2-yl)benzene (TFQB), and 1,3,5-tris(4-pyridinquinolin-2-yl)benzene (TPyQB), is outlined in Scheme 9.

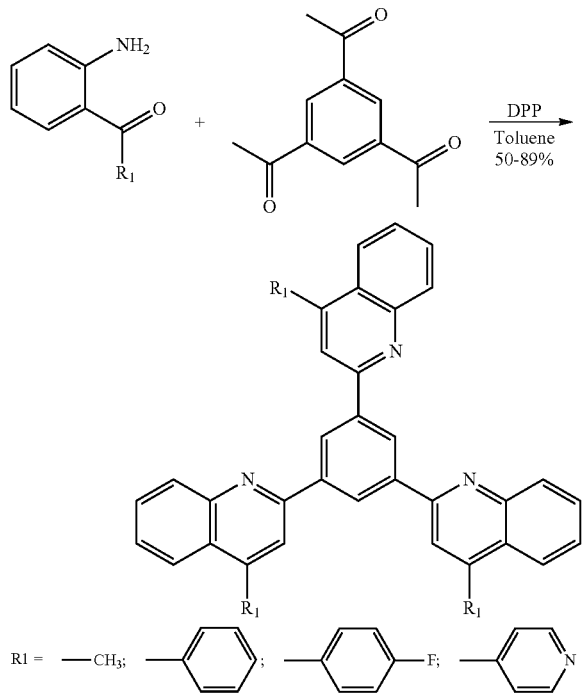

Scheme 9. Synthesis of Oligoquinolines.

The compounds were synthesized by acid-catalyzed Friedlander condensation using diphenyl phosphate (DPP). The products were precipitated from 10% methanol/triethylamine mixture. TMQB, TQB, and TFQB were purified by flash column chromatography followed by recrystallization to give the final products in 50-85% yield. TPyQB was purified by recrystallization from chloroform and methanol mixture to give the final product in 89% yield. The oligomers were soluble in chloroform, toluene, and tetrahydrofuran to varying degrees and they were readily soluble in formic acid. $^1$H NMR, $^{13}$C NMR and high-resolution mass spectrometry confirmed the proposed structure.

Figure 13:
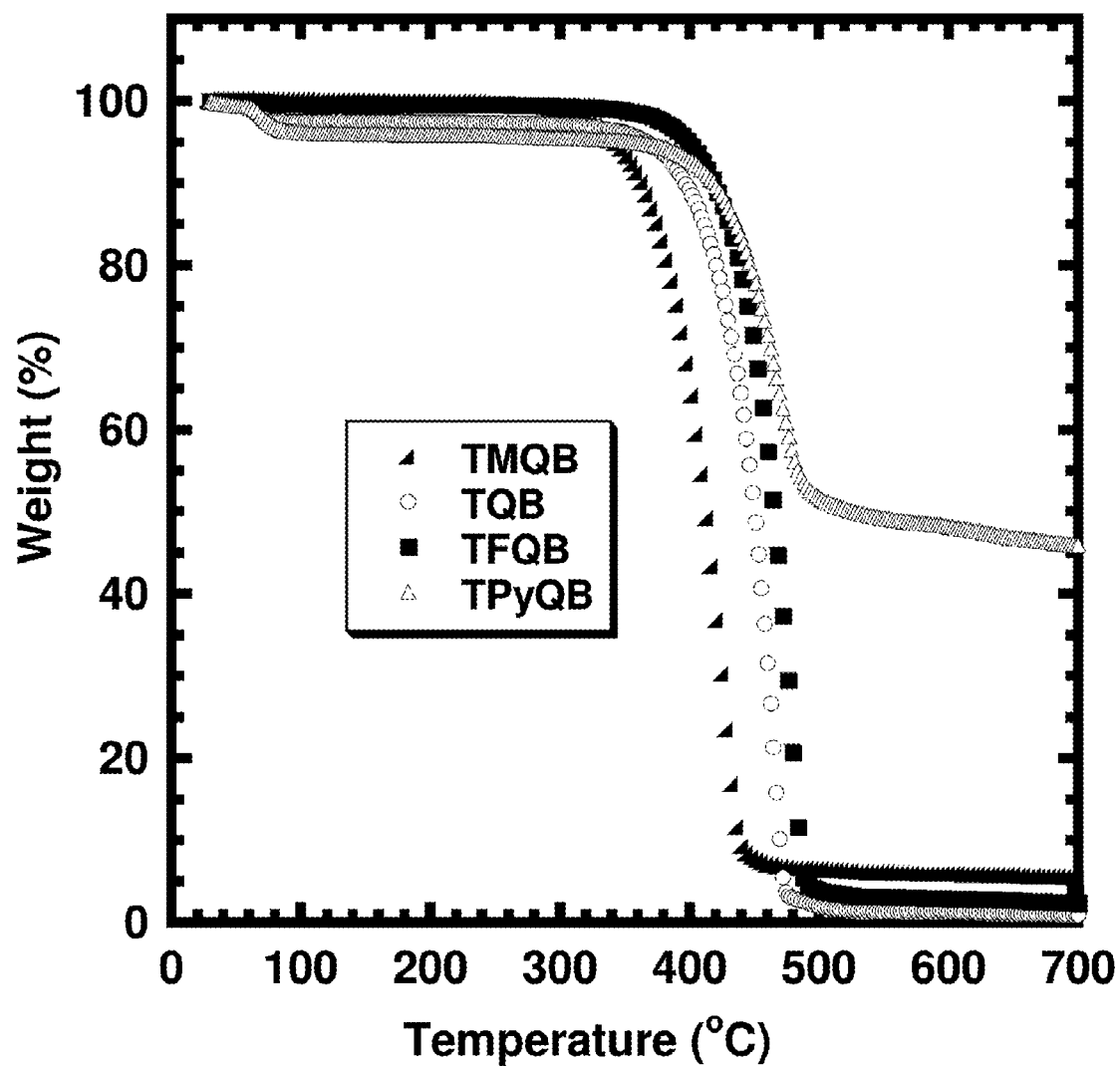
FIG. 13 graphically illustrates Thermogravimetric analysis (TGA) curves of oligoquinolines in accordance with the embodiments provided herein.

The thermal stability and thermal transition properties of the oligoquinolines were investigated by thermogravimetric analysis (TGA) and differential scanning calorimetry (DSC). The thermogravimetric analysis (TGA) scans illustrated in FIG. 13 show that the four oligoquinolines are thermally robust materials with onset decomposition temperatures ($T_D$) in the range of 378-437° C.

Figure 14A:
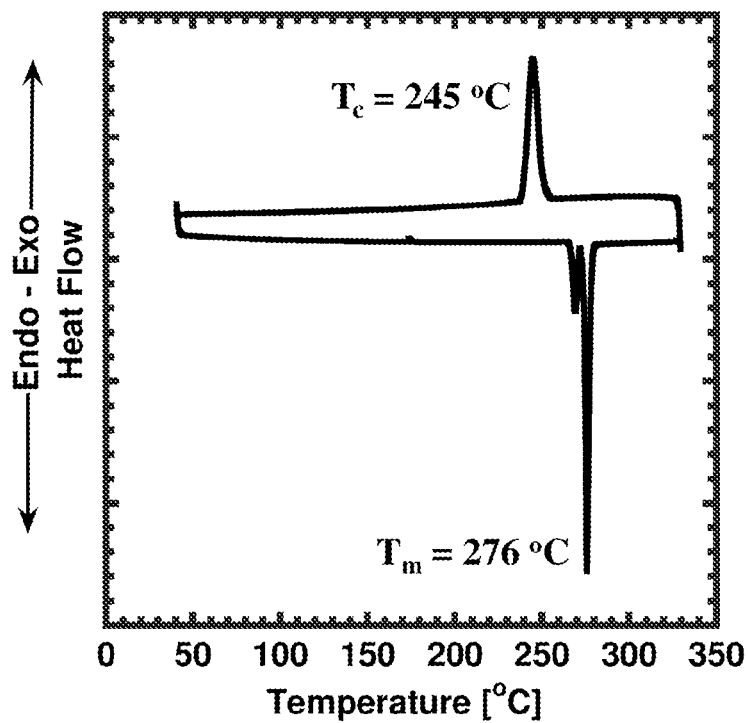
FIGS. 14A and 14B graphically illustrate DSC scans of TQB and TFQB, respectively, at a heating/cooling rate of 10° C. min⁻¹ in nitrogen.
Figure 14B:
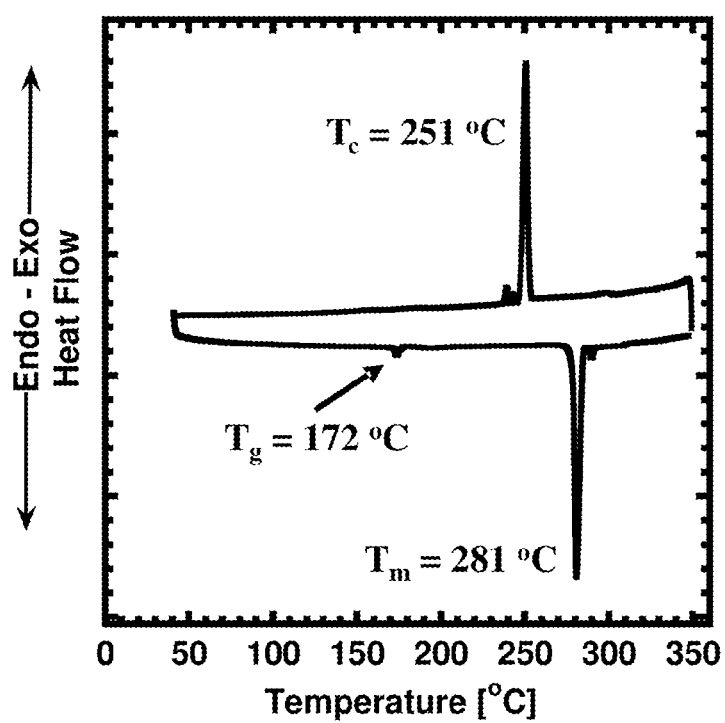
Figure 15A:
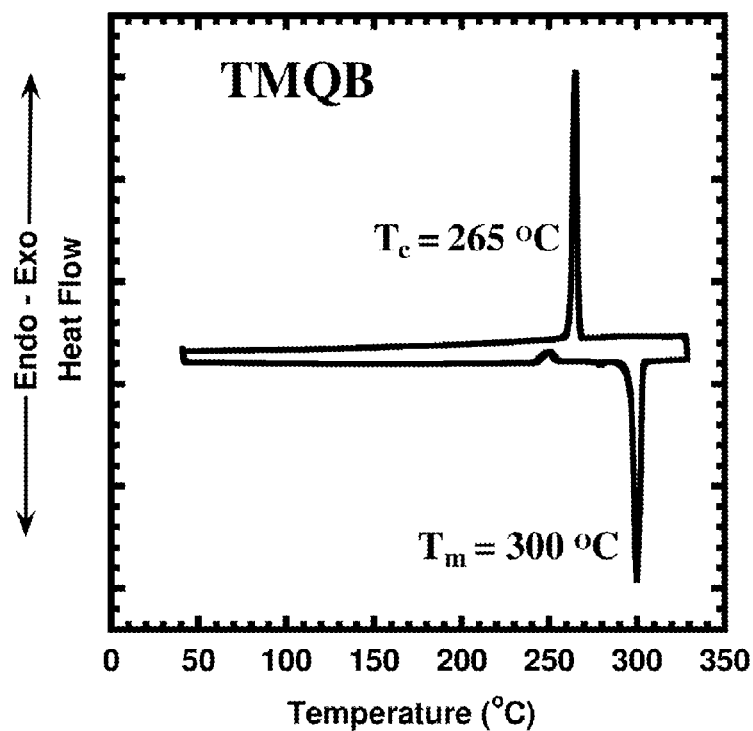
FIGS. 15A and 15B graphically illustrate DSC scans of TMQB and TPyQB, respectively, at a heating/cooling rate of 10° C. min⁻¹ in nitrogen.
Figure 15B:
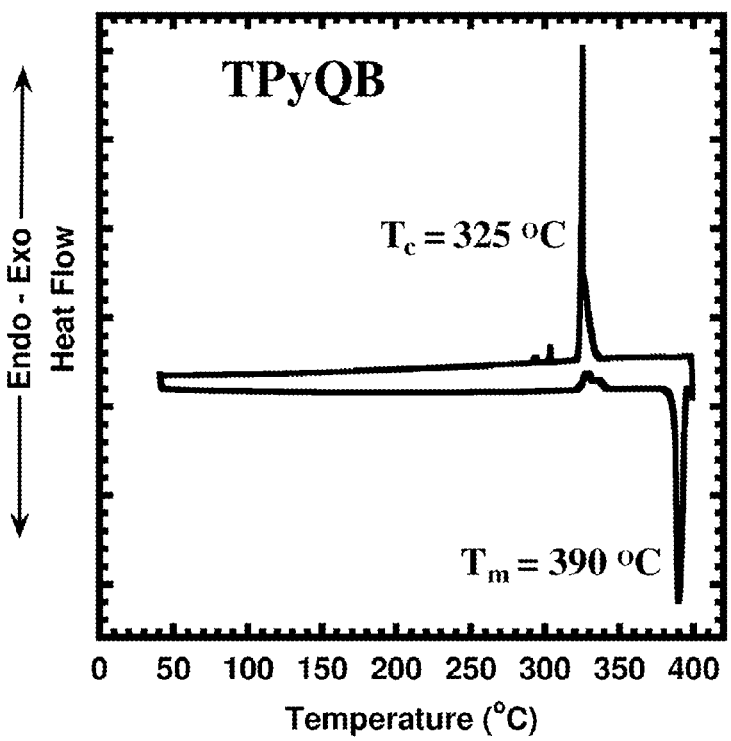

The observed $T_D$ values are slightly lower than those of para-substituted oligoquinolines ($T_D$~417-492° C.). The second-heating DSC scans of the oligoquinolines are exemplified by those of TQB (FIG. 14A) and TFQB (FIG. 14B) at a heating/cooling rate of 10° C. min$^{-1}$ in nitrogen; the DSC scans of TMQB and TPyQB are graphically illustrated in FIGS. 15A and 15B, respectively.

A clear glass transition temperature ($T_g$) of 172° C. was only observed in TPyQB. The thermal properties including the melting transition ($T_m$), crystallization transition ($T_c$) and onset decomposition temperature ($T_D$) are summarized in Table 3.

TABLE 3

Thermal and Photophysical Properties of Oligoquinolines.

|  | TMQB | TQB | TFQB | TPyQB |
|---|---|---|---|---|
| $T_D$ [° C.] | 378 | 429 | 437 | 427 |
| $T_m/T_c$ [° C.] | 300/265 | 276/245 | 281/251 | 390/325 |
| $\lambda_{max}^{abs}$ [soln] [nm] [a] | 249, 323 | 274, 325 | 276, 325 | 273, 326 |
| $\lambda_{max}^{abs}$ [film] [nm] [b] | 256, 329 | 261, 332 | 276, 332 | 276, 333 |
| $\lambda_{max}^{abs}$ [film] [nm] [c] | 256, 331 | 276, 332 | 274, 333 | 273, 337 |
| $E_g^{opt}$ [eV] | 3.38 | 3.40 | 3.39 | 3.33 |
| $\lambda_{max}^{PL}$ [film] [b], [fwhm] [nm] | 387 [100] | 391 [57] | 389 [57] | 395 [63] |
| $\lambda_{max}^{PL}$ [film] [c], [fwhm] [nm] | 468 [92] | 413 [88] | 505 [102] | 416 [84] |

[a] Absorption in dilute (1.3-1.8 × 10$^{-6}$ M) THF solution.
[b] Vacuum-deposited films.
[c] Solution-deposited films.

The $T_m$ slightly decrease from 300° C. in TMQB to 276° C. in TQB and 281° C. in TFQB and then significantly increase to 390° C. in TPyQB. The higher $T_m$ value observed in TMQB compared to TQB and TFQB suggest that TMQB has better intermolecular packing in the solid-state. On the other hand, the $T_m$ of TPyQB is higher by 114° C. than that of TQB, where the main difference between the two derivatives is the substitution of carbon atom with nitrogen. This suggest that in addition to the π-π intermolecular interactions, additional strong intermolecular interactions such as CH . . . N hydrogen-bonding is also present in TPyQB and likely responsible for the observed high $T_m$ value. All four oligomers showed clear thermal transitions during the cooling from the melt.

Photophysical Properties.

Figure 16A:
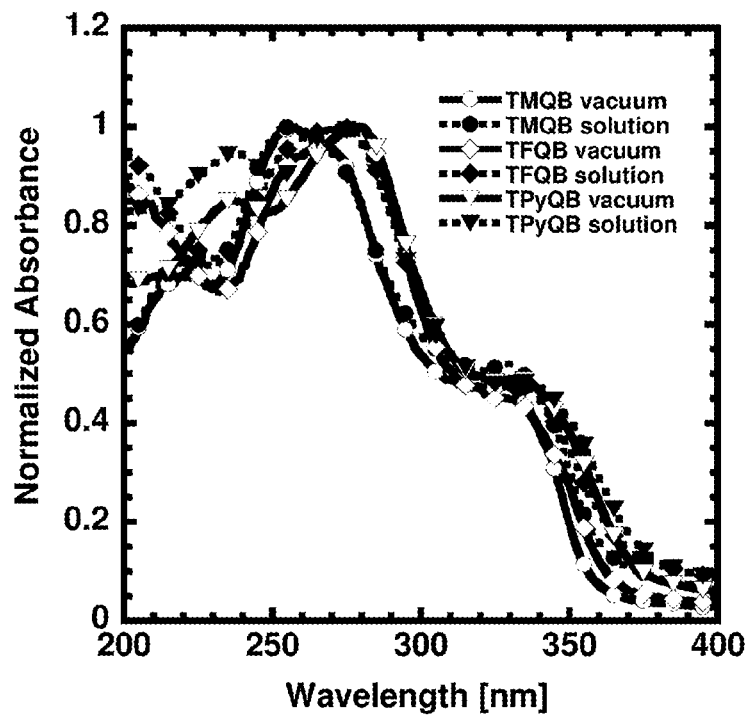
FIGS. 16A and 16B graphically illustrate optical absorption spectra and PL emission spectra, respectively, of vacuum-deposited and solution-deposited thin films of oligoquinolines in accordance with the embodiments provided herein.

The normalized optical absorption spectra of vacuum-deposited and solution-deposited thin films of the four oligoquinolines on quartz substrates are shown in FIG. 16A.

The thin film absorption spectra of the oligoquinolines show two bands, a lower intensity band in the range of 310-340 nm and a higher intensity band in the 250-280 nm range. These absorption bands in TMQB, TQB, TFQB and TPyQB spectra are associated with π-π* transitions. Absorption maxima ($\lambda_{max}$) of the oligoquinolines in solution and as thin films and the optical band gaps ($E_g^{opt}$) are listed in Table 1. The $\lambda_{max}$ values of the vacuum-deposited thin films of the materials are very similar ranging from 256 nm in TMQB to 276 nm in TFQB and TPyQB (Table 2). Solution-deposited thin films of TMQB, TQB, TFQB, and TPyQB have similar $\lambda_{max}$ (256, 276, 274, and 273 nm; respectively) to that of the vacuum-deposited films. Solution-deposited films of TMQB, TQB, and TFQB showed enhanced absorption at 330 nm compared to their vacuum-deposited films. In contrast, solution-deposited film of TPyQB showed enhanced absorption at 230 nm compared to the vacuum-deposited films. The enhanced absorption in solution-deposited films (e.g., at 330 nm) suggests the formation of aggregates due to improved intermolecular interactions. The solution- and vacuum-deposited films showed identical band gaps. The optical band gap from the absorption edge of the thin films was in the range of 3.40 eV in TQB to 3.33 eV in TPyQB. The $E_g^{opt}$ of these meta-substituted oligoquinolines is higher by 0.3-0.5 eV compared to previously reported para-substituted oligoquinolines.

Figure 16B:
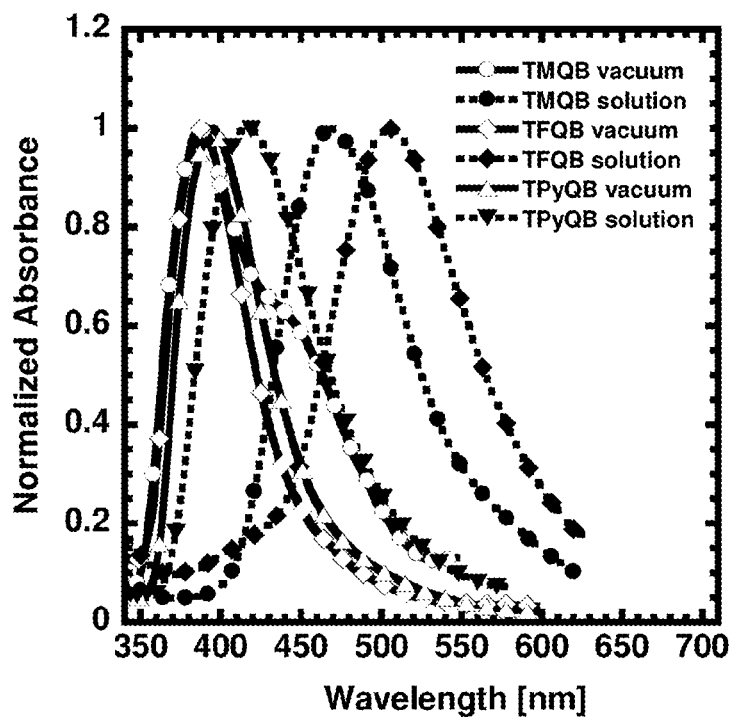

The photoluminescence (PL) emission spectra of the solution-deposited and vacuum-deposited thin films of oligoquoinolines are shown in FIG. 16B. Vacuum-deposited films of all four oligoquinolines showed violet PL emission spectra. TQB, TFQB, TPyQB have almost identical violet emission spectra with PL maximum in the range of 391-395 nm and a narrow full-width-half-maxim (fwhm) ranging from 57 nm in TQB to 63 nm in TPyQB. In contrast, TMQB has a broad PL spectrum with shoulder peak at 441 nm and a fwhm of 100 nm. The broad PL emission spectrum of TMQB suggests that it favors strong aggregation compared to the other three oligoquinolines. The PL emission spectra of the solution-deposited films were significantly different compared to the vacuum-deposited films. The PL spectra in solution-deposited films were red shifted and broader. TQB and TPyQB showed similar PL spectra with PL maximum of 413-416 nm with fwhm of 84-88 nm. In contrast, TMQB and TFQB PL spectra show significant bathochromic shift with PL maximum of 468 and 505 nm and fwhm of 92 and 102 nm, respectively. The significant bathochromic shift and broader PL spectra of the solution-deposited TMQB and TFQB films suggest that the photoluminescence originates from excimer or aggregate states formed as a result of aggregation from solution.

Electrochemical Properties.

Figure 17A:
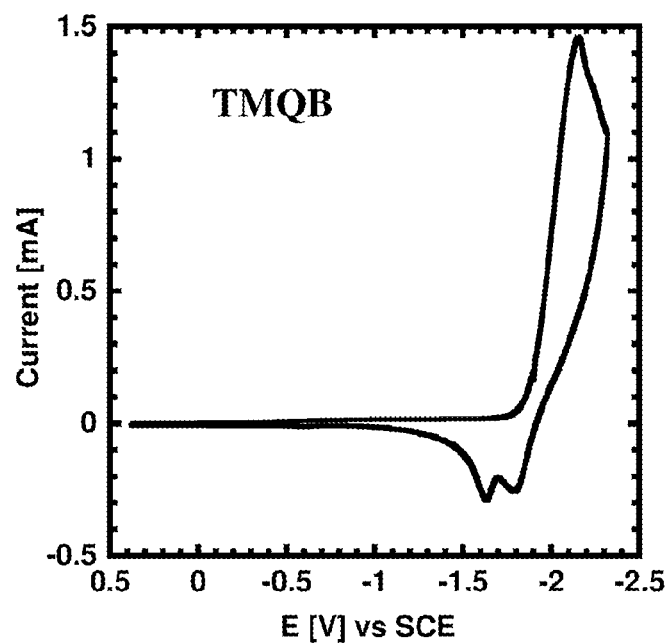
FIGS. 17A and 17B graphically illustrate reduction cyclic voltammograms of TMQB and TFQB, respectively, thin films in 0.1 M TBAPF$_6$/MeCN at a scan rate=50 mV s$^{-1}$.
Figure 17B:
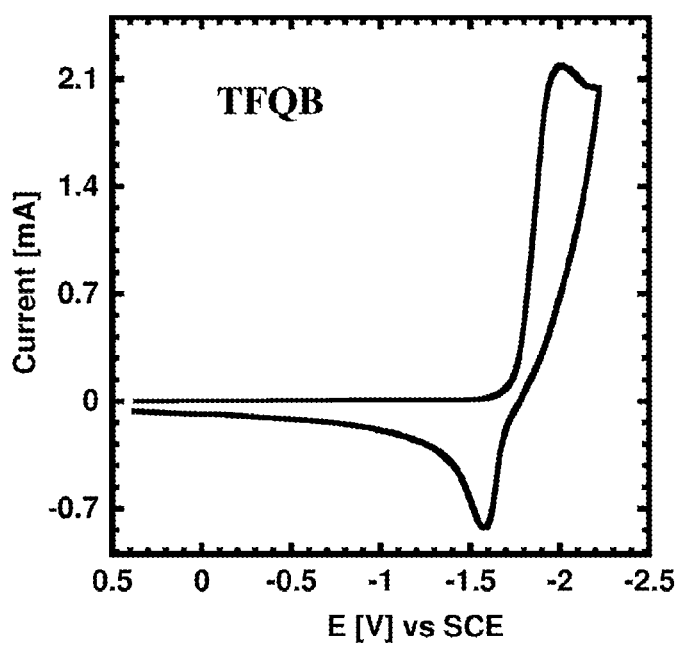
Figure 18A:
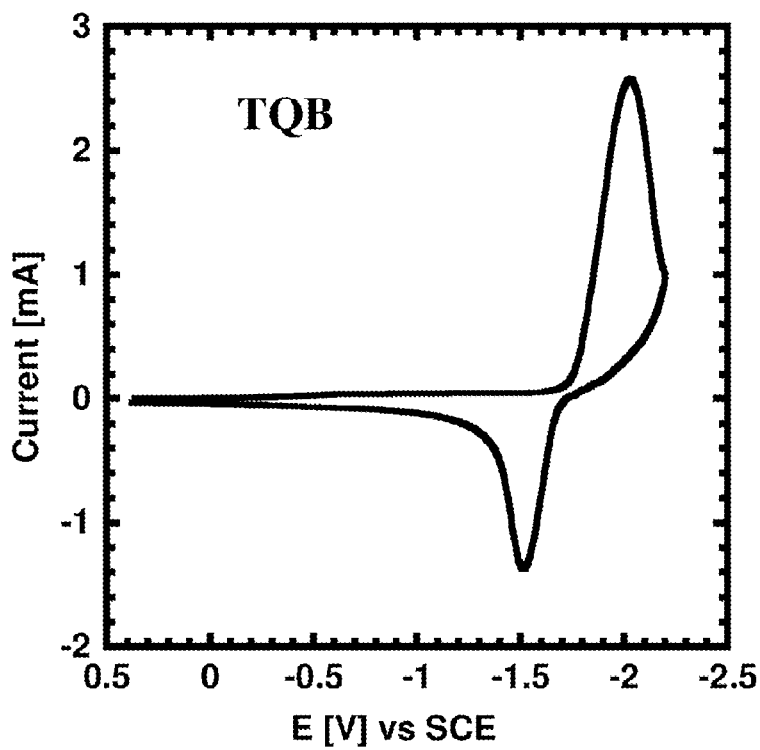
FIGS. 18A and 18B graphically illustrate reduction cyclic voltammograms of TQB and TPyQB, respectively, thin films in 0.1 M TBAPF$_6$/MeCN. Scan rate=50 mV s$^{-1}$.
Figure 18B:
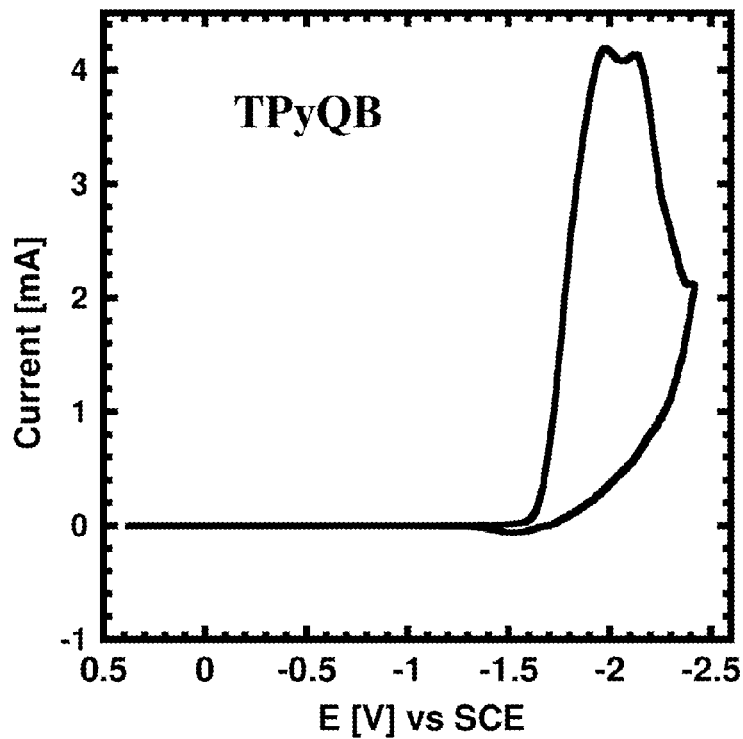

It is estimated that the lowest unoccupied molecular orbital (LUMO) levels or electron affinity (EA) and the highest occupied molecular orbital (HOMO) levels or the ionization potential (IP) of the oligoquinolines from cyclic voltammograms of thin films. The reduction CVs of the oligoquinolines exemplified by those of TMQB and TFQB are shown in FIGS. 17A and 17B, respectively, while the reduction CVs of TQB and TPyQB are shown in FIGS. 18A and 18B, respectively.

The onset reduction potentials of the oligomers are summarized in Table 4.

TABLE 4

Electrochemical Properties of Oligoquinolines.

| Compound | $E_{red}^{onset}$ [V] | $E_{ox}^{onset}$ [V] | EA [eV] | IP [eV] | $E_g^{el}$ [eV] |
|---|---|---|---|---|---|
| TMQB | −1.85 | 1.85 | 2.55 | 6.25 | 3.70 |
| TQB | −1.75 | 1.73 | 2.65 | 6.13 | 3.48 |
| TFQB | −1.73 | 1.68 | 2.67 | 6.08 | 3.41 |
| TPyQB | −1.60 | 1.74 | 2.80 | 6.14 | 3.34 |

The reduction CVs scans of TQB and TFQB show one reversible reduction wave, whereas a quasi-reversible reduction wave was observed in TMQB, and irreversible reduction wave was observed in TPyQB. The onset reduction potentials of the oligoquinolines are in the range of −1.85 V to −1.60 V (vs SCE). The various substitutions in the quinoline rings lead to a slightly more positive reduction potentials by 0.1-0.2 V. The EA values or LUMO levels, estimated from the onset reduction potential [$EA=E_{red}^{onset}+4.4$ eV], are in the range of −2.55 eV in TMQB to −2.8 eV in TPyQB. These values are similar to previously reported EA values of para-linked oligoquinolines and polyquinolines.

Figure 19A:
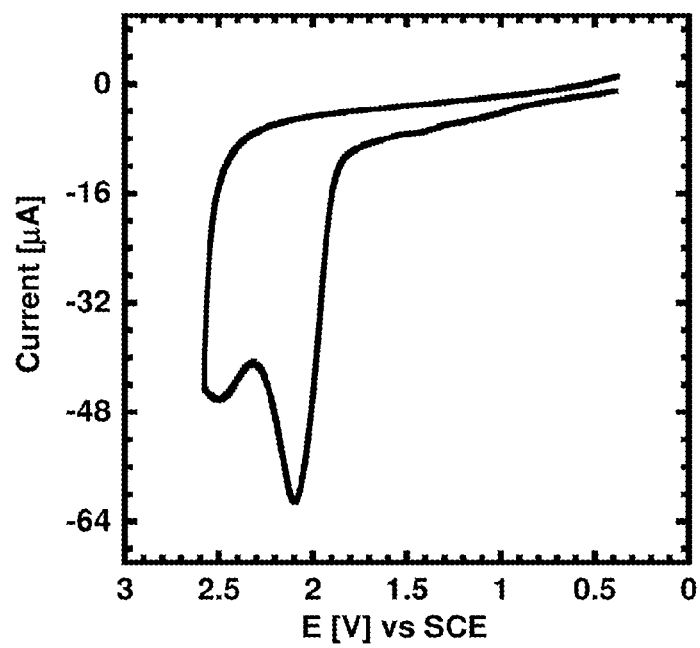
FIGS. 19A and 19B graphically illustrate oxidation cyclic voltammograms of TMQB and TFQB, respectively, thin films in 0.1 M TBAPF$_6$/MeCN at a scan rate=50 mV s$^{-1}$.
Figure 19B:
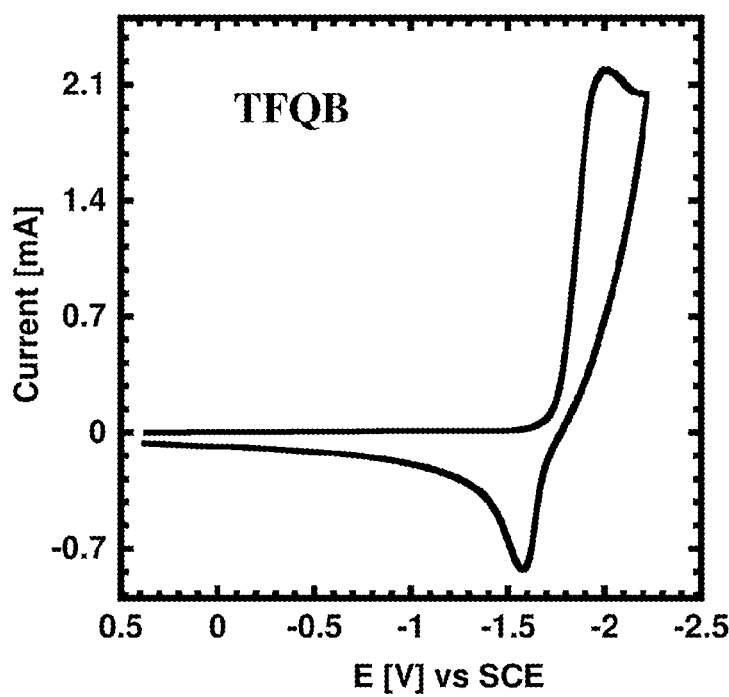
Figure 20A:
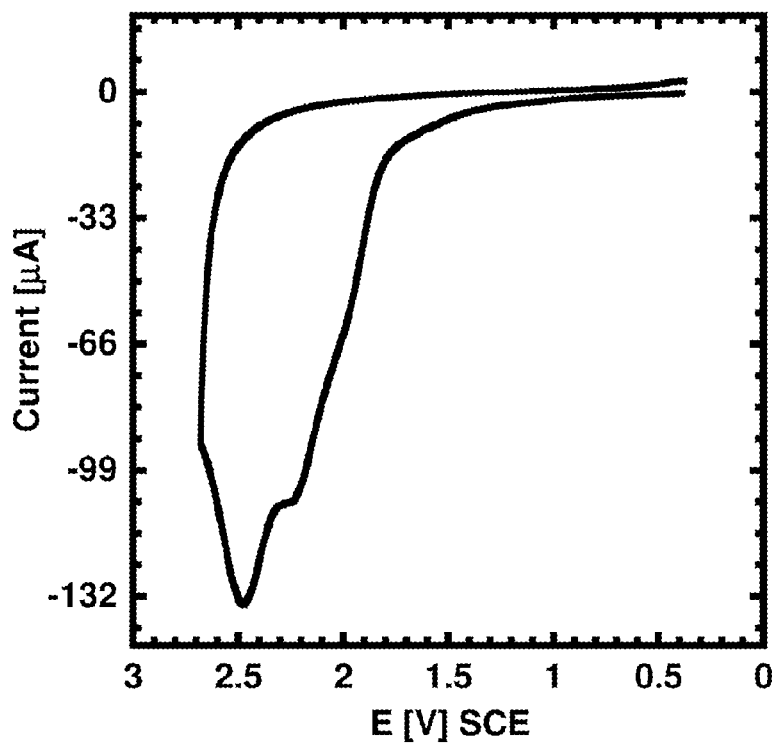
FIGS. 20A and 20B graphically illustrate oxidation cyclic voltammograms of TQB and TPyQB, respectively, thin films in 0.1 M TBAPF$_6$/MeCN at a scan rate=50 mV s$^{-1}$.
Figure 20B:
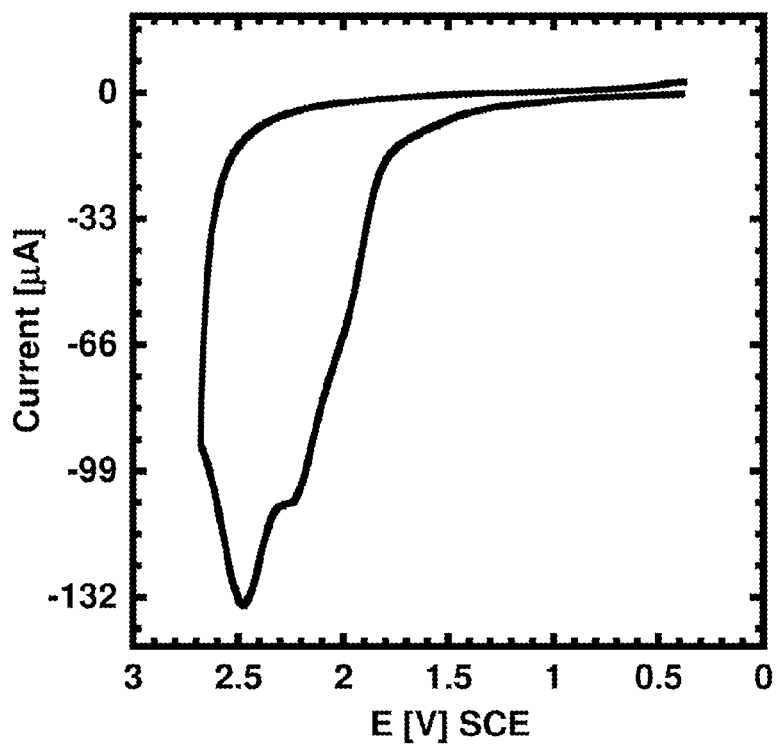
Figure 21A:
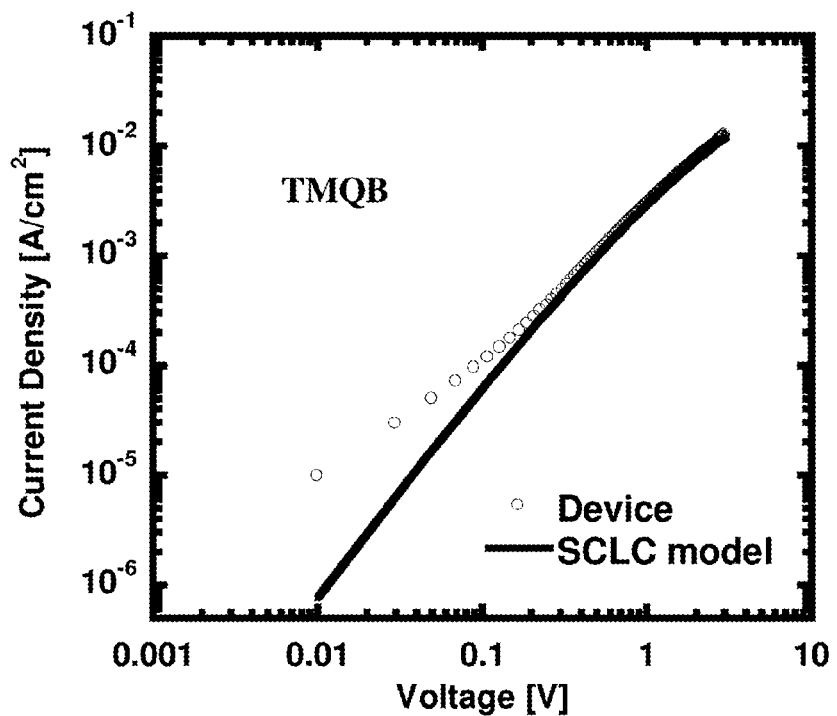
FIGS. 21A-21D graphically illustrate current density-voltage (J-V) curves of ITO/oligoquinoline/Al devices in ambient conditions, wherein the solid lines represent the SCLC model with field-dependent mobility.
Figure 21B:
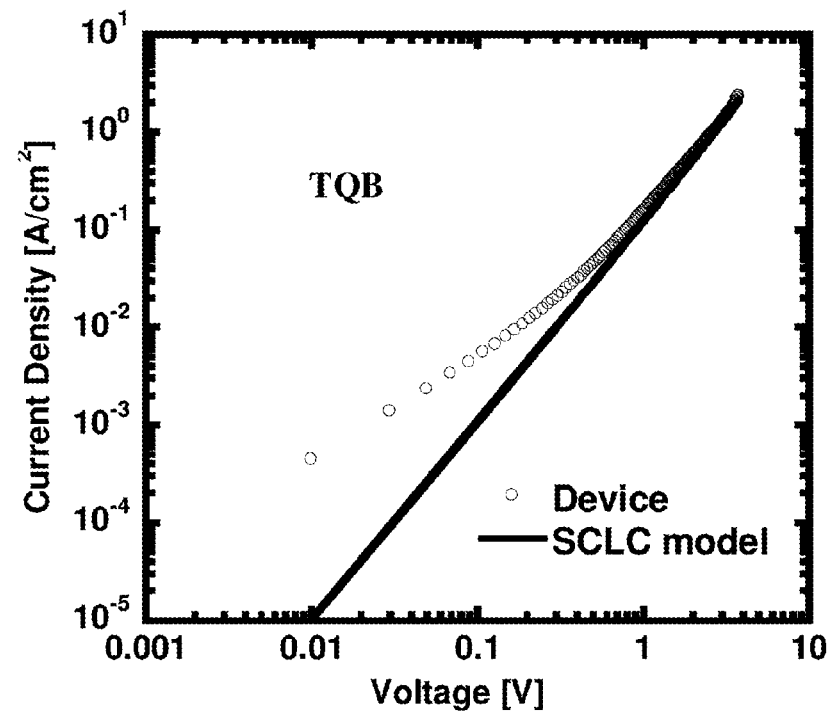
Figure 21C:
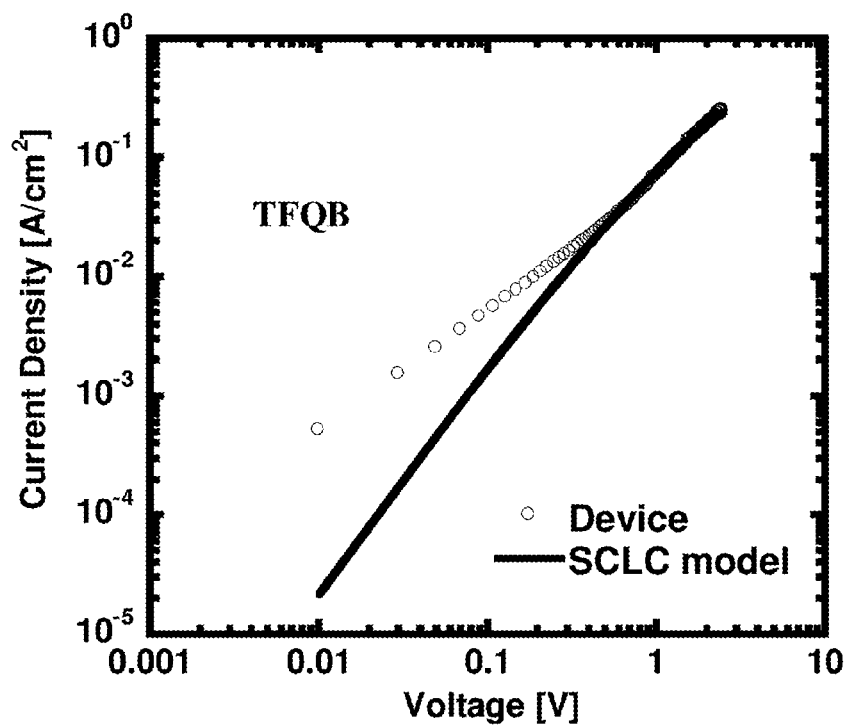
Figure 21D:
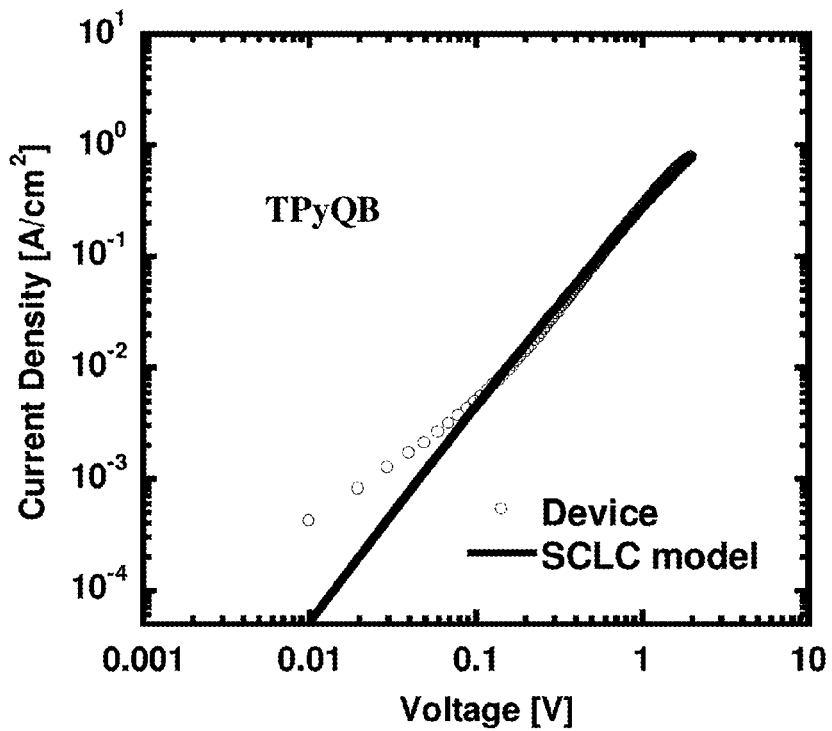

The oxidation CVs of the oligoquinoline thin films shown in FIG. 19A (TMQB), FIG. 19B (TFQB), FIG. 20A (TQB), and FIG. 20B (TPyQB), were similarly used to estimate the HOMO levels (IP values).

Irreversible oxidation waves were observed for all four materials with onset oxidation potential of 1.68-1.85 V (vs SCE) (Table 2). The estimated IP [$IP=E_{ox}^{onset}+4.4$ eV] values of 6.08-6.25 eV show rather deep HOMO levels for this class of electron transport materials. These IP values are significantly higher than that of well-known ETMs, including tris(8-hydroxyquinoline)aluminum ($Alq_3$) (IP=5.7-5.9 eV), and previously reported oligoquinolines (IP=5.53-5.81 eV). The IP values of the present meta-substituted oligoquinolines are higher by up to 0.7 eV compared to those of para-substituted oligoquinolines. This suggests that meta-substitution of the oligoquinolines mainly leads to a lowering of the HOMO levels while the LUMO levels essentially remain unchanged, which in turn leads to the desired wide-energy gap ETMs that could also function as an excellent hole-blocking layer in PhOLEDs. These results clearly demonstrate that the HOMO levels or IP values of oligoquinolines can be varied significantly (0.7 eV) by simply changing the substitution of the conjugated core from para-substitution to meta-substitution.

Charge Transport.

The electron mobilities of the oligoquinoline films by the space-charge-limited current (SCLC) method in ambient conditions was investigated. The current density-voltage (J-V) characteristics of the SCLC devices, which have the structure ITO/oligoquinoline/Al, are shown in FIGS. 21A-21D.

The electron mobility was extracted by fitting the J-V curves in the near quadratic region according to the modified Mott-Gurney equation (eq. 1), $$J = \frac{9}{8}\varepsilon\varepsilon_0\mu\frac{V^2}{L^3}\exp\left(0.89\beta\frac{\sqrt{V}}{\sqrt{L}}\right)$$

where J is the current density, $\varepsilon$ is the permittivity of free space, $\varepsilon_0$ is the relative permittivity, $\mu$ is the zero-field mobility, V is the applied voltage, L is the thickness of active layer, and $\beta$ is the field-activation factor (Table 5).

TABLE 5

SCLC Electron Mobilities of Oligoquinolines.

| Compound | L [nm] | B [$cm^{1/2}V^{-1/2}$] | $E_{max}$ [$V\,cm^{-1}$] | $\mu_e(E=0)$ [$cm^2\,V^{-1}\,s^{-1}$] |
|---|---|---|---|---|
| TMQB | 102 | $4.2 \times 10^{-4}$ | $3.3 \times 10^5$ | $5.0 \times 10^{-5}$ |
| TQB | 100 | $6.9 \times 10^{-4}$ | $3.8 \times 10^5$ | $3.6 \times 10^{-4}$ |
| TFQB | 107 | $5.5 \times 10^{-4}$ | $3.1 \times 10^5$ | $8.0 \times 10^{-4}$ |
| TPyQB | 120 | $2.9 \times 10^{-3}$ | $3.8 \times 10^5$ | $3.3 \times 10^{-3}$ |

The solid lines in FIGS. 21A-21D represent the SCLC fitting curves in the quadratic SCLC region.

The zero-field electron mobility of the solution-deposited oligoquinoline films varied from $5.0 \times 10^{-5}$ $cm^2\,V^{-1}\,s^{-1}$ in TMQB to $3.3 \times 10^{-3}$ $cm^2\,V^{-1}\,s^{-1}$ in TPyQB (Table 5). The electron mobility in TPyQB is an order of magnitude higher than that of TQB and two orders of magnitude higher than that of TMQB. However, the charge carrier mobility of TMQB and TPyQB is still about one to three orders of magnitude higher than those of conventional electron transport materials such as $Alq_3$, oxadiazole derivatives, and phenylphenanthroline. The general trend among the four molecules is an increase in carrier mobility as EA increased. However, it is unlikely that the high carrier mobility in TPyQB compared to TMQB is to due the slightly higher electron affinity. Based on the EA of the four molecules, the large energy barrier for electron injection from Al ($\Phi$=4.3 eV) is comparable in all four molecules. Thus, the observed two orders of magnitude variation in the SCLC electron mobility of the oligoquinoline series must be due to variation in the solid-state morphology of the materials and/or the relative ease of electron injection at oligoquinoline/Al interface. Attempt to measure the electron mobility of vacuum-deposited oligoquinoline films were unsuccessful due to a lack of clear SCL current. This could be due to poor interfacial contact between the vacuum-deposited oligoquinolines/Al interface.

PhOLED Characterization.

Figure 22A:
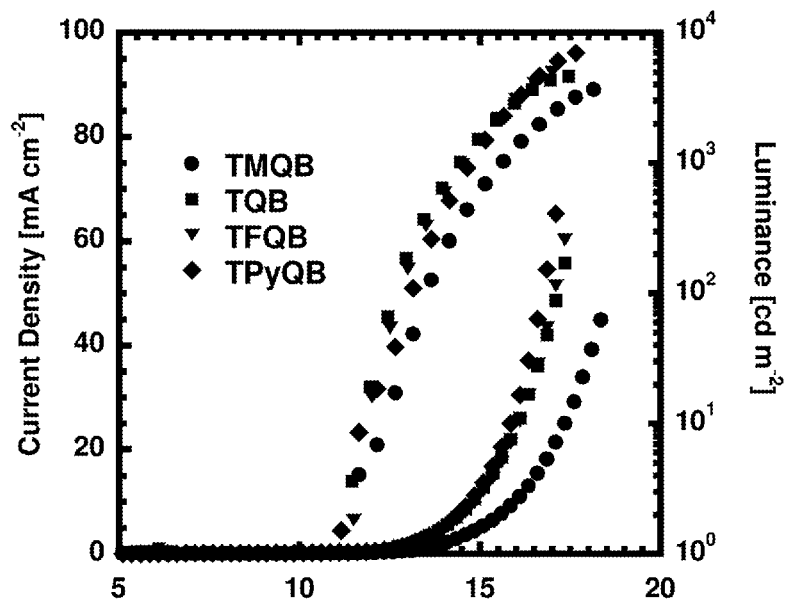
FIGS. 22A-22B graphically illustrate current density (J)-voltage (V) and luminance (L)-voltage (V) in FIG. 22A, and luminous efficiency (LE)-luminance (L) curves of PhOLEDs with vacuum-deposited ETLs in FIG. 22B.
Figure 22B:
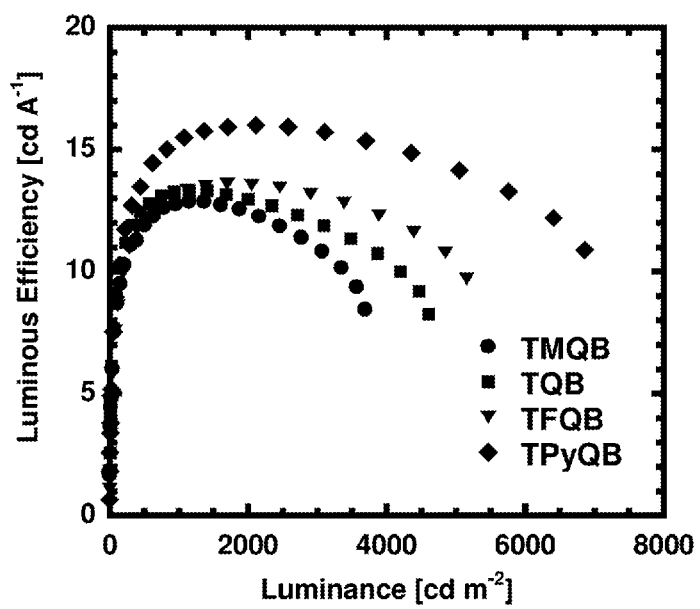

Blue PhOLEDs were fabricated using the oligoquinolines as electron-transport layers (ETLs) deposited by both vacuum-deposition and solution-processing methods. The emission layer (EML) consisted of blends of poly(N-vinyl-carbazole) (PVK) and 1,3-bis(2-(4-tert-butylphenyl)-1,3,4-oxadiazo-5-yl)benzene (OXD-7) as the polymeric host doped with the blue triplet emitter FIrpic as described in the Experimental Section. Initially, a series of four devices using different ETLs deposited by vacuum thermal evaporation were fabricated to verify and compare the effectiveness of oligoquinolines as electron-transport materials in blue PhOLEDs: device IA, ITO/PEDOT:PSS/EML/vacuum-deposited TMQB/Al; device IB, ITO/PEDOT:PSS/EML/vacuum-deposited TQB/Al; device IC, ITO/PEDOT:PSS/EML/vacuum-deposited TFQB/Al; and device ID, ITO/PEDOT:PSS/EML/vacuum-deposited TPyQB/Al. The current density-voltage-luminance (brightness) (J-V-L) and luminous efficiency-luminance (LE-L) characteristics of these series of diodes are shown in FIGS. 22A-22B.

Device IA with vacuum-deposited TMQB ETL showed the lowest device performance overall. This is likely due to the relatively low electron mobility ($\sim 10^{-5}$ cm$^2$ V$^{-1}$ s$^{-1}$) and small EA value (2.55 eV) of TMQB, which creates a large energy barrier for electrons to be injected from high work-function Al cathode (4.3 eV). Device IC with vacuum-deposited TFQB ETL showed a slightly better performance, giving a maximum brightness of 5240 cd m$^{-2}$ and an LE value of 13.6 cd A$^{-1}$ (at 1700 cd m$^{-2}$) whereas device IB with a TQB ETL had a maximum brightness of 4020 cd m$^{-2}$ (at 16.6 V) and an LE value of 12.2 cd A$^{-1}$ (at 1060 cd m$^{-2}$). Device ID with vacuum-deposited TPyQB ETL showed the highest performance, giving an LE value of 16.0 cd A$^{-1}$ (at 2200 cd m$^{-2}$) and a maximum brightness of 6970 cd m$^{-2}$ (at 17.8 V). These blue PhOLEDs with vacuum-deposited oligoquinoline ETLs have decent device performances with high LE values (>12 cd A$^{-1}$) and high brightness values (>3000 cd m$^{-2}$), demonstrating that the new of oligoquinolines can function as good electron-injection and electron-transport materials in blue PhOLEDs.

Towards the main goal of achieving highly efficient multilayered blue PhOLEDs by sequential solution-processing, a series of four devices was also fabricated with solution-processed oligoquinoline ETLs (device IIA to IID). The oligoquinoline ETMs were dissolved and spin-coated onto the EML from a formic acid/water mixture solvent (FA:H$_2$O=3:1) as introduced in our preliminarily report. For device II, the device structure and layer thicknesses were exactly the same as device I except that the ETLs were solution-processed onto the EML: ITO/PEDOT:PSS/EML/oligoquinoline ETL/Al. All the blue PhOLEDs with solution-processed ETLs (device IIA to IID) indeed show far superior performance compared to those with vacuum-deposited ETLs (device IA to ID).

The J-V, L-V and the LE-L characteristics of the PhOLEDs with solution-processed ETLs are shown in FIGS. 23A-23D.

Figure 23A:
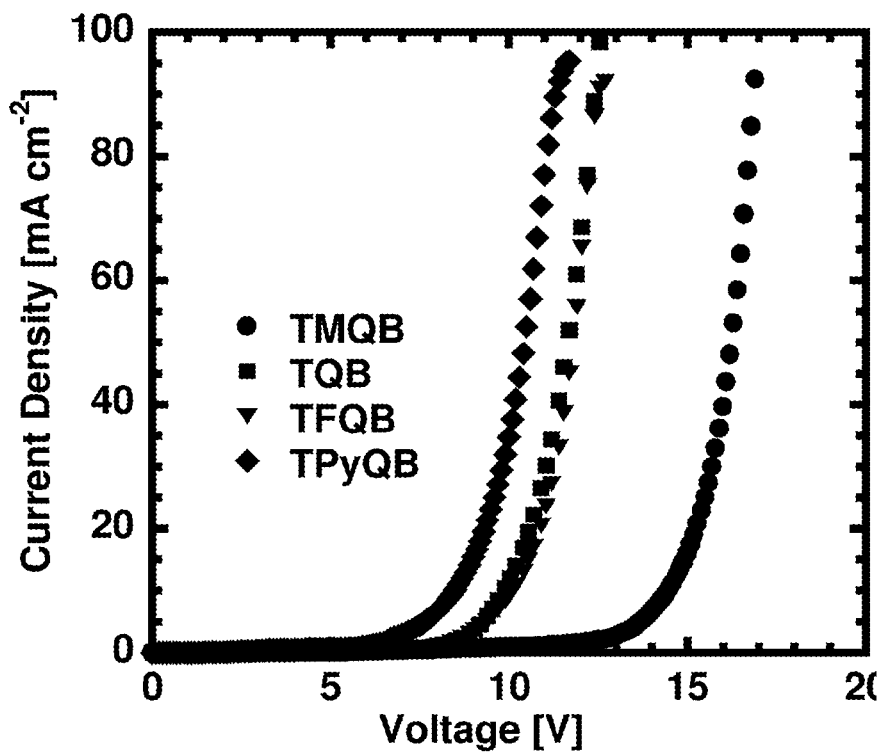
FIGS. 23A-23D graphically illustrate.
Figure 23B:
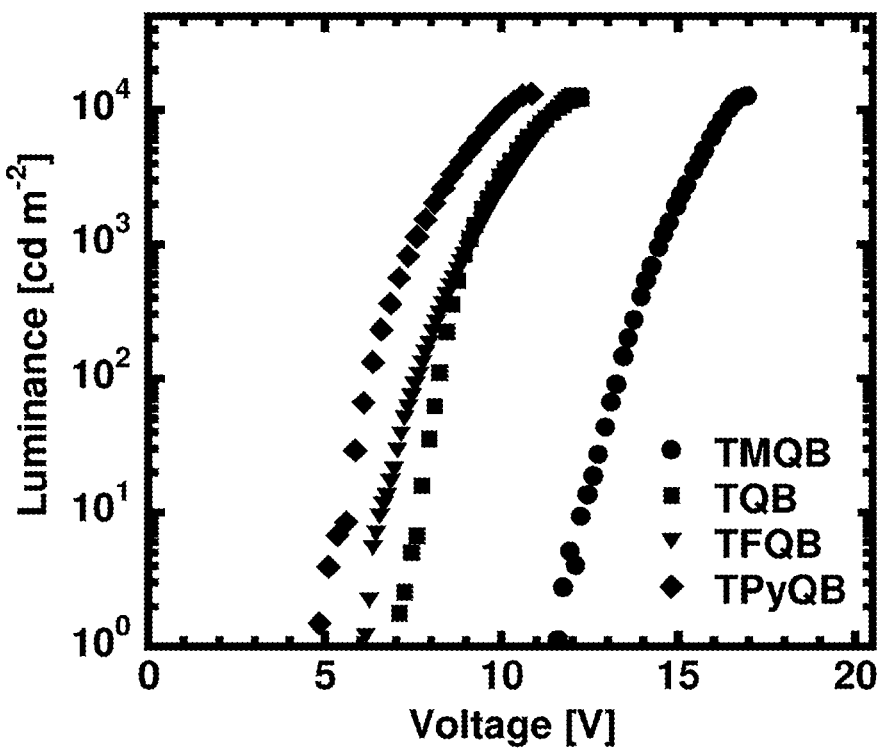
Figure 23C:
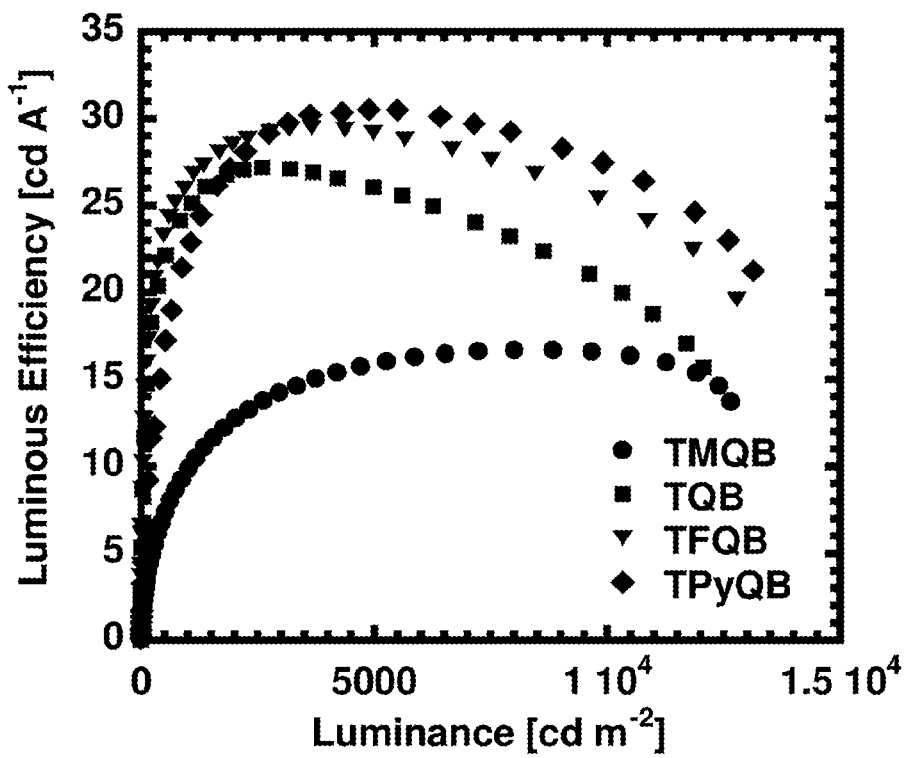

Although device IIA with a solution-processed TMQB ETL showed a similar turn-on voltage to device IA, it had increased efficiency and brightness with an LE value of 16.7 cd A$^{-1}$ (at 8420 cd m$^{-2}$) and a maximum brightness of 12700 cd m$^{-2}$ (at 17.0 V). Devices IIB and IIC with solution-processed TQB and TFQB ETLs also showed significant improvement in performance compared to devices IB and IC with vacuum-deposited ETLs. The LE value of device IIB was 27.2 cd A$^{-1}$ (at 2750 cd m$^{-2}$) with a maximum brightness of 12200 cd m$^{-2}$ (at 12.3 V) whereas the LE value of device IIC was 29.5 cd A$^{-1}$ (at 3660 cd m$^2$) with a maximum brightness of 12900 cd m$^{-2}$ (at 12.4 V), which is more than two-fold superior relative to the vacuum-deposited TQB (device IB) and TFQB (device IC). As shown in FIGS. 23A-23C and Table 4, the best performance was obtained in device IID with a solution-processed TPyQB ETL. The blue PhOLEDs of device IID had the lowest turn-on voltage (4.7 V) and highest brightness of 13300 cd m$^{-2}$ at lowest drive voltage (10.9 V). The LE value was 30.5 cd A$^{-1}$ (EQE of 16.0% and a power efficiency (PE) value of 10.9 lm W$^{-1}$) at a brightness of 4130 cd m$^{-2}$. Even at extremely high brightness ($\sim 10^4$ cd m$^{-2}$), device IID remained very efficient showing an LE value higher than 20 cd A$^{-1}$. The relatively large EA value (2.8 eV) and high electron mobility of TPyQB ($\sim 10^{-3}$ cm$^2$ V$^{-1}$ s$^{-1}$) should facilitate enhanced electron-injection and transport in the diode and thus can explain the high PhOLED performance. All fabricated device characteristics of the blue PhOLEDs are summarized in Table 6.

TABLE 6

Device Characteristics of Blue PhOLEDs. [a]

| Device [b] | ETL | ETL deposition method | $V_{on}$[c] [V] | Drive voltage [V] | Current density [mA cm$^{-2}$] | Luminance [cd m$^{-2}$] | Device efficiency [cd A$^{-1}$, (% EQE)] |
|---|---|---|---|---|---|---|---|
| Device IA | TMQB | Vacuum | 11.5 | 18.5 | 47.2 | 3710 | 7.9, (4.0) |
|  |  |  |  | 15.8 | 8.6 | 1110 | 12.9, (6.8) |
| Device IB | TQB | Vacuum | 9.6 | 16.6 | 54.9 | 4020 | 7.3, (4.0) |
|  |  |  |  | 14.0 | 8.7 | 1060 | 12.2, (6.9) |
| Device IC | TFQB | Vacuum | 11.2 | 17.4 | 60.2 | 5240 | 8.7, (4.3) |
|  |  |  |  | 15.2 | 12.5 | 1700 | 13.6, (7.2) |
| Device ID | TPyQB | Vacuum | 11.0 | 17.8 | 72.0 | 6970 | 9.7, (4.8) |
|  |  |  |  | 15.6 | 20.6 | 2200 | 16.0, (8.5) |
| Device IIA | TMQB | Solution | 11.6 | 17.0 | 96.2 | 12700 | 13.2, (6.9) |
|  |  |  |  | 16.3 | 50.4 | 8420 | 16.7, (8.9) |

TABLE 6-continued

Device Characteristics of Blue PhOLEDs. [a]

| Device [b] | ETL | ETL deposition method | $V_{on}$[c] [V] | Drive voltage [V] | Current density [mA cm$^{-2}$] | Luminance [cd m$^{-2}$] | Device efficiency [cd A$^{-1}$, (% EQE)] |
|---|---|---|---|---|---|---|---|
| Device IIB | TQB | Solution | 7.0 | 12.3 | 82.9 | 12200 | 14.7, (7.6) |
|  |  |  |  | *9.8* | *10.1* | *2750* | *27.2, (14.9)* |
| Device IIC | TFQB | Solution | 6.2 | 12.2 | 71.9 | 12900 | 17.9, (8.7) |
|  |  |  |  | *10.4* | *12.4* | *3660* | *29.5, (15.7)* |
| Device IID | TPyQB | Solution | 4.7 | 10.9 | 69.5 | 13300 | 19.2, (9.9) |
|  |  |  |  | *8.9* | *16.0* | *4130* | *50.5, (16.0)* |

[a] Values in italic correspond to those at maximum device efficiencies.
[b] Device I with vacuum-deposited ETL and device II with solution-deposited ETL (TMQB, TQB, TFQB, or TPyQB).
[c] Turn-on voltage (at brightness of 1 cd m$^{-2}$).

Figure 23D:
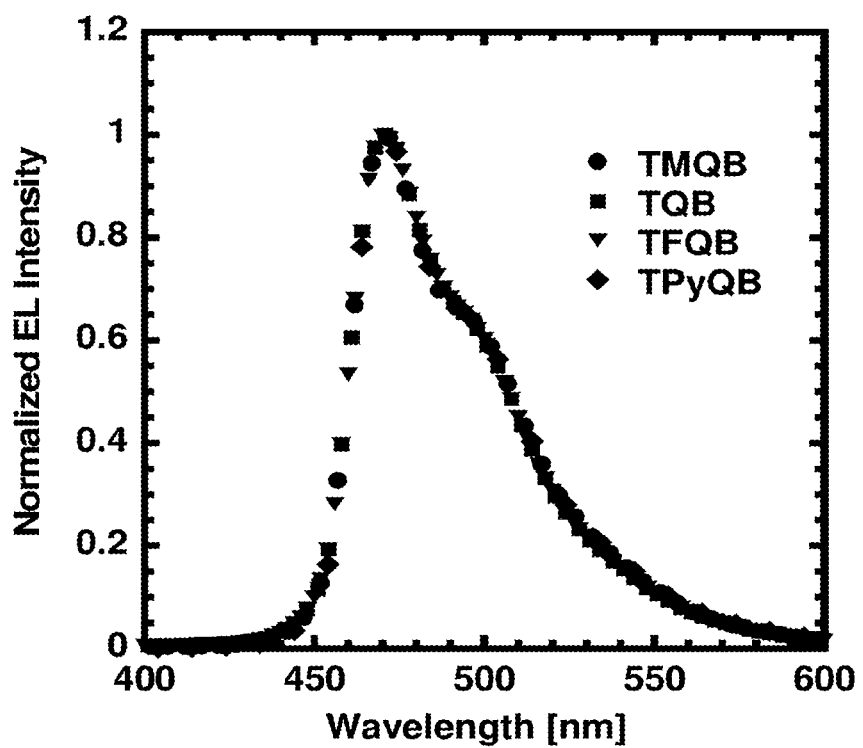

Electroluminescence (EL) spectra of the PhOLEDs with the solution-processed oligoquinoline ETL and without an ETL are shown in FIG. 23D. The EL emission of all the devices is identical with an EL maximum of 472 nm, corresponding to the EL of the blue triplet emitter FIrpic. The Commision Internationale de L'Eclairage (CIE) 1931 coordinates of all the devices were identical at the maximum brightness of ~12000 cd m$^{-2}$ (0.14, 0.28). This clearly demonstrate that the solution-processed oligoquinoline function solely as the electron-transport layer, efficiently confining charge carriers and exciton within the EML. These results demonstrate that high-performance multilayered blue PhOLEDs can be readily fabricated by sequential solution-processing while also eliminating the need for interface modification layers such as NaF, LiF, and CsF.

Surface Morphology of ETLs.

Figure 24A:
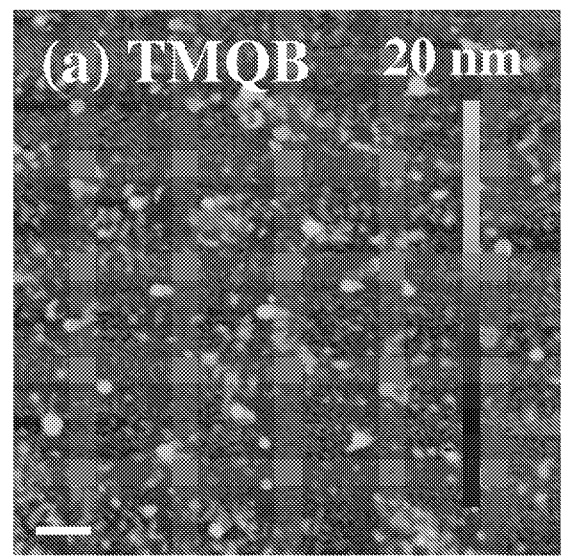
FIGS. 24A-24D are AFM micrographs of the 2D (5×5 μm; scale bar is 500 nm) and the corresponding 3D topological surface morphologies of the vacuum-deposited oligoquinoline thin films (FIG. 24A is TMQB, FIG. 24B is TQB, FIG. 24C is TFQB, and FIG. 24D is TPyQB)
Figure 24A:
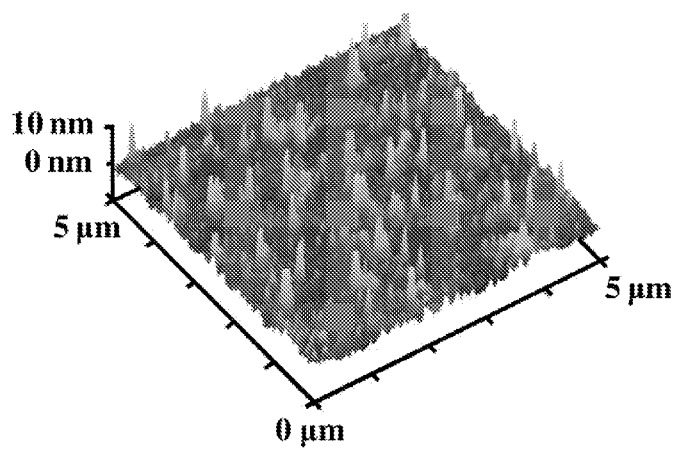
Figure 24B:
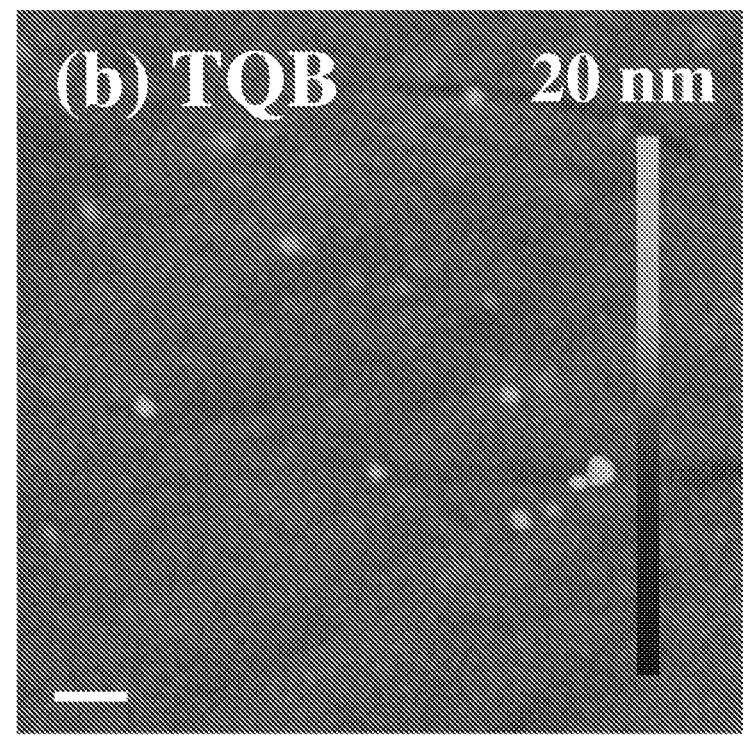
Figure 24B:
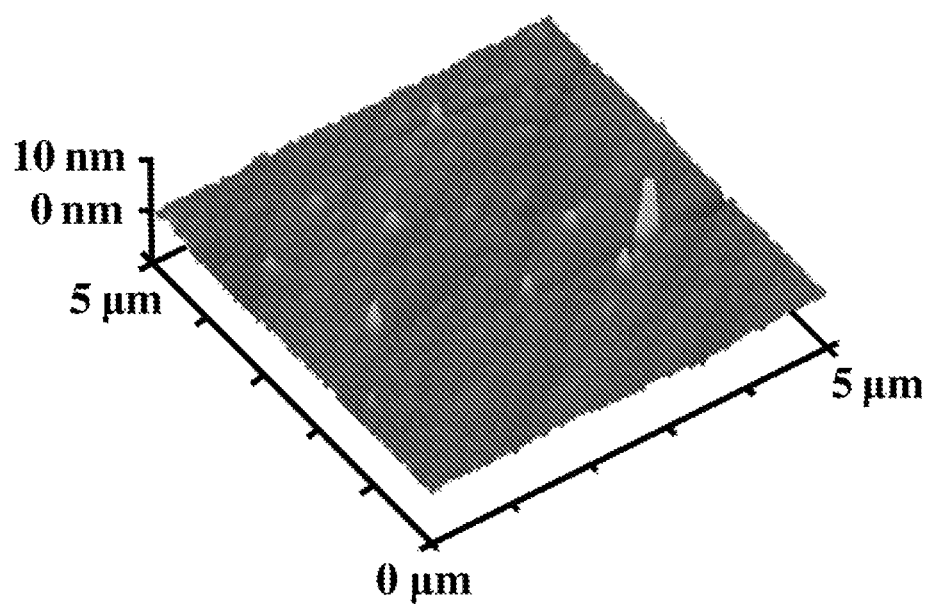
Figure 24C:
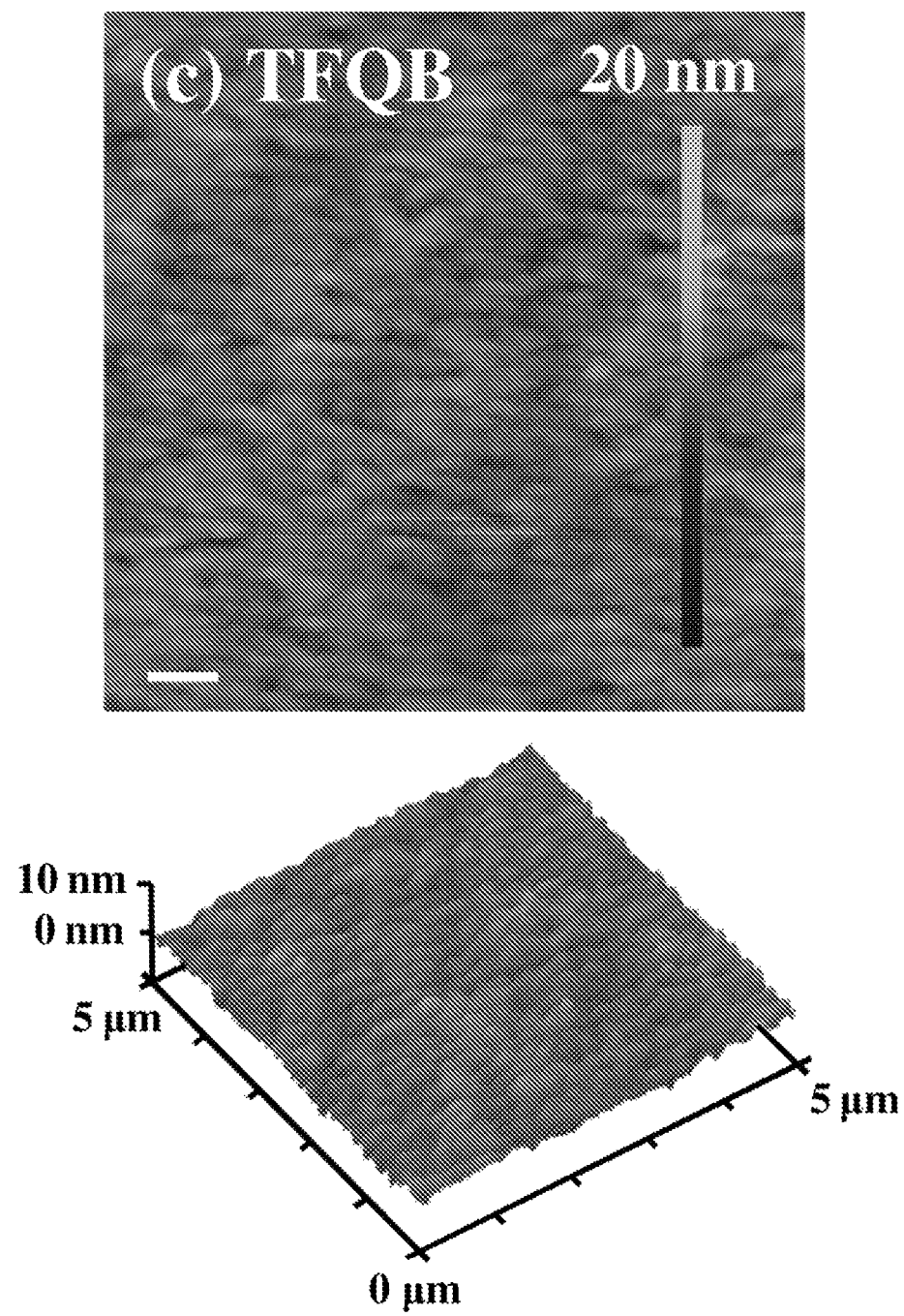
Figure 24D:
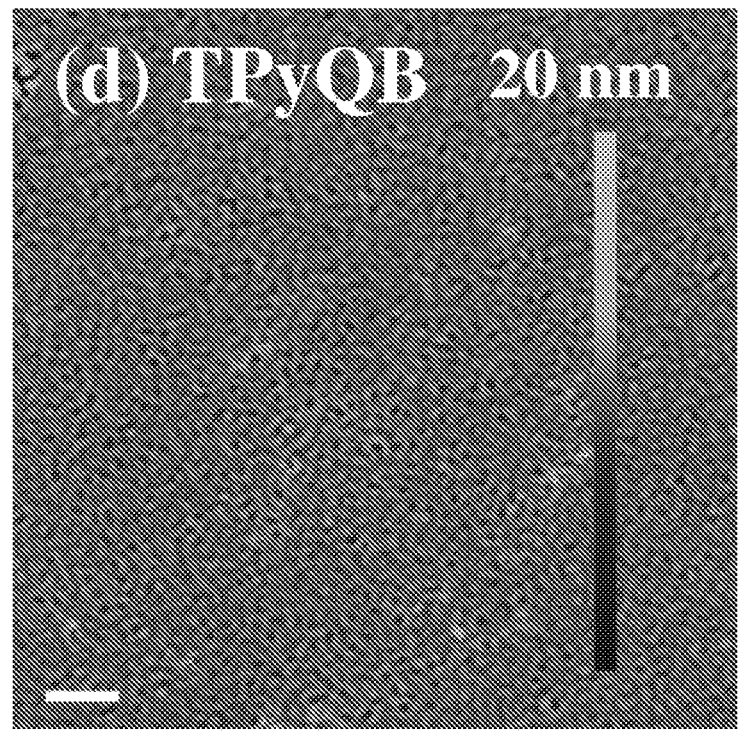
Figure 24D:
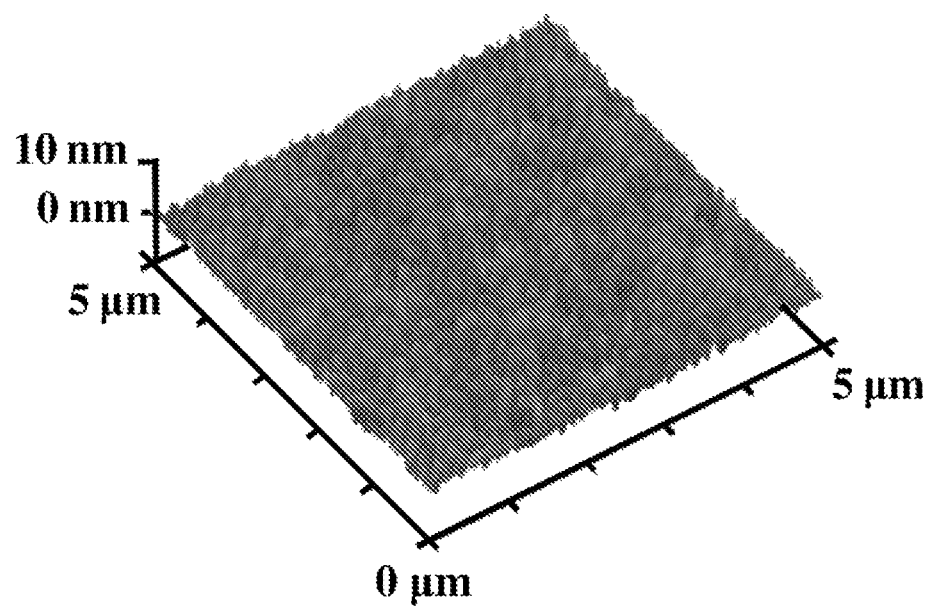

Atomic force microscopy (AFM) was used to investigate the surface morphology of both vacuum-deposited and solution-deposited oligoquinoline ETLs to understand the likely ETL/Al cathode interface morphology that underlies the observed trends in charge transport and the efficiency of the blue PhOLEDs. FIGS. 24A-24D are AFM micrographs of the 2D and the corresponding 3D topological surface morphologies of the vacuum-deposited oligoquinoline thin films (FIG. 24A is TMQB, FIG. 24B is TQB, FIG. 24C is TFQB, and FIG. 24D is TPyQB).

Figure 25A:
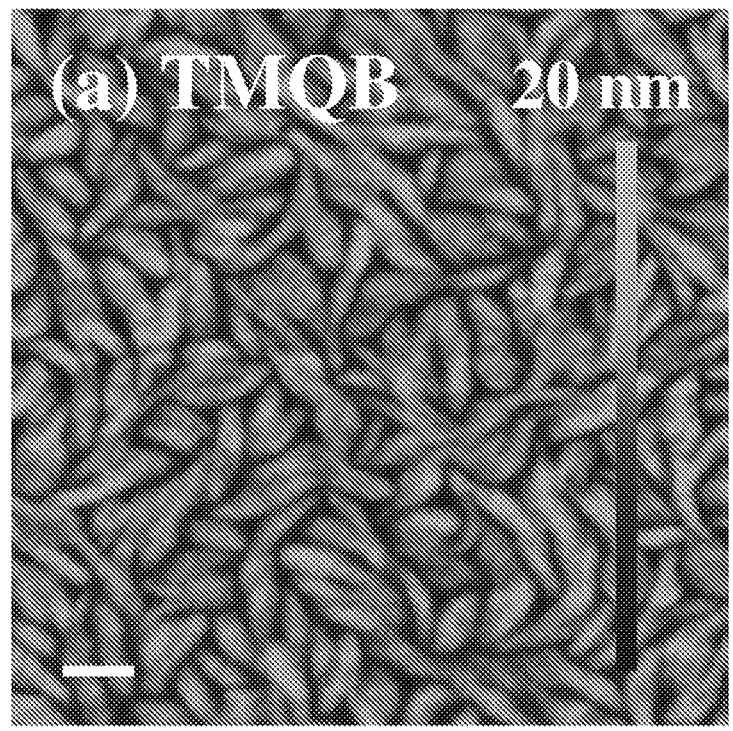
FIGS. 25A-25D are AFM micrographs of the 2D (5×5 μm; scale bar is 500 nm) and the corresponding 3D topological surface morphologies of the solution-deposited oligoquinoline thin films (FIG. 25A is TMQB, FIG. 25B is TQB, FIG. 25C is TFQB, and FIG. 25D is TPyQB)
Figure 25A:
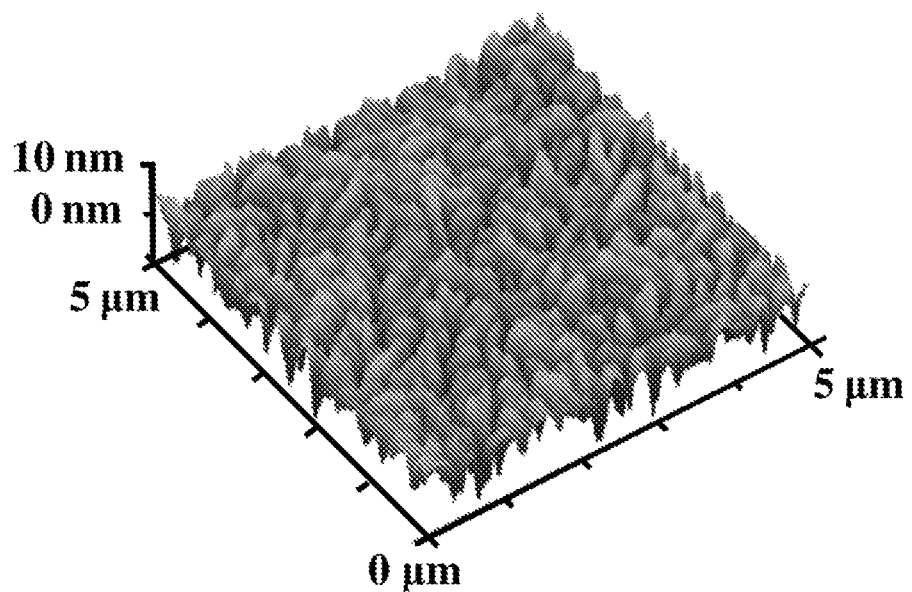
Figure 25B:
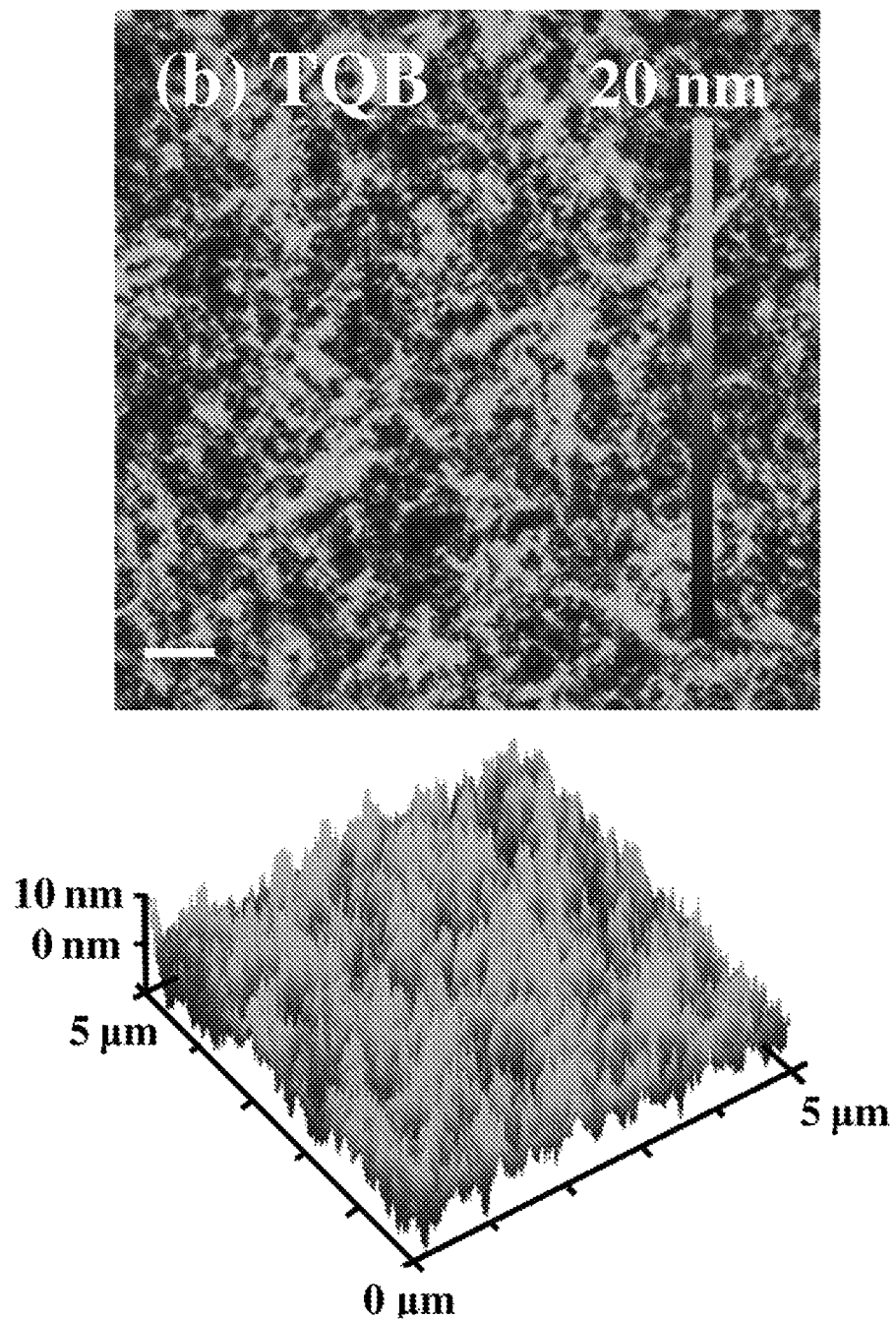
Figure 25C:
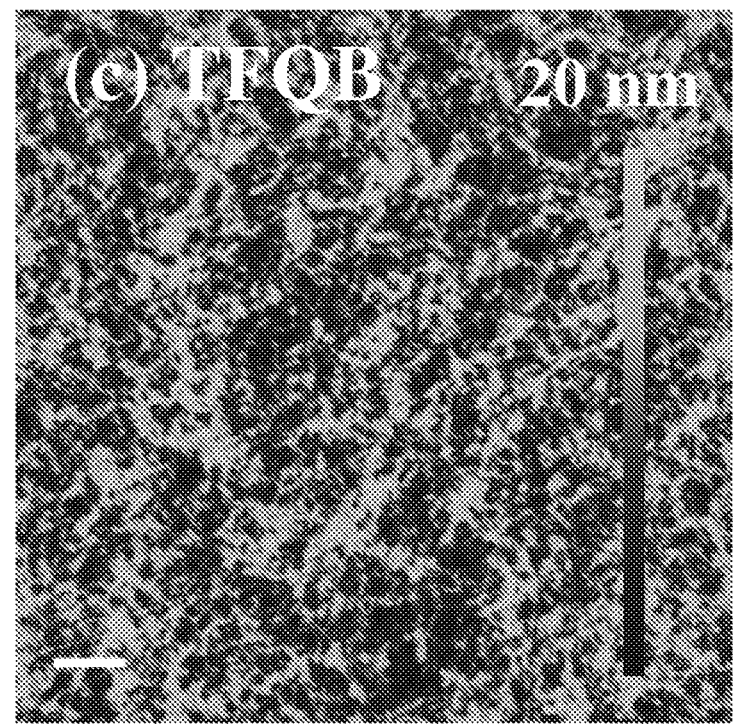
Figure 25C:
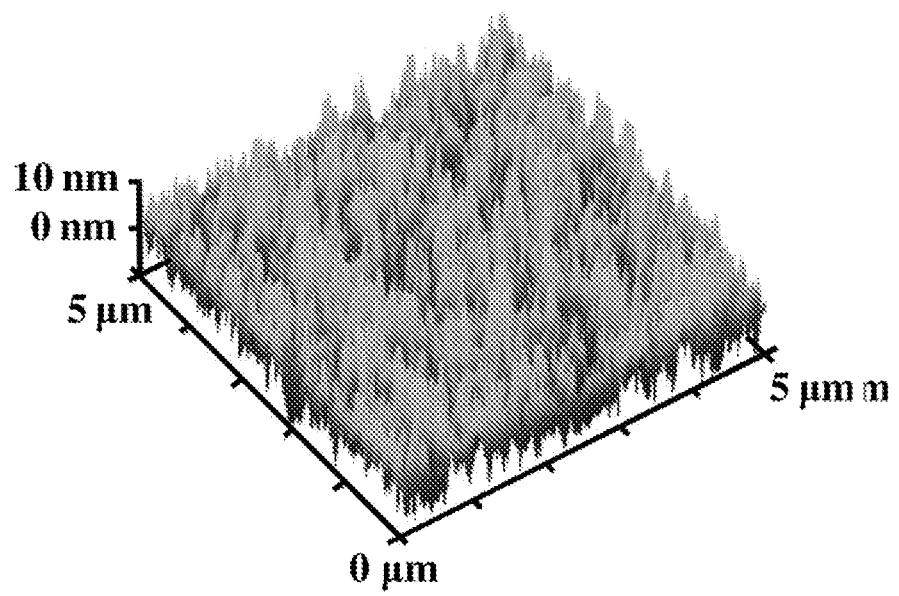
Figure 25D:
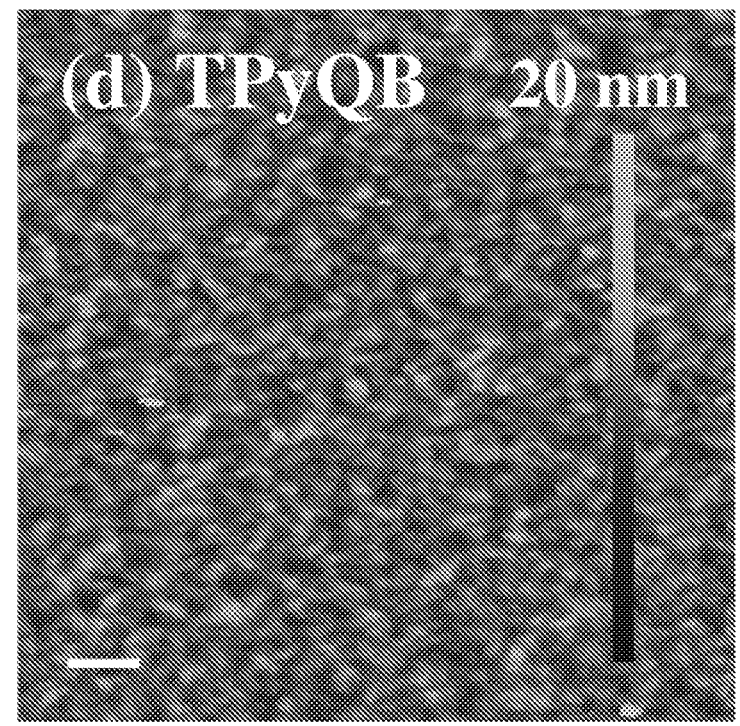
Figure 25D:
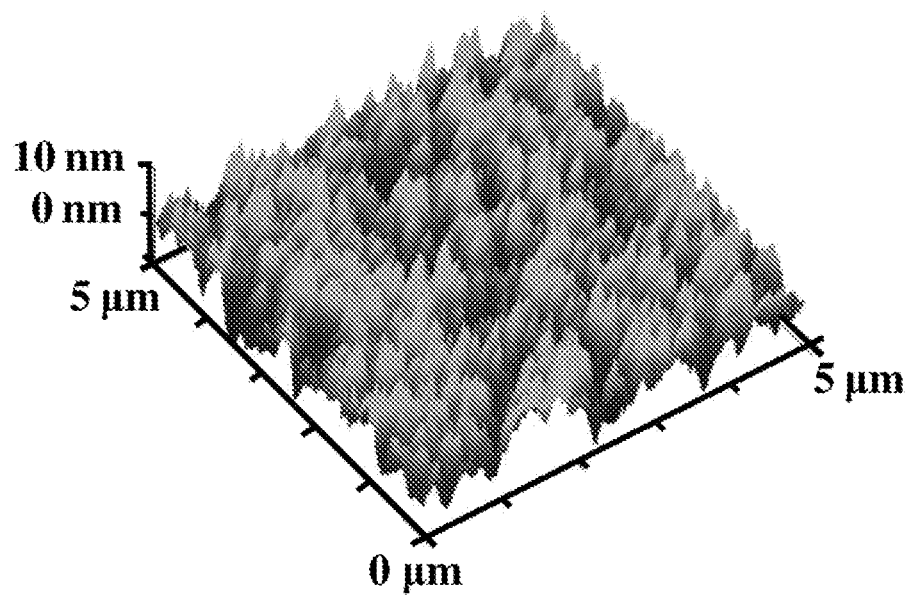

The thin films have smooth surfaces with RMS values of surface roughness of 1.75, 0.553, 0.754, and 0.867 nm for TMQB, TQB, TFQB and TPyQB, respectively. Vacuum-evaporated TMQB film shows some vertical aggregates dispersed on the surface, which likely resulted in the higher RMS value compared to the other vacuum-deposited thin films. In contrast, the surface morphologies of the solution-deposited oligoquinoline ETLs (FIGS. 25A-25D) are significantly different from those of the vacuum-deposited ETLs (FIG. 25A is TMQB, FIG. 25B is TQB, FIG. 25C is TFQB, and FIG. 25D is TPyQB). The RMS values of the solution-deposited ETLs increased to 2.35, 3.35, 4.01 and 3.75 nm for TMQB, TQB, TFQB and TPyQB films, respectively. As shown in the 3D surface morphology of FIGS. 25A-25D, that the solution-deposited thin films form a high density of vertically aligned nanopillars with the exception of TMQB.

The morphology of solution-processed TMQB thin films is characterized by horizontally oriented large crystallites or aggregates (~500 nm width). The observed morphology of TMQB thin films is consistent with its poor carrier mobility and poor PhOLED performance. On the other hand, the observed vertically oriented nanopillars in solution-deposited TQB, TFQB, and TPyQB thin films, and thus high surface roughness, suggest that the area of the ETL/cathode contact is maximized, facilitating efficient electron injection. The observed nanopillar morphology of the solution-deposited ETLs implies that maximum charge transport can be expected in the vertical direction, which is consistent with measured high electron mobility by the SCLC method. Furthermore, the oligoquinoline/Al interface is expected to involve a chemical bonding between Al metal and the nitrogen heteroatom in the organic electron-transport materials. The additional nitrogen and fluorine heteroatoms in TFQB and TPyQB are likely to result in improved interactions between the ETL and Al at the ETL/cathode interface, thus leading to improved electron injection and charge transport compared to TQB and TMQB.

In summary, novel wide-energy-gap n-type organic semi-conductors based on dendritic oligoquinolines were synthesized and were demonstrated to be effective solution-processable electron-transport layers in blue PhOLEDs. The new oligoquinolines have robust thermal stability with high decomposition temperatures and high melting temperatures. The new electron transport materials have enabled orthogonal sequential solution-processing of multilayered blue polymer-based PhOLEDs with the highest efficiency to date. The molecular design of the new n-type oligomers with meta-linkages enabled achievement of large band gaps (~3.4 eV) and low-lying HOMO levels (~−6.1 eV) that also facilitate excellent hole-blocking properties. The high electron affinity and high electron mobility ($3.3 \times 10^{-3}$ cm$^2$ V$^{-1}$ s$^{-1}$) of the solution-deposited thin films facilitated good electron-injection/transport properties. Blue PhOLEDs based on FIrpic triplet emitter-doped PVK host emission layer and a solution-processed oligoquinoline electron-transport layer gave a high luminous efficiency of 30.5 cd A$^{-1}$ at a brightness of 4130 cd m$^{-2}$ with an external quantum efficiency (EQE) of 16.0%. AFM imaging of the solution-deposited oligoquinoline ETLs revealed a high density of vertically oriented nanopillars which lead to a rough surface that enhance electron injection and transport compared to the smooth vacuum-deposited ETLs. These results demonstrate that small-molecule electron-transport layers can be readily processed from solution to fabricate high performance multilayered PhOLEDs. These results are also instructive in the design of ETMs with high electron mobilities, low-lying HOMO levels, and high performance solution-processable PhOLEDs for next-generation flat-panel displays and solid-state lighting.

Synthetic Procedures.

All commercially available reagents were used without further purification.

Synthesis of 1,3,5-Tris(4-methylquinolin-2-yl)benzene (TMQB)

A mixture of 2-aminoacetophenone (3.0 g, 14.7 mmol), 1,3,5-triacetylbenzene (6.2 g, 45.5 mmol) and diphenyl phosphate (8 equiv) in 12 mL of toluene were refluxed under argon for 18 h. The reaction mixture was precipitated from 10% methanol/triethylamine and the solid was collected by vacuum filtration. The product was purified by flash column chromatography using dichloromethane and acetonitrile mixture (9.5:0.5). The product was then recrystallized twice from dichloromethane and once from THF/MeOH mixture (2:1 v:v) to give a white solid (3.69 g, 50% yield). $^1$H NMR (300 MHz, CDCl$_3$): δ ppm=9.102 (s, 3H), 8.325 (d, J=8.0 Hz, 3H), 8.101-8.068 (m, 6H), 7.788 (t, J=8.1 Hz, 3H), 7.614 (m, 3H), 2.882 (s, 9H). $^{13}$C NMR (500 MHz, CDCl$_3$): δ ppm=156.76, 148.20, 144.99, 140.90, 130.40, 129.38, 127.53, 126.16, 123.73, 120.14, 19.08. HRMS (FAB) m/z calcd for [(M+H)$^+$] C$_{36}$H$_{28}$N$_3$ (502.22879). Found 502.22908.

Synthesis of
1,3,5-tris(4-phenylquinolin-2-yl)benzene (TQB)

A mixture of 2-aminobenzophenone (6 g, 30.5 mmol), 1,3,5-triacetylbenzene (2.0 g, 9.79 mmol) and diphenyl phosphate (DPP, 8 equiv.) in 12 mL of toluene was refluxed in argon for 18 h. The reaction mixture was precipitated into 10% methanol/triethylamine and the solid was collected by vacuum filtration. The product was purified by flash column chromatography using dichloromethane and acetonitrile mixture (9.5:0.5), followed by recrystallization from tetrahydrofuran/methanol solvent mixture (2:1, v/v) to give a white solid (5 g, 74% yield). $^1$H NMR (300 MHz, CDCl$_3$): δ ppm=9.175 (s, 3H), 8.3714 (d, 3H), 8.139 (s, 3H), 7.979 (d, 3H), 7.784 (t, 3H), 7.679-7.5067 (m, 18H). $^{13}$C NMR (300 MHz, CDCl$_3$): δ ppm=156.4905, 149.3806, 148.8507, 140.9459, 130.2619, 129.7142, 129.5713, 128.8807, 128.6283, 128.4425, 127.7615, 126.4845, 125.7167, 125.3298, 119.5872. HRMS (FAB) m/z calcd for [(M+H)$^+$] C$_{51}$H$_{34}$N$_3$ (688.27551). Found 688.27619.

Synthesis of 1,3,5-tris(4-(4-fluorophenyl)quinolin-2-yl)benzene (TFQB)

A mixture of 2-amino-4'-fluorobenzophenone (3.2 g, 14.9 mmol), 1,3,5-triacetylbenzene (1.0 g, 4.9 mmol) and diphenyl phosphate (8 equiv) in 12 mL of toluene were refluxed under argon for 18 h. The reaction mixture was precipitated from 10% methanol/triethylamine and the solid was collected by vacuum filtration. The product was purified by flash column chromatography using chloroform and acetonitrile mixture (9.5:0.5). The product was then recrystallized from chloroform/MeOH mixture (1:1 v:v) to give a white solid (3.1 g, 85% yield). $^1$H NMR (300 MHz, CDCl$_3$): δ ppm=9.158 (s, 3H), 8.352 (d, J=8.4 Hz, 3H), 8.106 (s, 3H), 7.927 (d, J=8.1 Hz, 2H), 7.787 (t, 3H), 7.620 (m, 9H), 7.328 (m, 6H), 2.882 (s, 9H). $^{13}$C NMR (500 MHz, CDCl$_3$): δ ppm=163.972, 161.997, 156.400, 148.824, 148.351, 140.845, 134.304, 131.452, 130.275, 129.744, 127.761, 126.717, 125.991, 125.479, 119.640, 115.816, 115.644. HRMS (FAB) m/z calcd for [(M+H)$^+$] C$_{51}$H$_{31}$F$_3$N$_3$ (742.24625). Found 742.24393.

Synthesis of
1,3,5-tris(4-pyridinquinolin-2-yl)benzene (TPyQB)

A mixture of 4-(2-aminobenzoyl)pyridine (1.0 g, 5.04 mmol), 1,3,5-triacetylbenzene (338 mg, 1.66 mmol) and diphenyl phosphate (8 equiv) in 12 mL of toluene were refluxed under argon for 18 h. The reaction mixture was precipitated from 10% methanol/triethylamine and the solid was collected by vacuum filtration. The product was then recrystallized from chloroform/MeOH mixture (1:1 v:v) to give a white solid (840 mg, 89% yield). $^1$H NMR (300 MHz, CDCl$_3$): δ ppm=9.184 (s, 3H), 8.887 (d, J=6.0 Hz, 6H), 8.391 (d, J=8.4 Hz, 3H), 8.120 (s, 3H), 7.886-7.813 (m, 6H), 7.602-7.582 (m, 9H). $^{13}$C NMR (500 MHz, CDCl$_3$): δ ppm=156.24, 150.25, 148.77, 146.60, 146.22, 140.70, 130.47, 130.18, 127.83, 127.28, 125.04, 124.96, 124.45, 119.12. HRMS (FAB) m/z calcd for [(M+H)$^+$] C$_{48}$H$_{31}$N$_6$ (691.26046). Found=691.25988.

Characterization.

$^1$H NMR spectra were recorded on a Bruker AV300 at 300 MHz, whereas $^{13}$C NMR spectra were recorder on a Brucker AV 500 at 500 MHz using CDCl$_3$ as the solvent. Mass spectra were obtained from Bruker Esquire LC/Ion Trap Mass spectrometer and JEOL/HX-110. Cyclic voltammetry was measured on an EG&G Princeton Applied Research Potentiostat/Galvanostat (Model 273A). Data were analyzed by Model 270 Electrochemical Analysis System Software on a PC computer. A three-electrode cell was used, consisting of platinum wire electrodes as both counter and working electrode. Silver/silver ion (Ag in 0.1M AgNO$_3$ solution, Bioanalytical System, Inc.) was used as a reference electrode. Ferrocene/ferrocenium (Fc/Fc$^+$) was used as an internal standard. The potential values obtained in reference to Ag/Ag$^+$ were converted to the saturated calomel electrode (SCE) scale. Thin film cyclic voltammetry was performed in acetonitrile containing 0.1M TBAPF$_6$. Thin films of each oligoquinoline were coated onto a platinum electrode from a concentrated solution (10 mg mL$^{-1}$) in formic acid and dried in vacuum for 2 hours. All solutions were purged with N$_2$ for 10-15 minutes before each experiment. UV-vis absorption spectra were collected on a Perkin-Elmer model Lambda 900 UV/vis/near-IR spectrophotometer. The photoluminescence (PL) spectra were obtained with a Photon Technology International (PTI) Inc. Model QM 2001-4 spectrofluorimeter.

Fabrication and Characterization of PhOLEDs.

The blue EML consisted of a blend of poly(N-vinyl carbazole) (PVK, M$_w$=135,600, M$_n$=56,400, Polysciences) and 1,3-bis(2-(4-tert-butylphenyl)-1,3,4-oxadiazo-5-yl)benzene (OXD-7, LumTec., Taiwan) (PVK:OXD-7=60:40, wt/wt) as a host and 10 wt % bis(3,5-difluoro-2-(2-pyridyl)phenyl-(2-carboxypyridyl)iridium (FIrpic, LumTec., Taiwan) as the dopant. A solution of PEDOT:PSS (poly-(ethylenedioxythiophene)-polystyrenesulfonate, H. C. Starck, Clevios PVP A14083) in water was spin-coated to make a 30-nm hole-injection layer onto a pre-cleaned ITO glass and annealed at 150° C. under vacuum. The 70-nm blue EML was obtained by spin coating of the PVK:OXD-7:FIrpic blends in cholorobenzene onto the PEDOT:PSS layer and vacuum dried at 100° C. A 20-nm film of each oligoquinoline was evaporated in a vacuum (<6.0×10$^{-7}$ torr) or spun cast from a 16 mg mL$^{-1}$ solution oligoquinoline in formic acid:water (3:1) mixture at a spin speed of 7000 rpm onto the EML, followed by vacuum drying at 50° C. overnight. After drying, 100-nm Al was deposited onto the ETL. The structure of devices I and II were identical: ITO/PEDOT:PSS (30 nm)/EML (70 nm)/oligoquinoline (20 nm)/Al (100 nm). Film thickness was measured by an Alpha-Step 500 profilometer (KLA-Tencor, San Jose, Calif.). EL (Electroluminescence) spectra were obtained using the same spectrofluorimeter described above. Current-voltage characteristics of the PhOLEDs were measured by using a HP4155A semiconductor parameter analyzer (Yokogawa Hewlett-Packard, Tokyo). The luminance was simultaneously measured by using a model 370 optometer (UDT Instruments, Baltimore, Md.) equipped with a calibrated luminance sensor head (Model 211) and a 5× objective lens. The device external quantum efficiencies (EQEs) were calculated from the luminance, current density and EL spectrum assuming a Lambertian distribution using procedures reported previously. All the device fabrication and device characterization steps were carried out under ambient laboratory condition.

Devices for space-charge-limited current (SCLC) measurement were fabricated with ITO/oligoquinoline/Al structure. The Al electrode and organic layer were obtained by the spin-coating of oligoquinolines onto the substrate followed by deposition of Al electrode. Current-voltage characteristics of SCLC devices were measured using the same semiconductor parameter analyzer as for PhOLED devices. The SCLC measurements were performed under dark and ambient conditions.

AFM characterization of surface morphology was done on a Veeco Dimension 3100 Scanning Probe Microscope (SPM) system. The AFM topographical images were measured with the same PhOLEDs used for device characterization.

Example 10

High-Performance Multilayered Solution-Processed PhOLEDs

In this example, high-performance multilayered PhOLEDs fabricated by orthogonal sequential solution-processing of a triplet-emitter-doped poly(N-vinylcarbazole)(PVK)-based emissive layer and widely used commercial small-molecule electron-transport materials are described. The results yield highly efficient multilayered green PhOLEDs based on solution-deposited triplet emitter-doped PVK emissive layer followed by sequential solution-deposition of commercial ETMs, including 1,3,5-tri(3-pyrid-3-yl-phenyl)benzene (TmPyPB), 4,7-diphenyl-1,10-phenanthroline (BPhen), and 2,9-dimethyl-4,7-diphenyl-1,10-phenanthroline (BCP) having the following structures:

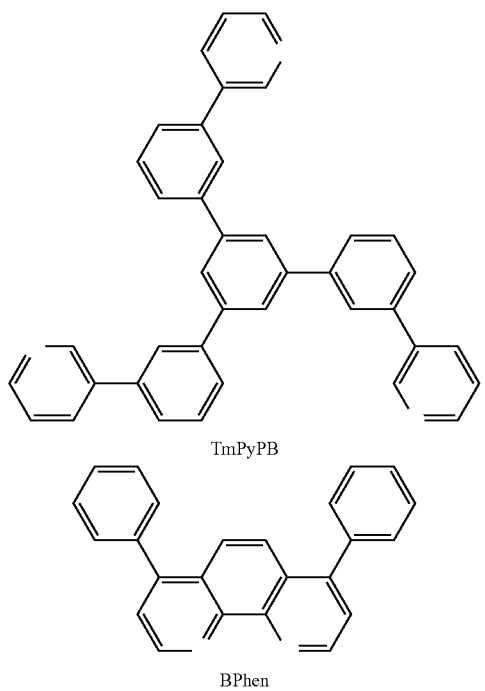

TmPyPB

BPhen

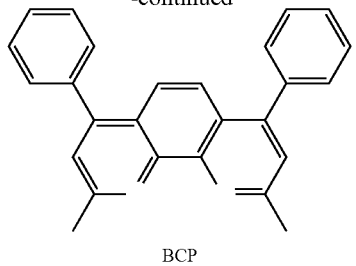

BCP

High-performance PhOLEDs with solution-deposited BPhen ETL showed a luminous efficiency (LE) value of 53.8 cd A$^{-1}$ with an external quantum efficiency (EQE) of 16.1% at a high brightness of 5900 cd m$^{-2}$. The results demonstrate that commercial small-molecule electron-transport materials can be readily solution-deposited to realize high-performance PhOLEDs. It was also determined that the surface morphology of an ETL can be tuned by solution-processing, facilitating improved charge-injection and transport and thus enhanced device performance by forming a better ETL/cathode interface compare to the vacuum-deposited ETL. The results demonstrate a general method for the orthogonal solution-deposition of widely used commercial small-molecule electron-transport materials in the fabrication of high-performance solution-processed multilayered organic electronic devices.

PhOLEDs with Vacuum-Deposited and Solution-Deposited ETMs

Multilayered PhOLEDs were fabricated using the commercial electron-transport materials (ETMs), TmPyPB, BPhen and BCP as the electron-transport layers (ETLs). The emissive polymer layer (EML) consisted of a blend of PVK and OXD-7, doped with triplet emitter tris(2-phenylpyridine)iridium(III) (Ir(ppy)$_3$) as described in Experimental Section. To facilitate comparison in PhOLED performance, the commercial ETMs were deposited by vacuum or solution methods to create an ETL thin film onto the EML. For the solution-processing method, the ETMs were deposited from formic acid (FA) and water (H$_2$O) solvent mixture (FA:H$_2$O=3:1) as previously reported, while varying the concentration of the ETM in solution. Three sets of PhOLEDs were fabricated using the different commercial ETMs: Device IA, ITO/PEDOT:PSS/EML/vacuum-deposited TmPyPB/Al; devices IB, IC, and ID, ITO/PEDOT:PSS/EML/solution-deposited TmPyPB/Al with different casting concentrations of TmPyPB; Device IIA, ITO/PEDOT:PSS/EML/vacuum-deposited BPhen/Al; devices IIB, IIC, and IID, ITO/PEDOT:PSS/EML/solution-deposited BPhen/Al with different casting concentrations of BPhen; Device IIIA, ITO/PEDOT:PSS/EML/vacuum-deposited BCP/Al; devices IIIB, IIIC, and IIID, ITO/PEDOT:PSS/EML/solution-deposited BCP/Al with different casting concentrations of BCP.

Figure 26A:
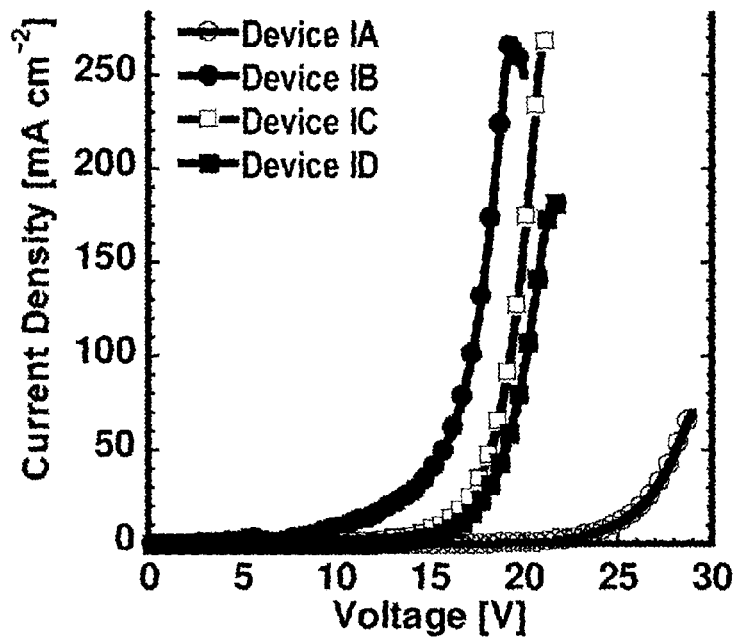
FIGS. 26A-26D graphically illustrate the performance of PhOLEDs with TmPyPB ETLs.
Figure 26B:
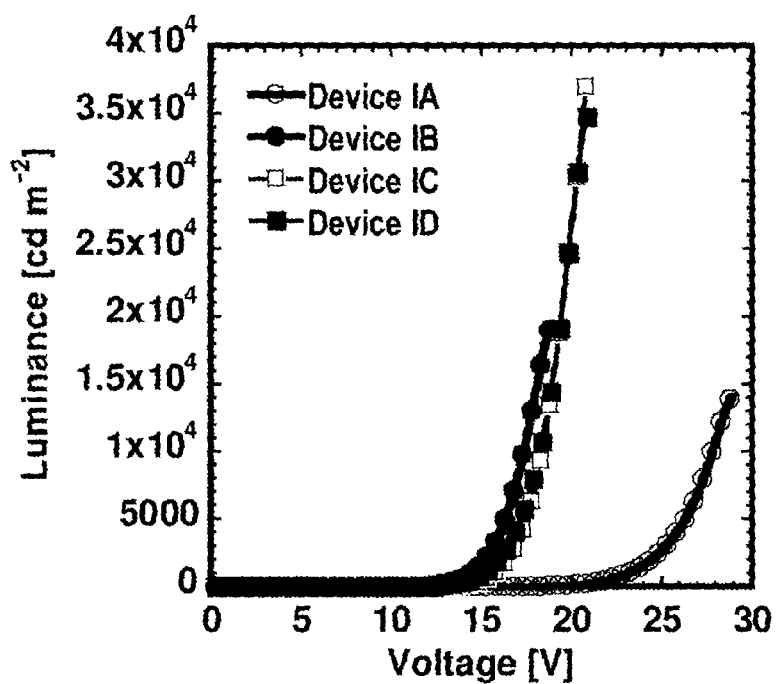
Figure 26C:
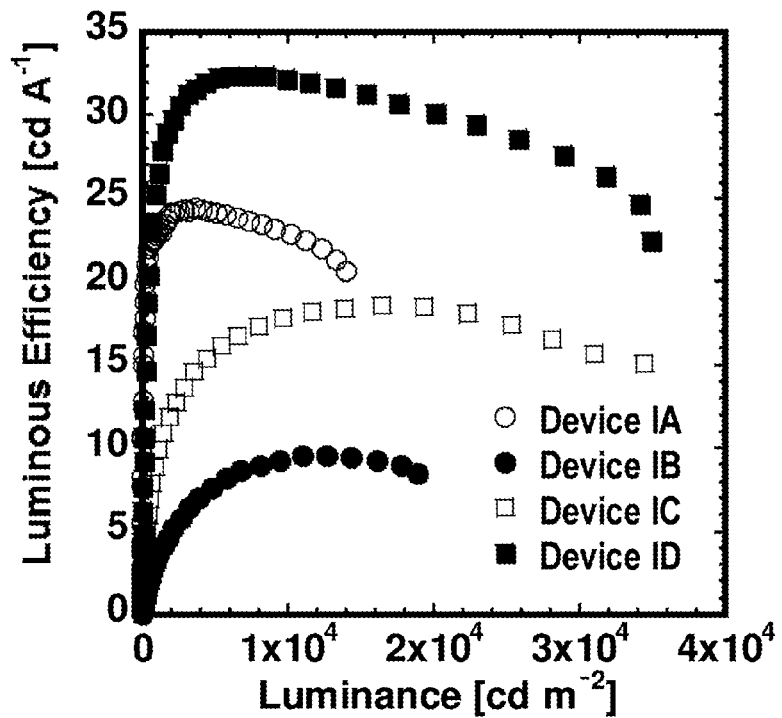
Figure 26D:
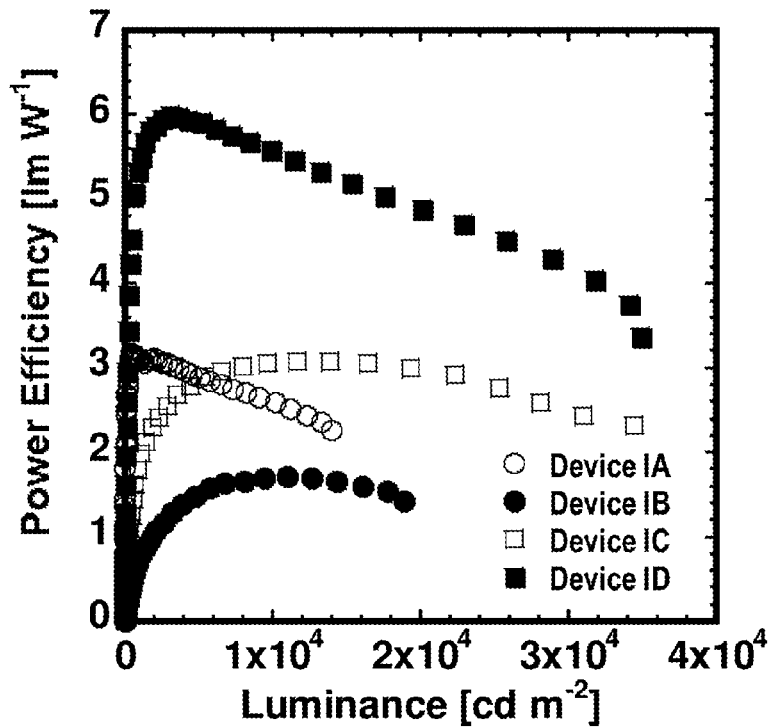

FIGS. 26A-26D show the performance of PhOLEDs using TmPyPB as an ETL. Devices IB, IC, and ID with solution-deposited TmPyPB were obtained by spin-coating onto the EML from 8, 16, and 24 mg mL$^{-1}$ solutions to deposit 15, 30, and 40 nm of TmPyPB ETL, respectively. Device IA included a vacuum-deposited 40-nm thick TmPyPB ETL. As shown in FIG. 26A, device IB with the ETL deposited from 8 mg mL$^{-1}$ solution showed a higher current density than devices IC and ID due to its smaller thickness (15 nm). On the other hand, device IA with vacuum-deposited TmPyPB showed very low current density even though it has the same ETL thickness (40 nm) as device ID with TmPyPB ETL deposited from 24 mg mL$^{-1}$ solution. Despite their different current densities, devices IC and ID showed similar turn-on voltages (9.1 and 8.5 V), and luminance (brightness)-voltage (L-V) characteristics with similar maximum brightness of 34900-35100 cd m$^{-2}$ (FIG. 26B). Device ID showed the highest luminous efficiency (LE) value of 32.4 cd A$^{-1}$ and power efficiency (PE) of 5.7 lm W$^{-1}$ (FIGS. 26B and 26C) with an external quantum efficiency (EQE) of 9.7% (Table 7). Surprisingly, device IA containing vacuum-deposited TmPyPB ETL had a very high turn-on voltage of 15.0 V and a very low maximum brightness of 14100 cd m$^{-2}$ at high drive voltage of 29.0 V. Device IA showed an LE value of 24.4 cd A$^{-1}$ and a power efficiency (PE) value of 3.0 lm W$^{-1}$ (EQE of 7.3%), higher than devices IB and IC but lower than device ID. However, device IA showed severe efficiency roll-off as the luminance increases (FIGS. 26C and 26D). Although devices IB and IC showed lower efficiencies than device IA, their turn-on voltages (9.4 and 9.1 V) and drive voltages (18.8 and 20.6 V) were much lower than device IA. These results clearly demonstrate that the PhOLEDs with solution-deposited TmPyPB ETLs show significantly decreased operating voltage, higher brightness and efficiency, depending on the solution-processing condition, compared to the device with vacuum-deposited TmPyPB ETL.

Figure 27A:
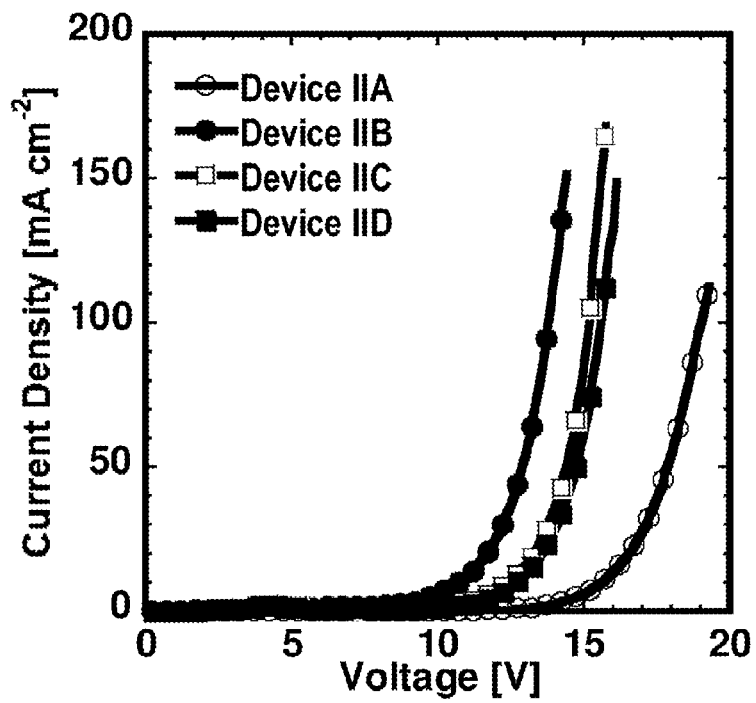
FIGS. 27A-27D graphically illustrate the performance of PhOLEDs with BPhen ETLs.
Figure 27B:
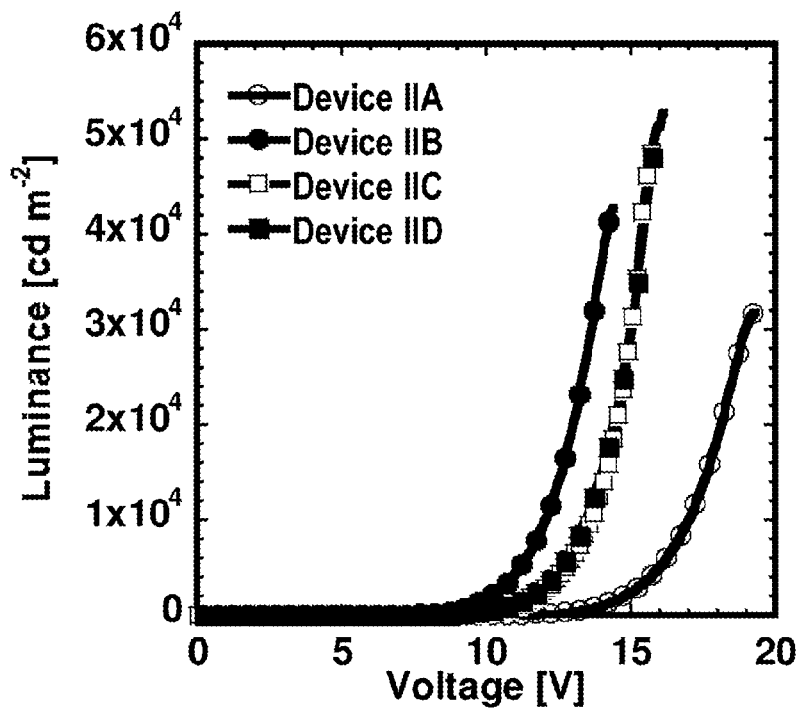
Figure 27C:
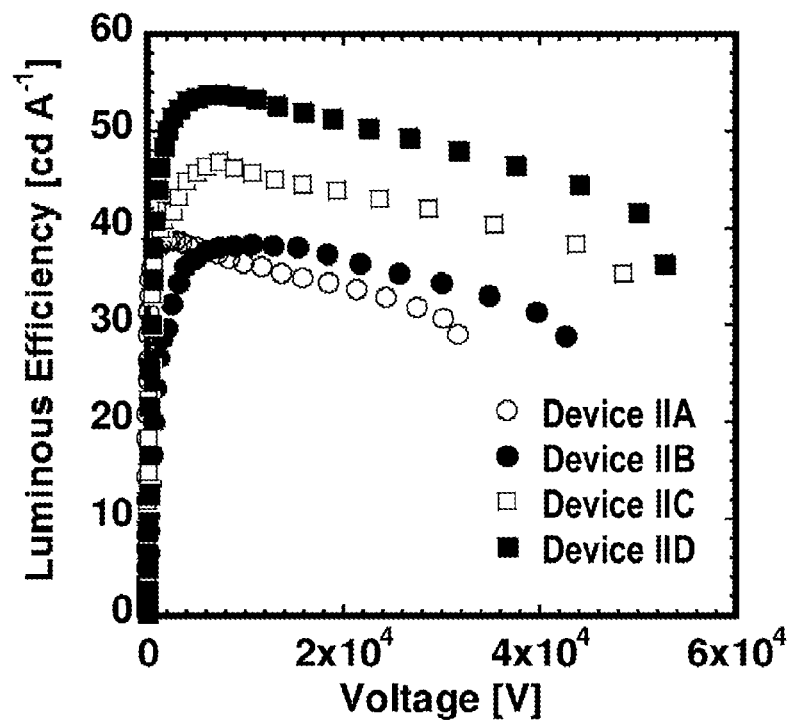
Figure 27D:
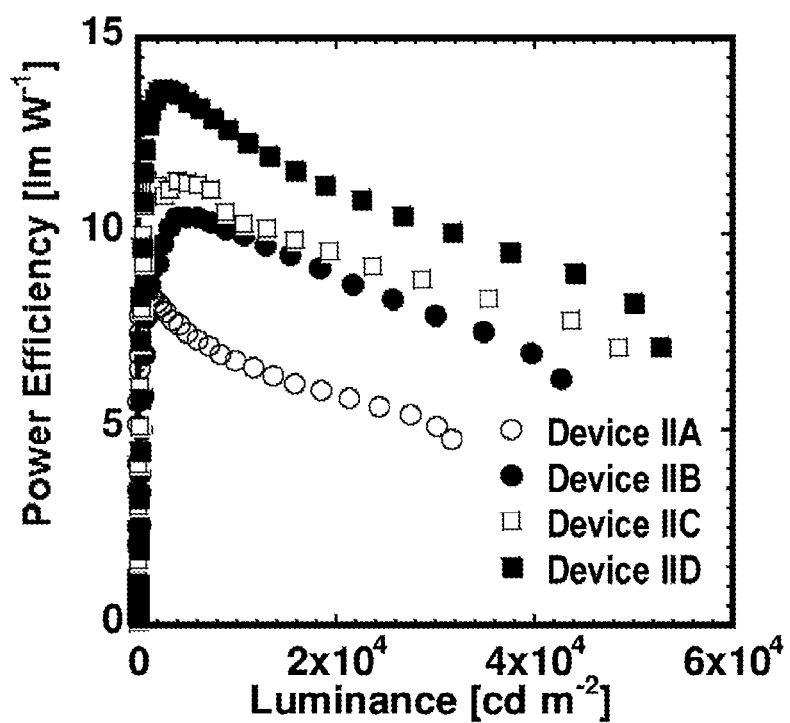

The J-V, L-V, LE-L, and the PE-L characteristics of PhOLEDs with BPhen ETLs are shown in FIGS. 27A-27D. In devices IIB, IIC, and IID, the solution-deposited BPhen ETL was spin-coated onto the EML from 16, 20, and 24 mg mL$^{-1}$ solutions to deposit 20, 30, and 40 nm of BPhen ETLs, respectively. Device IIA contained a 40-nm thick vacuum-deposited BPhen ETL. Similar to devices IB-ID, device IIB from a lower concentration of BPhen solution showed a higher current density than devices IIC and IID (FIG. 27A), whereas device IIA with vacuum-deposited BPhen showed a very low current density. As shown in FIGS. 27B-27D, devices IIC and IID with solution-processed BPhen ETL showed significant improvement in performance compared to device IIA containing vacuum-deposited BPhen. The operating voltages for devices IIC and IID were much lower with turn-on voltages of 5.8-6.0 V and drive voltages of 15.8-16.1 V, compared to device IIA with vacuum-deposited BPhen with a turn-on voltage of 8.8 V and a drive voltage of 19.3 V. The luminous efficiency of device IIC was 46.9 cd A$^{-1}$ (EQE of 14.1% at 8200 cd m$^{-2}$), showing a PE value of 11.1 lm W$^{-1}$ with a maximum brightness of 42800 cd m$^{-2}$ (at 15.8 V).

Device IID gave the best performance with a luminous efficiency of 53.8 cd A$^{-1}$ (EQE of 16.1% at 5900 cd m$^{-2}$) while showing a PE value of 13.3 lm W$^{-1}$ with a maximum brightness of 52800 cd m$^{-2}$ (at 16.1 V). It is noteworthy that device IID has a 40% higher efficiency and brightness than device IIA with vacuum-deposited BPhen (LE=38.7 cd A$^{-1}$, EQE=11.6% and PE=8.7 lm W$^{-1}$). We also note that device IIB with solution-deposited BPhen ETL from 16 mg mL$^{-1}$ solution also enhanced power efficiency and brightness.

Figure 28A:
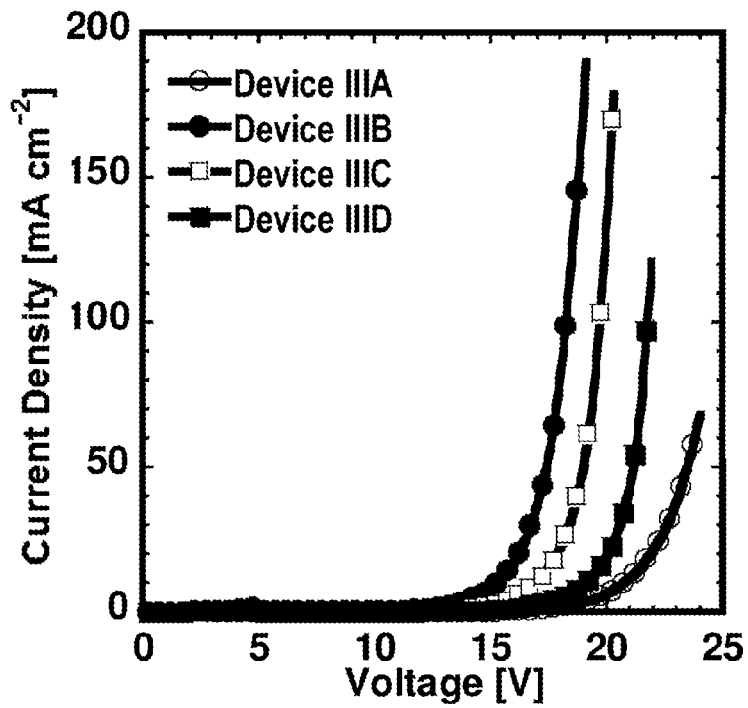
FIGS. 28A and 28B graphically illustrate the performance of PhOLEDs with BPhen ETLs.
Figure 28B:
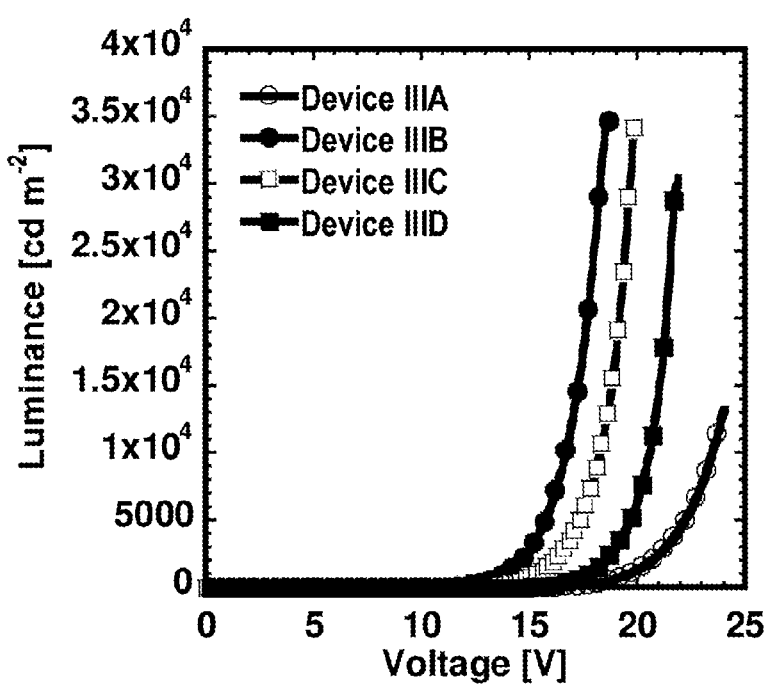

PhOLEDs with BCP ETL were also fabricated using vacuum- and solution-deposition methods. Devices IIIB, IIIC, and IIID had solution-deposited BCP ETLs, spin-coated onto the EML from 16, 20, and 24 mg mL$^{-1}$ of solutions to deposit 20, 30, and 40 nm ETLs, respectively. In the case of device IIIA, BCP was thermally deposited to form a 30-nm thick ETL onto the EML. Although the J-V and L-V characteristics of devices IIIB-D with BCP ETLs (FIGS. 28A and 28B) showed similar characteristics as devices IIB-D with solution-deposited BPhen ETLs, the luminous and power efficiencies did not significantly increase with increasing BCP solution concentration.

The LE value of device IIIB was 34.6 cd A$^{-1}$ (EQE of 10.4% at 5970 cd m$^{-2}$) with a maximum brightness of 34600 cd m$^{-2}$ whereas the LE value of device IIIC was only slightly higher at 36.5 cd A$^{-1}$ (EQE of 10.9% at 4880 cd m$^{-2}$) with a maximum brightness of 34600 cd m$^{-2}$. Device IIID with 30-nm thick solution-deposited BCP ETL showed a slightly lower LE value of 33.3 cd A$^{-1}$ (EQE of 10.0% at 8910 cd m$^{-2}$) with a maximum brightness of 30400 cd m$^{-2}$. Thus, the performance of all devices IIIB-D with solution-deposited BCP ETL is essentially comparable in LE values (33.3-36.5 cd A$^{-1}$), EQEs (10.0-10.9%) and maximum brightness (30400-34600 cd m$^{-2}$) in contrast to devices IIB-D with solution-deposited BPhen ETL which showed a significant increase of performance with increasing BPhen solution concentration. Compared to devices IIIB-D with solution-deposited BCP ETLs, device IIIA containing vacuum-deposited BCP ETL had a significantly lower performance in all measures with an LE value of 21.0 cd A$^{-1}$ (EQE of 6.3% at 2450 cd m$^{-2}$), a maximum brightness of 18100 cd m$^{-2}$ with very high turn-on (14.4 V) and drive voltage (25.0 V). These results demonstrate that the PhOLEDs with solution-deposited ETLs have superior performance compared to the corresponding devices with vacuum-deposited ETLs. Device characteristics of all PhOLEDs are summarized in Table 7.

TABLE 7

Device characteristics of PhOLEDs with commercial ETMs. [a]

| Device [b] | ETL | ETL deposition method | $V_{on}$[c] [V] | Drive voltage [V] | Current density [mA cm$^{-2}$] | Luminance [cd m$^{-2}$] | Device efficiency [cd A$^{-1}$, lm W$^{-1}$, (% EQE)] |
|---|---|---|---|---|---|---|---|
| Device IA | TmPyPB | Vacuum | 15.0 | 29.0 | 70.0 | 14100 | 20.1, 2.2, (6.0) |
|  |  |  |  | 25.5 | 14.1 | 3460 | 24.4, 3.0, (7.3) |
| Device IB | TmPyPB | Solution | 9.4 | 18.8 | 234.9 | 19100 | 8.1, 1.4, (2.4) |
|  |  | 8 mg mL$^{-1}$ |  | 9.6 | 132.2 | 12600 | 9.6, 1.7, (2.9) |
| Device IC | TmPyPB | Solution | 9.1 | 20.6 | 234.0 | 35100 | 15.0, 2.3, (4.5) |
|  |  | 16 mg mL$^{-1}$ |  | 19.1 | 88.9 | 16500 | 18.5, 3.0, (5.5) |
| Device ID | TmPyPB | Solution | 8.5 | 20.9 | 155.6 | 34900 | 22.4, 3.4, (6.7) |
|  |  | 24 mg mL$^{-1}$ |  | 19.6 | 24.5 | 7950 | 32.4, 5.7, (9.7) |
| Device IIA | BPhen | Vacuum | 8.8 | 19.3 | 112.8 | 31900 | 28.2, 4.6, (8.4) |
|  |  |  |  | 14.6 | 4.6 | 1800 | 38.7, 8.3, (11.6) |
| Device IIB | BPhen | Solution | 6.5 | 14.4 | 151.8 | 42800 | 28.2, 6.2, (8.4) |
|  |  | 16 mg mL$^{-1}$ |  | 12.1 | 26.8 | 10300 | 38.5, 10.0, (11.5) |
| Device IIC | BPhen | Solution | 6.0 | 15.8 | 168.6 | 48700 | 34.7, 6.7, (10.4) |
|  |  | 20 mg mL$^{-1}$ |  | 13.4 | 21.0 | 8200 | 46.9, 11.0, (14.1) |
| Device IID | BPhen | Solution | 5.8 | 16.1 | 148.8 | 52800 | 35.5, 7.0, (10.7) |
|  |  | 24 mg mL$^{-1}$ |  | 12.8 | 10.9 | 5860 | 53.8, 13.3, (16.1) |

TABLE 7-continued

Device characteristics of PhOLEDs with commercial ETMs. [a]

| Device [b] | ETL | ETL deposition method | $V_{on}$[c] [V] | Drive voltage [V] | Current density [mA cm$^{-2}$] | Luminance [cd m$^{-2}$] | Device efficiency [cd A$^{-1}$, lm W$^{-1}$, (% EQE)] |
|---|---|---|---|---|---|---|---|
| Device IIIA | BCP | Vacuum | 14.4 | 25.0 | 111.0 | 18100 | 16.3, 2.0, (4.9) |
|  |  |  |  | *20.9* | *11.7* | *2450* | *21.0, 3.1, (6.3)* |
| Device IIIB | BCP | Solution 16 mg mL$^{-1}$ | 9.1 | 18.7 | 145.8 | 34600 | 23.7, 4.0, (7.1) |
|  |  |  |  | *16.0* | *17.2* | *5970* | *34.6, 6.8, (10.4)* |
| Device IIIC | BCP | Solution 20 mg mL$^{-1}$ | 10.7 | 20.0 | 132.3 | 34600 | 26.2, 4.1, (7.8) |
|  |  |  |  | *17.3* | *13.8* | *5060* | *36.5, 6.1, (10.9)* |
| Device IIID | BCP | Solution 24 mg mL$^{-1}$ | 12.5 | 21.9 | 121.0 | 30400 | 25.2, 3.6, (7.6) |
|  |  |  |  | *20.4* | *26.7* | *8910* | *33.3, 5.1, (10.0)* |

[a] Values in italic correspond to those at maximum device efficiencies.
[b] Devices I with TmPyPB, devices II with BPhen, and devices III with BCP ETLs with the structure: ITO/PEDOT:PSS/EML/ETL/Al.
[c] Turn-on voltage (at brightness of 1 cd m$^{-2}$).

Surface Morphology of Vacuum-Deposited and Solution-Deposited ETLs.

Figure 29A:
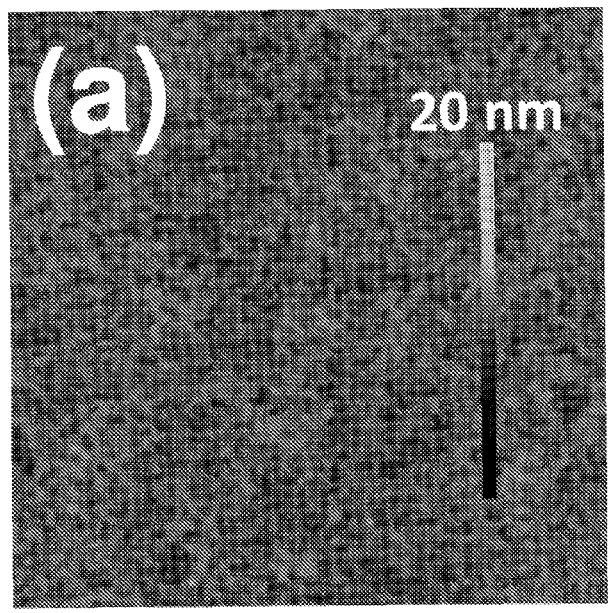
FIGS. 29A-29D show the 2D and the corresponding 3D topological surface morphologies of vacuum-deposited (FIG. 29A) and solution-deposited TmPyPB ETLs cast from different concentrations (FIGS. 29B-29D are TmPyPB from 8 mg mL$^{-1}$, 16 mg mL$^{-1}$, and 24 mg mL$^{-1}$, respectively)
Figure 29A:
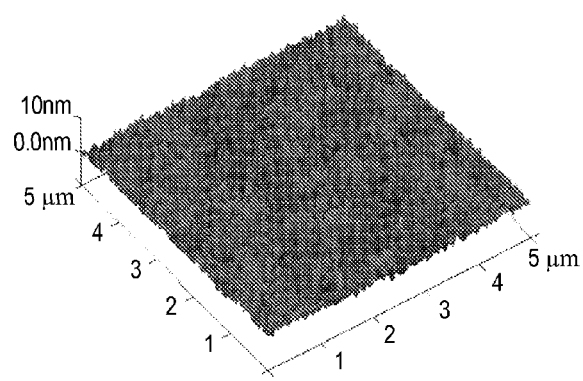
Figure 29B:
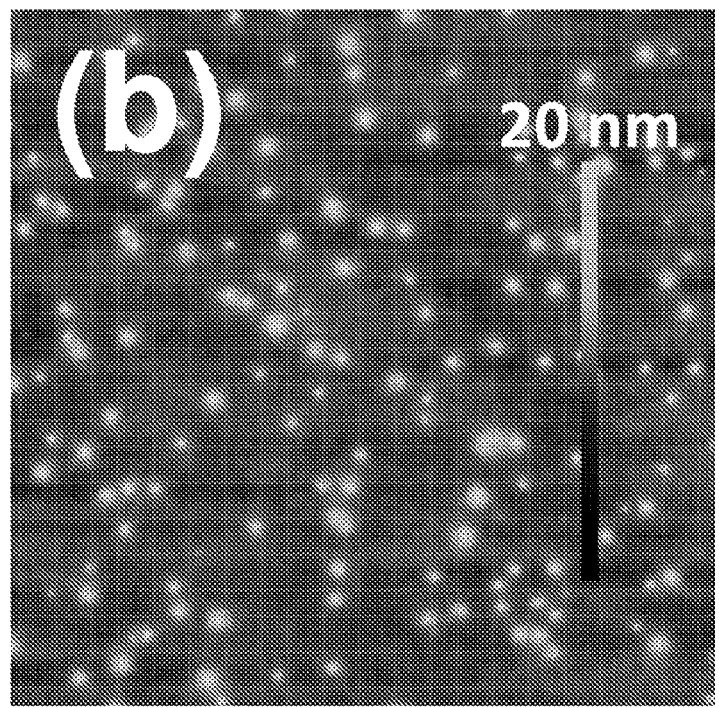
Figure 29B:
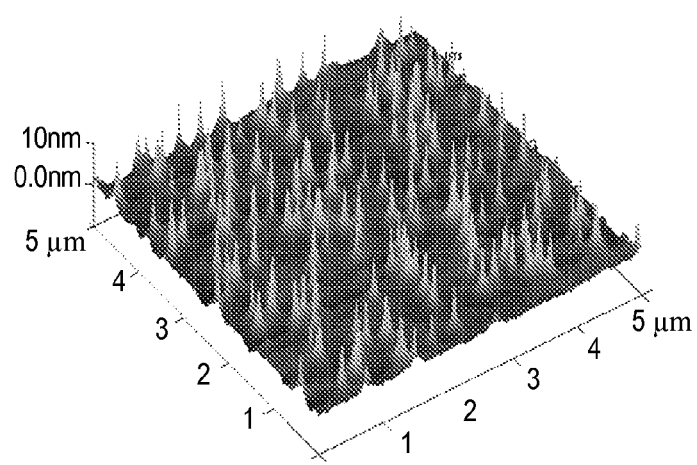
Figure 29C:
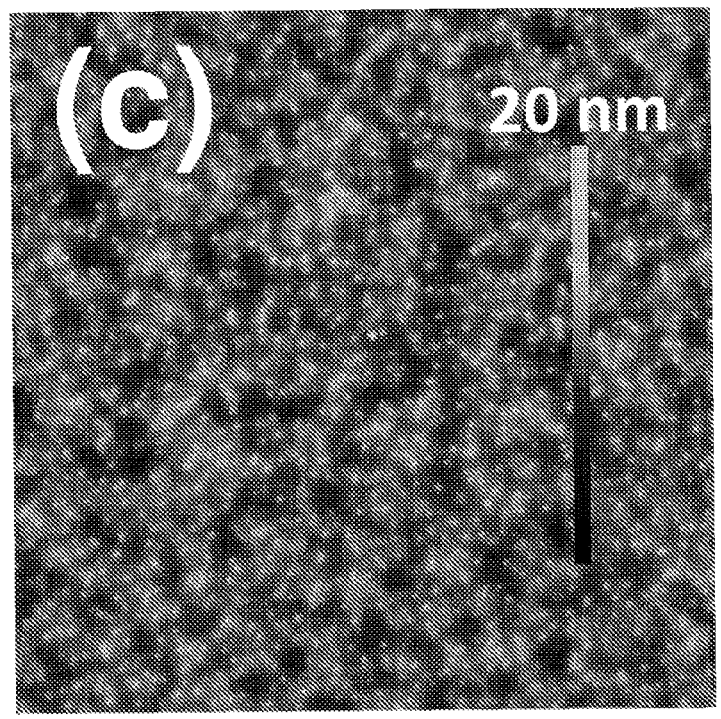
Figure 29C:
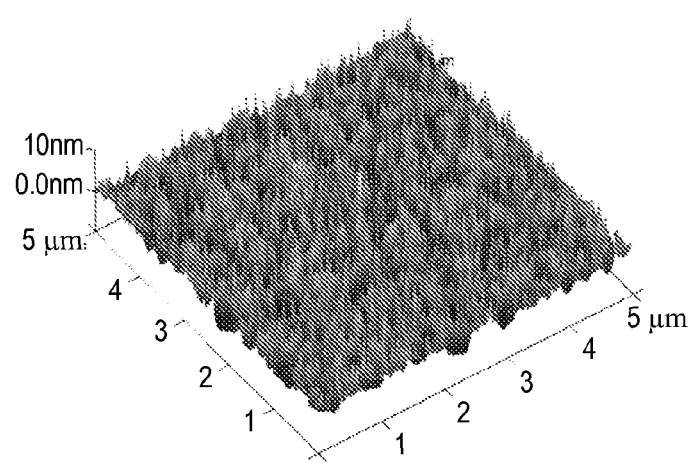
Figure 29D:
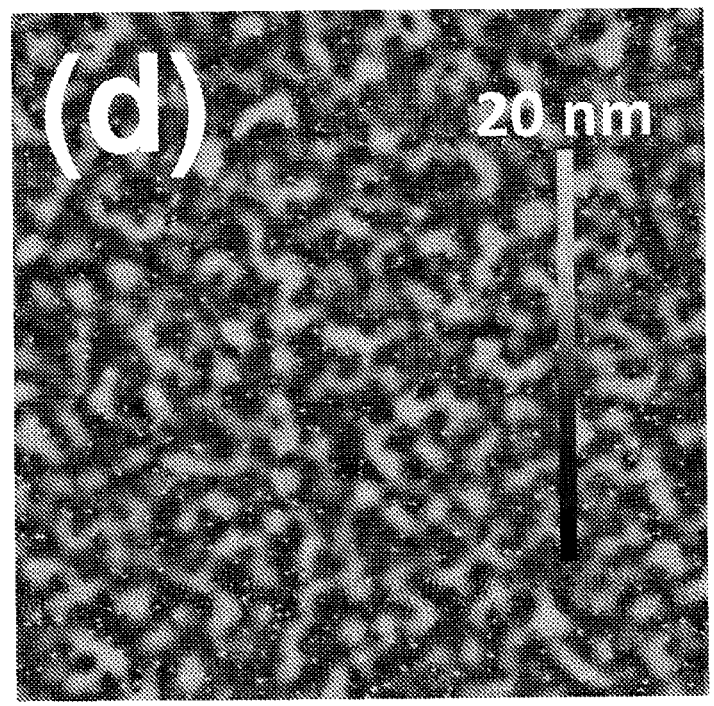
Figure 29D:
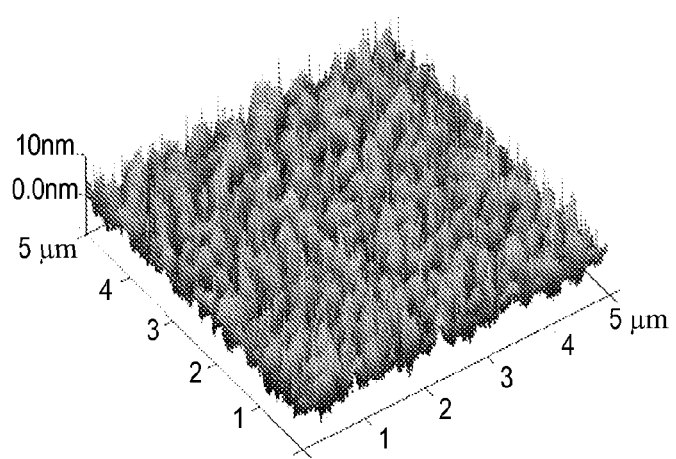

In order to understand the improved performance of the PhOLEDs with solution-deposited commercial ETMs, the surface morphology of both vacuum-deposited and solution-deposited ETLs was investigated by atomic force microscopy (AFM). FIGS. 29A-29D show the 2D and the corresponding 3D topological surface morphologies of vacuum-deposited (FIG. 29A) and solution-deposited TmPyPB ETLs cast from different concentrations (FIGS. 29B-29D are TmPyPB from 8 mg mL$^{-1}$, 16 mg mL$^{-1}$, and 24 mg mL$^{-1}$, respectively).

The vacuum-deposited TmPyPB ETL has a smooth surface with root-mean-square (RMS) roughness value of 0.792 nm whereas the solution-deposited thin films show a significant change in morphology as the casting solution concentration increases. TmPyPB ETL deposited from 8 mg mL$^{-1}$ solution shows a low density of vertically aligned nanopillars (FIG. 29B) throughout the surface while a progressively higher density of vertically aligned nanopillars was observed in TmPyPB ETLs that were solution-deposited from 16 and 24 mg mL$^{-1}$ (FIGS. 29C and 29D). The RMS roughness values were 1.41, 1.40, and 2.39 nm for solution-deposited TmPyPB ETLs from 8, 16, and 24 mg mL$^{-1}$, respectively. The relatively poor performance of device IB while device ID with solution-deposited TmPyPB from 24 mg mL$^{-1}$ has the highest performance among the PhOLEDs with TmPyPB ETLs suggest a good correlation of performance with the roughness and density of the vertical nanopillars on ETL surface.

Figure 30A:
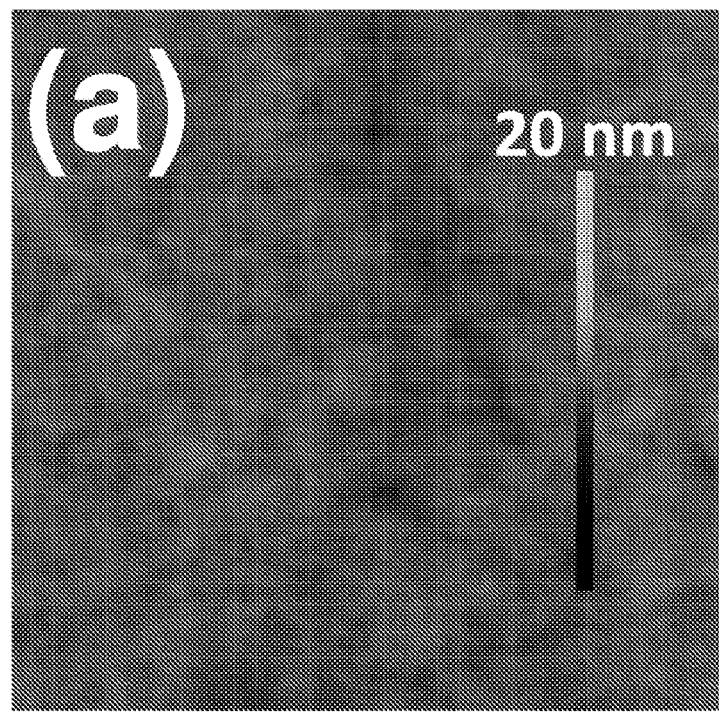
FIGS. 30A-30D show the 2D and the corresponding 3D topological surface morphologies of vacuum-deposited (FIG. 30A) and solution-deposited BPhen ETLs cast from different concentrations (FIGS. 30B-30D are from 16 mg mL$^{-1}$, 20 mg mL$^{-1}$, and 24 mg mL$^{-1}$, respectively)
Figure 30A:
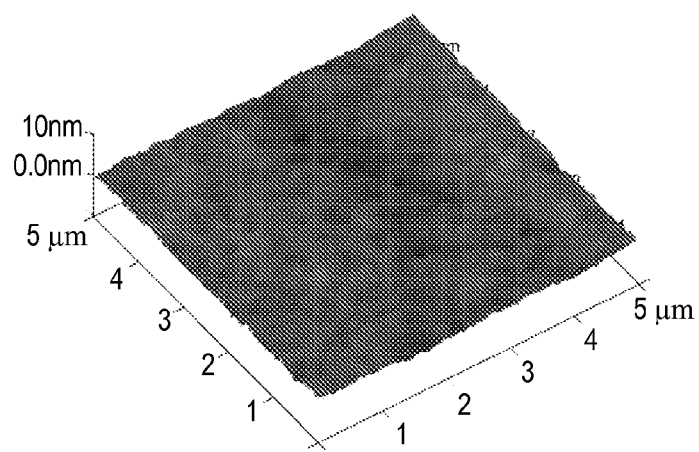
Figure 30B:
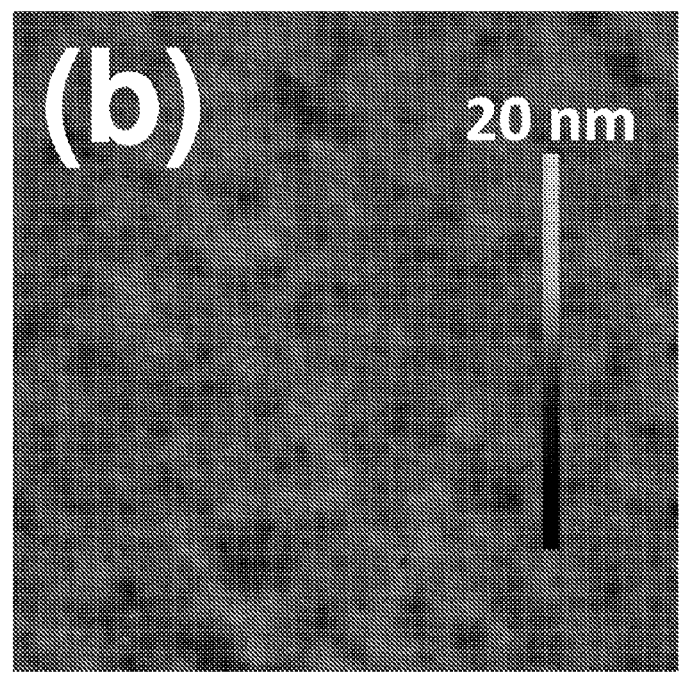
Figure 30B:
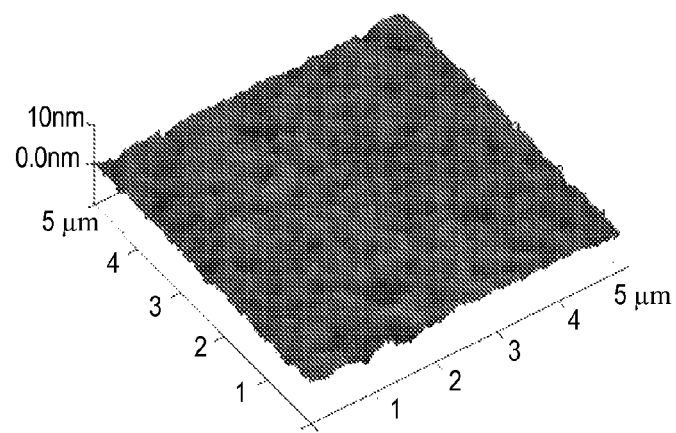
Figure 30C:
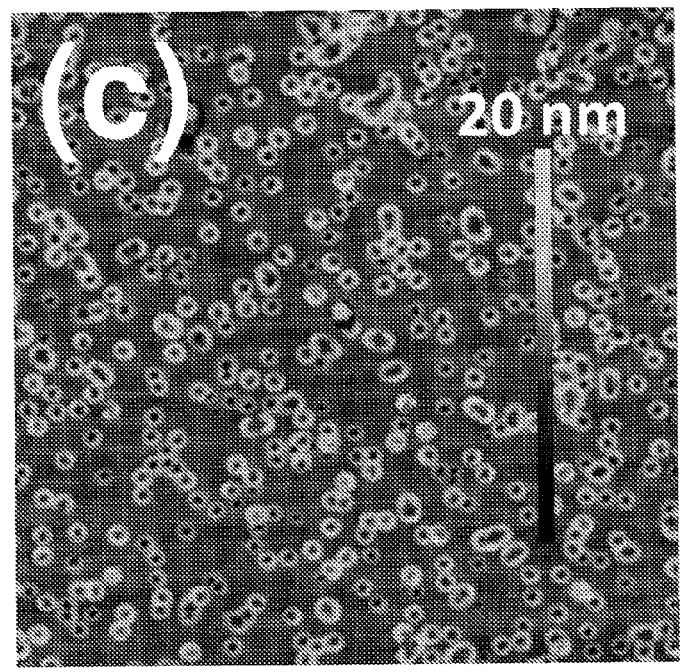
Figure 30C:
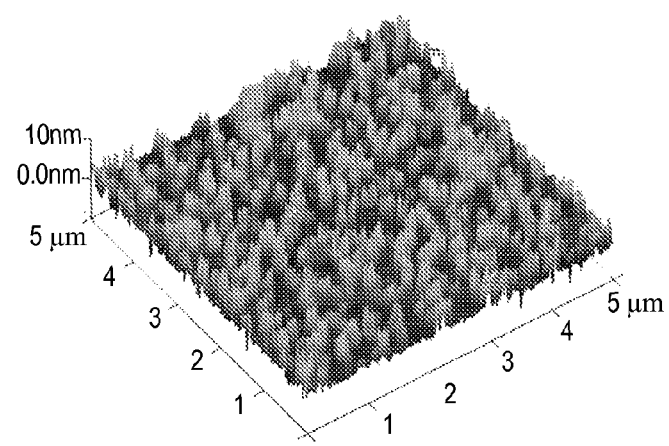
Figure 30D:
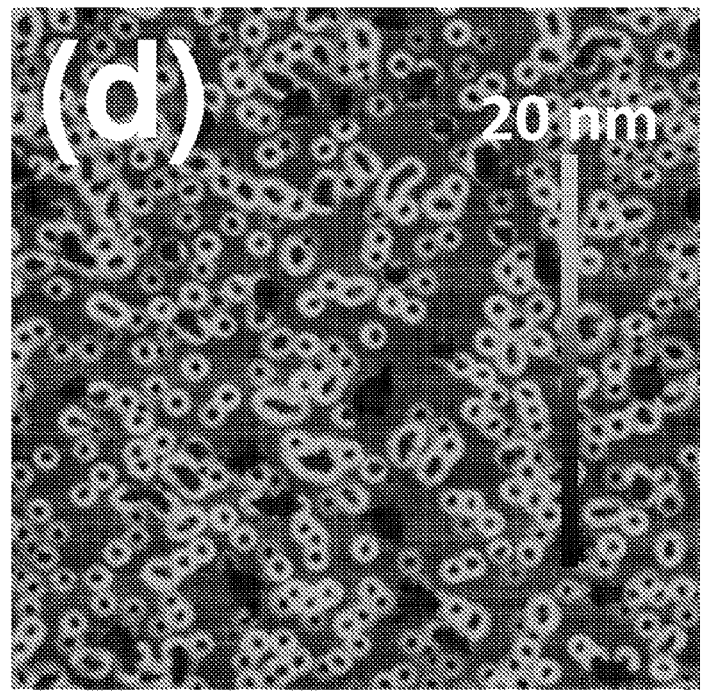
Figure 30D:
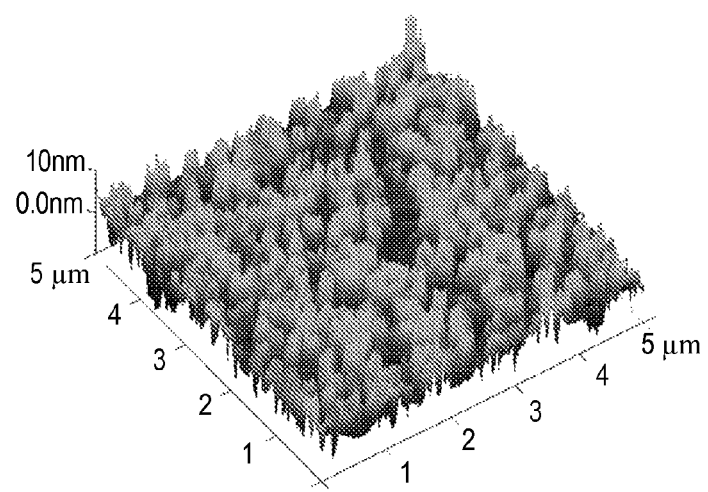

A similar trend in surface morphology was observed in the vacuum- and solution-deposited BPhen ETLs. A smooth surface was observed in the AFM images of the vacuum-deposited BPhen ETL (RMS value=0.459 nm, FIG. 30A) and the solution-deposited BPhen ETL from 16 mg mL$^{-1}$ (RMS value=0.545 nm, FIG. 30B). In contrast, a much rougher surface was observed in the solution-deposited BPhen ETL from higher concentrations of 20 (RMS value=1.84 nm, FIG. 30C) and 24 mg mL$^{-1}$ (RMS=2.63 nm, FIG. 30D).

It can be seen that the density of the vertical nanopillars on the ETL surface increases dramatically with increasing solution concentration. Similar to TmPyPB ETLs, the observed variation of the surface morphology of BPhen ETLs with solution concentration is consistent with the enhanced performance of the PhOLEDs with BPhen ETLs. The observed high surface roughness and high-density vertical nanopillars in the solution-deposited ETLs imply maximized area of ETL/Al cathode interface, which facilitates efficient electron-injection. Furthermore, it is expected that the vertically oriented nanopillars would result in improved charge-transport in the vertical direction.

Figure 31A:
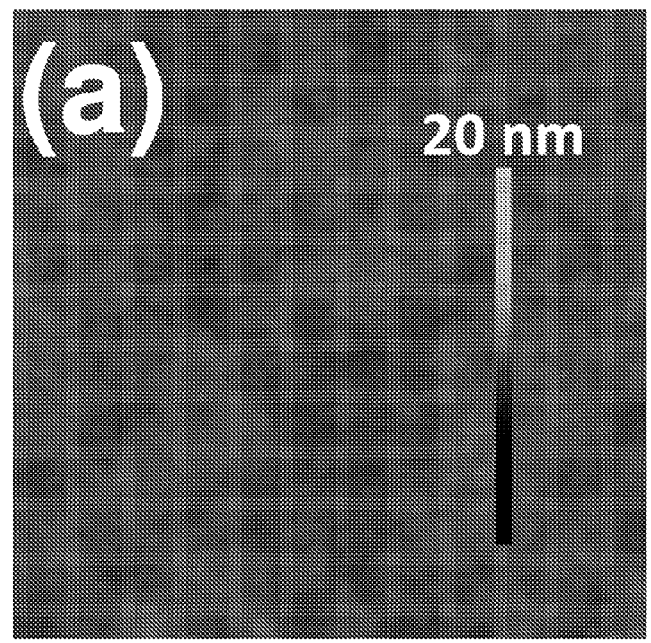
FIGS. 31A-31D show the 2D and the corresponding 3D topological surface morphologies of vacuum-deposited (FIG. 31A) and solution-deposited BPhen ETLs cast from different concentrations (FIGS. 31B-31D are from 16 mg mL$^{-1}$, 20 mg mL$^{-1}$, and 24 mg mL$^{-1}$, respectively)
Figure 31A:
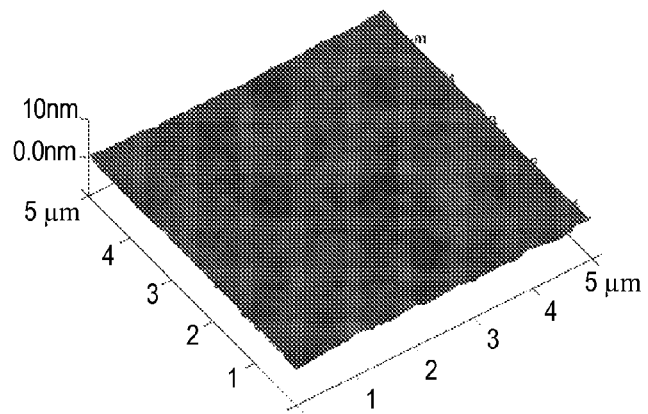
Figure 31B:
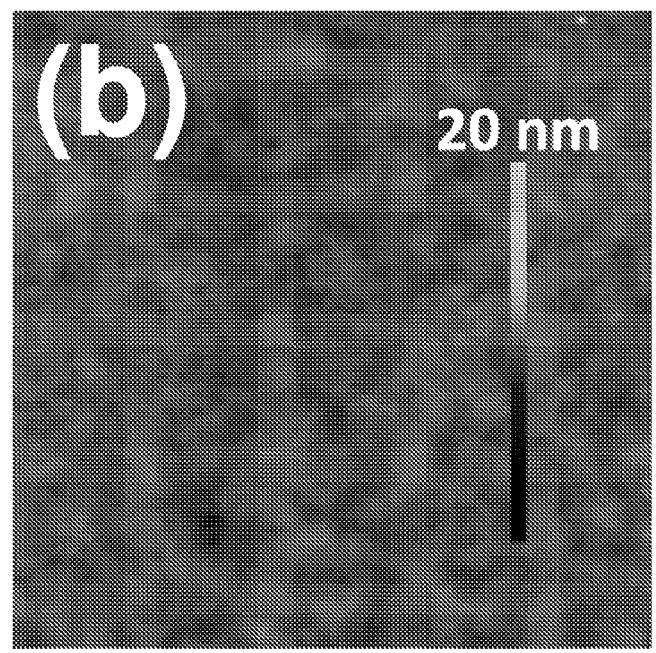
Figure 31B:
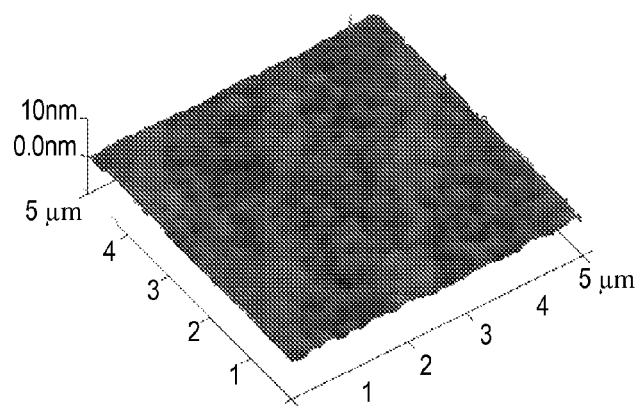
Figure 31C:
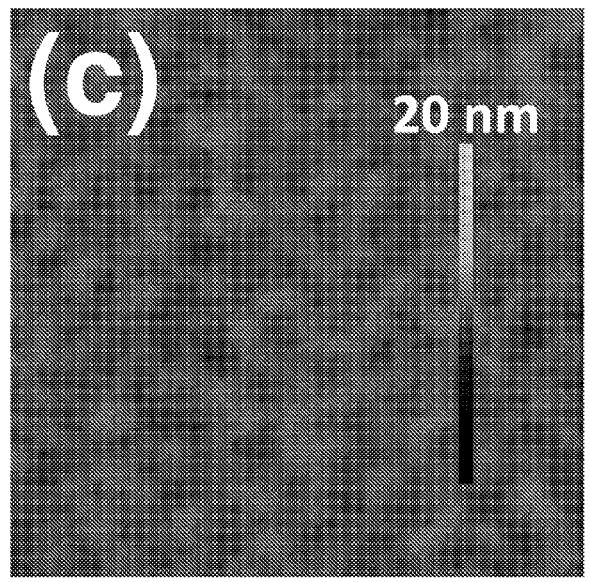
Figure 31C:
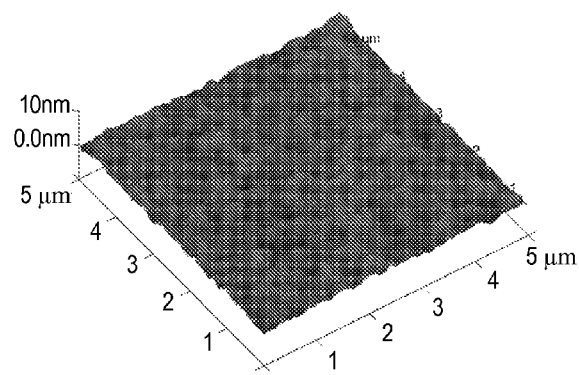
Figure 31D:
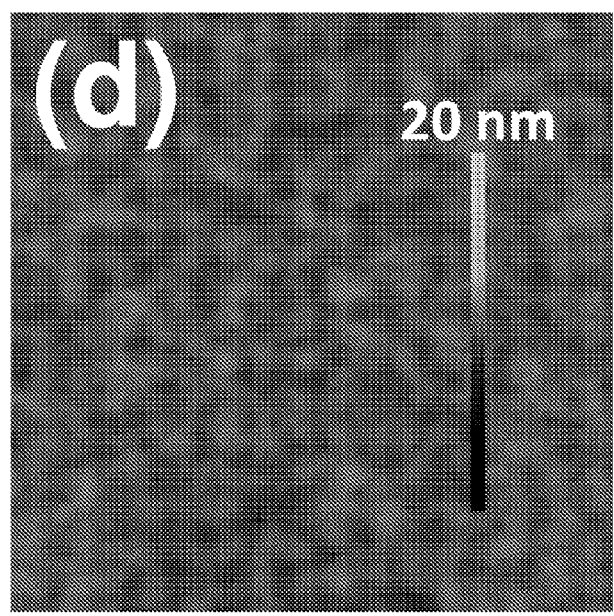
Figure 31D:
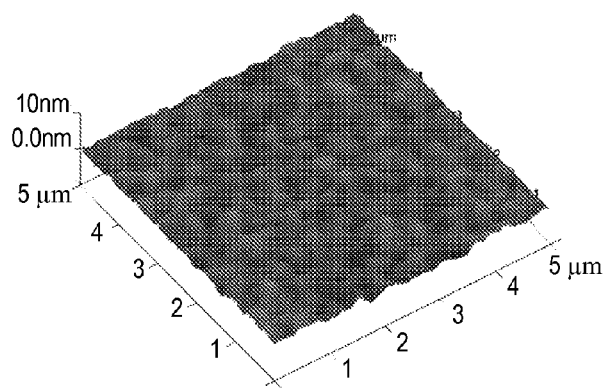

On the other hand, the surface morphology of BCP ETL did not show noticeable change by solution-processing (FIGS. 31A-31D). However, in contrast to the very smooth surface of vacuum-deposited BCP ETL (FIG. 31A), a relatively rougher surface of the solution-deposited BCP ETLs (FIGS. 31B-31D are 16 mg mL$^{-1}$, 20 mg mL$^{-1}$, and 24 mg mL$^{-1}$, respectively) can be seen.

The RMS roughness value of vacuum-deposited BCP was 0.311 nm whereas the RMS values of solution-deposited BCP ETLs was 0.467-0.504 nm. Although the change in surface morphology of the solution-processed BCP ETLs is small, the PhOLEDs with solution-deposited BCP ETLs showed superior performance compared with devices with vacuum-deposited BCP ETL. Thus, overall these results are consistent with the performance PhOLEDs with TmPyPB and BPhen ETLs, demonstrating that higher performance PhOLEDs can be achieved by solution-processing of ETLs compared to vacuum-processing.

Electron-Injection and Transport Properties.

Figure 32A:
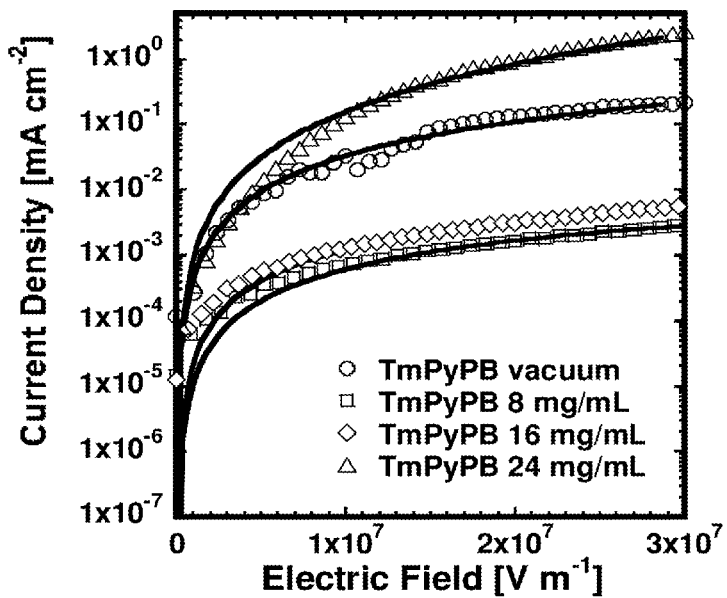
FIGS. 32A-32C graphically illustrate current density vs electric field (J vs E) of ITO/Al/PVK:OXD-7/commercial ETM/Al devices in ambient conditions, wherein the ETM is TmPyPB (FIG. 32A), BPhen (FIG. 32B), and BCP (FIG. 32C) ETLs.
Figure 32B:
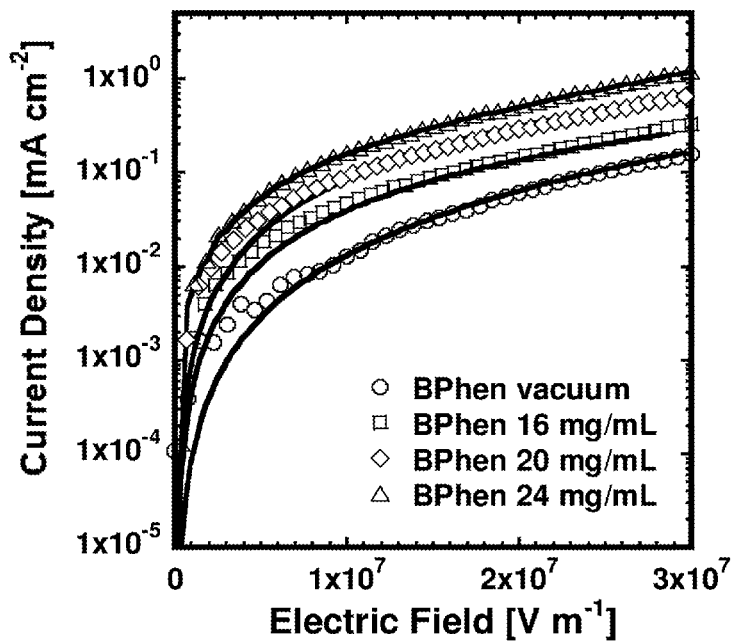
Figure 32C:
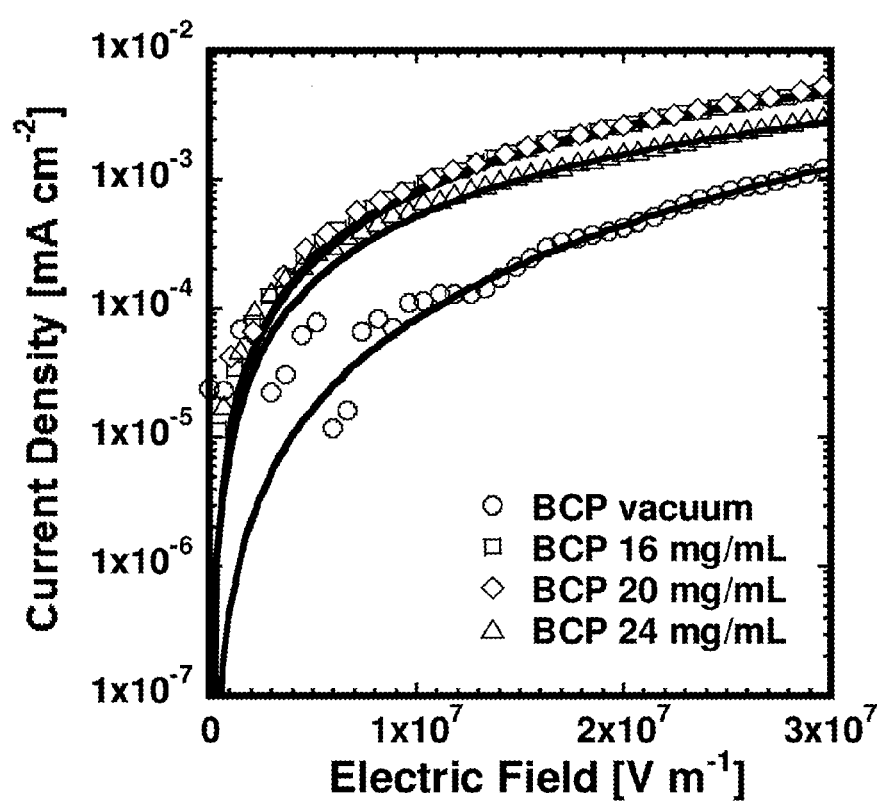

Electron-injection and transport in the vacuum- and solution-deposited commercial electron-transport materials was investigated by using electron-dominant devices: ITO/Al (100 nm)/PVK:OXD-7(60:40 wt/wt, 100 nm)/ETL(15-40 nm)/Al, which were fabricated and their current density-voltage (J-V) characteristics were measured and analyzed. The ETL thickness and deposition method were exactly the same as used in the PhOLEDs I-III with TmPyPB, BPhen, and BCP ETLs, as already discussed. The electron mobility of the devices was measured by the space-charge-limited current (SCLC) method under ambient conditions. In FIGS. 32A-32C, the current density-electric field (J-E) characteristics of the devices with TmPyPB (FIG. 32A), BPhen (FIG. 32B), and BCP (FIG. 32C) ETLs are shown.

Applied voltage (V) was converted to electric field (V cm$^{-1}$) by using the active layer thickness, allowing a relative comparison of electron-injection ability at the same electrical bias. The electron mobility was extracted by fitting the J-V curves in the near quadratic region according to the following modified Mott-Gurney equation, $$J = \frac{9}{8}\varepsilon\varepsilon_0\mu\frac{V^2}{L^3}\exp\left(0.89\beta\frac{\sqrt{V}}{\sqrt{L}}\right)$$

where J is the current density, $\epsilon 0$ is the permittivity of free space, $\epsilon$ is the relative permittivity, $\mu$ is the zero-field mobility, V is the applied voltage, L is the thickness of active layer, and $\beta$ is the field-activation factor (Table 8). The solid lines in FIGS. 32A-32C represent the SCLC fitting curves in the quadratic SCLC region.

TABLE 8

SCLC Electron Mobilities of Electron-Dominant Devices.

| ETL | Deposition method | $\mu$ (E = 0) [cm$^2$ V$^{-1}$ s$^{-1}$] | $\beta$ [cm$^{1/2}$ V$^{-1/2}$] | $E_{max}$ [V cm$^{-1}$] | Device layer thickness [nm] |
|---|---|---|---|---|---|
| TmPyPB | 8 mg mL$^{-1}$ | 6.1 × 10$^{-9}$ | 1.1 × 10$^{-5}$ | 3.5 × 10$^5$ | 115 |
| TmPyPB | 16 mg mL$^{-1}$ | 1.2 × 10$^{-8}$ | 1.2 × 10$^{-5}$ | 3.1 × 10$^5$ | 130 |
| TmPyPB | 24 mg mL$^{-1}$ | 3.7 × 10$^{-6}$ | 9.6 × 10$^{-6}$ | 2.9 × 10$^5$ | 140 |
| TmPyPB | Vacuum | 2.5 × 10$^{-7}$ | 5.9 × 10$^{-6}$ | 2.9 × 10$^5$ | 140 |
| BPhen | 16 mg mL$^{-1}$ | 1.6 × 10$^{-7}$ | 3.7 × 10$^{-6}$ | 3.3 × 10$^5$ | 120 |
| BPhen | 20 mg mL$^{-1}$ | 3.6 × 10$^{-6}$ | 2.8 × 10$^{-6}$ | 3.1 × 10$^5$ | 130 |
| BPhen | 24 mg mL$^{-1}$ | 1.3 × 10$^{-5}$ | 2.8 × 10$^{-5}$ | 3.1 × 10$^5$ | 140 |
| BPhen | Vacuum | 3.8 × 10$^{-8}$ | 6.0 × 10$^{-6}$ | 3.1 × 10$^5$ | 140 |
| BCP | 16 mg mL$^{-1}$ | 5.7 × 10$^{-9}$ | 7.7 × 10$^{-7}$ | 3.3 × 10$^5$ | 120 |
| BCP | 20 mg mL$^{-1}$ | 5.8 × 10$^{-9}$ | 8.9 × 10$^{-6}$ | 3.1 × 10$^5$ | 130 |
| BCP | 24 mg mL$^{-1}$ | 4.3 × 10$^{-9}$ | 7.0 × 10$^{-6}$ | 3.1 × 10$^5$ | 140 |
| BCP | Vacuum | 1.8 × 10$^{-10}$ | 8.0 × 10$^{-6}$ | 3.1 × 10$^5$ | 130 |

As shown by the highest current density in FIG. 32A, electron-injection was the most efficient in the device with TmPyPB ETL from 24 mg mL$^{-1}$ solution compared to other devices with a TmPyPB ETL. This trend matches well with the observed highest PhOLED performance compared to other devices with a TmPyPB ETL. The electron mobility estimated from these devices showed a three orders of magnitude increase, from ~10$^{-9}$ to ~10$^{-6}$ cm$^2$ V$^{-1}$ s$^{-1}$, with increasing TmPyPB solution concentration (Table 8). Devices with a BPhen ETL showed similar results, i.e., efficient electron-injection and increased electron mobility (from ~10$^{-7}$ to ~10$^{-5}$ cm$^2$ V$^{-1}$ s$^{-1}$) with increasing BPhen solution concentration (FIG. 32B, Table 8). The highest electron mobility of 1.3×10$^{-5}$ cm$^2$ V$^{-1}$ s$^{-1}$ was measured from the device with a BPhen ETL deposited from 24 mg mL$^{-1}$ solution, which also corresponds very well to the observed highest PhOLED performance. The previously discussed surface morphology, i.e. high surface roughness and high density of nanopillars of the surface of BPhen ETL deposited from a 24 mg mL$^{-1}$ solution, implies that maximum charge-transport can be expected, which is consistent with the measured high electron mobility of the electron-dominant device by the SCLC method. It is noted that it has been reported in the case of organic photovoltaic cells, that rough surface features of small-molecule thin films deposited from solution can increase the crystallinity and the roughness of the layer and thus increase device efficiency through improved charge-transport.

The J-E characteristics of electron-dominant devices with solution-deposited BCP ETL showed ETL are shown in FIG. 32C. The current density characteristics indicate similar electron-injection properties as of the devices with BCP ETL. The extracted electron mobilities of the devices were (4.3-5.8)× 10$^{-9}$ cm$^2$ V$^{-1}$ s$^{-1}$. However, the device with vacuum-deposited BCP ETL showed a relatively lower current density compared to the devices with solution-deposited BCP ETL as well as a significantly lower device electron mobility of 1.8×10$^{-10}$ cm$^2$ V$^{-1}$ s$^{-1}$, which explains the relatively poor performance of the corresponding PhOLED (device IIIA). The J-E characteristics of the electron-dominant devices with solution processed ETLs well-matched with the performance of the PhOLEDs and are also in accord with the observed AFM surface morphology of the ETLs. In general, the results suggest that the rough surface morphology with a high density of vertically aligned nanopillars formed by strong intermolecular interactions of solution-processed ETL maximize the contact area between the ETL and Al cathode, facilitating efficient electron-injection and transport, which lead to much higher device performance compared to PhOLEDs with vacuum-deposited ETL.

In summary, high-performance multilayered phosphorescent OLEDs have been successfully fabricated, for the first time, by sequential solution-processing of commercial small-molecule electron-transport materials (ETMs). The PhOLEDs with solution-processed electron-transport layers (ETLs) showed superior device performance compared to the devices with vacuum-deposited ETLs. Solution processing enabled the tuning and control of the ETL surface morphology by varying the solution concentration. The measured SCLC characteristics of the electron-dominant devices demonstrated that an ETL surface with a high density of vertically oriented nanopillars facilitated efficient electron-injection and transport, leading to enhanced PhOLED performance. The present approach of using a binary organic acid/water mixture as a solvent for the solution processing of ETMs is also applicable to the solution-deposition of many other commercial small-molecule ETMs, such as 2,2'2"-(1,3,5-benzinetriyl)-tris(1-phenyl-1-H-benzimidazole) (TPBI), and 3-(4-biphenyl)-4-phenyl-5-tert-butylphenyl-1,2,4-triazole (TAZ), since they also contain imine nitrogens which facilitate solubility in organic acids.

The results also suggest that control of the surface morphology of organic semiconductors by solution-processing is a very important and promising strategy to achieve efficient charge-injection and charge-transport properties. The density of vertically oriented nanopillars on the ETL surface and the device electron mobility strongly depend on the solution-processing condition and can be controlled to improve device performance. Furthermore, we expect that the orthogonal solution-processing approach demonstrated here has potential applications not limited to PhOLEDs but various other multilayered organic electronic devices.

Experimental

Materials

All commercially available materials were purchased and used as received without further purification.

Fabrication of PhOLEDs:

The phosphorescent emission layer (EML) consisted of a blend of Poly(N-vinyl carbazole) (PVK, M$_w$=1,100,000; Sigma-Aldrich) and 1,3-bis(2-(4-tert-butylphenyl)-1,3,4-oxadiazo-5-yl)benzene (OXD-7, LumTec., Taiwan) (PVK: OXD-7=60:40, wt/wt) as a host and 1.0 wt % fac-tris(2-phenylpyridine)iridium (Ir(ppy)$_3$, LumTec., Taiwan) as the dopant. A solution of PEDOT:PSS (poly-(ethylenedioxythiophene):polystyrenesulfonate, H. C. Starck, Clevios P VP Al 4083) in water was spin-coated to make a 30-nm hole-injection layer onto a pre-cleaned ITO glass and annealed at 150° C. under vacuum. The 70-nm polymer EML was obtained by spin coating of the PVK:OXD-7:Ir(ppy)$_3$ blends in cholorobenzene onto the PEDOT:PSS layer and vacuum dried at 100° C. Commercial small-molecule electron-transport materials (ETMs), 1,3,5-tri(3-pyrid-3-yl-phenyl)benzene (TmPyPB, LumTec., Taiwan), 4,7-diphenyl-1,10-phenanthroline (BPhen, sublimed grade, Sigma-Aldrich)

and 2,9-dimethyl-4,7-diphenyl-1,10-phenanthroline (BCP, sublimed grade, Sigma-Aldrich) were evaporated in a vacuum (<8.0×10$^{-7}$ torr) or spun cast from different concentration of ETMs in formic acid:water (FA:H$_2$O=3:1) mixture at a spin speed of 7000 rpm onto the EML followed by vacuum drying at 50° C. After drying, 100-nm Al was deposited onto the ETL. The structure of devices IA, HA, and IIIA was ITO/PEDOT:PSS(30 nm)/EML(70 nm)/vacuum-deposited ETM/Al (100 nm). The structure of devices IB-D, IIB-D, and IIIB-D was identical except electron-transport layer was solution-processed, ITO/PEDOT:PSS(30 nm)/EML(70 nm)/solution-deposited ETM/Al (100 nm). Film thickness was measured by an Alpha-Step 500 profilometer (KLA-Tencor, San Jose, Calif.).

Characterization of PhOLEDs:

Electroluminescence (EL) spectra were obtained using a Photon Technology International (PTI) Inc. Model QM 2001-4 spectrofluorimeter. Current-voltage (J-V) characteristics of the PhOLEDs were measured by using a HP4155A semiconductor parameter analyzer (Yokogawa Hewlett-Packard, Tokyo). The luminance was simultaneously measured by using a model 370 optometer (UDT Instruments, Baltimore, Md.) equipped with a calibrated luminance sensor head (Model 211) and a 5× objective lens. The device external quantum efficiency (EQE) was calculated from the luminance, current density and EL spectrum assuming a Lambertian distribution using procedures previously reported. All the device fabrication and device characterization steps were carried out under ambient laboratory conditions.

Devices for space-charge-limited current (SCLC) measurement were fabricated with electron-dominant device structure: ITO/Al(100 nm)/PVK:OXD-7(60:40, wt/wt, 100 nm)/ETL/Al. The 100-nm thick Al electrode was deposited onto ITO substrate followed by spin-coating of subsequent polymer host layer. ETL was vacuum-deposited or solution-deposited using the exact same condition as for PhOLED fabrication followed by deposition of Al electrode. Current-voltage characteristics of SCLC devices were measured using the same semiconductor parameter analyzer as for the characterization of PhOLED devices. The SCLC measurements were performed under dark and ambient conditions.

AFM characterization of ETL surface morphology was done on a Veeco Dimension 3100 Scanning Probe Microscope (SPM) system. The AFM topographical images were measured with the same PhOLEDs used for device characterization.

While illustrative embodiments have been illustrated and described, it will be appreciated that various changes can be made therein without departing from the spirit and scope of the invention.

The embodiments of the invention in which an exclusive property or privilege is claimed are defined as follows:

1. An optoelectronic device, comprising:
 a first electrode;
 a second electrode;
 an active layer intermediate the first and second electrodes; and
 a transport layer intermediate the second electrode and the active layer, wherein the transport layer comprises a compound of (1):

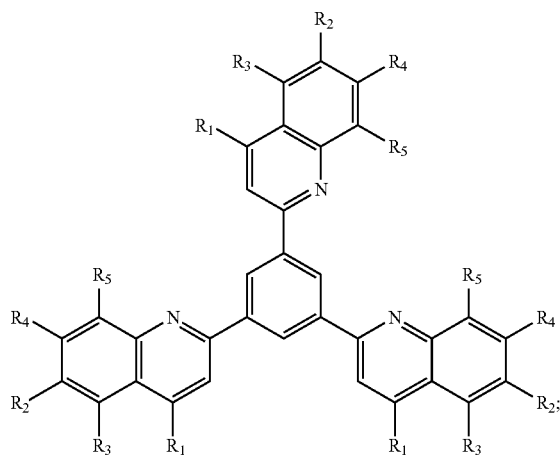

wherein R$_1$ is independently selected from the group consisting of H, alkyl, aromatic, heteroaromatic,

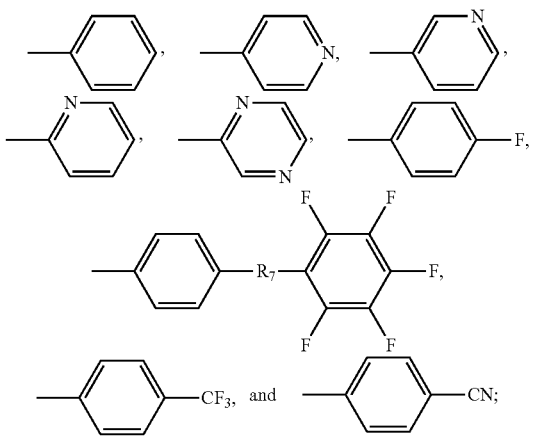

wherein R$_7$ is any one of R$_1$ or R$_2$;

wherein R$_2$ is independently selected from the group consisting of H, alkyl, aromatic, heteroaromatic,

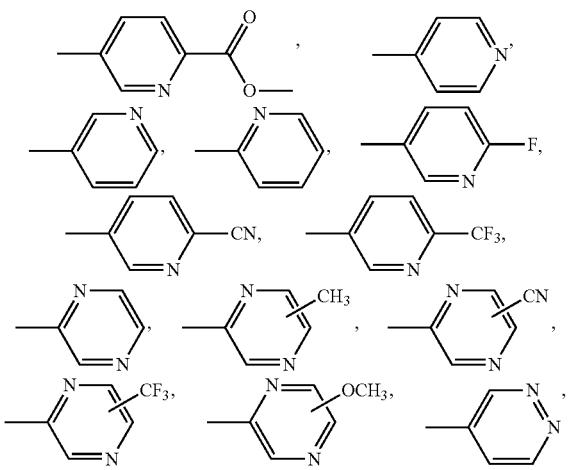

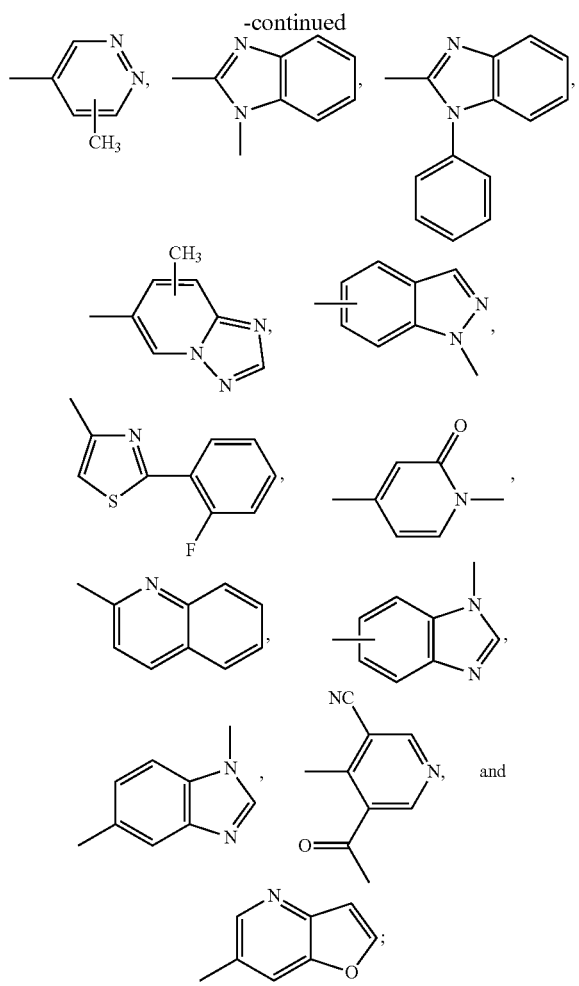

wherein $R_3$, $R_4$ and $R_5$ are each independently selected from the group consisting of H and $R_1$; and wherein all of $R_1$-$R_5$ are not H.

2. The device of claim 1, wherein the transport layer has solubility orthogonal to the solubility of the active layer.

3. The device of claim 1, wherein the first electrode is an anode.

4. The device of claim 1, wherein the first electrode comprises a material selected from the group consisting of indium-tin-oxide and fluorine-tin-oxide.

5. The device of claim 1, wherein the second electrode is a cathode.

6. The device of claim 1, wherein the second electrode comprises a material selected from the group consisting of aluminum, silver, and gold.

7. The device of claim 1, further comprising a substrate adjacent the first or second electrode.

8. The device of claim 7, wherein the substrate is glass or plastic.

9. The device of claim 7, wherein the substrate is adjacent to the first electrode, wherein the substrate is glass, and wherein the first electrode is indium-tin-oxide.

10. The device of claim 1, further comprising a hole-injection buffer layer intermediate the active layer and the first electrode.

11. The device of claim 10, wherein the hole-injection buffer layer comprises poly(3,4-ethylene dioxythiophene):poly(styrene sulfonic acid) or polyaniline.

12. The device of claim 1, wherein the active layer is a phosphorescent light-emitting material.

13. The device of claim 12, wherein the active layer is a blue light-emitting material.

14. The device of claim 1, wherein the active layer comprises a triplet emitter-doped poly(N-vinylcarbazole).

15. A method of fabricating a portion of an optoelectronic device comprising forming a transport layer on an active layer from a solution comprising a compound of (1) and a solvent, wherein the compound has a solubility in the solvent orthogonal to the solubility of the active layer in the solvent, and wherein the active layer is not solvated during forming of the transport layer wherein the compound (1) is:

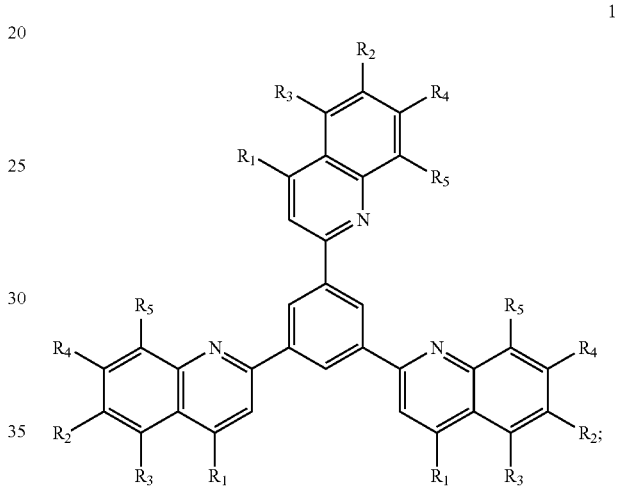

wherein $R_1$ is independently selected from the group consisting of H, alkyl, aromatic, heteroaromatic,

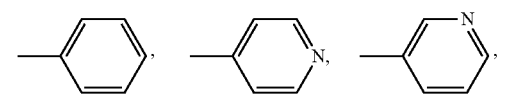

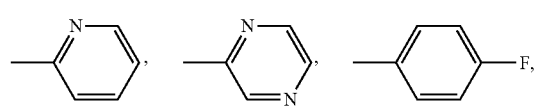

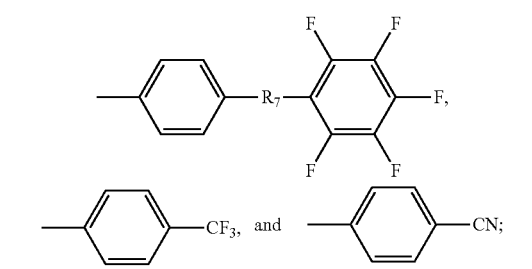

wherein $R_7$ is any one of $R_1$ or $R_2$;

wherein $R_2$ is independently selected from the group consisting of H, alkyl, aromatic, heteroaromatic,

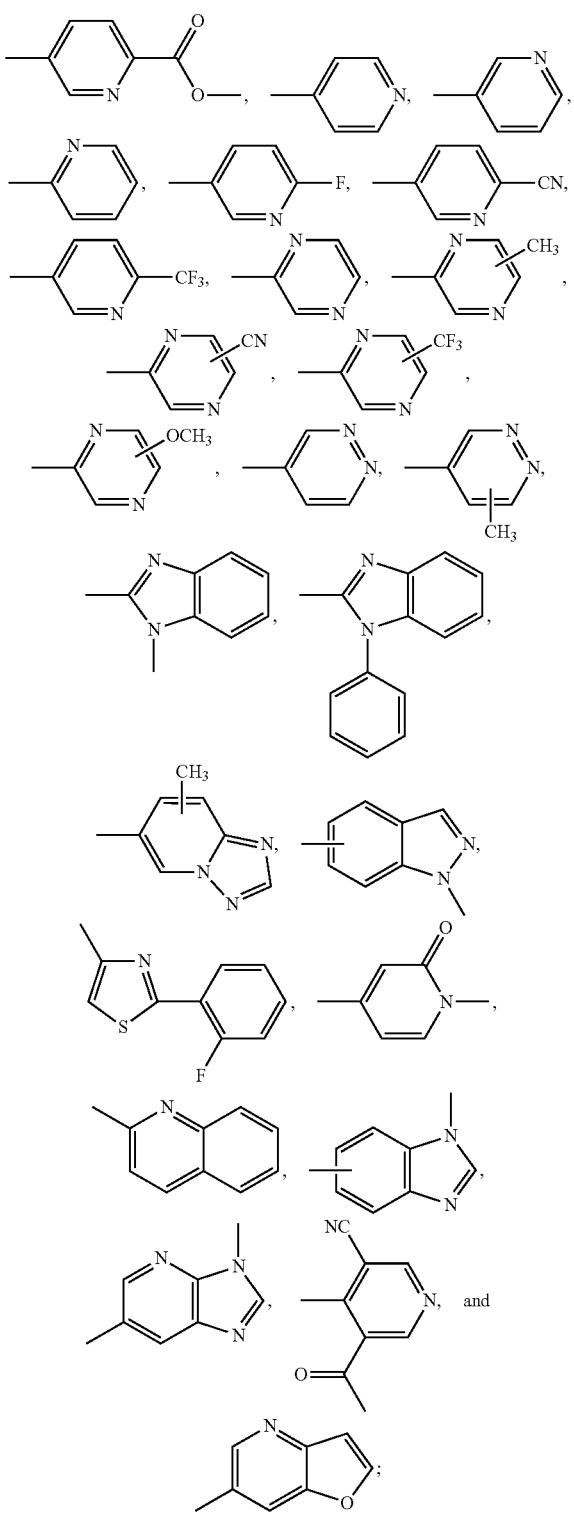

wherein $R_3$, $R_4$, and $R_5$ are each independently selected from the group consisting of H and $R_1$; and wherein all of $R_1$-$R_5$ are not H.

16. The method of claim 15 further comprising providing a first electrode abutting the active layer and a second electrode abutting the transport layer to provide an optoelectronic device.

17. The method of claim 16, wherein the optoelectronic device is a blue, green, red and white phosphorescent light-emitting diode.

18. The method of claim 15, wherein the solvent is a binary solvent.

19. The method of claim 18, wherein the binary solvent comprises a mixture of water and formic acid.

20. The method of claim 19, wherein the binary solvent is about one part water and from about 2 to about 10 parts formic acid.

21. The method of claim 19, wherein the binary solvent is about one part water and about three parts formic acid.

22. The method of claim 18, wherein the binary solvent comprises a mixture of water and one or more acids, each having a boiling point in the range of from about 70-160° C. and a pKa lower than 4.97.

23. The method of claim 22, wherein the acid is a $C_1$-$C_4$ carboxylic acid; wherein the carboxylic acid is selected from the group consisting of hydrogen-substituted, halogenated, fluorinated, and combinations thereof.

24. The method of claim 15, wherein the solvent is a carboxylic acid selected from the group consisting of formic acid, acetic acid, 2-propenoic acid, 2-propynoic acid, lactic acid, maleic acid, trifluoroacetic acid, trifluorobutanoic acid, and trifluoropropionic acid, and combinations thereof.

25. The method of claim 24, wherein the carboxylic acid has a boiling point in the range of from about 70-160° C. and a pKa lower than 4.97.

26. A method of fabricating a portion of an optoelectronic device, comprising forming a transport layer on an active layer from a solution comprising a charge-transport compound and a non-ionic solvent, wherein the charge-transport compound has a solubility in the solvent orthogonal to the solubility of the active layer in the solvent, wherein the charge-transport compound is a heterocyclic compound containing two or more imine nitrogens, and wherein the active layer is not solvated during forming of the transport layer.

27. The method of claim 26, wherein the solvent is a binary solvent.

28. The method of claim 27, wherein the binary solvent comprises a mixture of water and formic acid.

29. The method of claim 28, wherein the binary solvent is about one part water and from about 2 to about 10 parts formic acid.

30. The method of claim 28, wherein the binary solvent is about one part water and about three parts formic acid.

31. The method of claim 27, wherein the binary solvent comprises a mixture of water and one or more acids, each having a boiling point in the range of from about 70-160° C. and a pKa lower than 4.97.

32. The method of claim 31, wherein the acid is a $C_1$-$C_4$ carboxylic acid; wherein the carboxylic acid is selected from the group consisting of hydrogen-substituted, halogenated, fluorinated, and combinations thereof.

33. The method of claim 26, wherein the solvent is a carboxylic acid selected from the group consisting of formic acid, acetic acid, 2-propenoic acid, 2-propynoic acid, lactic acid, maleic acid, trifluoroacetic acid, trifluorobutanoic acid, and trifluoropropionic acid, and combinations thereof.

34. The method of claim 33, wherein the carboxylic acid has a boiling point in the range of from about 70-160° C. and a pKa lower than 4.97.

35. The method of claim 26, wherein the charge-transport compound is a heterocyclic compound containing three or more imine nitrogens.

36. The method of claim 26, wherein the charge-transport compound is selected from the group consisting of:

(a) compound (1):

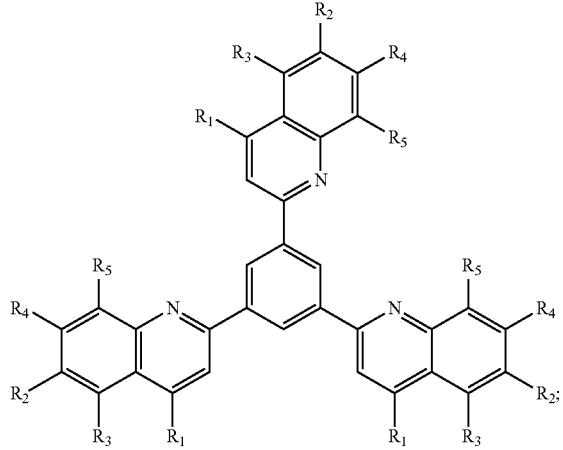

wherein R₁ is independently selected from the group consisting of H, alkyl, aromatic, heteroaromatic,

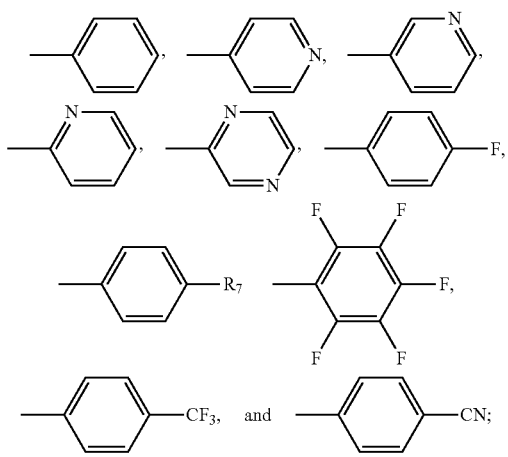

wherein R₇ is any one of R₁ or R₂;

wherein R₂ is independently selected from the group consisting of H, alkyl, aromatic, heteroaromatic,

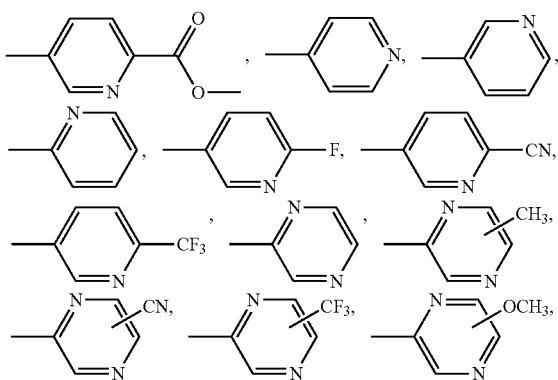

-continued

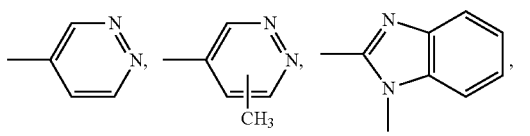

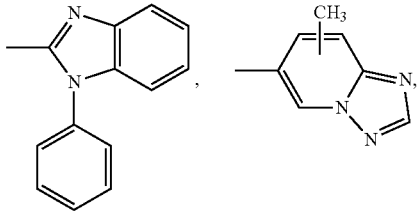

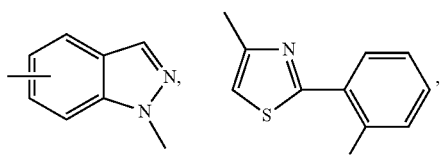

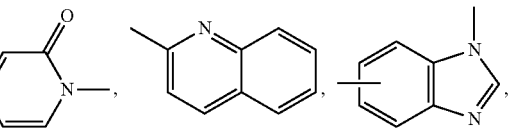

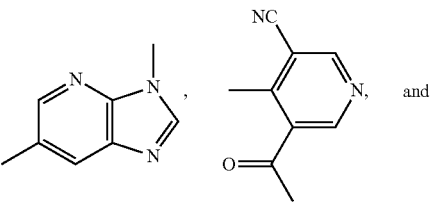

wherein R₃, R₄, and R₅ are each independently selected from the group consisting of H and R₁; and wherein all of R₁-R₅ are not H (b) compound (2):

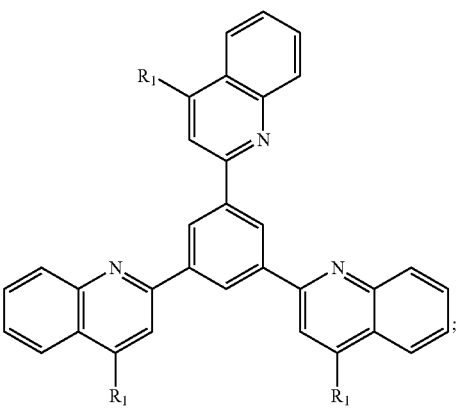

wherein R₁ is selected from the group consisting of alkyl, aromatic, heteroaromatic,

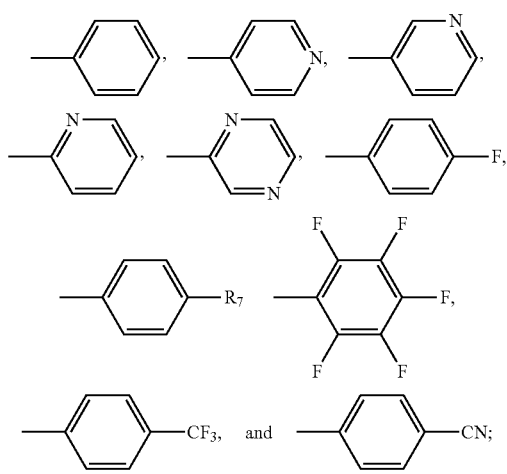
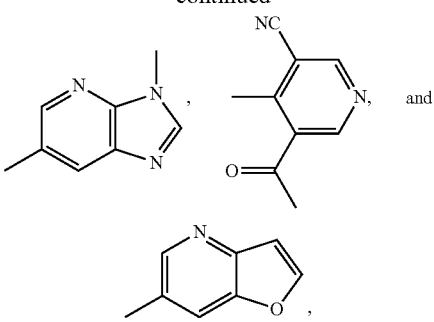
(c) compound (3):
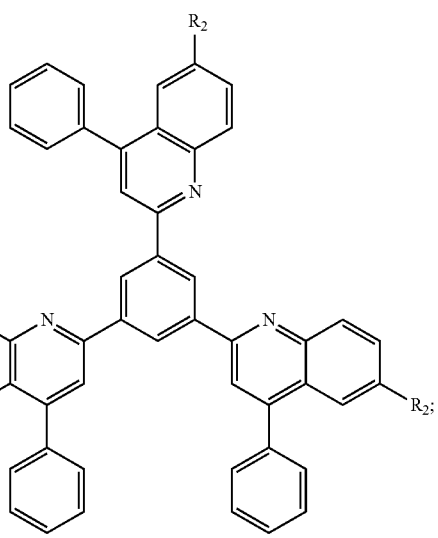
wherein $R_7$ is any one of $R_1$ or $R_2$; and
wherein $R_2$ is independently selected from the group consisting of H, alkyl, aromatic, heteroaromatic,
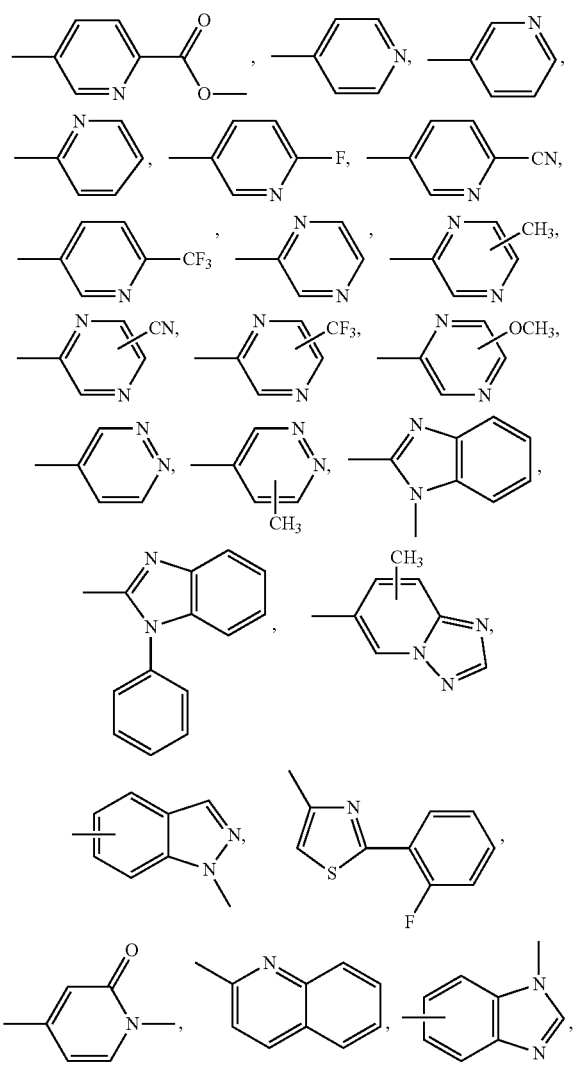
wherein $R_2$ is independently selected from the group consisting of H, alkyl, aromatic, heteroaromatic,
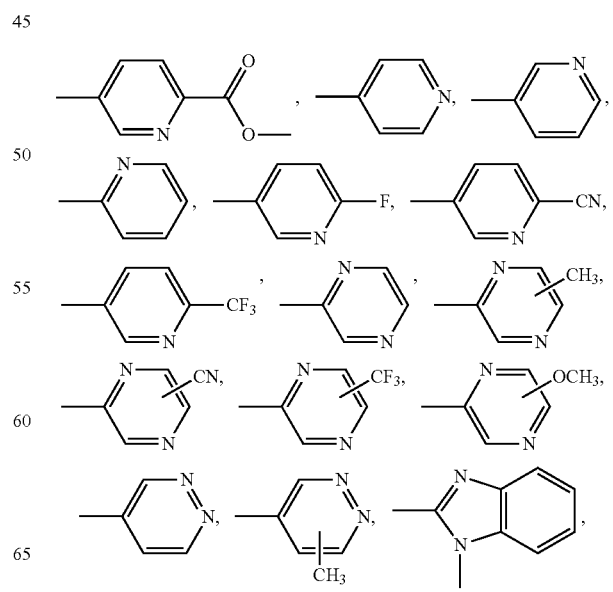

-continued
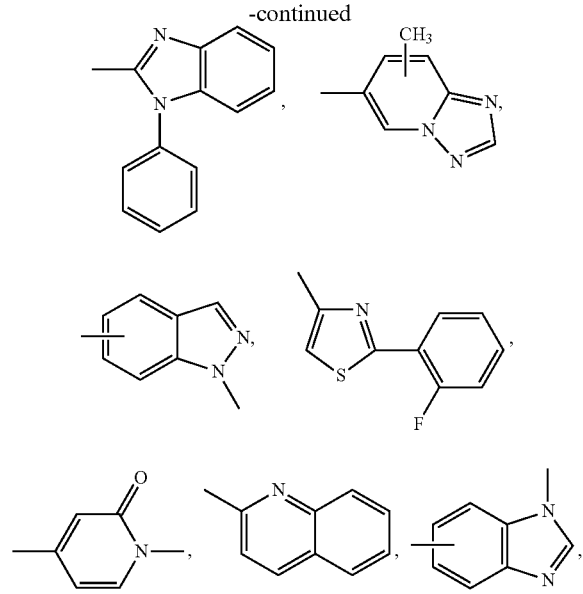
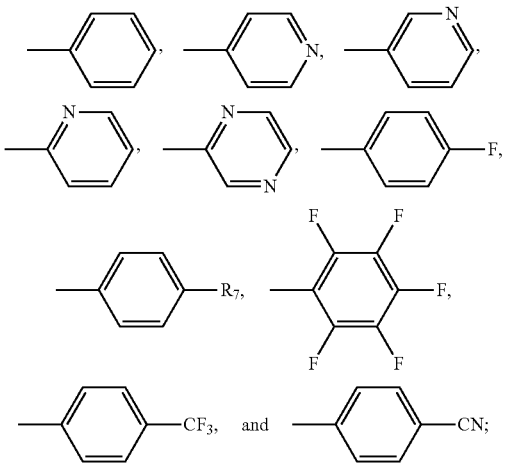
wherein $R_1$ is independently selected from the group consisting of H, alkyl, aromatic, heteroaromatic,
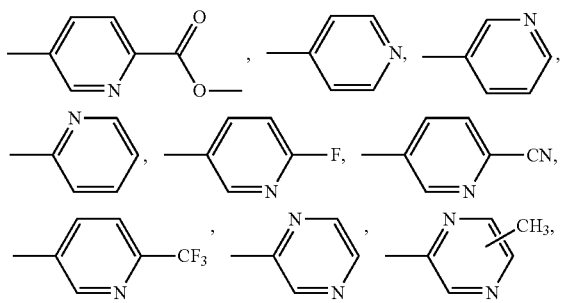
wherein $R_7$ is any one of $R_1$ or $R_2$;
wherein $R_2$ is any of H, alkyl, aromatic, heteroaromatic,
(d) compound (4):
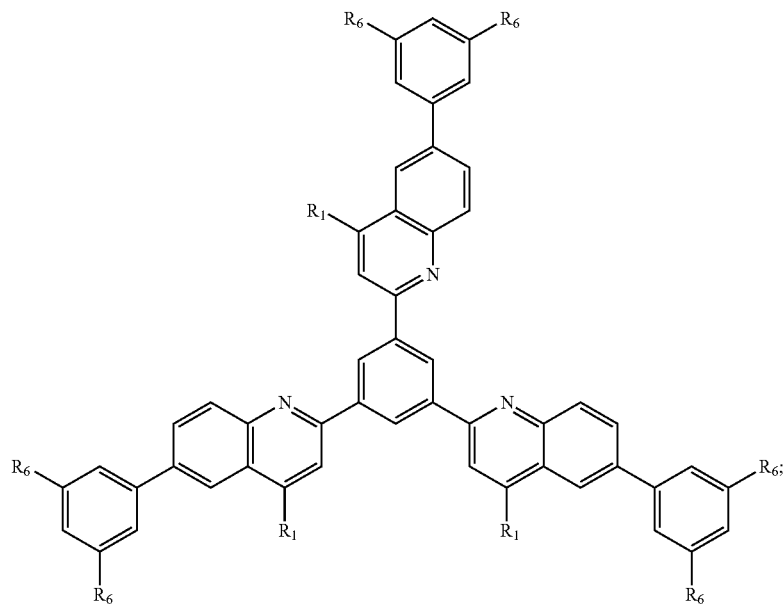

-continued

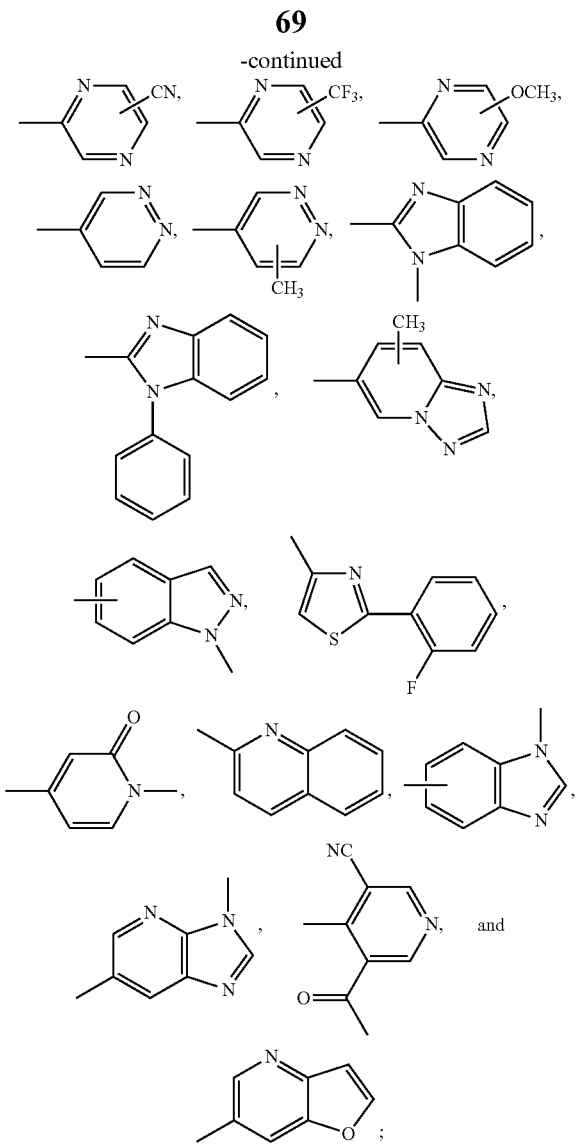

and
wherein R₆ is independently selected from the group consisting of:

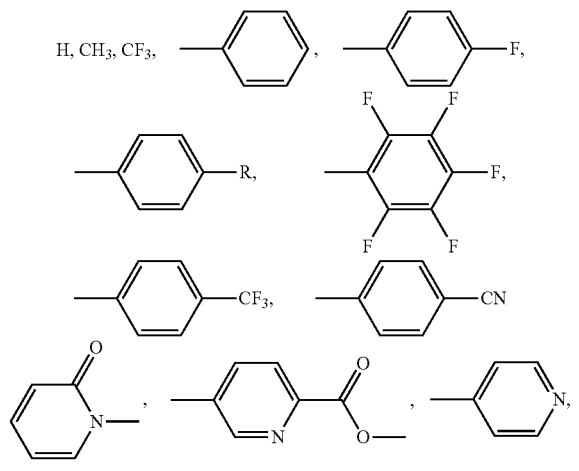

-continued

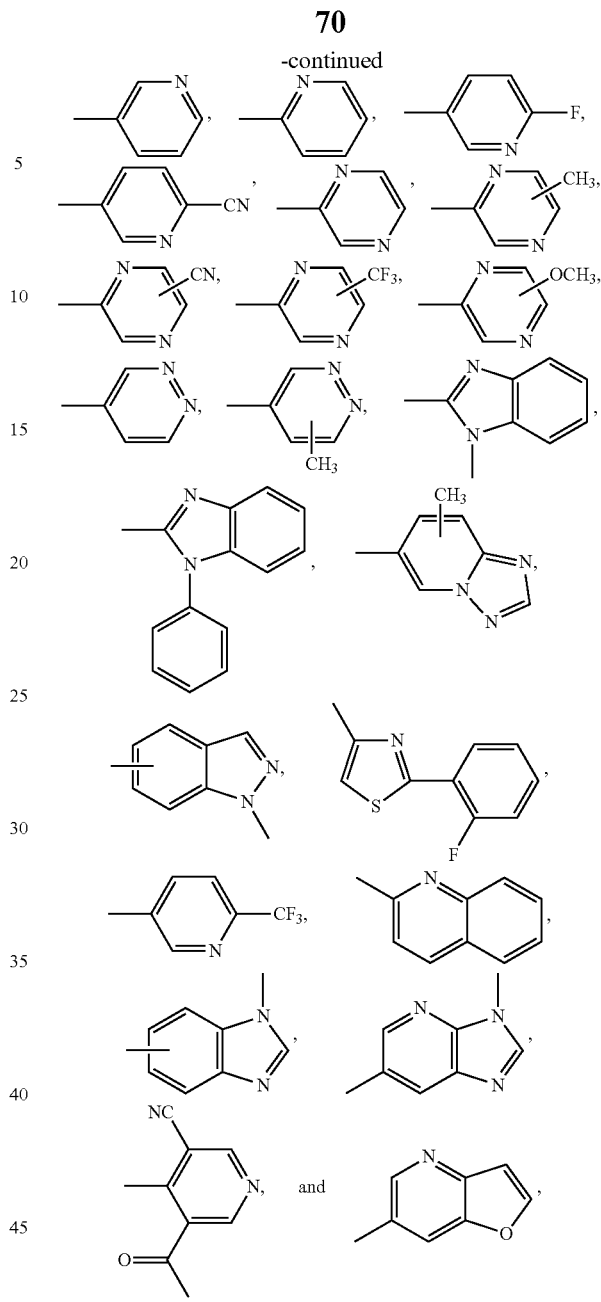

(e) 2,9-dimethyl-4,7-diphenyl-1,10-phenanthroline (BCP),
(f) (2,2',2''-(1,3,5-Benzinetriyl)-tris(1-phenyl-1-H-benzimidazole) (TPBI),
(g) 4,7-diphenyl-1,10-phenanthroline (BPhen),
(h) 2-(4-biphenyl)-5-(4-tert-butylphenyl)-1,3,4-oxadiazole (PBD),
(i) 3-(4-biphenyl)-4-phenyl-5-tert-butylphenyl-1,2,4-triazole (TAZ),
(j) 1,3-bis[2-(4-tert-butylphenyl)-1,3,4-oxadiazo-5-yl]benzene (OXD-7),
(k) tris(2,4,6-trimethyl-3-(pyridine-3-yl)phenyl)borane (3 TPYMB),
(l) 3,3',5,5'-tetra[(m-pyridyl)-phen-3-yl]biphenyl (BP4mPy), (m) 1,3,5-tri[(3-pyridyl)phen-3-yl]benzene (TmPyPB),
(n) 1,3-bis[3,5-di(pyridine-3-yl)phenyl]benzene (BmPy-PhB), and
(o) combinations thereof.

37. The method of claim 26, wherein the organic active layer comprises a mixture of one or more polymers and one or more phosphorescent triplet emitters.

38. The method of claim 37, wherein the polymer is selected from the group consisting of poly(N-vinylcarbazole) (PVK), poly(alkylfluorene) (PFO), and poly(p-phenylene) (PPP).

39. The method of claim 37 wherein the polymer has the band gap ($E_g$) greater than 2.5 eV.

40. The method of claim 37, wherein the phosphorescent triplet emitter is selected from the group consisting of Iridium-, Ruthenium-, and Osmium-based metal-complexes.

41. The method of claim 37, wherein the phosphorescent triplet emitter is selected from the group consisting of Tris(2-phenylpyridine)iridium(III) (Ir(ppy)$_3$), Bis(2-phenylpyridine)(acetylacetonate)iridium(III) (Ir(ppy)$_2$(acac)), Tris[2-(p-tolyl)pyridine] iridium(III) (Ir(mppy)$_3$), Bis(3,5-difluoro-2-(2-pyridyl)phenyl-(2-carboxypyridyl)iridium III (FIrpic), Bis(2,4-difluorophenylpyridinato)tetrakis(1-pyrazolyl)borate iridium III (FIr6), Bis(2-benzo[b]thiophen-2-yl-pyridine)(acetylacetonate)iridium(III) (Ir(btp)2(acac)), Tris(1-phenylisoquinoline)iridium(III) (Ir(piq)$_3$) Bis(1-phenylisoquinoline)(acetylacetonate)iridium (III) (Ir(piq)$_2$(acac)), Bis[1-(9,9-dimethyl-9H-fluoren-2-yl)-isoquinoline](acetylacetonate)iridium(III) (Ir(fliq)$_2$(acac)), Bis[2-(9,9-dimethyl-9H-fluoren-2-yl)-quinoline](acetylacetonate) iridium(III) (Ir(flq)$_2$(acac)), Bis(2-phenylbenzothiazolato)(acetylacetonate)iridium(III) (Bt$_2$Ir(acac)), Osmium(II) bis (3-trifluoromethyl-5-(2-pyridyl)-pyrazolate) dimethylphenylphosphine (Os(fppz)$_2$(PPhMe$_2$)$_2$) Osmium (II) bis(3-(trifluoromethyl)-5-(4-tert-butylpyridyl)-1,2,4-triazolate)diphenylmethylphosphine (Os(bpftz)$_2$ (PPh2Me)$_2$), and combinations thereof.

42. The method of claim 37, wherein the organic active layer further comprises a charge transport compound.

43. The method of claim 42, wherein the charge transport compound is selected from the group consisting of 1,3-bis(2-(4-tert-butylphenyl)-1,3,4-oxadiazo-5-yl)benzene (OXD-7), 2-(4-Biphenyl)-5-(4-tert-butylphenyl)-1,3,4-oxadiazole (PBD), 3-(4-Biphenyl)-4-phenyl-5-tert-butylphenyl-1,2,4-triazole (TAZ), and combinations thereof.

44. The method of claim 42, wherein the charge transport compound is selected from the group consisting of N,N'-Bis(3-methylphenyl)-N,N'-bis(phenyl)-benzidine (TPD), Di-[4-(N,N-ditolyl-amino)-phenyl]cyclohexane (TAPC), 4,4'-Bis(carbazol-9-yl)biphenyl (CBP), N, N'-Bis(naphthalen-1-yl)-N,N'-bis(phenyl)-benzidine (NPB), and combinations thereof.

45. The method of claim 42, wherein the charge transport compound has ionization potential value (IP) lower than 6.0 eV.

46. The method of claim 26, wherein the organic active layer is selected from the group consisting of poly(N-vinylcarbazole) (PVK), N,N'-Bis(3-methylphenyl)-N,N'-bis(phenyl)-benzidine (TPD), Di-[4-(N,N-ditolyl-amino)-phenyl] cyclohexane (TAPC), 4,4'-Bis(carbazol-9-yl)biphenyl (CBP), 1,3-bis(2-(4-tert-butylphenyl)-1,3,4-oxadiazo-5-yl) benzene (OXD-7), 2-(4-Biphenyl)-5-(4-tert-butylphenyl)1,3,4-oxadiazole (PBD), and combinations thereof.

47. The method of claim 15, wherein the solvent has a neutral charge.

48. A compound (2):

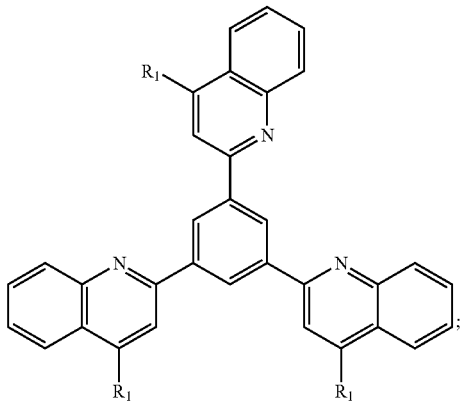

wherein R$_1$ is selected from the group consisting of alkyl, aromatic, heteroaromatic,

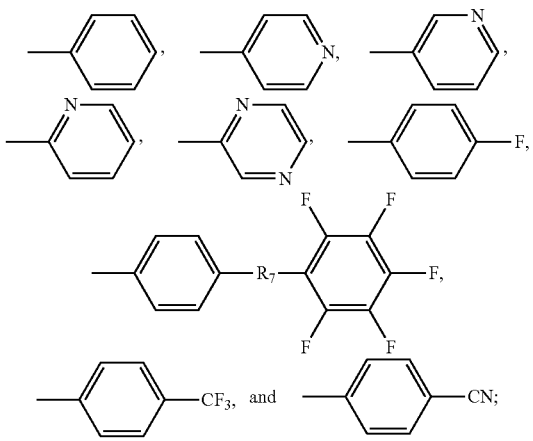

wherein R$_7$ is any one of R$_1$ or R$_2$; and
wherein R$_2$ is independently selected from the group consisting of H, alkyl, aromatic, heteroaromatic,

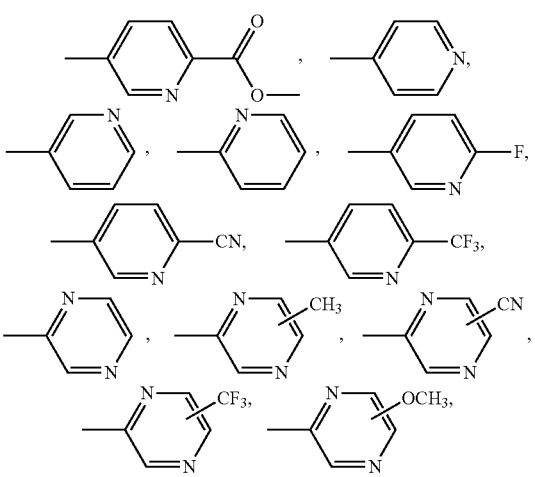

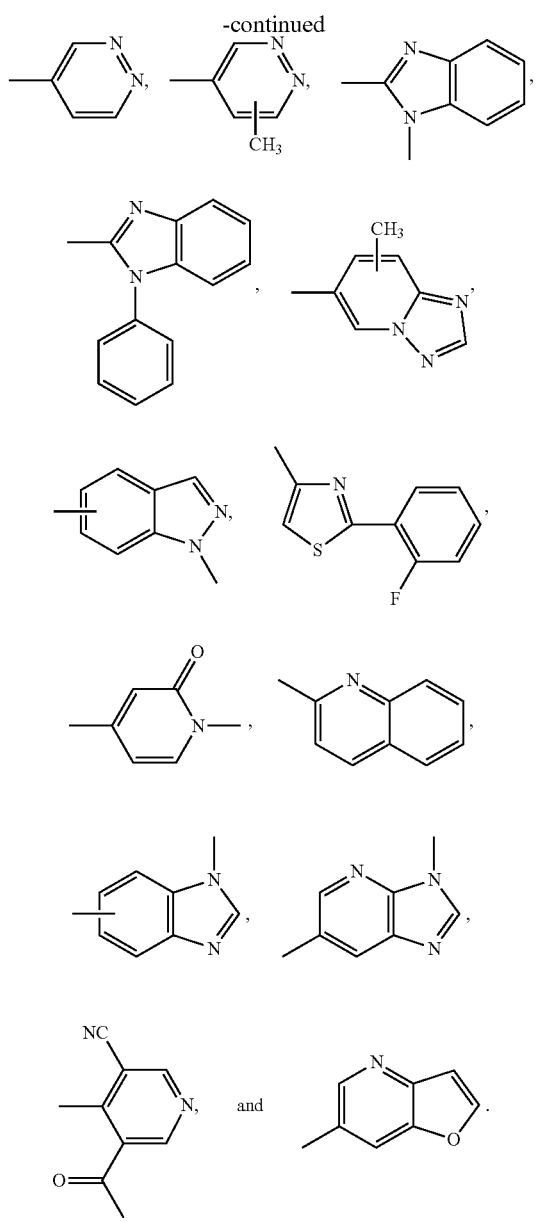
49. The compound of claim 48, wherein the compound is:
50. The compound of claim 48, wherein the compound is:
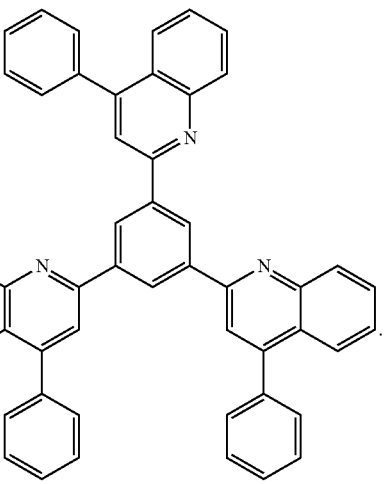
51. The compound of claim 48, wherein the compound is:
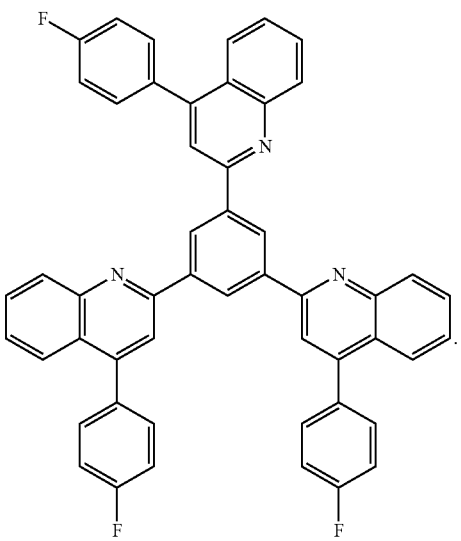 [SMILES: Fc1ccc(-c2cc(-c3cc(-c4cc(-c5ccc(F)cc5)c5ccccc5n4)cc(-c4cc(-c5ccc(F)cc5)c5ccccc5n4)c3)nc3ccccc23)cc1]
52. The compound of claim 48, wherein the compound is:
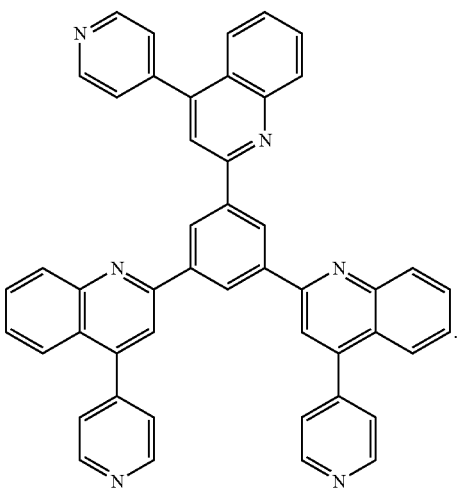 [SMILES: c1ccc2c(-c3ccncc3)cc(-c3cc(-c4cc(-c5ccncc5)c5ccccc5n4)cc(-c4cc(-c5ccncc5)c5ccccc5n4)c3)nc2c1]
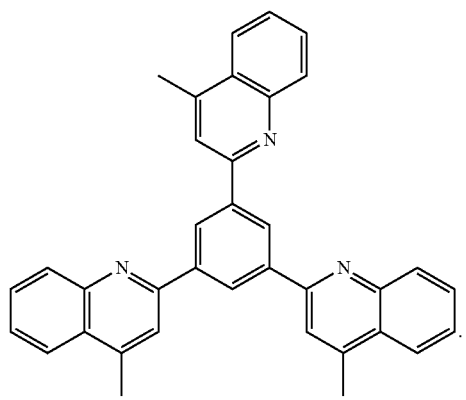

53. A compound (3):
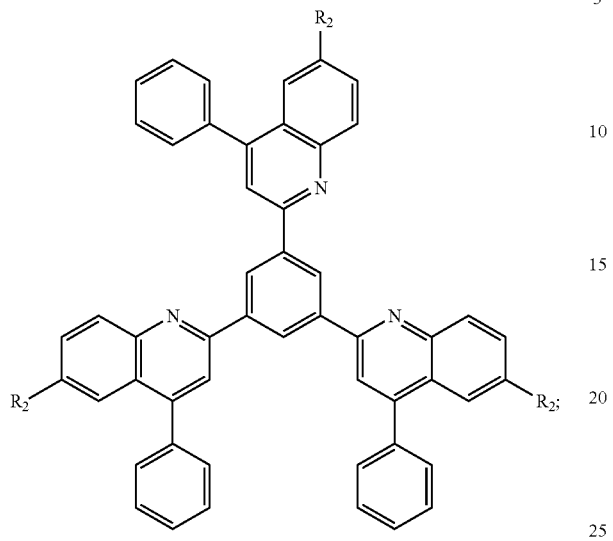
wherein R₂ is independently selected from the group consisting of H, alkyl, aromatic, heteroaromatic,
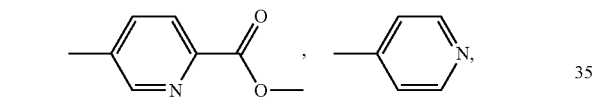
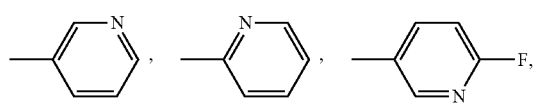
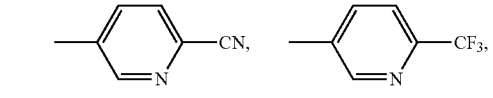
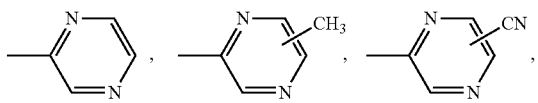
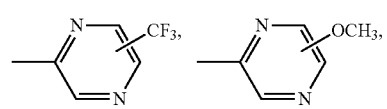
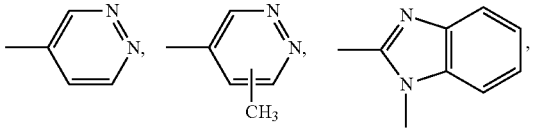
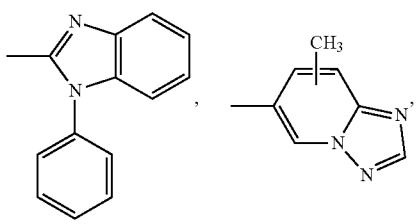
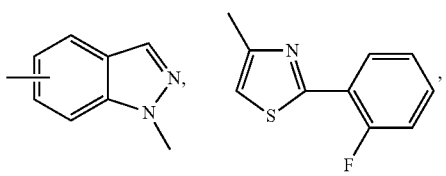
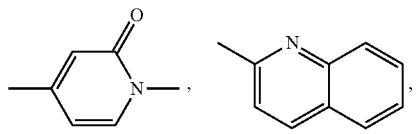
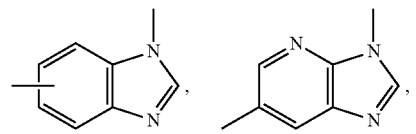
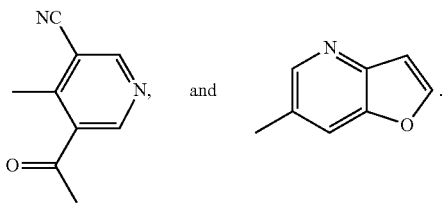

54. A compound (4):
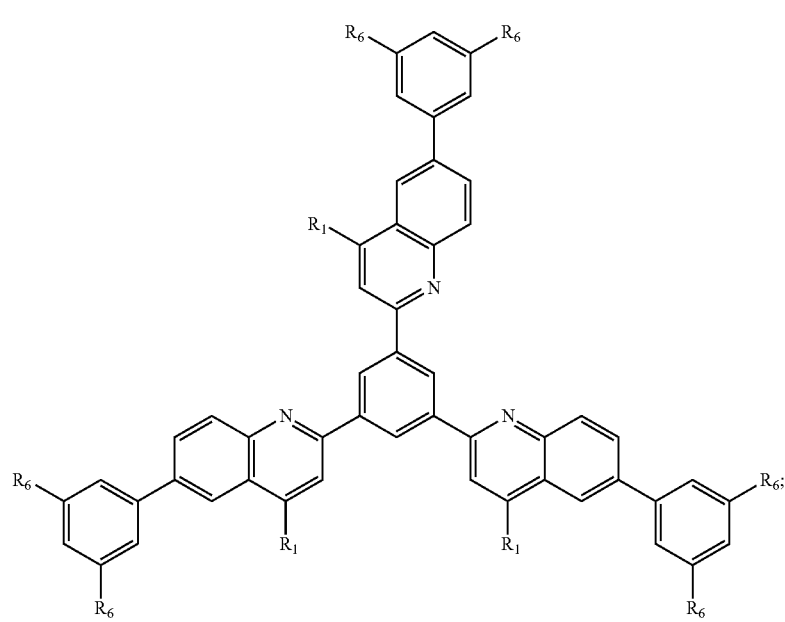
wherein $R_1$ is independently selected from the group consisting of H, alkyl, aromatic, heteroaromatic,
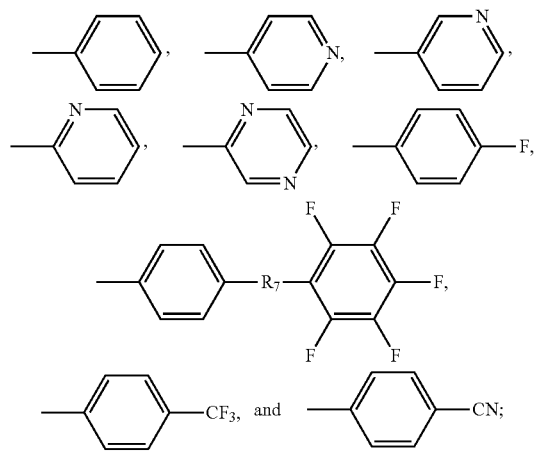
wherein $R_7$ is any one of $R_1$ or $R_2$;
wherein $R_2$ is any of H, alkyl, aromatic, heteroaromatic,
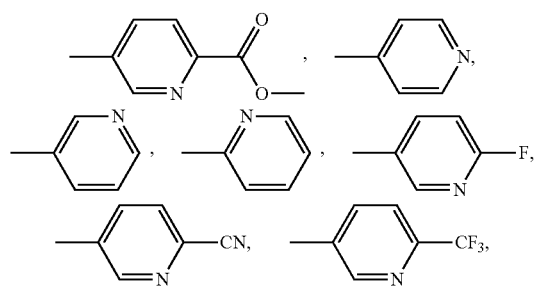
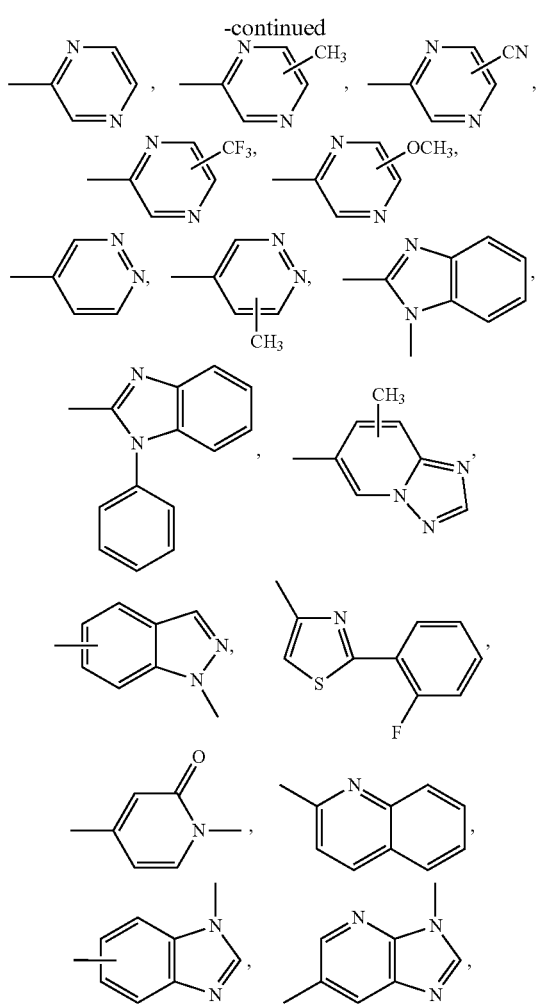

-continued
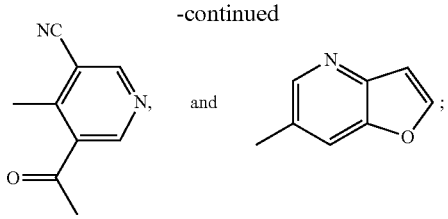
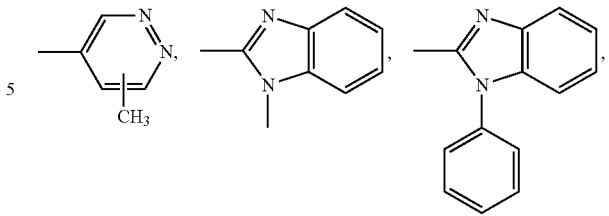
and wherein $R_6$ is independently selected from the group consisting of
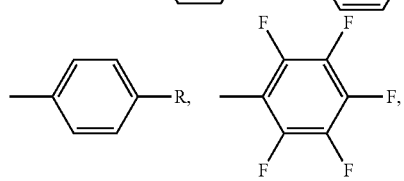
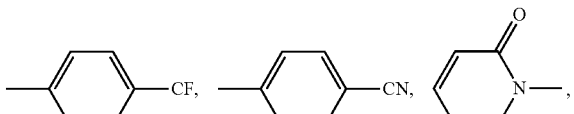
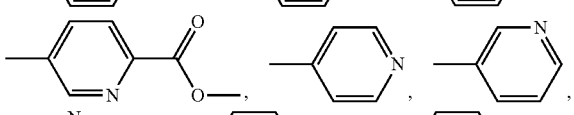
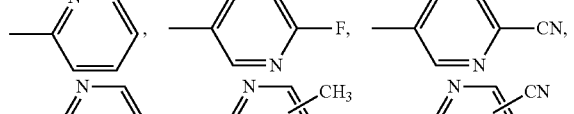
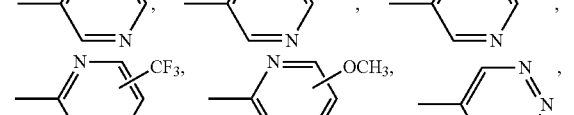
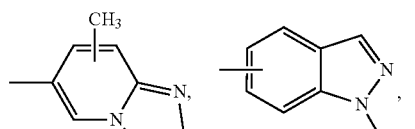
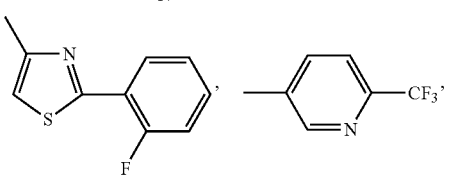
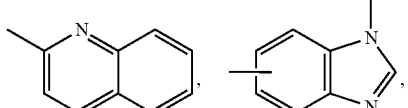
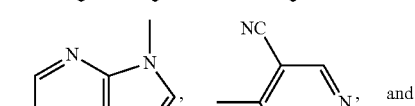
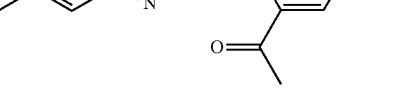
* * * * *